(12) United States Patent
Moinet et al.

(10) Patent No.: US 8,269,026 B2
(45) Date of Patent: Sep. 18, 2012

(54) LUPANE DERIVATIVES USEFUL FOR TREATING HIV

(75) Inventors: Christophe Moinet, Noyal Chatillon (FR); Liliane Halab, Laval (CA); Nathalie Turcotte, Rosemere (CA); Monica Bubenik, Mascouche (CA); Marc Courchesne, Laval (CA); Carl Poisson, Montreal (CA); Oswy Z. Pereira, Kirkland (CA); Paul Nguyen-Ba, Laprairie (CA); Bingcan Liu, Laval (CA); Nathalie Chauret, Ile Bizard (CA); Caroline Cadilhac, Montreal (CA); Laval Chan Chun Kong, Kirkland (CA)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 0 days.

(21) Appl. No.: 12/830,293

(22) Filed: Jul. 3, 2010

(65) Prior Publication Data

US 2011/0077227 A1    Mar. 31, 2011

Related U.S. Application Data

(63) Continuation of application No. PCT/CA2008/002291, filed on Dec. 23, 2008.

(60) Provisional application No. 61/018,759, filed on Jan. 3, 2008, provisional application No. 61/039,660, filed on Mar. 26, 2008.

(51) Int. Cl.
*C07J 53/00*    (2006.01)
(52) U.S. Cl. ......... 552/510; 552/502; 514/177; 514/169
(58) Field of Classification Search ................. None
See application file for complete search history.

(56) References Cited

U.S. PATENT DOCUMENTS

| | | | |
|---|---|---|---|
| 6,172,110 B1 * | 1/2001 | Lee et al. ............... | 514/530 |
| 7,026,305 B2 * | 4/2006 | Chen et al. ............. | 514/169 |
| 2006/0019934 A1 * | 1/2006 | Saxena et al. .......... | 514/169 |
| 2006/0205697 A1 * | 9/2006 | Robinson et al. ...... | 514/129 |

OTHER PUBLICATIONS

"Synthesis and Antiviral Activity of Ureides and Carbamates of Betulinic Acid and Its Derivatives" by Flekhter et al., Russian J. Bioorg. Chem. 29, 594-600 (2003).*
"Betulinic Acid Derivatives: A New Class of Human Immunodeficiency Virus Type 1 Specific Inhibitors with a New Mode of Action" by Evers et al., J. Med. Chem. 39, 1056-68 (1996).*
International Search Report PCT/CA2008/002291 dated Jan. 28, 2009.
Sun, et al., "Anti-AIDS Agents. 34. Synthesis and Structure-Activity Relationships of Betulin Derivatives as Anti-HIV Agents", J. Med. Chem., 1998, 41(23), p. 4648-4657.
Sun et al., "Anti-AIDS Agents. 32. Synthesis and Anti-HIV Activity of Betullin Derivatives", Biorg. Med. Chem. Lett., 1998, 8(10), p. 1267-1272.
Kashiwada, et al., "3, 28-Di-O-(dimethylsuccinyl)-betulin Isomers as Anti-HIV Agents", Bioorg. Med. Chem. Lett., 2001, 11(2), p. 183-185.

* cited by examiner

*Primary Examiner* — Anish Gupta
*Assistant Examiner* — Theodore R West
(74) *Attorney, Agent, or Firm* — Daniel A. Pearson

(57) ABSTRACT

The invention relates to 21-keto triterpene compounds of formula (I): wherein $R^1$, X, and Y are as defined herein, and pharmaceutically acceptable salts and solvates thereof. These compounds exhibit significant anti-HIV activity. Thus, the invention also relates to methods for prevention or treatment of HIV infections by administering therapeutically effective amounts of a compound of formula (I), or a pharmaceutically acceptable salt or solvate thereof to a subject in need of such treatment.

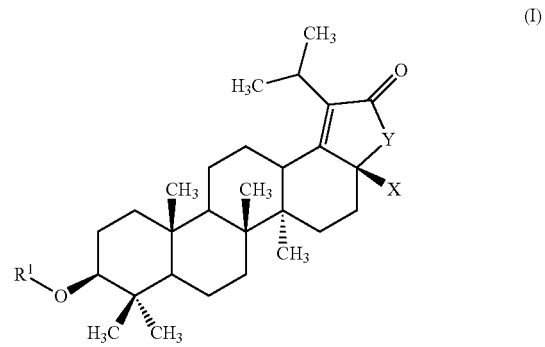

20 Claims, No Drawings

LUPANE DERIVATIVES USEFUL FOR TREATING HIV

CROSS-REFERENCE TO RELATED APPLICATIONS

This application is a continuation of International Patent Application No. PCT/CA2008/002291, filed Dec. 23, 2008, which claims benefit, under 35 U.S.C. §119, to United States Provisional Application No. 61/018,759, filed Jan. 3, 2008 and U.S. Provisional Application No. 61/039,660, filed Mar. 26, 2008, the entire disclosure of each of which are incorporated herein by reference.

Infection by the Human immunodeficiency virus (HIV) can lead to the Acquired ImmunoDeficiency Syndrome (AIDS), an incurable and life threatening condition which requires life-long treatment. It is estimated that the HIV/AIDS pandemic has resulted in the deaths of more than 25 million people since it was first recognized in 1981 and according to a UNAIDS report, an estimated 40 million people worldwide are infected with HIV and about 2.5 million lost their lives to AIDS in 2005. There is presently no effective vaccine for HIV. HIV primarily infects T cells, macrophages and other important components of the immune system resulting in the gradual loss of cell-mediated immunity and as result, HIV patients become increasingly more susceptible to numerous opportunistic infections and tumors and if left untreated, death usually results within 10 years following infection.

The viral life cycle initiates with attachment of HIV gp120 surface protein to the CD4 receptors present of the T-cells. This event triggers a conformational change which exposes an additional binding site on gp120 and results with an interaction with the chemokine co-receptors (CCR5 and CXCR4). Another conformational change arising from co-receptor binding results in fusion of the cellular and viral membranes and release of the virion into the cell. After uncoating and release of the viral genome in the cytoplasm, viral reverse transcriptase (RT) then converts RNA into double stranded DNA which is then integrated into the host genome by the action of HIV integrase. The proviral DNA is then transcribed and translated by host cellular system to express HIV RNA and HIV proteins which are then directed to the cell membrane where they assemble and bud as immature virions. During or soon after the budding process, the viral protease cleaves specific sites in Gag and Gag-Pol releasing essential viral proteins and enzymes such as capsid, nucleocapsid, reverse transcriptase, integrase and spacer peptides SP1 and SP2. This last step is crucial for generating functional viral enzymes and also for the formation of the mature conical HIV capsid.

A number of antiviral agents have been developed to interfere with various stages of viral replication. For example, viral entry can be blocked with T-20 or Maraviroc and post entry steps such as reverse transcription can be blocked with nucleoside RT inhibitors (examples: Lamivudine, Tenofovir, Zidovudine, Didanosine, Emtricitabine, Abacavir) or non-nucleoside RT inhibitors (examples: Nevirapine, Efavirenz and Delavirdine). Integration can be blocked by Raltegravir and HIV proteolytic activity can be inhibited by protease inhibitors such as Saquinavir, Indinavir, Amprenavir, Darunavir, Lopinavir, Atazanavir, and Nelfinavir. Other experimental agents such as Vicriviroc (CCR5), Elvitegravir (integrase), Etravirine (RT), Apricitabine (RT), Bevirimat (maturation) are presently under investigation. The use of combinations of antiretroviral agents have been particularly effective in halting replication to undetectable levels and have led to markedly improved health and life span of HIV/AIDS patients. Nevertheless the appearance of drug resistant viruses after long term therapy is a major concern and there is still a major need for additional drugs in order to provide additional options for these patients facing these issues.

Triterpenoid derivatives have been shown to possess anti-retroviral properties. For example, moronic acid (D. Yu, et al. J. Med. Chem. 2006, 49, 5462-5469), oleanolic acid (H. Assefa, et al. Bioorg. Med. Chem. Lett. 1999, 9, 1889-1894), platanic acid (T. Fujioka, et al. J. Nat. Prod. 1994, 57, 243-247), betulonic acid (O. B. Flekhter, et al. Russ. J. Bioorg. Chem. 2004, 30, 80-88) and betulinic acid (I.-C. Sun, et al. Bioorg. Med. Chem. Lett. 1998, 8, 1267-1272) derivatives were shown to have anti-HIV-1 activities. Other triterpenes arising from the modification of natural product precursors such as betulin have been described, for example 21-keto derivatives shown in references (M. Urban, et al. J. Nat. Prod. 2007, 70, 526-532; M. Urban, et al. Synthesis 2006, 23, 3979-3986; J. Sarek, et al. Bioorg. Med. Chem. Lett. 2005, 15, 4196-4200; J. Sarek, et al. J. Med. Chem. 2003, 46, 5402-5414; M. Hajduch, J. Sarek WO 2001/090046). However, data pertaining to their anti-HIV properties are either absent or are related to uses other than for the treatment of HIV/AIDS conditions. Furthermore, the cytotoxicity of these compounds is unsuitable for the treatment of a chronic disease such as HIV/AIDS.

This invention relates to 21-keto triterpenes and the discovery that these novel modified triterpenoid derivatives possess significant anti-HIV activity.

The present invention relates to a compound of formula (I):

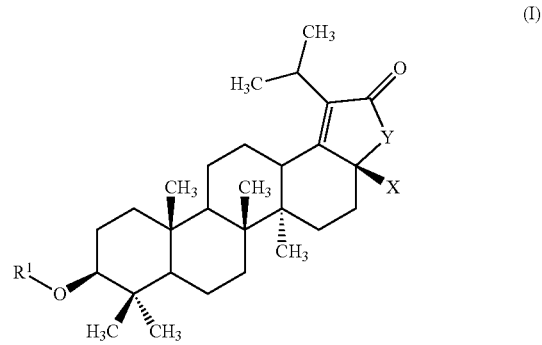

(I)

wherein;

$R^1$ is H, hydroxy protecting group or

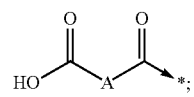

A is $C_{1-8}$ alkyl, $C_{2-8}$ alkenyl, or —$(CH_2)_{1-2}O(CH_2)_{1-2}$—;
Y is C═O or C—$R_{y1}R_{y2}$;
$R_{y1}$ and $R_{y2}$ are each independently H or —$CH_3$;
X is $NR_2R_3$;

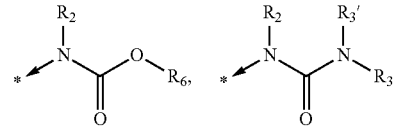

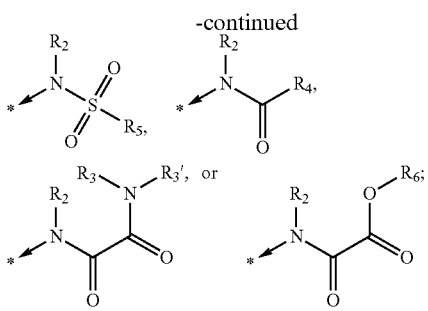

R$_2$ is H, C$_{1-12}$ alkyl which is unsubstituted or substituted one or more times by R$^{10}$, C$_{2-12}$ alkenyl which is unsubstituted or substituted one or more times by R$^{10}$, or C$_{2-12}$ alkynyl which is unsubstituted or substituted one or more times by R$^{10}$;

R$_3$ and R$_3$' are each independently H, C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;

R$_3$ and R$_3$' can also be taken together to form 5-12 member heteroaryl which is unsubstituted or substituted one or more times by R$^{11}$, or a 3-12 member heterocycle which is unsubstituted or substituted one or more times by R$^{12}$;

R$_4$ is C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;

R$_5$ and R$_6$ are each independently C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;

R$^{10}$ is halogen, oxo, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl)C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino;

R$^{11}$ is halogen, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl)C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)ON, —P(O)(OC$_{1-4}$alkyl)$_2$, amidino, or guanidino; and R$^{12}$ is halogen, oxo, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$—N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl)C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino;

or a pharmaceutically acceptable salt thereof.

In further embodiments, the compounds of the inventions are represented by formula (I) wherein the following embodiments are present alone or in combination:

Y is C═O.
Y is C—R$_{y1}$R$_{y2}$ and R$_{y1}$ and R$_{y2}$ are each —CH$_3$.
Y is C—R$_{y1}$R$_{y2}$ and R$_{y1}$ and R$_{y2}$ are each H.
R$_1$ is

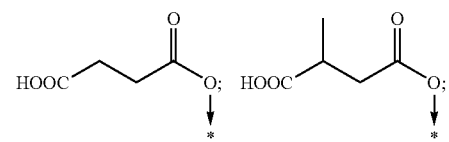

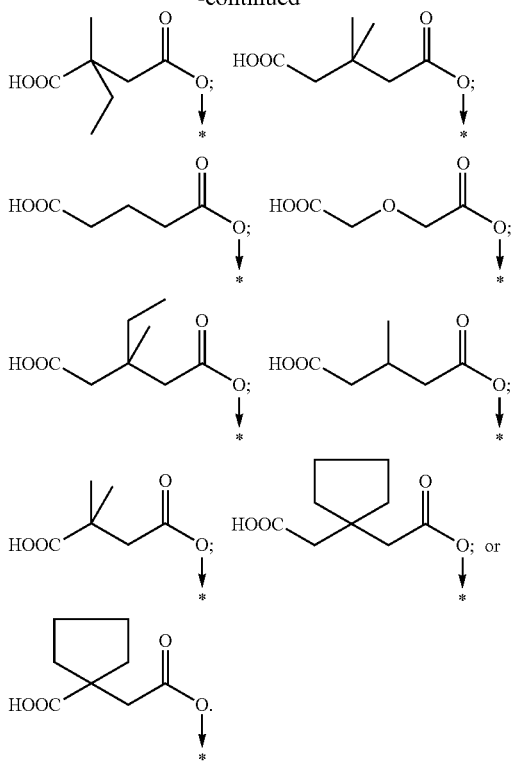

$R_1$ is succinyl, glutaryl, 3'-methylglutaryl, 3'-methylsuccinyl, 3',3'-dimethylsuccinyl, 3',3'-dimethylglutaryl, 2',2'-dimethylmalonyl, 2',3'-dihydroxysuccinyl, 2',3'-dimethylsuccinyl, 2', 2', 3', 3'-tetramethylsuccinyl, 2'-methylsuccinyl, or 2',2'-dimethylsuccinyl.

$R_1$ is succinyl, glutaryl, 3'-methylglutaryl, 3'-methylsuccinyl, 3',3'-dimethylsuccinyl, 3',3'-dimethylglutaryl, 2',2'-dimethylmalonyl, 2',3'-dihydroxysuccinyl, 2', 2', 3', 3'-tetramethylsuccinyl or 2',2'-dimethylsuccinyl.

$R_1$ is 3',3'-dimethylsuccinyl.

In a further embodiment, $R_1$ is H, or a hydroxy protecting group.

In a further embodiment, $R_1$ is H.

$R_2$ is H or $C_{1-12}$ alkyl which is unsubstituted or substituted one or more times by $R^{10}$.

$R_2$ is H or $C_{1-6}$ alkyl which is unsubstituted or substituted one or more times by $R^{10}$.

$R_2$ is H, methyl, ethyl, propyl, isopropyl, butyl, sec-butyl, tert-butyl, cyclopropyl, cyclobutyl, cyclopentyl, or cyclohexyl.

$R_2$ is methyl, ethyl, propyl, isopropyl, butyl, sec-butyl, or tert-butyl.

$R_2$ is H.

$R_3'$ is H.

$R_3$ and $R_3'$ can also be taken together to form a 5-6 member heteroaryl which is unsubstituted or substituted one or more times by $R^{11}$ or a 5-6 member heterocycle which is unsubstituted or substituted one or more times by $R^{12}$.

$R_3$ and $R_3'$ can also be taken together to form a piperidyl, a piperazinyl, or a morpholinyl which is unsubstituted or substituted one or more times by $R_{11}$.

$R_3$ is $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 member heteroaryl which is unsubstituted or substituted one or more times by $R^{11}$, 6-18 member heteroaralkyl which is unsubstituted or substituted one or more times by $R^{11}$, 3-12 member heterocycle which is unsubstituted or substituted one or more times by $R^{12}$, or 4-18 member heterocycle-alkyl which is unsubstituted or substituted one or more times by $R^{12}$.

$R_3$ is $C_{1-12}$ alkyl which is unsubstituted or substituted one or more times by $R^{10}$, $C_6$ aryl which is unsubstituted or substituted one or more times by $R^{11}$, $C_{7-9}$ aralkyl which is unsubstituted or substituted one or more times by $R^{11}$, 5-6 member heteroaryl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_3$ is $C_{1-6}$ alkyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 member heteroaryl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_4$ is $C_{1-12}$ alkyl which is unsubstituted or substituted one or more times by $R^{10}$, $C_{2-12}$ alkenyl which is unsubstituted or substituted one or more times by $R^{10}$, $C_{2-12}$ alkynyl which is unsubstituted or substituted one or more times by $R^{10}$, $C_{6-14}$ aryl which is unsubstituted or substituted one or more times by $R^{11}$, $C_{7-16}$ aralkyl which is unsubstituted or substituted one or more times by $R^{11}$, 5-12 member heteroaryl which is unsubstituted or substituted one or more times by $R^{11}$, 6-18 member heteroaralkyl which is unsubstituted or substituted one or more times by $R^{11}$, 3-12 member heterocycle which is unsubstituted or substituted one or more times by $R^{12}$, or 4-18 member heterocycle-alkyl which is unsubstituted or substituted one or more times by $R^{12}$, $R_4$ is $C_{1-12}$ alkyl which is unsubstituted or substituted one or more times by $R^{10}$, $C_6$ aryl which is unsubstituted or substituted one or more times by $R^{11}$, $C_{7-9}$ aralkyl which is unsubstituted or substituted one or more times by $R^{11}$, 5-6 member heteroaryl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_4$ is $C_{1-6}$ alkyl which is unsubstituted or substituted one or more times by $R^{10}$, phenyl which is unsubstituted or substituted one or more times by $R^{11}$, benzyl which is unsubstituted or substituted one or more times by $R^{11}$, 5-6 member heteroaryl which is unsubstituted or substituted one or more times by $R^{11}$, 7-8 member heteroaralkyl which is unsubstituted or substituted one or more times by $R^{11}$, 5-6 member heterocycle which is unsubstituted or substituted one or more times by $R^{12}$, or 7-8 member heterocycle-alkyl which is unsubstituted or substituted one or more times by $R^{12}$.

$R_3$, $R_4$, $R_5$ or $R_6$ are $C_{1-12}$ alkyl which is unsubstituted or substituted one or more times by $R^{10}$.

$R_3$, $R_4$, $R_5$ or $R_6$ are $C_{1-6}$ alkyl which is unsubstituted or substituted one or more times by $R^{10}$.

$R_3$, $R_4$, $R_5$ or $R_6$ are each independently methyl, ethyl, propyl, isopropyl, butyl, sec-butyl, tert-butyl, cyclopropyl, cyclobutyl, cyclopentyl, or cyclohexyl.

$R_3$, $R_4$, $R_5$ or $R_6$ are each independently is methyl, ethyl, propyl, isopropyl, butyl, sec-butyl, or tert-butyl.

$R_3$, $R_4$, $R_5$ or $R_6$ are phenyl which is unsubstituted or substituted one or more times by $R_{11}$.

$R_3$, $R_4$, $R_5$ or $R_6$ are phenyl.

$R_3$, $R_4$, $R_5$ or $R_6$ are 5-6 member heteroaryl which is unsubstituted or substituted one or more times by $R^{11}$.

$R_3$, $R_4$, $R_5$ or $R_6$ are is pyridyl which is unsubstituted or substituted one or more times by $R^{11}$.

$R^3$, $R^4$, $R^5$ or $R_6$ are is 7-8 member heteroaralkyl which is unsubstituted or substituted one or more times by $R^{11}$.

$R^3$, $R^4$, $R^5$ or $R_6$ are —CH$_2$-pyridyl which is unsubstituted or substituted one or more times by $R^{11}$.

$R_3$, $R_4$, $R_5$ or $R_6$ are 5-6 member heterocycle which is unsubstituted or substituted one or more times by $R^{12}$.

$R_3$, $R_4$, $R_5$ or $R_6$ are piperidine which is unsubstituted or substituted one or more times by $R^{12}$.

$R_3$, $R_4$, $R_5$ or $R_6$ are 7-8 member heterocycle-alkyl which is unsubstituted or substituted one or more times by $R^{12}$ $R_3$, $R_4$, $R_5$ or $R_6$ are —CH$_2$-piperidine which is unsubstituted or substituted one or more times by $R^{12}$.

$R_3$, $R_4$, $R_5$ or $R_6$ are each independently ethyl, iso-propyl, tert-butyl, cyclopentyl, —CH$_2$-cyclopentyl, cyclohexyl, —CH$_2$-cyclohexyl, phenyl, benzyl, Pyridinyl, —CH$_2$-pyridinyl, piperidynyl, piperazinyl, thienyl, morpholino, oxadiazole, pyrimidinyl, pyranyl, pyrazinyl, thiazole, and pyrazole, which are unsubstituted or substituted by one or more substituents chosen from a halogen, $C_{1-4}$ alkyl, $C_{1-4}$ alkyloxy, $CF_3$, $COC_{1-4}$ alkyl, COON, $COOC_{1-4}$ alkyl, cyano, $NH_2$, nitro, $NH(C_{1-6}$ alkyl), and $N(C_{1-6}$ alkyl$)_2$.

$R_3$ is 5-6 member heteroaryl which is unsubstituted or substituted one or more times by $R^{11}$.

$R_3$ is 5-6 member heterocycle which is unsubstituted or substituted one or more times by $R^{12}$.

$R_3$ is pyridine which is unsubstituted or substituted one or more times by halogen, $C_{1-3}$ alkyl, $C_{1-3}$ alkoxy, or halogenated $C_{1-3}$ alkyl.

$R_3$ is pyrimidine which is unsubstituted or substituted one or more times by halogen, $C_{1-3}$ alkyl, $C_{1-3}$ alkoxy, or halogenated $C_{1-3}$ alkyl.

$R_3$ is pyrazole which is unsubstituted or substituted one or more times by halogen, $C_{1-3}$ alkyl, $C_{1-3}$ alkoxy, or halogenated $C_{1-3}$ alkyl.

$R_3$ is phenyl which is unsubstituted or substituted one or more times by halogen, $C_{1-3}$ alkyl, $C_{1-3}$ alkoxy, or halogenated $C_{1-3}$ alkyl.

$R_3$ is benzyl which is unsubstituted or substituted one or more times by halogen, $C_{1-3}$ alkyl, $C_{1-3}$ alkoxy, or halogenated $C_{1-3}$ alkyl.

$R_3$ is oxadiazole which is unsubstituted or substituted one or more times by halogen, $C_{1-3}$ alkyl, $C_{1-3}$ alkoxy, or halogenated $C_{1-3}$ alkyl.

$R_3$ is imidazole which is unsubstituted or substituted one or more times by halogen, $C_{1-3}$ alkyl, $C_{1-3}$ alkoxy, or halogenated $C_{1-3}$ alkyl.

$R_3$ is pyrrolidine which is unsubstituted or substituted one or more times by halogen, $C_{1-3}$ alkyl, $C_{1-3}$ alkoxy, or halogenated $C_{1-3}$ alkyl.

$R_3$ is piperidine which is unsubstituted or substituted one or more times by halogen, $C_{1-3}$ alkyl, $C_{1-3}$ alkoxy, or halogenated $C_{1-3}$ alkyl.

$R_3$ is cyclohexyl which is unsubstituted or substituted one or more times by halogen, $C_{1-3}$ alkyl, $C_{1-3}$ alkoxy, or halogenated $C_{1-3}$ alkyl.

$R_3$ is pyridine.
$R_3$ is methylpyridine.
$R_3$ is pyrimidine.
$R_3$ is pyrazine.
$R_3$ is pyrazole.
$R_3$ is methylpyrazole.
$R_3$ is thiadiazole.
$R_3$ is methylthiadiazole.
$R_3$ is oxadiazole.
$R_3$ is methyloxadiazole.
$R_3$ is piperidine.
$R_3$ is methylpiperidine.
$R_3$ is N-acetyl piperidine.
$R_3$ is cyclohexyl.
$R_3$ is difluorocyclohexyl.

$R_4$ is 5-6 member heteroaryl which is unsubstituted or substituted one or more times by $R^{11}$.

$R_4$ is 5-6 member heterocycle which is unsubstituted or substituted one or more times by $R_{12}$.

$R_4$ is pyridine which is unsubstituted or substituted one or more times by halogen, $C_{1-3}$ alkyl, $C_{1-3}$ alkoxy, or halogenated $C_{1-3}$ alkyl.

$R_4$ is pyrimidine which is unsubstituted or substituted one or more times by halogen, $C_{1-3}$ alkyl, $C_{1-3}$ alkoxy, or halogenated $C_{1-3}$ alkyl.

$R_4$ is pyrazine which is unsubstituted or substituted one or more times by halogen, $C_{1-3}$ alkyl, $C_{1-3}$ alkoxy, or halogenated $C_{1-3}$ alkyl.

$R_4$ is pyrazole which is unsubstituted or substituted one or more times by halogen, $C_{1-3}$ alkyl, $C_{1-3}$ alkoxy, or halogenated $C_{1-3}$ alkyl.

$R_4$ is phenyl which is unsubstituted or substituted one or more times by halogen, $C_{1-3}$ alkyl, $C_{1-3}$ alkoxy, or halogenated $C_{1-3}$ alkyl.

$R_4$ is benzyl which is unsubstituted or substituted one or more times by halogen, $C_{1-3}$ alkyl, $C_{1-3}$ alkoxy, or halogenated $C_{1-3}$ alkyl.

$R_4$ is thiazole which is unsubstituted or substituted one or more times by halogen, $C_{1-3}$ alkyl, $C_{1-3}$ alkoxy, or halogenated $C_{1-3}$ alkyl.

$R_4$ is oxadiazole which is unsubstituted or substituted one or more times by halogen, $C_{1-3}$ alkyl, $C_{1-3}$ alkoxy, or halogenated $C_{1-3}$ alkyl.

$R_4$ is imidazole which is unsubstituted or substituted one or more times by halogen, $C_{1-3}$ alkyl, $C_{1-3}$ alkoxy, or halogenated $C_{1-3}$ alkyl.

$R_4$ is pyrrolidine which is unsubstituted or substituted one or more times by halogen, $C_{1-3}$ alkyl, $C_{1-3}$ alkoxy, or halogenated $C_{1-3}$ alkyl.

$R_4$ is piperidine which is unsubstituted or substituted one or more times by halogen, $C_{1-3}$ alkyl, $C_{1-3}$ alkoxy, or halogenated $C_{1-3}$ alkyl.

$R_4$ is cyclohexyl which is unsubstituted or substituted one or more times by halogen, $C_{1-3}$ alkyl, $C_{1-3}$ alkoxy, or halogenated $C_{1-3}$ alkyl.

$R_4$ is pyridine.
$R_4$ is methylpyridine.
$R_4$ is pyrimidine.
$R_4$ is pyrazine.
$R_4$ is pyrazole.
$R_4$ is methylpyrazole.
$R_4$ is phenyl.
$R_4$ is fluorophenyl.
$R_4$ is benzyl.
$R_4$ is fluorobenzyl.
$R_4$ is thiazote.
$R_4$ is methylthiazote.
$R_4$ is oxadiazote.
$R_4$ is methyloxadiazote.
$R_4$ is imidazole.

$R_4$ is methylimidazote.

$R_4$ is piperidine.

$R_4$ is methylpiperidine.

$R_4$ is N-acetyl piperidine.

$R_4$ is thienyl.

$R_5$ is $C_{1-12}$ alkyl which is unsubstituted or substituted one or more times by $R^{10}$.

$R_5$ is $C_{1-6}$ alkyl which is unsubstituted or substituted one or more times by $R_{10}$.

$R_5$ is methyl, ethyl, propyl, isopropyl, butyl, sec-butyl, tert-butyl, cyclopropyl, cyclobutyl, cyclopentyl, or cyclohexyl.

$R_5$ is methyl, ethyl, propyl, isopropyl, butyl, sec-butyl, or tert-butyl. $R_6$ is $C_{1-12}$ alkyl which is unsubstituted or substituted one or more times by $R_{10}$.

$R_6$ is $C_{1-6}$ alkyl which is unsubstituted or substituted one or more times by $R^{10}$.

$R_6$ is methyl, ethyl, propyl, isopropyl, butyl, sec-butyl, tert-butyl, cyclopropyl, cyclobutyl, cyclopentyl, or cyclohexyl.

$R_6$ is methyl, ethyl, propyl, isopropyl, butyl, sec-butyl, or tert-butyl.

$R^{10}$ is halogen, oxo, $C_{1-6}$ alkoxy, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$, alkyl, —$NHCOC_{1-4}$ alkyl, —$NHCOOC_{1-4}$ alkyl, —$NHCONHC_{1-4}$ alkyl, —$N(O)C_{1-4}$ alkyl)$CONHC_{1-4}$ alkyl, —$N(C_{1-4}$ alkyl)$CON(C_{1-4}$ alkyl)$_2$, —$NHCON(C_{1-4}$ alkyl)$_2$, —C(O)H, —$C(O)C_{1-4}$ alkyl, carboxy, —$C(O)OC_{1-4}$ alkyl, —$C(NOH)C_{1-4}$ alkyl, —C(NOH)H, —$C(NOC_{1-4}$ alkyl)$C_{1-4}$ alkyl, —$C(NOC_{1-4}$ alkyl)H, hydroxyl, nitro, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$N(C_{1-4}$ alkyl)$SO_2C_{1-4}$ alkyl, —$NHSO_2C_{1-4}$ alkyl, —$P(O)(OH)_2$ or $P(O)(OC_{1-4}$alkyl)$_2$;

$R^{10}$ is halogen, oxo, $C_{1-6}$ alkoxy, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —$N(C_{1-4}$ alkyl)$CONHC_{1-4}$ alkyl, —$N(C_{1-4}$ alkyl)$CON(C_{1-4}$ alkyl)$_2$, —$NHCON(C_{1-4}$ alkyl)$_2$, —C(O)H, —$C(O)C_{1-4}$ alkyl, carboxy, —$C(O)OC_{1-4}$ alkyl, —$C(NOH)C_{1-4}$ alkyl, —C(NOH)H, hydroxyl, nitro, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$N(C_{1-4}$ alkyl)$SO_2C_{1-4}$ alkyl, —$NHSO_2C_{1-4}$ alkyl, or —$P(O)(OH)_2$.

$R^{10}$ is halogen, oxo, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —C(O)H, —$C(O)C_{1-4}$ alkyl, carboxy, —$C(O)OC_{1-4}$ alkyl, hydroxyl, $C_{1-4}$ alkoxy, nitro, nitroso, azido, or cyano.

$R^{10}$ is halogen, oxo, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —C(O)H, —$C(O)C_{1-4}$ alkyl, carboxy, —$C(O)OC_{1-4}$ alkyl, hydroxyl, $C_{1-4}$ alkoxy, nitro, azido, or cyano.

$R^{10}$ is halogen, oxo, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —C(O)H, —$C(O)C_{1-4}$ alkyl, carboxy, —$C(O)OC_{1-4}$ alkyl, hydroxyl, or $C_{1-4}$ alkoxy.

$R^{10}$ is halogen, oxo, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —$N(C_{1-4}$ alkyl)$COC_{1-4}$ alkyl, —$NHCOC_{1-4}$ alkyl, carboxy, —$C(O)OC_{1-4}$ alkyl, hydroxyl, $C_{1-4}$ alkoxy, or cyano.

$R^{11}$ is halogen, $C_{1-6}$ alkyl, halogenated $C_{1-6}$ alkyl, $C_{2-6}$ alkenyl, $C_{2-6}$ alkynyl, $C_{1-6}$ alkoxy, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, alkyl)$COC_{1-4}$, alkyl, —$NHCOC_{1-4}$ alkyl, —$NHCOOC_{1-4}$ alkyl, —$NHCONHC_{1-4}$ alkyl, —$N(C_{1-4}$ alkyl)$CONHC_{1-4}$ alkyl, —$N(C_{1-4}$ alkyl)$CON(C_{1-4}$ alkyl)$_2$, —$NHCON(C_{1-4}$ alkyl)$_2$, —C(O)H, —$C(O)C_{1-4}$ alkyl, carboxy, —$C(O)OC_{1-4}$ alkyl, —$C(NOH)C_{1-4}$ alkyl, —C(NOH)H, —$C(NOC_{1-4}$ alkyl)$C_{1-4}$ alkyl, —$C(NOC_{1-4}$ alkyl)H, hydroxyl, nitro, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$N(C_{1-4}$ alkyl)$SO_2C_{1-4}$ alkyl, —$NHSO_2C_{1-4}$ alkyl, —$P(O)(OH)_2$ or $P(O)(OC_{1-4}$ alkyl)$_2$;

$R^{11}$ is halogen, $C_{1-6}$ alkyl, halogenated $C_{1-6}$ alkyl, $C_{2-6}$ alkenyl, $C_{2-6}$ alkynyl, $C_{1-6}$ alkoxy, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —$N(C_{1-4}$ alkyl)$CONHC_{1-4}$ alkyl, —$N(C_{1-4}$ alkyl)$CON(C_{1-4}$ alkyl)$_2$, —$NHCON(C_{1-4}$ alkyl)$_2$, —C(O)H, —$C(O)C_{1-4}$ alkyl, carboxy, —$C(O)OC_{1-4}$ alkyl, —$C(NOH)C_{1-4}$ alkyl, —C(NOH)H, hydroxyl, nitro, azido, cyano, —$S(O)_{0-2}H$, —$S(O)_{0-2}C_{1-4}$ alkyl, —$SO_2NH_2$, —$SO_2NH(C_{1-4}$ alkyl), —$SO_2N(C_{1-4}$ alkyl)$_2$, —$N(C_{1-4}$ alkyl)$SO_2C_{1-4}$ alkyl, —$NHSO_2C_{1-4}$ alkyl, or —$P(O)(OH)_2$.

$R^{11}$ is halogen, $C_{1-6}$ alkyl, halogenated $C_{1-6}$ alkyl, $C_{2-6}$ alkenyl, $C_{2-6}$ alkynyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —C(O)H, —$C(O)C_{1-4}$ alkyl, carboxy, —$C(O)OC_{1-4}$ alkyl, hydroxyl, $C_{1-6}$ alkoxy, nitro, nitroso, azido, or cyano.

$R^{11}$ is halogen, $C_{1-6}$ alkyl, halogenated $C_{1-6}$ alkyl, $C_{2-6}$ alkenyl, $C_{2-6}$ alkynyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, $N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —C(O)H, —$C(O)C_{1-4}$ alkyl, carboxy, —$C(O)OC_{1-4}$ alkyl, hydroxyl, $C_{1-6}$ alkoxy, nitro, azido, or cyano.

$R^{11}$ is halogen, $C_{1-6}$ alkyl, halogenated $C_{1-6}$ alkyl, $C_{2-6}$ alkenyl, $C_{2-6}$ alkynyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$ alkyl, —$NHCOC_{1-4}$ alkyl, —$NHCOOC_{1-4}$ alkyl, —$NHCONHC_{1-4}$ alkyl, —C(O)H, —$C(O)C_{1-4}$ alkyl, carboxy, —$C(O)OC_{1-4}$ alkyl, hydroxyl, or $C_{1-6}$ alkoxy.

$R^{11}$ is halogen, $C_{1-6}$ alkyl, halogenated $C_{1-6}$ alkyl, $C_{2-6}$ alkenyl, $C_{2-6}$ alkynyl, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —$N(C_{1-4}$ alkyl)$COC_{1-4}$ alkyl, —$NHCOC_{1-4}$ alkyl, carboxy, —$C(O)OC_{1-4}$ alkyl, hydroxyl, or $C_{1-6}$ alkoxy.

$R^{12}$ is halogen, oxo, $C_{1-6}$ alkyl, halogenated $C_{1-6}$ alkyl, $C_{2-6}$ alkenyl, $C_{2-6}$ alkynyl, $C_{1-6}$ alkoxy, —$NH_2$, —$NH(C_{1-4}$ alkyl), —$N(C_{1-4}$ alkyl)$_2$, —$CONH_2$, —$CONH(C_{1-4}$ alkyl), —$CON(C_{1-4}$ alkyl)$_2$, —NHCOH, —$N(C_{1-4}$ alkyl)COH, —$N(C_{1-4}$ alkyl)$COC_{1-4}$, alkyl, —$NHCOC_{1-4}$ alkyl, —$NHCOOC_{1-4}$ alkyl, —$NHCONHC_{1-4}$ alkyl, —$N(C_{1-4}$ alkyl)$CONHC_{1-4}$ alkyl, —$N(C_{1-4}$ alkyl)$CON(C_{1-4}$ alkyl)$_2$, —$NHCON(C_{1-4}$ alkyl), —C(O)H, —$C(O)C_{1-4}$ alkyl, carboxy, —$C(O)OC_{1-4}$ alkyl, —C(NOH)$C_{1-4}$ alkyl, —C(NOH)H, —C(NO$C_{1-4}$ alkyl)$C_{1-4}$ alkyl, —C(NO$C_{1-4}$ alkyl)H, hydroxyl, nitro, azido, cyano, —S(O)$_{0-2}$H, —S(O)$_{0-2}$$C_{1-4}$ alkyl, —SO$_2$NH$_2$, —SO$_2$NH($C_{1-4}$ alkyl), —SO$_2$N($C_{1-4}$ alkyl)$_2$, —N($C_{1-4}$ alkyl)SO$_2$$C_{1-4}$ alkyl, —NHSO$_2$$C_{1-4}$ alkyl, —P(O)(OH)$_2$ or P(O)(O$C_{1-4}$alkyl)$_2$.

$R^{12}$ is halogen, oxo, $C_{1-6}$ alkyl, halogenated $C_{1-6}$ alkyl, $C_{2-6}$ alkenyl, $C_{2-6}$ alkynyl, $C_{1-6}$ alkoxy, —NH$_2$, —NH($C_{1-4}$ alkyl), —N($C_{1-4}$ alkyl)$_2$, —CONH$_2$, —CONH($C_{1-4}$ alkyl), —CON($C_{1-4}$ alkyl)$_2$, —NHCOH, alkyl)COH, —N($C_{1-4}$ alkyl)COC$_{1-4}$, alkyl, —NHCOC$_{1-4}$ alkyl, —NHCOOC$_{1-4}$ alkyl, —NHCONHC$_{1-4}$ alkyl, —N($C_{1-4}$ alkyl)CONHC$_{1-4}$ alkyl, —N($C_{1-4}$ alkyl)CON($C_{1-4}$ alkyl)$_2$, —NHCON($C_{1-4}$ alkyl)$_2$, —C(O)H, —C(O)$C_{1-4}$ alkyl, carboxy, —C(O)O $C_{1-4}$ alkyl, —C(NOH)$C_{1-4}$ alkyl, —C(NOH)H, hydroxyl, nitro, azido, cyano, —S(O)$_{0-2}$H, —S(O)$_{0-2}$$C_{1-4}$ alkyl, —SO$_2$NH$_2$, —SO$_2$NH($C_{1-4}$alkyl), —SO$_2$N($C_{1-4}$alkyl)$_2$, —N($C_{1-4}$alkyl)SO$_2$$C_{1-4}$ alkyl, —NHSO$_2$$C_{1-4}$ alkyl, or —P(O)(OH)$_2$.

$R^{12}$ is halogen, oxo, $C_{1-6}$ alkyl, halogenated $C_{1-6}$ alkyl, $C_{2-6}$ alkenyl, $C_{2-6}$ alkynyl, —NH$_2$, —NH($C_{1-4}$ alkyl), —N($C_{1-4}$ alkyl)$_2$, —CONH$_2$, —CONH($C_{1-4}$ alkyl), —CON($C_{1-4}$ alkyl)$_2$, —NHCOH, —N($C_{1-4}$ alkyl)COH, —N($C_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)$C_{1-4}$ alkyl, carboxy, —C(O)O$C_{1-4}$ alkyl, hydroxyl, $C_{1-6}$ alkoxy, nitro, nitroso, azido, or cyano.

$R^{12}$ is halogen, oxo, $C_{1-6}$ alkyl, halogenated $C_{1-6}$ alkyl, $C_{2-6}$ alkenyl, $C_{2-6}$ alkynyl, —NH$_2$, —NH($C_{1-4}$ alkyl), —N($C_{1-4}$ alkyl)$_2$, —CONH$_2$, —CONH($C_{1-4}$ alkyl), —CON($C_{1-4}$ alkyl)$_2$, —NHCOH, —N($C_{1-4}$ alkyl)COH, —N($C_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)$C_{1-4}$ alkyl, carboxy, —C(O)O$C_{1-4}$ alkyl, hydroxyl, $C_{1-6}$ alkoxy, nitro, azido, or cyano.

$R^{12}$ is halogen, oxo, $C_{1-6}$ alkyl, halogenated $C_{1-6}$ alkyl, $C_{2-6}$ alkenyl, $C_{2-6}$ alkynyl, —NH$_2$, —NH($C_{1-4}$ alkyl), —N($C_{1-4}$ alkyl)$_2$, —CONH$_2$, —CONH($C_{1-4}$ alkyl), —CON($C_{1-4}$ alkyl)$_2$, —NHCOH, —N($C_{1-4}$ alkyl)COH, —N($C_{1-4}$ alkyl)COC$_{1-4}$ alkyl, —NHCOC$_{1-4}$ alkyl, —NHCOOC$_{1-4}$ alkyl, —NHCONHC$_{1-4}$ alkyl, —C(O)H, —C(O)$C_{1-4}$ alkyl, carboxy, —C(O)O$C_{1-4}$ alkyl, hydroxyl, or $C_{1-6}$ alkoxy.

$R^{12}$ is halogen, oxo, $C_{1-6}$ alkyl, halogenated $C_{1-6}$ alkyl, —NH$_2$, —NH($C_{1-4}$ alkyl), —N($C_{1-4}$ alkyl)$_2$, —CONH$_2$, —CONH($C_{1-4}$ alkyl), —CON($C_{1-4}$ alkyl)$_2$, —N($C_{1-4}$ alkyl)COC$_{1-4}$ alkyl, —NHCOC$_{1-4}$ alkyl, carboxy, —C(O)O$C_{1-4}$ alkyl, hydroxyl, or $C_{1-6}$ alkoxy.

In a further embodiment, the present invention relates to a compound of formula (II) or formula (IIa):

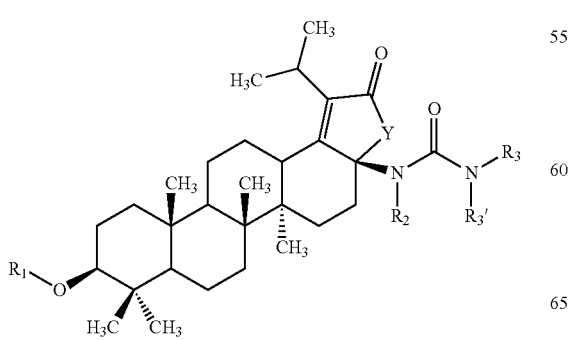

(II)

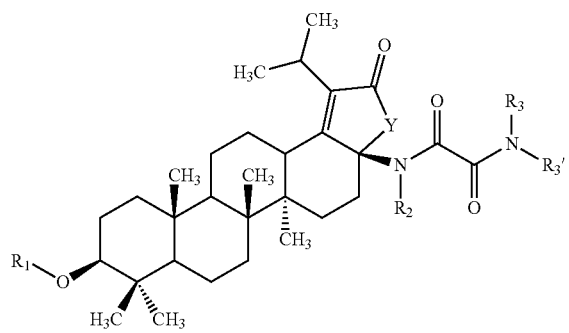

(IIa)

or a pharmaceutically acceptable salt thereof, wherein $R_1$, $R_2$, $R_3$, and $R_3'$ are defined above.

In a further embodiment, the present invention relates to a compound of formula (II):

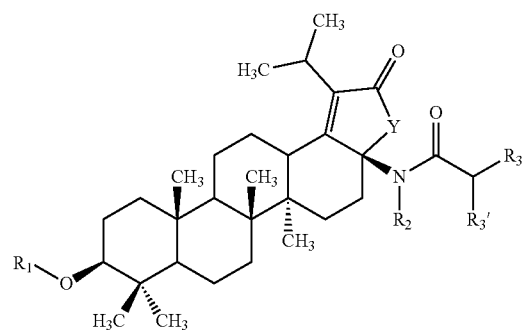

(II)

or a pharmaceutically acceptable salt thereof, wherein $R_1$, $R_2$, $R_3$, and $R_3'$ are defined above.

In a further embodiment, the present invention relates to a compound of formula (III):

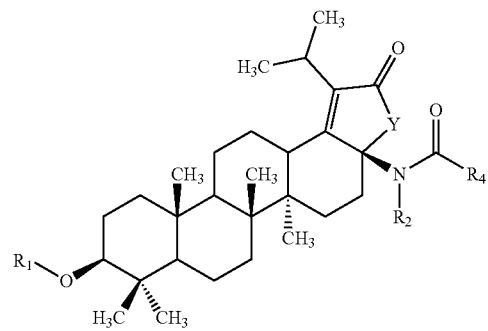

(III)

or a pharmaceutically acceptable salt thereof, wherein $R_1$, $R_2$, and $R_4$ are defined above.

In a further embodiment, the present invention relates to a compound of formula (IV):

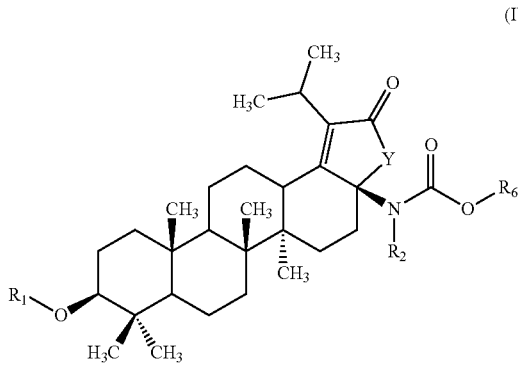

(IV)

or a pharmaceutically acceptable salt thereof, wherein $R_1$, $R_2$, and $R_6$ are defined above.

It will be appreciated by those skilled in the art that the compounds in accordance with the present invention can exists as stereoisomers, for example, optical (+ and −), geometrical (cis and trans) and conformational isomers (axial and equatorial). All such stereoisomers are included in the scope of the present invention.

It will be appreciated by those skilled in the art that the compounds in accordance with the present invention can contain a chiral center. The compounds of formula (I) may thus exist in the form of two different optical isomers (i.e. (+) or (−) enantiomers). All such enantiomers and mixtures thereof including racemic mixtures are included within the scope of the invention. The single optical isomers or enantiomers can be obtained by methods well known in the art, such as chiral HPLC, enzymatic resolution and chiral auxiliary.

In one embodiment, the compounds of the present invention are provided in the form of a single enantiomer at least 95%, at least 97% and at least 99% free of the corresponding enantiomer.

In a further embodiment the compound of the present invention are in the form of the (+) enantiomer at least 95% free of the corresponding (−) enantiomer.

In a further embodiment the compound of the present invention are in the form of the (+) enantiomer at least 97% free of the corresponding (−) enantiomer.

In a further embodiment the compound of the present invention are in the form of the (+) enantiomer at least 99% free of the corresponding (−) enantiomer.

In a further embodiment, the compounds of the present invention are in the form of the (−) enantiomer at least 95% free of the corresponding (+) enantiomer.

In a further embodiment the compound of the present invention are in the form of the (−) enantiomer at least 97% free of the corresponding (+) enantiomer.

In a further embodiment the compound of the present invention are in the form of the (−) enantiomer at least 99% free of the corresponding (+) enantiomer.

There is also provided pharmaceutically acceptable salts of the compounds of the present invention. By the term pharmaceutically acceptable salts of compounds are meant those derived from pharmaceutically acceptable inorganic and organic acids and bases. Examples of suitable acids include hydrochloric, hydrobromic, sulphuric, nitric, perchloric, fumaric, maleic, phosphoric, glycollic, lactic, salicylic, succinic, toluene-p-sulphonic, tartaric, acetic, trifluoroacetic, citric, methanesulphonic, formic, benzoic, malonic, naphthalene-2-sulphonic and benzenesulphonic acids. Other acids such as oxalic, while not themselves pharmaceutically acceptable, may be useful as intermediates in obtaining the compounds of the invention and their pharmaceutically acceptable acid addition salts.

Salts derived from amino acids are also included (e.g. L-Arginine, L-Lysine).

Salts derived from appropriate bases include alkali metals (e.g. sodium, lithium, potassium), alkaline earth metals (e.g. calcium, magnesium), ammonium, $NR_4+$ (where R is $C_{1-4}$ alkyl) salts, choline, meglumine and tromethamine.

A reference hereinafter to a compound according to the invention includes that compound and its pharmaceutically acceptable salts.

In one embodiment of the invention, the pharmaceutically acceptable salt is a sodium salt.

In one embodiment of the invention, the pharmaceutically acceptable salt is a lithium salt.

In one embodiment of the invention, the pharmaceutically acceptable salt is a potassium salt.

In one embodiment of the invention, the pharmaceutically acceptable salt is a tromethamine salt.

In one embodiment of the invention, the pharmaceutically acceptable salt is an L-Arginine salt.

In one embodiment of the invention, the pharmaceutically acceptable salt is a meglumine salt.

It will be appreciated by those skilled in the art that the compounds in accordance with the present invention can exist in different polymorphic forms. As known in the art, polymorphism is the ability of a compound to crystallize as more than one distinct crystalline or "polymorphic" species. A polymorph is a solid crystalline phase of a compound with at least two different arrangements or polymorphic forms of that compound molecule in the solid state. Polymorphic forms of any given compound are defined by the same chemical formula or composition and are as distinct in chemical structure as crystalline structures of two different chemical compounds.

It will further be appreciated by those skilled in the art that the compounds in accordance with the present invention can exist in different solvate forms, for example hydrates. Solvates of the compounds of the invention may also form when solvent molecules are incorporated into the crystalline lattice structure of the compound molecule during the crystallization process.

Unless otherwise defined, all technical and scientific terms used herein have the same meaning as commonly understood by one of ordinary skill in the art to which this invention belongs. All publications, patent applications, patents, and other references mentioned herein are incorporated by reference in their entirety. In case of conflict, the present specification, including definitions, will control. In addition, the materials, methods, and examples are illustrative only and not intended to be limiting.

The term "alkyl" represents a linear, branched or cyclic hydrocarbon moiety. The terms "alkenyl" and "alkynyl" represent a linear, branched or cyclic hydrocarbon moiety which has one or more double bonds or triple bonds in the chain, respectively. Examples of alkyl, alkenyl, and alkynyl groups include but are not limited to methyl, ethyl, propyl, isopropyl, butyl, isobutyl, sec-butyl, tert-butyl, pentyl, isopentyl, neopentyl, tert-pentyl, hexyl, isohexyl, neohexyl, allyl, vinyl, acetylenyl, ethylenyl, propenyl, isopropenyl, butenyl, isobutenyl, butadienyl, pentenyl, pentadienyl, hexenyl, hexadienyl, hexatrienyl, heptenyl, heptadienyl, heptatrienyl, octenyl, octadienyl, octatrienyl, octatetraenyl, propynyl, butynyl, pentynyl, hexynyl, cyclopropyl, cyclobutyl, cyclopentyl, cyclohexenyl, cyclohexdienyl and cyclohexyl. Where indicated the "alkyl," "alkenyl," and "alkynyl" can be optionally substituted such as in the case of haloalkyls in which one or more hydrogen atom is replaced by a halogen, e.g., an alkylhalide. Examples of haloalkyls include but are not limited to trifluoromethyl, difluoromethyl, fluoromethyl, trichloromethyl, dichloromethyl, chloromethyl, trifluoroethyl, difluoroethyl, fluoroethyl, trichloroethyl, dichloroethyl, chloroethyl, chlorofluoromethyl, chlorodifluoromethyl, dichlorofluoroethyl. Aside from halogens, where indicated, the alkyl, alkenyl or alkynyl groups can also be optionally substituted by, for example, oxo, —$NR_dR_e$, —$CONR_dR_e$, =NO—$R_e$, —$NR_dCOR_e$, carboxy, —$C(=NR_d)NR_eR_f$, azido, cyano, $C_{1-6}$ alkyloxy, $C_{2-6}$ alkenyloxy, $C_{2-6}$ alkynyloxy, —$N(R_d)C(=NR_e)$—$NR_fR_g$, hydroxyl, nitro, nitroso, —$N(R_h)CONR_iR_j$, —$S(O)_{0-2}R_a$, —$C(O)R_a$, —$C(O)OR_a$, —$SO_2NR_aR_b$, —$NR_aSO_2R_b$, —$NR_aSO_2NR_bR_c$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl, or $C_{2-4}$ alkynyl.

The terms "cycloalkyl" and "cycloalkenyl" represent a cyclic hydrocarbon alkyl or alkenyl, respectively, and are meant to include monocyclic (e.g., cyclohexyl), spiro (e.g., spiro[2.3]hexanyl), fused (e.g., bicyclo[4.4.0]decanyl), and bridged (e.g., bicyclo[2.2.1]heptanyl)hydrocarbon moieties. Where indicated, the "cycloalkyl", and "cycloalkenyl" groups can also be optionally substituted as defined in "alkyl" and "alkenyl" definition, The terms "alkoxy," "alkenyloxy," and "alkynyloxy" represent an alkyl, alkenyl or alkynyl moiety, respectively, which is covalently bonded to the adjacent atom through an oxygen atom. Like the alkyl, alkenyl and alkynyl groups, where indicated the alkoxy (—O-alkyl), alkenyloxy (—O-alkenyl) and alkynyloxy (—O-alkynyl) groups can also be optionally substituted. Examples include but are not limited to methoxy, ethoxy, propoxy, isopropoxy, butoxy, isobutoxy, sec-butoxy, tert-butoxy, pentyloxy, isopentyloxy, neopentyloxy, tert-pentyloxy, hexyloxy, isohexyloxy, trifluoromethoxy and neohexyloxy. The alkoxy, alkenyloxy, and alkynyloxy groups can be optionally substituted by, for example, halogens, oxo, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, $C_{1-6}$ alkyl, $C_{2-6}$ alkenyl, $C_{2-6}$ alkynyl, —$N(R_6)CONR_iR_j$, —$S(O)_{0-2}R_a$, —$C(O)R_a$, —$C(O)OR_a$, =NO—$R_e$, —$SO_2NR_aR_b$, —$NR_aSO_2R_b$, —$NR_aSO_2NR_bR_c$, —$CR_aN=OR_b$, —$OCONR_eR_f$ and/or —$NR_aCOOR_6$, wherein $R_a$-$R_j$ are each independently H, $C_{1-4}$ alkyl, $C_{2-4}$ alkenyl, or $C_{2-4}$ alkynyl.

The term "aryl" represents a carbocyclic moiety containing at least one benzenoid-type ring (i.e., may be monocyclic or polycyclic), and which where indicated may be optionally substituted with one or more substituents. Examples include but are not limited to phenyl, tolyl, dimethylphenyl, aminophenyl, anilinyl, naphthyl, anthryl, phenanthryl or biphenyl. The aryl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, —$C(O)R_a$, —$C(O)OR_a$, —$SO_2NR_aR_b$, —$NR_aSO_2R_b$, —$NR_aSO_2NR_bk$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl, or $C_{2-4}$ alkynyl.

The terms "aryloxy," represent an aryl moiety substituted with an oxygen, wherein the point of attachment to the molecule it substitutes is on the oxygen. Where indicated the aryloxy group (—O-aryl) can also be optionally substituted by one or more substituents, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, $C(O)R_a$, $C(O)OR_a$, $SO_2NR_aR_b$, $NR_aSO_2R_b$, $NR_aSO_2NR_bR_c$, $CR_aN=OR_b$, —$OCONR_eR_f$ or $NR_aCOOR_b$, wherein $R_a$-$R_j$ are each independently H, $C_{1-4}$ alkyl, $C_{2-4}$ alkenyl, or $C_{2-4}$ alkynyl.

The term "aralkyl" represents an aryl group attached to the adjacent atom by an alkyl, alkenyl, or alkynyl. Like the aryl groups, where indicated the aralkyl groups can also be optionally substituted. Examples include but are not limited to benzyl, benzhydryl, trityl, phenethyl, 3-phenylpropyl, 2-phenylpropyl, 4-phenylbutyl and naphthylmethyl. Where indicated, the aralkyl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, optionally substituted 5-12 member heteroaryl, optionally substituted 6-18 member heteroaralkyl, optionally substituted 3-12 member heterocycle, optionally substituted 4-18 member heterocycle-alkyl, —$C(O)R_a$, —$C(O)OR_a$, —$SO_2NR_aR_b$, —$NR_aSO_2R_b$, —$NR_aSO_2NR_bk$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl, or $C_{2-4}$ alkynyl.

The term "heterocycle" represents an optionally substituted, non aromatic, saturated or partially saturated wherein said cyclic moiety is interrupted by at least one heteroatom selected from oxygen (O), sulfur (S) or nitrogen (N). It is understood that in a 3-12 member heterocycle moiety, the 3-12 member represents the total of the ring atoms present in the heterocycle moiety. Heterocycles may be monocyclic or polycyclic rings. Examples include but are not limited to azetidinyl, dioxolanyl, morpholinyl, morpholino, oxetanyl, piperazinyl, piperidyl, piperidino, cyclopentapyrazotyl, cyclopentaoxazinyl, cyclopentafuranyl, tetrahydrofuranyl, tetrahydrothiofuranyl, tetrahydrothiofuranyl, tetrahydropyranyl, tetrahydrothiopyranyl, tetrahydrothiopyranyl dioxyde, thiazolinyl, oxazolinyl, pyranyl, thiopyranyl, aziridinyl, azepinyl, dioxazepinyl, diazepinyl, oxyranyl, oxazinyl, pyrrolidinyl, thiopyranyl, thiolane, pyrazolidinyl, dioxanyl, and imidazolidinyl. Where indicated, the heterocyclic groups can be optionally substituted by, for example, halogens, oxo, —$NR_dR_e$, —$CONR_dR_e$, =NO—$R_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{7-12}$ aralkyl, $C_{6-12}$ aryl, $C_{1-6}$ alkyloxy, $C_{2-6}$ alkenyloxy, $C_{2-6}$ alkynyloxy, $S(O)_{0-2}R_a$, $C_{6-10}$ aryl, $C_{6-10}$ aryloxy, $C_{7-10}$ arylalkyl, $C_{6-10}$ aryl-$C_{1-10}$ alkyloxy, —$C(O)R_a$, —$C(O)OR_a$, —$SO_2NR_aR_b$, —$NR_aSO_2R_b$, —$NR_aSO_2NR_bR_c$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl or $C_{2-4}$ alkynyl.

The term "heterocycle-alkyl" represents an optionally substituted heterocycle group attached to the adjacent atom by an alkyl, alkenyl, or alkynyl group. It is understood that in a 5-18 member heterocycle-alkyl moiety, the 5-18 member represents the total of the ring atoms present in the heterocycle moiety and the carbon atoms present in the alkyl, alkenyl or alkynyl group. For example, the following groups are encompassed by a 7 member heterocycle-alkyl (* represents the attachment point):

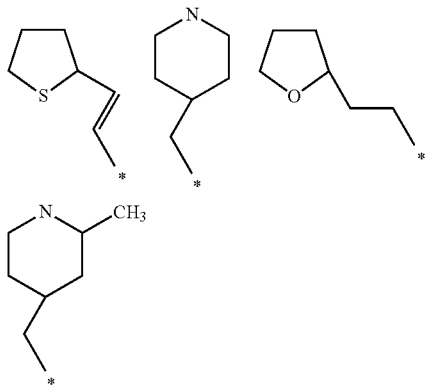

Where indicated the heterocycle-alkyl groups can be optionally substituted by, for example, halogens, oxo, $NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, $C_{6-10}$ aryl, $C_{6-10}$ aryloxy, $C_{2-10}$ arylalkyl, $C_{6-10}$ aryl-$C_{1-10}$ alkyloxy, —$C(O)R_a$, —$C(O)OR_a$, =NO—$R_e$, —$SO_2NR_aR_b$, —$NR_aSO_2R_b$, —$NR_aSO_2NR_bR_c$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl or $C_{2-4}$ alkynyl.

The term "heteroaryl" represents an optionally substituted aromatic cyclic moiety wherein said cyclic moiety is interrupted by at least one heteroatom selected from oxygen (O), sulfur (S) or nitrogen (N). It is understood that in a 5-12 member heteroaryl moiety, the 5-12 member represents the total of the ring atoms present in the heteroaryl moiety. Heteroaryls may be monocyctic or polycyclic rings. Examples include but are not limited to dithiadiazinyt, furanyl, isooxazolyl, isothiazolyl, imidazolyl, oxadiazolyl, dioxazole, oxatriazole, oxazolyl, pyrazinyl, pyridazinyl, pyrimidinyl, pyridyl, pyrazotyl, pyrrotyl, thiatriazotyl, tetrazolyl, thiadiazotyl, triazolyl, thiazolyl, thienyl, tetrazinyl, thiadiazinyl, trinity, thiazinyl, furoisoxazolyl, imidazothiazolyl, thienoisothiazolyl, thienothiazolyl, imidazopyrazotyl, pyrrolopyrrotyl, thienothienyl, thiadiazotopyrimidinyl, thiazolothiazinyl, thiazolopyrimidinyl, thiazotopyridinyl, oxazotopyrimidinyl, oxazolopyridyl, benzoxazolyl, benzisothiazolyl, benzothiazolyl, imidazopyrazinyl, purinyl, pyrazotopyrimidinyl, imidazopyridinyl, benzimidazotyl, indazolyl, benzoxathiotyl, benzodioxotyl, benzodithiolyl, indolizinyl, indolinyl, isoindotinyl, furopyrimidinyl, furopyridyl, benzofuranyl, isobenzofuranyl, thienopyrimidinyl, thienopyridyl, benzothienyl, benzoxazinyl, benzothiazinyl, quinazolinyl, naphthyridinyl, quinolinyl, isoquinolinyl, benzopyranyl, pyridopyridazinyl and pyridopyrimidinyl. Where indicated the heteroaryl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, $C_{6-10}$ aryl, $C_{6-10}$ aryloxy, $C_{7-10}$ arylalkyl, $C_{6-10}$ aryl-$C_{1-10}$ alkyloxy, —$C(O)R_a$, —$C(O)OR_a$, —$SO_2NR_aR_b$, —$NR_aSO_2R_b$, —$NR_aSO_2NR_bR_c$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl or $C_{2-4}$ alkynyl.

The term "heteroaralkyl" represents an optionally substituted heteroaryl group attached to the adjacent atom by an alkyl, alkenyl, or alkynyl group. Where indicated the heteroaralkyl groups can be optionally substituted by, for example, halogens, —$NR_dR_e$, —$CONR_dR_e$, —$NR_dCOR_e$, carboxy, —$C(=NR_d)NR_eR_f$, azido, cyano, —$N(R_d)C(=NR_e)NR_fR_g$, hydroxyl, nitro, nitroso, —$N(R_h)CONR_iR_j$, $C_{1-6}$ alkyl, $C_{2-6}$ alkenyl, $C_{2-6}$ alkynyl, $C_{1-6}$ alkyloxy, $C_{2-6}$ alkenyloxy, $C_{2-6}$ alkynyloxy, $S(O)_{0-2}R_a$, $C_{6-10}$ aryl, $C_{6-10}$ aryloxy, $C_{7-10}$ arylalkyl, $C_{6-10}$ aryl-$C_{1-10}$ alkyloxy, —$C(O)R_a$, —$C(O)OR_a$, —$SO_2NR_aR_b$, —$NR_aSO_2R_b$, —$NR_aSO_2NR_bk$, —$CR_aN=OR_b$, —$OCONR_eR_f$ and/or —$NR_aCOOR_b$, wherein $R_a$-$R_j$ are each independently H, $C_{1-4}$ alkyl, $C_{2-4}$ alkenyl, or $C_{2-4}$ alkynyl. It is understood that in a 6-18 member heteroaralkyl moiety, the 5-18 member represents the total of the ring atoms present in the heteroaryl moiety and the carbon atoms present in the alkyl, alkenyl or alkynyl group. For example, the following groups are encompassed by a 7 member heteroaralkyl (* represents the attachment point):

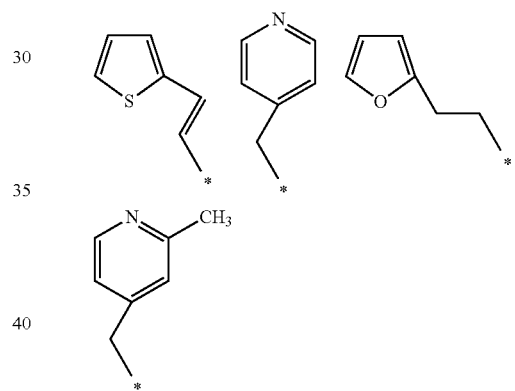

"Halogen atom" is specifically a fluorine atom, chlorine atom, bromine atom or iodine atom.

The term "oxo" represents =O.

A dash ("-") that is not between two letters or symbols is used to indicate a point of attachement for a substitutent. For example, —$CONR_dR_e$ is attached through the carbon of the amide.

A bond represented by a combination of a solid and dashed line, ie. ═══ may be either a single or double bond.

The term "guanidino" represents —$N(R_d)C(=NR_e)NR_fR_g$ wherein $R_d$, $R_e$, $R_f$ and $R_g$ are each independently selected from H, $C_{1-10}$ alkyl, $C_{2-10}$ alkenyl, $C_{2-10}$ alkynyl, $C_{6-12}$ aryl, and $C_{7-12}$ aralkyl, or $R_f$ and N are taken together with the nitrogen to which they are attached to form an optionally substituted 4 to 10 member heterocycle or an optionally substituted 5-12 member heteroaryl.

The term "amidino" represents —$C(=NR_d)NR_eR_f$ wherein $R_d$, $R_e$ and $R_f$ are each independently selected from H, $C_{1-10}$ alkyl, $C_{2-10}$ alkenyl, $C_{2-10}$ alkynyl, $C_{6-12}$ aryl, and $C_{7-12}$ aralkyl, or $R_e$ and $R_f$ are taken together with the nitrogen to which they are attached to form an optionally substituted 4 to 10 member heterocycle or an optionally substituted 5-12 member heteroaryl.

The term "hydroxyl protecting group" is well known in the field of organic chemistry. Such protecting groups may be found in "Protective Groups in Organic Synthesis" second edition, Wiley-interscience publication, by T. W. Greene and P. G. M. Wuts. Examples of hydroxy protecting groups include but are not limited to benzyl, acetyl, benzoyl, pivaloyl and isopropyloxycarbonyl.

When there is a sulfur atom present, the sulfur atom can be at different oxidation levels, i.e., S, SO, or $SO_2$. All such oxidation levels are within the scope of the present invention.

The term "independently" means that a substituent can be the same or a different definition for each item.

In still another aspect, there is provided a method for prevention or treatment of HIV infections in a subject in need of such treatment comprising administering to the subject a therapeutically effective amount of a compound of formula (I) or composition of the invention.

In still another aspect, there is provided a method for delaying the onset of AIDS or treating AIDS in a subject in need of such treatment comprising administering to the subject a therapeutically effective amount of a compound of formula (I) or composition of the invention.

In another embodiment, there is provided the use of a compound, composition or combination of the invention for the manufacture of a medicament for treating or preventing HIV infections in a subject in need of such treatment.

In another embodiment, there is provided the use of a compound, composition or combination of the invention for the manufacture of a medicament for blocking cellular entry of HIV in a subject.

In another embodiment, there is provided the use of a compound, composition or combination of the invention for the manufacture of a medicament for delaying the onset of AIDS or treating AIDS in a subject in need of such treatment.

In still another aspect, there is provided a method for blocking cellular entry of HIV in a subject or for the prevention or treatment of HIV infections in a subject in need of such treatment comprising administering to the subject a pharmaceutical combination comprising at least one compound of formula (I) and at least one further therapeutic agent.

In still another aspect, there is provided a method for delaying the onset of AIDS or treating AIDS in a subject in need of such treatment comprising administering to the subject a pharmaceutical combination comprising at least one compound of formula (I) and at least one further therapeutic agent.

In another embodiment, the pharmaceutical combination of this invention may contain at least one further therapeutic agent which is an antiviral agent.

In one embodiment, the pharmaceutical combination of this invention may contain at least one further antiviral agent which is chosen from nucleoside and nucleotide analog reverse transcriptase inhibitors, non-nucleoside reverse transcriptase inhibitors, protease inhibitors, attachment and fusion inhibitors, integrase inhibitors, and maturation inhibitors.

In one embodiment, the pharmaceutical combinations of this invention may contain at least one other antiviral agent which is a nucleoside and nucleotide analog reverse transcriptase inhibitors chosen from 3TC (lamivudine, Epivir®), AZT (zidovudine, Retrovir®), Emtricitabine (Coviracil®, formerly FTC), d4T (2',3'-dideoxy-2',3'-didehydro-thymidine, stavudine and Zerit®), tenofovir (Viread®), 2',3'-dideoxyinosine (ddI, didanosine, Videx®), 2',3'-dideoxycytidine (ddC, zalcitabine, Hivid®), Combivir® (AZT/3TC or zidovudine/lamivudine combination), Trivizir® (AZT/3TC/abacavir or zidovudine/lamivudine/abacavir combination), abacavir (1592U89, Ziagen®), Epzicom® (abacavir and lamivudine), Truvada® (Tenofovir and emtricitabine), SPD-754 (apricitabine), Elvucitabine (ACH-126,443, (Beta-L-Fd4C), Alovudine (MIV-310), DAPD (amdoxovir), Racivir, phosphazid, stampidine, CMX-157, PPI-801/802 (formerly MIV-410), MIV-210, fozivudine tidoxil, KP-1461, Fosalvudine (HDP 99.0003), 9-[(2-hydroxymethyl)-1,3-dioxolan-4-yl]guanine, and 2-amino-9-[(2-hydroxymethyl)-1,3-dioxolan-4-yl]adenine.

In another embodiment, the pharmaceutical combination of this invention may contain at least one other antiviral agent which is a non-nucleoside reverse transcriptase inhibitor chosen from Nevirapine (Viramune®, NVP, BI-RG-587), delavirdine (Rescriptor®, DLV), efavirenz (DMP 266, Sustiva®), (+)-Calanolide A, Capravirine (AG1549, formerly S-1153), DPC083, MIV-150, TMC120, Intelence (Etravirine®, TMC125), TMC-278 or BHAP (delavirdine), calanolides, GW695634, RDEA806, RDEA427, RDEA640, UK-453061, BILR355, VRX 840773 and L-697,661 (2-Pyridinone 3-benzoxazolMeNH derivative).

In another embodiment, the pharmaceutical combination of this invention may contain at least one other antiviral agent which is a protease inhibitor chosen from nelfinavir (Viracept®, NFV), amprenavir (141W94, Agenerase®), indinavir (MK-639, IDV, Crixivan®), saquinavir (Invirase®, Fortovase®, SQV), ritonavir (Norvir®, RTV), lopinavir (ABT-378, Kaletra®), Atazanavir (Reyataz®, BMS232632), mozenavir (DMP-450), fosamprenavir (GW433908), RO033-4649, Tipranavir (Aptivus®, PNU-140690), Darunavir (Prezista®, TMC114), SPI-256, Brecanavir (GW640385), P-1946, MK-8122 (formerly PPL-100) and VX-385.

In another embodiment, the pharmaceutical combination of this invention may contain at least one other antiviral agent which is an attachment and fusion inhibitor chosen from T-20 (enfuvirtide, Fuzeon®), T-1249, TRI-999, TRI-1144, Schering C(SCH-C), Vicriviroc (Schering D, SCH-D), FP21399, PRO-140, PRO 542, PRO 452, TNX-355, Aplaviroc (GW873140, AK602), TBR-220 (formerly TAK-220), TBR-652 (formerly TAK-652), PF-232798, Maraviroc (Selzentry®, UK-427,857) or soluble CD4, CD4 fragments, CD4-hybrid molecules, BMS-806, BMS-488043, AMD3100, AMD070, AMD887, INCB9471, INCB15050, KRH-2731, KRH-3140, SJ-3366, SP-01A, sifuvirtide, and KRH-3955.

In another embodiment, the pharmaceutical combination of this invention may contain at least one other antiviral agent which is an integrase inhibitor chosen from S-1360, L-870, 810, elvitegravir (GS9137, JKT 303), GS9137, L-870,812, raltegravir (Isentress®, MK-0518), MK-2048, GSK1349572, and C-2507.

In another embodiment, the pharmaceutical combination of this invention may contain at least one other antiviral agent which is a maturation inhibitor chosen from Vivecon (MPC-9055) and Bevirimat PA-457.

In another embodiment, the pharmaceutical combination of this invention may contain at least one other antiviral agent which is a zinc finger inhibitor and is azodicarbonamide (ADA).

In another embodiment, the pharmaceutical combination of this invention may contain at least one other antiviral agent which is an antisense drug and is HGTV43.

In another embodiment, the pharmaceutical combination of this invention may contain at least one other antiviral agent which is an immunomodutator, immune stimulator or cytokine chosen from interleukin-2 (IL-2, Aldesleukin, Proleukin), granulocyte macrophage colony stimulating factor (GM-CSF), erythropoietin, Multikine, Ampligen, thymomodulin, thymopentin, foscarnet, HE2000, Reticulose, Murabutide, Resveratrol, HRG214, HIV-1 Immunogen (Remune), WF10 and EP HIV-1090.

In another embodiment, the pharmaceutical combination of this invention may contain at least one other antiviral agent chosen from: 2',3'-dideoxyadenosine, 3'-deoxythymidine, 2',3'-dideoxy-2',3'-didehydrocytidine and ribavirin; acyclic nucleosides such as acyclovir, and ganciclovir; interferons such as alpha-, beta- and gamma-interferon; glucuronation inhibitors such as probenecid; and TIBO drugs, HEPT, Pictovir® (VGX-410) and TSAO derivatives.

In another embodiment, the pharmaceutical combination of this invention may contain an inhibitor of the cytochrome P450.

In another embodiment, the pharmaceutical combination of this invention may contain an inhibitor of the cytochrome P450 chosen from atazanavir, clarithromycin, indinavir, itraconazole, ketoconazole, nefazodone, nelfinavir, ritonavir, saquinavir, telithromycin, amprenavir, erythromycin, fluconazole, fosamprenavir, grapefruit juice, fluvoxamine, fluoxetine, macrolide antibiotics, sertraline sulfaphenazole, Troleandomycin, cyclosporine, clomethiazole, atazanavir, mibefradil, vitamin E, bergamottin, dihydroxybergamottin, and pharmaceutically acceptable salts thereof.

In another embodiment, the pharmaceutical combination of this invention may contain an inhibitor of the cytochrome P450 which is ritonavir or a pharmaceutically acceptable salt thereof.

The combinations referred to above may conveniently be presented for use in the form of a pharmaceutical formulation and thus pharmaceutical formulations comprising a combination as defined above together with a pharmaceutically acceptable carrier thereof comprises a further aspect of the invention.

The individual components of such combinations may be administered either sequentially or simultaneously in separate or combined pharmaceutical formulations.

In a further embodiment, the compound of formula (I) and at least one further therapeutic agent are administered sequentially.

In a further embodiment, the compound of formula (I) and at least one further therapeutic agent are administered simultaneously.

Thus, a further embodiment of the invention is a kit for use in administering a combination, the kit comprising: a first containment means for storing a compound according to formula I in the form of a pharmaceutical formulation further comprising a pharmaceutically acceptable carrier; and a second containment means for storing at least one further therapeutic agent in the form of a pharmaceutical formulation further comprising a pharmaceutically acceptable carrier.

In one embodiment, the present invention further provides a pharmaceutical composition comprising at least one compound having the formula (I) or a pharmaceutically acceptable salt thereof, or a pharmaceutically acceptable hydrate thereof, or a pharmaceutically acceptable solvate thereof, and at least one pharmaceutically acceptable carrier or excipient.

The terms "host" or "patient" or "subject" means a human, male or female, for example, a child, an adolescent, or an adult.

It will be appreciated that the amount of a compound of the invention required for use in treatment will vary not only with the particular compound selected but also with the route of administration, the nature of the condition for which treatment is required and the age and condition of the patient and will be ultimately at the discretion of the attendant physician. In general, however, a suitable dose will be in the range of from about 0.1 to about 750 mg/kg of body weight per day, for example, in the range of 0.5 to 60 mg/kg/day, or, for example, in the range of 1 to 20 mg/kg/day.

The desired dose may conveniently be presented in a single dose or as divided dose administered at appropriate intervals, for example as two, three, four or more doses per day.

The compound is conveniently administered in unit dosage form; for example containing 10 to 1500 mg, conveniently 20 to 1000 mg, most conveniently 50 to 700 mg of active ingredient per unit dosage form.

Ideally the active ingredient should be administered to achieve peak plasma concentrations of the active compound of from about 1 to about 75 µM, about 2 to 50 µM, about 3 to about 30 µM. This may be achieved, for example, by the intravenous injection of a 0.1 to 5% solution of the active ingredient, optionally in saline, or orally administered as a bolus containing about 1 to about 500 mg of the active ingredient. Desirable blood levels may be maintained by a continuous infusion to provide about 0.01 to about 5.0 mg/kg/hour or by intermittent infusions containing about 0.4 to about 15 mg/kg of the active ingredient.

When a compound of the present invention or a pharmaceutically acceptable salt thereof is used in combination with a second therapeutic agent active against the same virus, the dose of each compound may be either the same as or differ from that when the compound is used alone. Appropriate doses will be readily appreciated by those skilled in the art.

While it is possible that, for use in therapy, a compound of the invention may be administered as the raw chemical, it is preferable to present the active ingredient as a pharmaceutical composition. The invention thus further provides a pharmaceutical composition comprising a compound of the present invention or a pharmaceutically acceptable salt thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

Pharmaceutical compositions include those suitable for oral, rectal, nasal, topical (including buccal and sub-lingual), transdermal, vaginal or parenteral (including intramuscular, sub-cutaneous and intravenous) administration or in a form suitable for administration by inhalation or insufflation. The formulations may, where appropriate, be conveniently presented in discrete dosage units and may be prepared by any of the methods well known in the art of pharmacy. All methods include the step of bringing into association the active compound with liquid carriers or finely divided solid carriers or both and then, if necessary, shaping the product into the desired formulation.

Pharmaceutical compositions suitable for oral administration may conveniently be presented as discrete units such as capsules, cachets or tablets each containing a predetermined amount of the active ingredient; as a powder or granules; as a solution, a suspension, or as an emulsion. The active ingredient may also be presented as a bolus, electuary or paste. Tablets and capsules for oral administration may contain conventional excipients such as binding agents, fillers, lubricants, disintegrants, or wetting agents. The tablets may be coated according to methods well known in the art. Oral liquid preparations may be in the form of, for example, aqueous or oily suspensions, solutions, emulsions, syrups or elixirs, or may be presented as a dry product for constitution with water or other suitable vehicle before use. Such liquid preparations may contain conventional additives such as suspending agents, emulsifying agents, non-aqueous vehicles (which may include edible oils), or preservatives.

The compounds according to the invention may also be formulated for parenteral administration (e.g. by injection, for example, bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

For topical administration to the epidermis, the compounds according to the invention may be formulated as ointments, creams or lotions, or as a transdermal patch. Such transdermal patches may contain penetration enhancers such as linalool, carvacrol, thymol, citral, menthol and t-anethole. Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Compositions suitable for topical administration in, the mouth include lozenges comprising active ingredient in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Pharmaceutical compositions suitable for rectal administration wherein the carrier is a solid are, for example, presented as unit dose suppositories. Suitable carriers include cocoa butter and other materials commonly used in the art, and the suppositories may be conveniently formed by admixture of the active compound with the softened or melted carrier(s) followed by chilling and shaping in moulds.

Compositions suitable for vaginal administration may be presented as pessaries, tampons, creams, gels, pastes, foams or sprays containing in addition to the active ingredient such carriers as are known in the art to be appropriate.

For intra-nasal administration the compounds of the invention may be used as a liquid spray or dispersible powder or in the form of drops. Drops may be formulated with an aqueous or non-aqueous base also comprising one more dispersing agents, solubilizing agents, or suspending agents. Liquid sprays are conveniently delivered from pressurized packs.

For administration by inhalation the compounds according to the invention are conveniently delivered from an insufflator, nebulizer or a pressurized pack or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount.

Alternatively, for administration by inhalation or insufflation, the compounds according to the invention may take the form of a dry powder composition, for example a powder mix of the compound and a suitable powder base such as lactose or starch. The powder composition may be presented in unit dosage form in, for example, capsules or cartridges or, e.g., gelatin or blister packs from which the powder may be administered with the aid of an inhalator or insufflator.

When desired the above described formulations adapted to give sustained release of the active ingredient may be employed.

Compounds according to the present invention include:

| Cpd# | Name |
|---|---|
| 14-1 | 3β-O-(3',3'-Dimethylsuccinyl)-17β-tert-butyloxycarbonylamino-21-oxolup-18-ene; |
| 14-2 | 3β-O-(cis-Cyclohexane-3'-carboxylic acid-1'-carboxyl)-17β-[N-tert-butyloxycarbonyl-amino]-21-oxolup-18-ene; |
| 14-3 | 3β-O-[(1'R,3'S)-1',2',2'-Trimethyl-cyclopentane-3'-carboxylic acid-1'-carboxyl]-17β-[N-tert-butyloxycarbonyl-amino]-21-oxolup-18-ene; |
| 15-1 | 3β-O-(3',3'-Dimethylsuccinyl)-17β-amino-21-oxolup-18-ene; |
| 15-2 | 3β-O-(cis-Cyclohexane-3'-carboxylic acid-1'-carboxyl)-17β-amino-21-oxolup-18-ene; |
| 15-3 | 3β-O-[(1'R,3'S)-1',2',2'-Trimethyl-cyclopentane-3'-carboxylic acid-1'-carboxyl]-17β-amino-21-oxolup-18-ene; |
| 16-1 | 3β-O-(3',3'-Dimethylsuccinyl)-17β-(1-tert-butyloxycarbonylpiperidine-4-amino]-21-oxolup-18-ene; |
| 16-2 | 3β-O-(3',3'-Dimethylsuccinyl)-17β-(methylamino)-21-oxolup-18-ene; |
| 17-1 | 3β-O-(3',3'-Dimethylsuccinyl)-17β-[N'-(benzyl)ureido]-21-oxolup-18-ene; |
| 17-2 | 3β-O-(3',3'-Dimethylsuccinyl)-17β-[N'-(ethyl)ureido]-21-oxolup-18-ene; |
| 17-3 | 3β-O-(3',3'-Dimethylsuccinyl)-17β-[N'-(phenyl)ureido]-21-oxolup-18-ene; |
| 17-4 | 3β-O-(3',3'-Dimethylsuccinyl)-17β-[N'-(isopropyl)ureido]-21-oxolup-18-ene; |
| 17-5 | 3β-O-(3',3'-Dimethylsuccinyl)-17β-[N'-(tert-butyl)ureido]-21-oxolup-18-ene; |
| 17-6 | 3β-O-(3',3'-Dimethylsuccinyl)-17β-[N'-(pyridin-3-yl)ureido]-21-oxolup-18-ene; |
| 17-7 | 3β-O-(3',3'-Dimethylsuccinyl)-17β-[N'-(cyclohexyl)ureido]-21-oxolup-18-ene; |
| 17-8 | 3β-O-(3',3'-Dimethylsuccinyl)-17β-[N'-(cyclohexylmethyl)ureido]-21-oxolup-18-ene; |
| 17-9 | 3β-O-(3',3'-Dimethylsuccinyl)-17β-[N'-(1-tert-butyloxycarbonyl-piperidin-4-yl)-ureido]-21-oxolup-18-ene; |
| 17-10 | 3β-O-(3',3'-Dimethylsuccinyl)-17β-(N'-piperidin-4-yl-ureido)-21-oxolup-18-ene; |
| 17-11 | 3β-O-(3',3'-Dimethylsuccinyl)-17β-[N'-(1-acetyl-piperidin-4-yl)-ureido]-21-oxolup-18-ene; |
| 17-12 | 3β-O-(3',3'-Dimethylsuccinyl)-17β-[N'-(pyridin-3-ylmethyl)ureido]-21-oxolup-18-ene; |
| 17-13 | 3β-O-(3',3'-Dimethylsuccinyl)-17β-[(morpholine-4-carbonyl)-amino]-21-oxolup-18-ene; |
| 17-14 | 3β-O-(3',3'-Dimethylsuccinyl)-17β-[(4-tert-butyloxycarbonyl-piperazine-1-carbonyl)-amino]-21-oxolup-18-ene; |
| 17-15 | 3β-O-(3',3'-Dimethylsuccinyl)-17β-[(piperazine-1-carbonyl)-amino]-21-oxolup-18-ene; |
| 17-16 | 3β-O-(3',3'-Dimethylsuccinyl)-17β-[(4-methyl-piperazine-1-carbonyl)-amino]-21-oxolup-18-ene; |
| 17-17 | 3β-O-(3',3'-Dimethylsuccinyl)-17β-[(4-acetyl-piperazine-1-carbonyl)-amino]-21-oxolup-18-ene; |
| 17-18 | 3β-O-(3',3'-Dimethylsuccinyl)-17β-[N'-isopropyl-N'-methyl-ureido]-21-oxolup-18-ene; |
| 17-19 | 3β-O-(3',3'-Dimethylsuccinyl)-17β-(N'-5-methyl-[1,3,4]oxadiazol-2-yl-ureido)-21-oxolup-18-ene; |
| 17-20 | 3β-O-(3',3'-Dimethylsuccinyl)-17β-[(4-tert-butoxycarbonylamino-piperidine-1-carbonyl)-amino]-21-oxolup-18-ene; |
| 17-21 | 3β-O-(3',3'-Dimethylsuccinyl)-17β-(N'-cyclopropylmethyl-ureido)-21-oxolup-18-ene; |
| 17-22 | 3β-O-(3',3'-Dimethylsuccinyl)-17β-(N'-cyclopropyl-ureido)-21-oxolup-18-ene; |
| 17-23 | 3β-O-(3',3'-Dimethylsuccinyl)-17β-[(4-amino-piperidine-1-carbonyl)-amino]-21-oxolup-18-ene trifluoroacetate; |
| 17-24 | 3β-O-(3',3'-Dimethylsuccinyl)-17β-[(4-amino-piperidine-1-carbonyl)-amino]-21-oxolup-18-ene; |
| 17-25 | 3β-O-(3',3'-Dimethylsuccinyl)-17β-(N'-pyridin-2-yl-ureido)-21-oxolup-18-ene; |
| 17-26 | 3β-O-(3',3'-Dimethylsuccinyl)-17β-(N'-pyridin-4-yl-ureido)-21-oxolup-18-ene; |
| 17-27 | 3β-O-(3',3'-Dimethylsuccinyl)-17β-[N'-(pyridin-2-ylmethyl)ureido]-21-oxolup-18-ene; |
| 17-28 | 3β-O-(3',3'-Dimethylsuccinyl)-17β-[N'-(1-methyl-piperidin-4-ylmethyl)-ureido]-21-oxolup-18-ene; |
| 17-29 | 3β-O-(3',3'-Dimethylsuccinyl)-17β-[(4-isopropyl-piperazine-1-carbonyl)-amino]-21-oxolup-18-ene; |

-continued

| Cpd# | Name |
|---|---|
| 17-30 | 3β-O-(3',3'-Dimethylsuccinyl)-17β-[N'-(1-methyl-piperidin-4-yl)-ureido]-21-oxolup-18-ene; |
| 17-31 | 3β-O-(3',3'-Dimethylsuccinyl)-17β-[N'-(pyridin-4-ylmethyl)ureido]-21-oxolup-18-ene; |
| 17-32 | 3β-O-(3',3'-Dimethylsuccinyl)-17β-(N'-pyrimidin-2-yl-ureido)-21-oxolup-18-ene; |
| 17-33 | 3β-O-(3',3'-Dimethylsuccinyl)-17β-[N'-(1-tert-butyloxycarbonyl-azetidin-3-yl)-ureido]-21-oxolup-18-ene; |
| 17-34 | 3β-O-(3',3'-Dimethylsuccinyl)-17β-[(3-(S)-1-tert-butyloxycarbonyl-pyrrolidin-2-ylmethyl)-ureido]-21-oxolup-18-ene; |
| 17-35 | 3β-O-(3',3'-Dimethylsuccinyl)-17β-[azetidin-3-yl-ureido)]-21-oxolup-18-ene; |
| 17-36 | 3β-O-(3',3'-Dimethylsuccinyl)-17β-[(4-(tert-butyloxycarbonyl-methyl-amino)-piperidine-1-carbonyl)-amino]-21-oxolup-18-ene; |
| 17-37 | 3β-O-(3',3'-Dimethylsuccinyl)-17β-[N'-(1-methyl-1H-pyrazol-4-yl)ureido]-21-oxolup-18-ene; |
| 17-38 | 3β-O-(3',3'-Dimethylsuccinyl)-17β-(3-(S)-1-pyrrolidin-2-ylmethyl-ureido)-21-oxolup-18-ene; |
| 17-39 | 3β-O-(3',3'-Dimethylsuccinyl)-17β-[(4-methylamino-piperidine-1-carbonyl)-amino]-21-oxolup-18-ene; |
| 17-40 | 3β-O-(3',3'-Dimethylsuccinyl)-17β-[((R)-3-tert-butyloxycarbonyl amino-pyrrolidine-1-carbonyl)-amino]-21-oxolup-18-ene; |
| 17-41 | 3β-O-(3',3'-Dimethylsuccinyl)-17β-[((S)-3-tert-butyloxycarbonyl amino-pyrrolidine-1-carbonyl)-amino]-21-oxolup-18-ene; |
| 17-42 | 3β-O-(3',3'-Dimethylsuccinyl)-17β-[((R)-3-amino-pyrrolidine-1-carbonyl)-amino]-21-oxolup-18-ene; |
| 17-43 | 3β-O-(3',3'-Dimethylsuccinyl)-17β-[((S)-3-amino-pyrrolidine-1-carbonyl)-amino]-21-oxolup-18-ene; |
| 17-44 | 3β-O-(3',3'-Dimethylsuccinyl)-17β-(N'-pyrimidin-5-yl-ureido)-21-oxolup-18-ene; |
| 17-45 | 3β-O-(3',3'-Dimethylsuccinyl)-17β-(N'-5-methyl-[1,3,4]thiadiazol-2-yl-ureido)-21-oxolup-18-ene; |
| 17-46 | 3β-O-(3',3'-Dimethylsuccinyl)-17β-(N'-pyrimidin-4-yl-ureido)-21-oxolup-18-ene; |
| 17-47 | 3β-O-(3',3'-Dimethylsuccinyl)-17β-(N'-2-methylpyridin-4-yl-ureido)-21-oxolup-18-ene; |
| 17-48 | 3β-O-(3',3'-Dimethylsuccinyl)-17β-[N',N'-dimethyl-ureido]-21-oxolup-18-ene; |
| 17-50 | 3β-O-(3',3'-Dimethylsuccinyl)-17β-[N'-((S)-2,2,2-trifluoro-1-methyl-ethyl)-ureido]-21-oxolup-18-ene; |
| 17-51 | 3β-O-(3',3'-Dimethylsuccinyl)-17β-[N'-((R)-2,2,2-trifluoro-1-methyl-ethyl)-ureido]-21-oxolup-18-ene; |
| 17-52 | 3β-O-(3',3'-Dimethylsuccinyl)-17β-[N'-(pyrimidin-4-ylmethyl)ureido]-21-oxolup-18-ene; |
| 17-53 | 3β-O-(3',3'-Dimethylsuccinyl)-17β-[N'-(1-methyl-1-pyridin-2-yl-ethyl)ureido]-21-oxolup-18-ene; |
| 17-54 | 3β-O-(3',3'-Dimethylsuccinyl)-17β-[N'-((S)-1-cyclohexyl-ethyl)ureido]-21-oxolup-18-ene; |
| 17-55 | 3β-O-(3',3'-Dimethylsuccinyl)-17β-[N'-((R)-1-cyclohexyl-ethyl)ureido]-21-oxolup-18-ene; |
| 17-56 | 3β-O-(3',3'-Dimethylsuccinyl)-17β-[N'-(2,2,2-trifluoro-1,1-dimethyl-ethyl)ureido]-21-oxolup-18-ene; |
| 17-57 | 3β-O-(3',3'-Dimethylsuccinyl)-17β-[N'-(4,4-difluorocyclohexyl)ureido]-21-oxolup-18-ene; |
| 17-58 | 3β-O-(3',3'-Dimethylsuccinyl)-17β-(3,3-difluoro-pyrrolidine-1-carbonyl)-amino]-21-oxolup-18-ene; |
| 17-59 | 3β-O-(3',3'-Dimethylsuccinyl)-17β-[(4,4-difluoro-piperidine-1-carbonyl)-amino]-21-oxolup-18-ene; |
| 17-60 | 3β-O-(3',3'-Dimethylsuccinyl)-17β-[N'-(4,4-difluoro-cyclohexyl-methyl)ureido]-21-oxolup-18-ene; |
| 17-61 | 3β-O-(3',3'-Dimethylsuccinyl)-17β-[N'-((S)-1-phenyl-ethyl)-ureido]-21-oxolup-18-ene; |
| 17-62 | 3β-O-(3',3'-Dimethylsuccinyl)-17β-[N'-((R)-1-phenyl-ethyl)-ureido]-21-oxolup-18-ene; |
| 17-63 | 3β-O-(3',3'-Dimethylsuccinyl)-17β-[N'-(1-methyl-1-phenyl-ethyl)-ureido]-21-oxolup-18-ene; |
| 17-64 | 3β-O-(3',3'-Dimethylsuccinyl)-17β-[N'-(thiophen-2-ylmethyl)-ureido]-21-oxolup-18-ene; |
| 17-65 | 3β-O-(3',3'-Dimethylsuccinyl)-17β-[N'-(2-methyl-[1,3,4]oxadiazol-2-ylmethyl)-ureido]-21-oxolup-18-ene; |
| 17-66 | 3β-O-(3',3'-Dimethylsuccinyl)-17β-[N'-(1-phenyl-cyclopropyl)-ureido]-21-oxolup-18-ene; |
| 17-67 | 3β-O-(3',3'-Dimethylsuccinyl)-17β-[N'-(pyrimidin-2-ylmethyl)ureido]-21-oxolup-18-ene; |
| 17-68 | 3β-O-(3',3'-Dimethylsuccinyl)-17β-[N'-(pyrimidin-5-ylmethyl)ureido]-21-oxolup-18-ene; |
| 17-69 | 3β-O-(3',3'-Dimethylsuccinyl)-17β-[N'-(1-pyridin-2-yl-cyclopropyl)-ureido]-21-oxolup-18-ene; |
| 17-70 | 3β-O-(3',3'-Dimethylsuccinyl)-17β-[N'-(1-methyl-1-cyclohexyl-ethyl)-ureido]-21-oxolup-18-ene; |
| 17-72 | 3β-O-(3',3'-Dimethylsuccinyl)-17β-[N'-(1-pyridin-2-yl-ethyl)-ureido]-21-oxolup-18-ene; |
| 17-73 | 3β-O-(3',3'-Dimethylsuccinyl)-17β-[N'-(1-methyl-1H-imidazol-2-yl-methyl)-ureido]-21-oxolup-18-ene; |
| 17-74 | 3β-O-(3',3'-Dimethylsuccinyl)-17β-[N'-(4-methyl-4H-[1,2,4]triazol-3-yl-methyl)-ureido]-21-oxolup-18-ene; |
| 17-75 | 3β-O-(3',3'-Dimethylsuccinyl)-17β-[N'-(thiophen-3-ylmethyl)-ureido]-21-oxolup-18-ene; |
| 17-76 | 3β-O-(3',3'-Dimethylsuccinyl)-17β-[N'-(2-methyl-2H-pyrazol-3-yl-methyl)-ureido]-21-oxolup-18-ene; |
| 18-1 | 3β-O-(3',3'-Dimethylsuccinyl)-17β-methylsulfonylamino-21-oxolup-18-ene; |
| 19-1 | 3β-O-(3',3'-Dimethylsuccinyl)-17β-acetylamino-21-oxolup-18-ene; |
| 19-2 | 3β-O-(3',3'-Dimethylsuccinyl)-17β-benzamido-21-oxolup-18-ene; |
| 19-3 | 3β-O,17β-N-bis(3',3'-dimethylsuccinyl)-21-oxolup-18-ene; |
| 19-4 | 3β-O-(3',3'-Dimethylsuccinyl)-17β-(5-methyl-[1,3,4]oxadiazole-2-amido)-21-oxolup-18-ene; |
| 19-5 | 3β-O-(3',3'-Dimethylsuccinyl)-17β-(1-tert-butyloxycarbonylpiperidine-4-amido)-21-oxolup-18-ene; |
| 19-6 | 3β-O-(3',3'-Dimethylsuccinyl)-17β-(piperidine-4-amido)-21-oxolup-18-ene; |
| 19-7 | 3β-O-(3',3'-Dimethylsuccinyl)-17β-(1-acetylpiperidine-4-amido)-21-oxolup-18-ene; |
| 19-8 | 3β-O-(3',3'-Dimethylsuccinyl)-17β-(pyridin-3-yl)amido-21-oxolup-18-ene; |
| 19-9 | 3β-O-(3',3'-Dimethylsuccinyl)-17β-(4-fluorobenzyl)amido-21-oxolup-18-ene; |
| 19-10 | 3β-O-(3',3'-Dimethylsuccinyl)-17β-benzamido-21-oxolup-18-ene; |
| 19-11 | 3β-O-(3',3'-Dimethylsuccinyl)-17β-(2-fluorobenzamido)-21-oxolup-18-ene; |
| 19-12 | 3β-O-(3',3'-Dimethylsuccinyl)-17β-(3-fluorobenzamido)-21-oxolup-18-ene; |
| 19-13 | 3β-O-(3',3'-Dimethylsuccinyl)-17β-(4-fluorobenzamido)-21-oxolup-18-ene; |
| 19-14 | 3β-O-(3',3'-Dimethylsuccinyl)-17β-(pyridin4-yl)amido-21-oxolup-18-ene; |
| 19-15 | 3β-O-(3',3'-Dimethylsuccinyl)-17β-(pyridin-2-yl)amido-21-oxolup-18-ene; |
| 19-16 | 3β-O-(3',3'-Dimethylsuccinyl)-17β-(pyrazin-2-yl)amido-21-oxolup-18-ene; |
| 19-17 | 3β-O-(3',3'-Dimethylsuccinyl)-17β-(1-methyl-1H-pyrazole-3-amido)-21-oxolup-18-ene; |
| 19-18 | 3β-O-(3',3'-Dimethylsuccinyl)-17β-(1-methyl-1H-imidazole-5-amido)-21-oxolup-18-ene; |
| 19-19 | 3β-O-(3',3'-Dimethylsuccinyl)-17β-(1-methyl-1H-imidazole-4-amido)-21-oxolup-18-ene; |
| 19-20 | 3β-O-(3',3'-Dimethylsuccinyl)-17β-(2-thiophene)amido-21-oxolup-18-ene; |
| 19-21 | 3β-O-(3',3'-Dimethylsuccinyl)-17β-(1,3-thiazole-2-amido)-21-oxolup-18-ene; |
| 19-22 | 3β-O-(3',3'-Dimethylsuccinyl)-17β-(pyrimidine-2-amido)-21-oxolup-18-ene; |
| 19-23 | 3β-O-(3',3'-Dimethylsuccinyl)-17β-(pyrimidine-5-amido)-21-oxolup-18-ene; |
| 19-24 | 3β-O-(3',3'-Dimethylsuccinyl)-17β-(5-methylisoxazole-3-amido)-21-oxolup-18-ene; |
| 19-25 | 3β-O-(3',3'-Dimethylsuccinyl)-17β-(pyrimidine-4-amido)-21-oxolup-18-ene; |
| 19-26 | 3β-O-(3',3'-Dimethylsuccinyl)-17β-(1-methyl-1H-imidazole-2-amido)-21-oxolup-18-ene; |
| 19-27 | 3β-O-(3',3'-Dimethylsuccinyl)-17β-(1,3-thiazole-4-amido)-21-oxolup-18-ene; |
| 19-28 | 3β-O-(3',3'-Dimethylsuccinyl)-17β-(1,3-thiazole-5-amido)-21-oxolup-18-ene; |
| 19-29 | 3β-O-(3',3'-Dimethylsuccinyl)-17β-phenylacetamido-21-oxolup-18-ene; |
| 19-30 | 3β-O-(3',3'-Dimethylsuccinyl)-17β-tetrahydro-pyran-4-carbonylamino-21-oxolup-18-ene; |

| Cpd# | Name |
|---|---|
| 19-31 | 3β-O-(3',3'-Dimethylsuccinyl)-17β-isopropylamido-21-oxolup-18-ene; |
| 19-32 | 3β-O-(3',3'-Dimethylsuccinyl)-17β-tert-butylamido-21-oxolup-18-ene; |
| 19-33 | 3β-O-(3',3'-Dimethylsuccinyl)-17β-cyclohexylamido-21-oxolup-18-ene; |
| 19-34 | 3β-O-(3',3'-Dimethylsuccinyl)-17β-(1-methyl-1H-pyrazole-5-amido)-21-oxolup-18-ene; |
| 19-35 | 3β-O-(3',3'-Dimethylsuccinyl)-17β-(1-methyl-1H-pyrazole-4-amido)-21-oxolup-18-ene; |
| 19-36 | 3β-O-(3',3'-Dimethylsuccinyl)-17β-(1-methylpiperidine-4-amido)-21-oxolup-18-ene; |
| 19-37 | 3β-O-(3',3'-Dimethylsuccinyl)-17β-(3-pyrrolidin-1-yl-propionamido)-21-oxolup-18-ene; |
| 19-38 | 3β-O-(3',3'-Dimethylsuccinyl)-17β-(2-pyrrolidin-1-yl-acetamido)-21-oxolup-18-ene; |
| 19-39 | 3β-O-(3',3'-Dimethylsuccinyl)-17β-(4-pyrrolidin-1-yl-butyramido)-21-oxolup-18-ene; |
| 19-40 | 3β-O-(3',3'-Dimethylsuccinyl)-17β-(3-piperidin-1-yl-propionamido)-21-oxolup-18-ene; |
| 19-41 | 3β-O-(3',3'-Dimethylsuccinyl)-17β-[3-(2-oxo-pyrrolidin-1-yl)-propionamido]-21-oxolup-18-ene; |
| 19-42 | 3β-O-(3',3'-Dimethylsuccinyl)-17β-(S)-1-methyl-pyrrolidine-2-amido)-21-oxolup-18-ene; |
| 19-43 | 3β-O-(3',3'-Dimethylsuccinyl)-17β-(4-methylbenzamido)-21-oxolup-18-ene; |
| 19-44 | 3β-O-(3',3'-Dimethylsuccinyl)-17β-(3-methylbenzamido)-21-oxolup-18-ene; |
| 19-45 | 3β-O-(3',3'-Dimethylsuccinyl)-17β-(2-methylbenzamido)-21-oxolup-18-ene; |
| 19-46 | 3β-O-(3',3'-Dimethylsuccinyl)-17β-(2-methylpyridin-3-yl)amido-21-oxolup-18-ene; |
| 19-47 | 3β-O-(3',3'-Dimethylsuccinyl)-17β-(5-methylpyridin-3-yl)amido-21-oxolup-18-ene; |
| 19-48 | 3β-O-(3',3'-Dimethylsuccinyl)-17β-(6-methylpyridin-3-yl)amido-21-oxolup-18-ene; |
| 19-49 | 3β-O-(3',3'-Dimethylsuccinyl)-17β-(4-methylpyridin-3-yl)amido-21-oxolup-18-ene; |
| 19-50 | 3β-O-(3',3'-Dimethylsuccinyl)-17β-(4-hydroxypyridin-3-yl)amido-21-oxolup-18-ene; |
| 19-51 | 3β-O-(3',3'-Dimethylsuccinyl)-17β-(2-hydroxypyridin-3-yl)amido-21-oxolup-18-ene; |
| 19-52 | 3β-O-(3',3'-Dimethylsuccinyl)-17β-(2-methylpyridin-4-yl)amido-21-oxolup-18-ene; |
| 19-53 | 3β-O-(3',3'-Dimethylsuccinyl)-17β-(2-dimethylamino-acetamido)-21-oxolup-18-ene; |
| 19-54 | 3β-O-(3',3'-Dimethylsuccinyl)-17β-(4-methylpiperazine-1-acetamido)-21-oxolup-18-ene; |
| 19-55 | 3β-O-(3',3'-Dimethylsuccinyl)-17β-(R)-1-methyl-pyrrolidine-2-amido]-21-oxolup-18-ene; |
| 19-56 | 3β-O-(3',3'-Dimethylsuccinyl)-17β-(S)-1-isopropyl-pyrrolidine-2-amido]-21-oxolup-18-ene; |
| 19-57 | 3β-O-(3',3'-Dimethylsuccinyl)-17β-(S)-1-tert-butyloxycarbonyl-pyrrolidine-2-amido]-21-oxolup-18-ene; |
| 19-58 | 3β-O-(3',3'-Dimethylsuccinyl)-17β-(R)-1-tert-butyloxycarbonyl-pyrrolidine-2-amido]-21-oxolup-18-ene; |
| 19-59 | 3β-O-(3',3'-Dimethylsuccinyl)-17β-((RS)-2-dimethylamino-propionamido)-21-oxolup-18-ene; |
| 19-60 | 3β-O-(3',3'-Dimethylsuccinyl)-17β-(1-imidazole-acetamido)-21-oxolup-18-ene; |
| 19-61 | 3β-O-(3',3'-Dimethylsuccinyl)-17β-(2-carboxy-benzamido)-21-oxolup-18-ene; |
| 19-62 | 3β-O-(3',3'-Dimethylsuccinyl)-17β-(5-cyclopropyl-[1,3,4]oxadiazole-2-amido)-21-oxolup-18-ene; |
| 19-63 | 3β-O-(3',3'-Dimethylsuccinyl)-17β-(5-phenyl-[1,3,4]oxadiazole-2-amido)-21-oxolup-18-ene; |
| 19-64 | 3β-O-(3',3'-Dimethylsuccinyl)-17β-(2,6-dimethylpyridin-4-yl)amido-21-oxolup-18-ene; |
| 19-65 | 3β-O-(3',3'-Dimethylsuccinyl)-17β-((S)-1-methylpiperidine-2-amido)-21-oxolup-18-ene; |
| 19-66 | 3β-O-(3',3'-Dimethylsuccinyl)-17β-((R)-1-methylpiperidine-2-amido)-21-oxolup-18-ene; |
| 19-67 | 3β-O-(3',3'-Dimethylsuccinyl)-17β-(3-methyl-[1,2,4]oxadiazole-5-amido)-21-oxolup-18-ene; |
| 19-68 | 3β-O-(3',3'-Dimethylsuccinyl)-17β-(5-methyl-[1,2,4]oxadiazole-3-amido)-21-oxolup-18-ene; |
| 19-69 | 3β-O-(3',3'-Dimethylsuccinyl)-17β-(5-methyl-[1,3,4]oxadiazole-2-methyl-amido)-21-oxolup-18-ene; |
| 19-70 | 3β-O-(3',3'-Dimethylsuccinyl)-17β-(8β-oxa-bicyclo[3.2.1]octane-3-amido)-21-oxolup-18-ene; |
| 19-71 | 3β-O-(3',3'-Dimethylsuccinyl)-17β-(8α-oxa-bicyclo[3.2.1]octane-3-amido)-21-oxolup-18-ene; |
| 19-72 | 3β-O-(3',3'-Dimethylsuccinyl)-17β-(2-methyl-1,3-thiazole-4-amido)-21-oxolup-18-ene; |
| 19-73 | 3β-O-(3',3'-Dimethylsuccinyl)-17β-(1-azetidin-acetamido)-21-oxolup-18-ene; |
| 19-74 | 3β-O-(3',3'-Dimethylsuccinyl)-17β-(N',N'-dimethyl-oxalamido)-21-oxolup-18-ene; |
| 19-75 | 3β-O-(3',3'-Dimethylglutaryl)-17β-(5-methyl-[1,3,4]oxadiazole-2-amido)-21-oxolup-18-ene; |
| 19-76 | 3β-O-(3',3'-Dimethylsuccinyl)-17β-(2-methyl-1,3-oxazole-4-amido)-21-oxolup-18-ene; |
| 19-77 | 3β-O-(3',3'-Dimethylsuccinyl)-17β-(5-methyl-thiophene-2-amido)-21-oxolup-18-ene; |
| 19-78 | 3β-O-(3',3'-Dimethylsuccinyl)-17β-(thiophene-3-amido)-21-oxolup-18-ene; |
| 19-79 | 3β-O-(3',3'-Dimethylsuccinyl)-17β-(5-ethyl-[1,3,4]-oxadiazole-2-amido)-21-oxolup-18-ene; |
| 19-80 | 3β-O-(3',3'-Dimethylsuccinyl)-17β-(5-methyl-[1,3]-oxazole-2-amido)-21-oxolup-18-ene; |
| 19-81 | 3β-O-(cis-Cyclohexane-3'-carboxylic acid-1'-carboxyl)-17β-[(5-methyl-[1,3,4]oxadiazol-2-carbonyl)-amino]-21-oxolup-18-ene; |
| 19-82 | 3β-O-(3',3'-Dimethylsuccinyl)-17β-(1H-pyrazole-4-amido)-21-oxolup-18-ene; |
| 19-84 | 3β-O-(3',3'-Dimethylsuccinyl)-17β-(5-isopropyl-[1,3,4]-oxadiazole-2-amido)-21-oxolup-18-ene; |
| 20-1 | 3β-O-(3',3'-Dimethylsuccinyl)-17β-methoxycarbonylamino-21-oxolup-18-ene; |
| 20-2 | 3β-O-(3',3'-Dimethylsuccinyl)-17β-isopropyloxycarbonylamino-21-oxolup-18-ene; |
| 20-3 | 3β-O-(3',3'-Dimethylsuccinyl)-17β-cyclopropylmethoxycarbonylamino-21-oxolup-18-ene; |
| 20-4 | 3β-O-(3',3'-Dimethylsuccinyl)-17β-cyclopentyloxycarbonylamino-21-oxolup-18-ene; |
| 20-5 | 3β-O-(3',3'-Dimethylsuccinyl)-17β-cyclohexyloxycarbonylamino-21-oxolup-18-ene; |
| 20-6 | 3β-O-(3',3'-Dimethylsuccinyl)-17β-[(1-carboxylic acid tert-butyl ester)-piperidine-4-oxycarbonylamino]-21-oxolup-18-ene; |
| 20-7 | 3β-O-(3',3'-Dimethylsuccinyl)-17β-cyclohexylmethoxycarbonylamino-21-oxolup-18-ene; |
| 20-8 | 3β-O-(3',3'-Dimethylsuccinyl)-17β-benzyloxycarbonylamino-21-oxolup-18-ene; |
| 20-9 | 3β-O-(3',3'-Dimethylsuccinyl)-17β-cyclobutyloxycarbonylamino-21-oxolup-18-ene; |
| 20-10 | 3β-O-(3',3'-Dimethylsuccinyl)-17β-(1-cyclopropylethoxycarbonylamino)-21-oxolup-18-ene; |
| 20-11 | 3β-O-(3',3'-Dimethylsuccinyl)-17β-(1-methyl-cyclopropylmethoxycarbonylamino)-21-oxolup-18-ene; |
| 20-12 | 3β-O-(3',3'-Dimethylsuccinyl)-17β-(1-amino-cyclopropylmethoxycarbonylamino)-21-oxolup-18-ene; |
| 20-13 | 3β-O-(3',3'-Dimethylsuccinyl)-17β-((R)-1-methylpyrrolidine-3-oxycarbonylamino)-21-oxolup-18-ene; |
| 20-14 | 3β-O-(3',3'-Dimethylsuccinyl)-17β-(tetrahydro-thiopyran-4-oxycarbonylamino)-21-oxolup-18-ene; |
| 20-15 | 3β-O-(3',3'-Dimethylsuccinyl)-17β-(1,1-dioxo-tetrahydro-thiopyran-4-oxycarbonylamino)-21-oxolup-18-ene; |
| 20-16 | 3β-O-(3',3'-Dimethylsuccinyl)-17β-(piperidine-4-oxycarbonylamino)-21-oxolup-18-ene; |
| 20-17 | 3β-O-(3',3'-Dimethylsuccinyl)-17β-(1-methylpiperidine-4-oxycarbonylamino)-21-oxolup-18-ene; |
| 20-18 | 3β-O-(3',3'-Dimethylsuccinyl)-17β-(1-methylpiperidine-4-methoxycarbonylamino)-21-oxolup-18-ene; |
| 20-19 | 3β-O-(3',3'-Dimethylsuccinyl)-17β-(1-methylpiperidine-3-methoxycarbonylamino)-21-oxolup-18-ene; |
| 20-20 | 3β-O-(3',3'-Dimethylsuccinyl)-17β-((S)1-methylpyrrolidine-2-methoxycarbonylamino)-21-oxolup-18-ene; |
| 20-21 | 3β-O-(3',3'-Dimethylsuccinyl)-17β-(1-methylpyrrolidine-3-methoxycarbonylamino)-21-oxolup-18-ene; |
| 20-22 | 3β-O-(3',3'-Dimethylsuccinyl)-17β-(2-cyclopropyl-1-ethoxycarbonylamino)-21-oxolup-18-ene; |
| 20-23 | 3β-O-(3',3'-Dimethylsuccinyl)-17β-(2-pyrrolidin-1-ethoxycarbonylamino)-21-oxolup-18-ene; |
| 20-24 | 3β-O-(3',3'-Dimethylsuccinyl)-17β-(2-(2-oxo-pyrrolidin)-1-ethoxycarbonylamino)-21-oxolup-18-ene; |

-continued

| Cpd# | Name |
|---|---|
| 24-1 | 17β-Benzamido-3β-hydroxy-21-oxolup-18-ene; |
| 24-2 | 17β-(pyridin-2-yl)amido-3β-hydroxy-21-oxolup-18-ene; and |
| 25-1 | 17β-(isopropylcarbonylamino)-3β-hydroxy-21-oxolup-18-ene; | and pharmaceutically acceptable salts thereof.

EXAMPLES

The following general schemes and examples are provided to illustrate various embodiments of the present invention and shall not be considered as limiting in scope. It will be appreciated by those of skill in the art that other compounds of the present invention can be obtained by substituting the generically or specifically described reactants and/or operating conditions used in the following examples.

In the foregoing and in the following examples, all temperatures are set forth uncorrected in degrees Celsius; and, unless otherwise indicated, all parts and percentages are by weight.

Analytical HPLC is carried out under standard conditions using a Phenomenex Gemini C18 column, 250×4.6 mm, 3 µm, 110 Å for the methods A, B, C, D and E, a Varian pursuit XRs C18 column, 50×4.6 mm, 3 µm, for the methods F, G, H and I and a Waters SymmetryShield C18 column, 250×4.6 mm, 5 µm for the method J. Elution is performed using a linear gradient with a flow rate of 1 mL/min. as described in the following table (Solvent A is 0.01% TFA in H$_2$O; solvent B is 0.01% TFA in CH$_3$CN):

| Methods | A | B | C | D | E |
|---|---|---|---|---|---|
| Solvent B | 50 to 90% over 40 min | 60 to 100% over 40 min | 30 to 70% over 40 min | 20 to 60% over 40 min | 40 to 80% over 40 min |
| Methods | F | G | H | I | J |
| Solvent B | 50 to 95% over 15 min | 15 to 45% over 15 min | 30 to 75% over 15 min | 15 to 60% over 15 min | 80 to 90% over 20 min |

The following abbreviations may be used as follows:
Ac acetyl
AcOEt Ethyl acetate
AcOH Acetic acid
Ac$_2$O Acetic anhydride
(Boc)$_2$O di-tert-butyldicarbonate
br broad
DABCO 1,4-diazabicyclo[2.2.2]octane
DCM dichloromethane
DIPEA Diisopropylethylamine
DMAP 4-Dimethylaminopyridine
DPPA Diphenylphosphoryl azide
NaOAc Sodium acetate
PCC Pyridinium chlorochromate
q Quadruplet
Sept. Septuplet
TEA Triethylamine
TFA Trifluoroacetic acid
THF Tetrahydrofuran
Hal Halogen

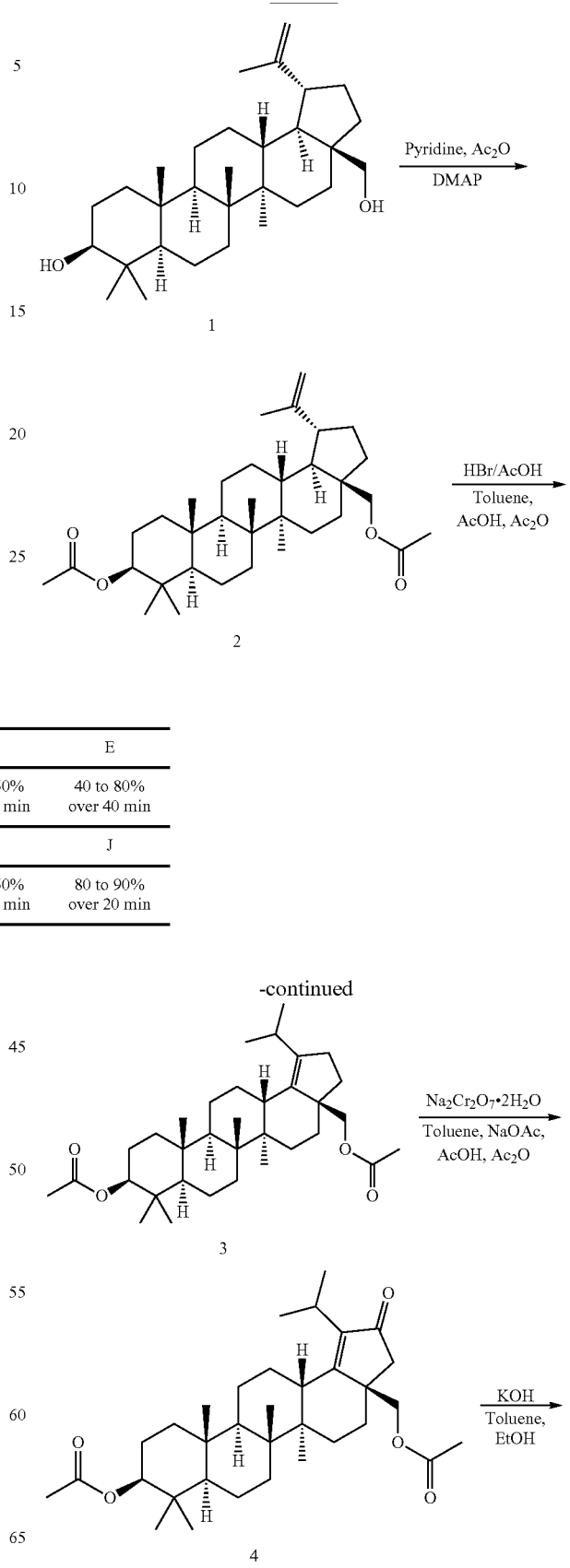

Scheme 1

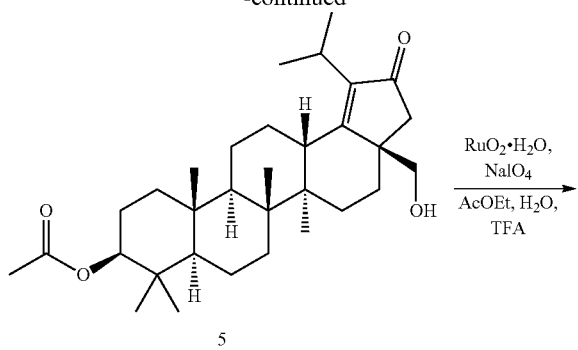

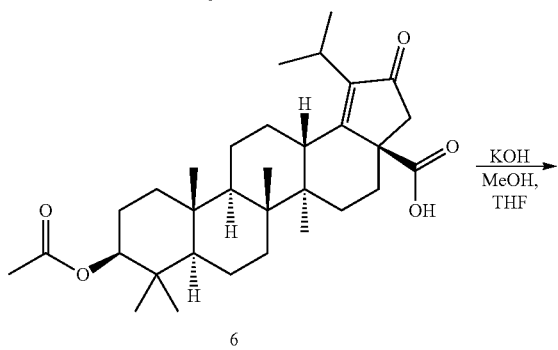

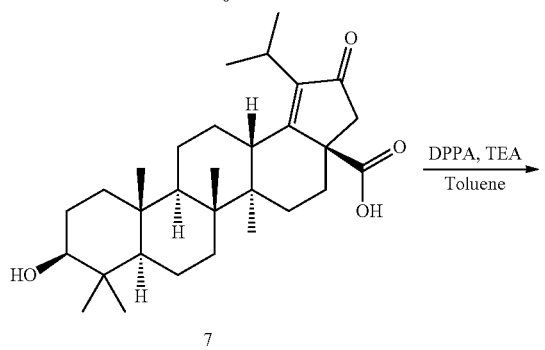

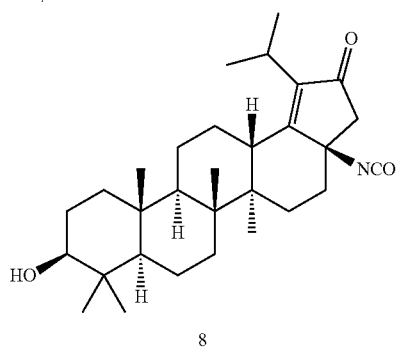

Lup-20(29)-ene-3β,28-diyl diacetate 2

To a mixture of betulin 1 (100 g, 0.225 mot) in 120 mL of anhydrous pyridine is added DMAP (2.68 g, 0.022 mot) and 48 mL (0.495 mol) of acetic anhydride. The reaction mixture is stirred at room temperature for 5 hours and diluted with iced water. The mixture is then extracted with DCM (3×200 mL) and the combined organic layers are washed back with aqueous HCl 1N (3×200 mL), brine and dried over sodium sulfate. The pale yellow solid is taken up with methanol (400 mL), filtered off and rinsed with methanol (2×400 mL) to give the title compound 2 (102.35 g, 86.3%) as a colorless solid.

Lup-18-ene-3β,28-diyl diacetate 3

A solution of 90 mL of HBr in acetic acid (33%) is added to a mixture of 2 (45.03 g, 85.48 mmol) in 90 mL of toluene, 90 mL of acetic anhydride and 90 mL of acetic acid previously heated at 90° C. The reaction mixture is stirred and heated at this temperature for 4 hours. After cooling, 46 g of sodium acetate is added and the mixture is evaporated to dryness. The pale brownish residue is re-evaporated from methanol (50 mL) and the residue is triturated with methanol, filtered off and washed with methanol to obtain 42.35 g of a pale brownish solid. After recrystallization in ethyl acetate (0.5 L) and cooling on ice for 0.5 hour, the title compound 3 (25.78 g, 60.4%) is isolated as a colorless solid.

21-Oxo-lup-18-ene-3β,28-diyl diacetate 4

A mixture of 3 (22 g, 41.76 mmol), sodium acetate (19.5 g, 238 mmol) and sodium dichromate dihydrate (14.9 g, 50.1 mmol) in 280 mL of anhydrous toluene, 350 mL of acetic acid and 76 mL of acetic anhydride is stirred overnight at 60° C. After cooling, water (500 mL) and ethyl acetate (350 mL) are added and the layers are separated. The organic layer is washed successively with water (500 mL), a saturated solution of sodium carbonate (3×250 mL), water (500 mL) and brine (3×200 mL), dried over sodium sulfate and concentrated in vacuum. The gummy yellow solid is triturated with methanol and filtered off to yield the title compound 4 (21.41 g, 94.8%) as a colorless solid.

28-Hydroxy-21-oxolup-18-en-3β-yl acetate 5

A solution of compound 4 (12.07 g, 22.3 mmol) and potassium hydroxide (1.49 g, 26.76 mmol) in a mixture 1:1 of toluene and ethanol (0.72 L) is stirred vigorously at room temperature for 1 hour. The reaction mixture is neutralized with aqueous HCl 1N (27 mL) and evaporated to dryness. The solid is taken up with water and a minimum of acetone then filtered off. The precipitate is washed with water and dried to yield the title compound 5 (10.24 g, 92%) as a colorless solid.

3β-Acetoxy-21-oxolup-18-en-28-oic acid 6

A suspension of compound 5 (10.24 g, 20.5 mmol) in ethyl acetate (720 mL) is added to a mixture of ruthenium oxide (IV) hydrate (272 mg, 2.05 mmol) and sodium periodate (26.3 g, 123 mmol) in water (650 mL) and TFA (11 mL). The biphasic mixture is stirred vigorously overnight at room temperature. Ethanol (100 mL) is added and the separated organic layer is filtered through a short column of silica gel. Water (400 mL) is added and the organic layer is dried over sodium sulfate, and concentrated in vacuo. The yellow solid is taken up with diethyl ether, filtered off and washed with diethyl ether to give the title compound 6 (4.96 g, 47.2%) as a colorless solid.

3β-Hydroxy-21-oxolup-18-en-28-oic acid 7

To a solution of compound 6 (300 mg, 0.58 mmol) in 3 mL of methanol and 10 mL of THF is added an aqueous 4N solution of potassium hydroxide (1.45 mL, 5.8 mmol). The reaction mixture is stirred for 2 days at room temperature, neutralized with HCl 1N (6 mL) and extracted with DCM (20 mL). The organic layer is washed with water (3×20 mL), brine (20 mL) and dried over sodium sulfate to yield the title compound 7 (201.4 mg, 73.7%).

¹H NMR (400 MHz, CDCl₃): δ [ppm] 3.20 (m, 2H), 2.74 (d×d, 1H), 2.57 (d, 1H), 2.46 (m, 1H), 2.17 (d, 1H), 2.06 (br d, 1H), 1.90-1.24 (m, 15H), 1.21 (s, 3H), 1.19 (s, 3H), 1.04 (s, 3H), 0.98-0.83 (m, 2H), 0.96 (s, 3H), 0.93 (s, 3H), 0.87 (s, 3H), 0.76 (s, 3H), 0.70 (br d, 1H).

LC/MS: m/z=471.46 (M+H⁺).

3β-Hydroxy-21-oxolup-18-en-17β-isocyanate 8

To a stirring suspension of compound 7 (124 mg, 0.26 mmol) in dry toluene (2.2 mL) is added TEA (40 μL, 0.32 mmol) and DPPA (68 μL, 0.32 mmol). The mixture is stirred for 24 hours at room temperature and concentrated to dryness. The residue is purified by flash chromatography on silica gel (ethyl acetate/hexanes 0% to 20%) to afford the title compound 8 (70.3 mg, 57%) as a white solid.

¹H NMR (400 MHz, CDCl₃): δ [ppm] 3.19 (m, 1H), 3.11 (m, 1H), 3.01 (d×d, 1H), 2.58 (d, 1H), 2.40 (d×d, 1H), 2.11-1.22 (m, 17H), 1.17 (m, 9H), 0.96 (s, 3H), 0.90 (s, 3H), 0.89 (s, 3H), 0.76 (s, 3H), 0.68 (m, 1H).

LC/MS: m/z=468.57 (M+H⁺).

Scheme 2

3β-Acetoxy-21-oxolup-18-en-28-oic acid azide 9

To a stirring suspension of compound 6 (1.11 g, 2.17 mmol) in dry toluene (16 mL) is added TEA (0.33 mL, 2.6 mmol) and DPPA (0.56 mL, 2.6 mmol). The mixture is stirred for 3 hours at room temperature and concentrated to dryness. The residue is purified by flash chromatography on silica gel (ethyl acetate/hexanes 0% to 20%) to afford the title compound 9 (967 mg, 83%) as a white solid.

$^1$H NMR (400 MHz, CDCl$_3$): δ [ppm] 4.45 (dxd, 1H); 3.18 (m, 1H), 2.60 (dxd, 1H), 2.48 (d, 1H), 2.44 (m, 1H), 2.11 (d, 1H), 2.21 (s, 3H), 2.0 (m, 1H), 1.92-1.22 (m, 14H), 1.20 (d, 3H), 1.18 (d, 3H), 1.04 (m, 1H), 1.03 (s, 3H), 0.90 (s, 3H), 0.89 (s, 3H), 0.83 (s, 3H), 0.82 (s, 3H), 0.79 (m, 1H).

LC/MS: m/z=538.58 (M+H$^+$).

3β-Acetoxy-21-oxolup-18-en-17β-isocyanate 10

A solution of compound 9 (960 mg, 1.78 mmol) in toluene (18 mL) is stirred at 80° C. for 2 hours and concentrated to dryness to afford the title compound 10 (784 mg, 86%) as a white solid.

$^1$H NMR (400 MHz, CDCl$_3$): δ [ppm] 4.46 (dxd, 1H), 3.11 (m, 1H), 3.01 (dxd, 1H), 2.58 (d, 1H), 2.41 (d, 1H), 2.09 (m, 1H), 2.04 (s, 3H), 2.0-1.24 (m, 15H), 1.18 (d, 3H), 1.70 (m, 6H), 1.04 (m, 1H), 0.92 (s, 3H), 0.89 (s, 3H), 0.84 (s, 3H), 0.83 (s, 3H), 0.80 (m, 1H).

LC/MS: m/z=510.48 (M+H$^+$).

3β-Acetoxy-17β-amino-21-oxolup-18-ene hydrochloride 11

To a stirring solution of compound 10 (784 mg, 1.54 mmol) in DCM (15 mL) is added concentrated HCl (5 mL). The biphasic mixture is stirred 48 hours at room temperature, and then concentrated to dryness to give the title compound 11 (765 mg, 96%) as a white solid.

$^1$H NMR (400 MHz, DMSO-d$_6$): δ [ppm] 8.40 (br s, 2H), 4.37 (dxd, 1H), 3.16 (m, 1H), 2.83 (dxd, 1H), 2.43 (m, 2H), 2.08 (m, 1H), 1.97 (s, 3H), 1.92-1.0 (m, 25H), 0.86 (s, 3H), 0.82 (s, 3H), 0.81 (m, 1H), 0.77 (s, 6H).

17β-Amino-3β-hydroxy-21-oxolup-18-ene hydrochloride 12

To a solution of compound 11 (760 mg, 1.46 mmol) in 3.8 mL of methanol and 11.2 mL of THF is added an aqueous 4N solution of potassium hydroxide (3.6 mL, 14.6 mmol). The reaction mixture is stirred for 24 hours at room temperature and acidified with 4N HCl. The precipitate formed is collected by filtration to yield the title compound 12 (705 mg, 100%) as a white solid.

$^1$H NMR (400 MHz, DMSO-d$_6$): δ [ppm] 4.28 (dxd, 1H), 3.14 (m, 1H), 2.95 (m, 1H), 2.86 (br d, 1H), 2.48 (m, 2H), 2.42 (d, 2H), 2.06 (m, 1H), 1.90-1.07 (m, 24H), 0.91 (m, 1H), 0.84 (s, 3H), 0.81 (s, 3H), 0.80 (s, 3H), 0.65 (m, 1H), 0.63 (s, 3H).

LC/MS: m/z=442.56 (M+H$^+$).

17β-tent-Butyloxycarbonylamino-3β-hydroxy-21-oxolup-18-ene 13

To a stirring suspension of compound 12 (600 mg, 1.25 mmol) in DCM (13 mL) is added successively TEA (0.4 mL, 3.14 mmol) and (Boc)$_2$O (411 mg, 1.88 mmol). The solution is stirred overnight at room temperature then another 1.56 mmol of TEA and 0.94 mmol of (Boc)$_2$O is added and stirring is continued for 3 hours. The mixture is diluted with DCM and washed with HCl (1N) and water, dried over sodium sulfate and concentrated to dryness. The residue is purified by flash chromatography on silica gel (methanol/DCM 0% to 8%) to afford the title compound 13 as foam (564 mg, 83%).

$^1$H NMR (400 MHz, CDCl$_3$): δ [ppm] 4.62 (br s, 1H), 3.19 (dxd, 1H), 3.11 (m, 1H), 2.83 (br d, 1H), 2.62 (d, 1H), 2.23 (br d, 1H), 1.88 (m, 3H), 1.73 (m, 1.68-1.10 (m, 30H), 0.98 (m, 1H), 0.96 (s, 3H), 0.92 (s, 3H), 0.88 (s, 3H), 0.76 (s, 3H), 0.70 (m, 1H).

LC/MS: m/z=542.61 (M+H$^+$).

3β-O-(3',3'-Dimethylsuccinyl)-17β-tert-butyloxycarbonylamino-21-oxolup-18-ene 14-1

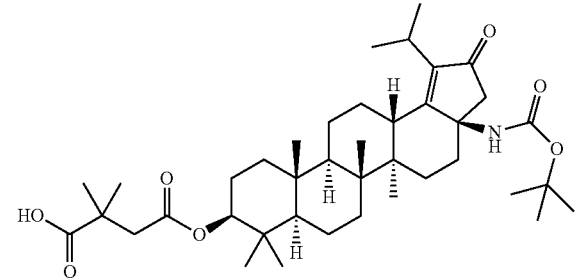

A stirring solution of compound 13 (557 mg, 1.03 mmol), DMAP (151 mg, 1.23 mmol) and 2,2-dimethylsuccinic anhydride (527 mg, 4.12 mmol) in dry pyridine (11 mL) is heated overnight at 120° C. Another 3.12 mmol of 2,2-dimethylsuccinic anhydride is added and heating at 120° C. is continued for 4 hours. The mixture is cooled down to room temperature and concentrated to dryness. The residue is diluted in ethyl acetate, washed twice with HCl 1N, water and brine, dried over sodium sulfate and concentrated to dryness. The residue is purified by flash column chromatography on silica gel (ethyl acetate/hexanes 0% to 40%) to yield the title compound 14-1 as a white solid (467 mg, 68%).

$^1$H NMR (400 MHz, CDCl$_3$): δ [ppm] 4.50 (dxd, 1H), 3.11 (m, 1H), 2.84 (br s, 1H), 2.60 (m, 3H), 2.24 (br s, 1H), 1.98-0.95 (m, 39H), 0.92 (s, 3H), 0.90 (s, 3H), 0.83 (s, 3H), 0.80 (s, 3H), 0.79 (m, 2H).

LC/MS: m/z=670.69 (M+H$^+$).

3β-O-(3',3'-Dimethylsuccinyl)-17β-amino-21-oxolup-18-ene hydrochloride 15-1

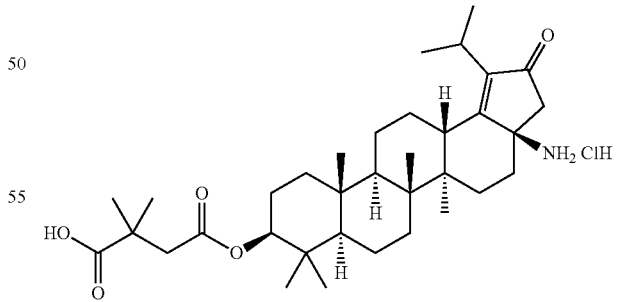

To a stirring solution of compound 14-1 (414 mg, 0.62 mmol) in dioxane (5 mL) is added 4N HCl in dioxane (1.5 mL). The mixture is stirred 24 hours at room temperature. Another 1.5 mL of 4N HCl in dioxane is added and the mixture is stirred for 2 days and then concentrated to dryness to give the title compound 15-1 (390 mg, 100%) as a white solid. An aliquot (80 mg) is purified by flash column chromatography on silica gel (methanol/DCM 0% to 10%) to give the title compound 15-1 as a white solid (38 mg).

$^1$H NMR (400 MHz, DMSO-d$_6$): δ [ppm] 4.36 (d×d, 1H), 3.18 (d×d, 1H), 3.05 (m, 1H), 2.48 (m, 2H), 2.13 (d, 2H), 2.0-1.18 (m, 16H), 1.17-0.94 (m, 17H), 0.84 (s, 3H), 0.82 (s, 3H), 0.76 (s, 6H).

LC/MS: m/z=570.59 (M+H$^+$).

To a stirring suspension of compound 15-1 (54.6 mg, 0.09 mmol) and N-Boc-4-piperidine (21.5 mg, 0.11 mmol) in dichloroethane (0.6 mL) is added TEA (17 µL, 0.13 mmol). After stirring the mixture at room temperature for 1 hour, sodium triacetoxyborohydride (28.6 mg, 0.13 mmol) is added and the reaction is stirred for 24 hours at room temperature. The mixture is diluted with ethyl acetate, washed with aque-

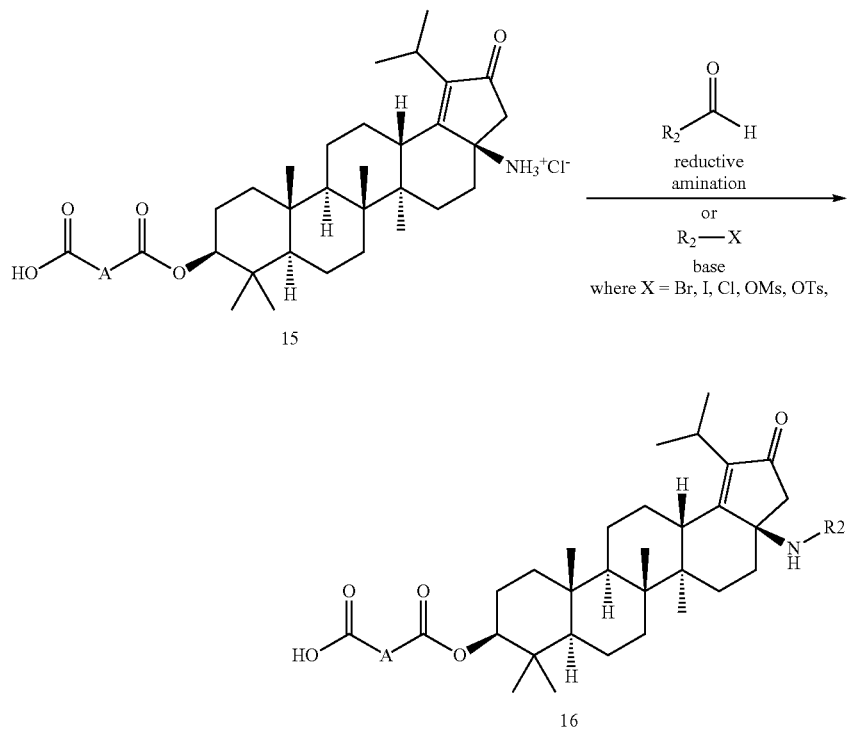

Scheme 3

General Procedure for the Preparation of Compound 16:

An alkyl R$_2$ group is introduced to compound 15 by conventional reductive amination with an aldehyde or a ketone (see A. F. Abdel-Magid, et al. *J. Org. Chem.* (1996), 61, 3849-3862) or by alkylation with an alkyl halide in presence of a base such as TEA, DIPEA or NaH in a solvent such as THF or DMF to give compound 16.

3β-O-(3',3'-Dimethylsuccinyl)-17β-(1-tert-butyloxy-carbonylpiperidine-4-amino]-21-oxolup-18-ene 16-1 ous sodium bicarbonate, water and brine, dried over sodium sulfate and concentrated to dryness. The residue is purified by flash column chromatography on silica gel (methanol/DCM 0% to 10%) to give the title compound 16-1 as a white solid (39 mg, 68%).

$^1$H NMR (400 MHz, DMSO-d$_6$): δ [ppm] 4.49 (m, 1H), 4.10 (q, 1H), 3.90 (m, 4H), 3.18 (m, 1H), 3.0 (t, 1H), 2.77 (m, 1H), 2.60 (m, 2H), 2.35 (m, 1H), 2.08 (m, 2H), 1.84 (m, 3H), 1.78-0.94 (m, 47H), 0.90 (s, 3H), 0.88 (s, 3H), 0.81 (m, 7H).

LC/MS: m/z=753.7 (M+H$^+$).

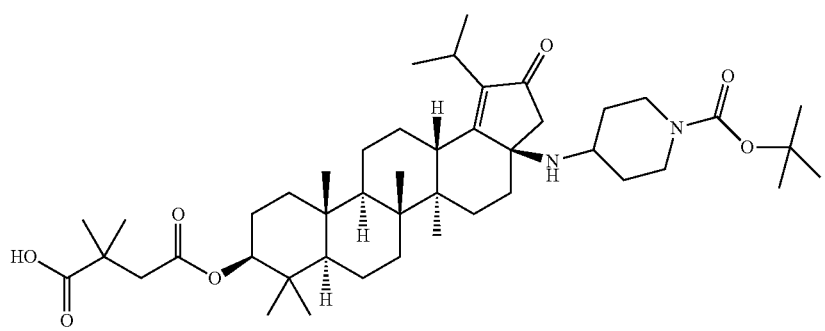

Scheme 4

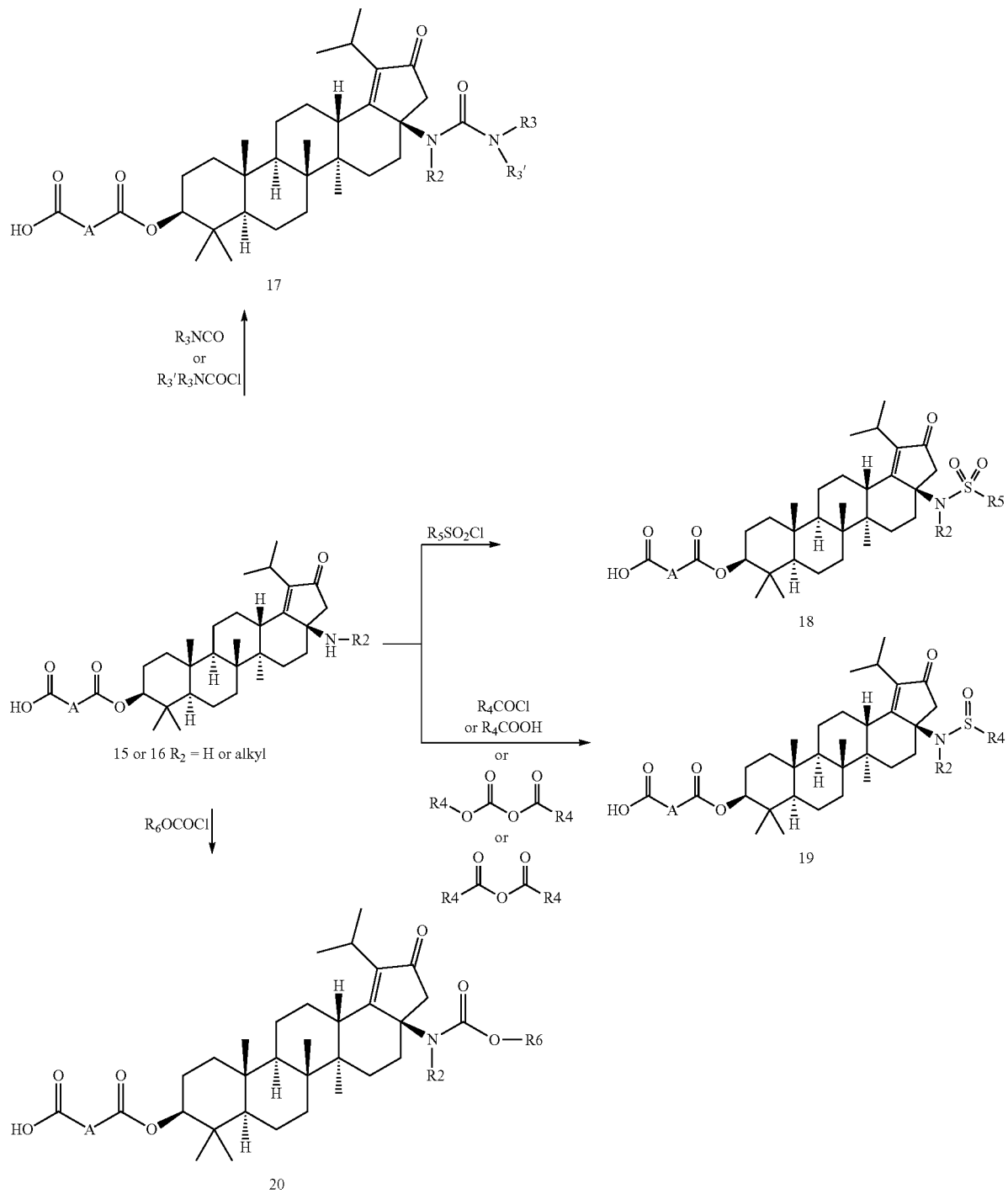

General Procedures

Ureas 17 are made by treatment of compound 15 or 16 with an isocyanate (1 to 3 eq.), carbamoyl chloride or phosgene or triphosgene followed by an amine in a solvent such as toluene or THF.

Sulfonamides 18 are obtained by coupling compound 15 or 16 with the appropriate sulfonyl chloride (1 to 3 eq.) in solvents such as THF or DCM and in the presence of a base such as TEA or DIPEA.

Amides 19 are prepared by coupling compound 15 or 16 with the appropriate acyl chloride (1 to 3 eq.), preactivated carboxylic acid, mixed anhydride or anhydride in solvents such as THF or DCM and in the presence of a base such as TEA or DIPEA.

Carbamates 20 are obtained by reacting compound 15 or 16 with the appropriate chloroformate (1 to 3 eq.) in solvents such as THF or DCM and in the presence of a base such as TEA or DIPEA.

3β-O-(3',3'-Dimethylsuccinyl)-17β[N'-(benzyl)ureido]-21-oxolup-18-ene 17-1

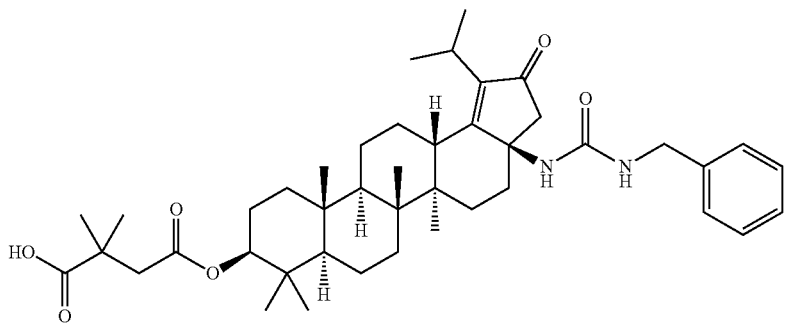

To a stirring suspension of compound 15-1 (49.2 mg, 0.08 mmol) in DCM (1 mL) is added TEA (23 μL, 0.18 mmol) and benzyl isocyanate (15 μL, 0.12 mmol). The mixture is stirred for 24 hours at room temperature, diluted with DCM, washed twice with water and brine, dried over sodium sulfate and concentrated to dryness. The residue is purified by flash column chromatography on silica gel (methanol/DCM 0% to 10%) to give the title compound 17-1 as a white solid (39 mg, 68%).

$^1$H NMR (400 MHz, DMSO-d$_6$): δ [ppm] 12.2 (br s, 1H), 7.25 (m, 2H), 7.20 (m, 3H), 6.28 (s, 1H), 6.21 (t, 1H), 4.35 (d×d, 1H), 4.20 (d×d, 1H), 4.07 (d×d, 1H), 3.04 (m, 1H), 2.83 (d×d, 1H), 2.43 (m, 2H), 2.09 (d, 2H), 1.90 (m, 2H), 1.75-0.94 (m, 30H), 0.87 (s, 3H), 0.85 (s, 3H), 0.80 (m, 1H), 0.76 (s, 6H).

LC/MS: m/z=703.68 (M+H$^+$).

3β-O-(3',3'-Dimethylsuccinyl)-17β-methylsulfonylamino-21-oxolup-18-ene 18-1

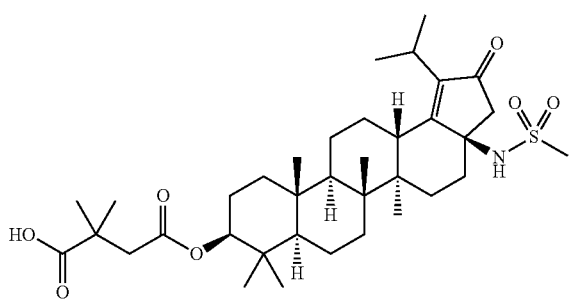

A solution of compound 15-1 (48.6 mg, 0.08 mmol) in DCM (0.8 mL) is treated with TEA (51 μL, 0.4 mmol) and methanesulfonyl chloride (25 μL, 0.128 mmol). The mixture is stirred in microwave at 100° C. for 5 minutes. The mixture is diluted with DCM, washed twice with water and brine, dried over sodium sulfate. The residue is purified by flash column chromatography on silica gel (methanol/DCM 0% to 10%) to yield the title compound 18-1 (26.5 mg, 51%) as a pale yellow solid.

$^1$H NMR (400 MHz, CDCl$_3$): δ [ppm] 4.62 (s, 1H), 4.48 (d×d, 1H), 3.14 (m, 1H), 3.05 (m, 1H), 2.98 (s, 3H), 2.88 (d, 1H), 2.60 (q, 2H), 2.33 (d, 1H), 2.27 (br d, 1H), 2.02-1.82 (m, 2H), 1.78-1.1 (m, 28H), 1.02 (m, 1H), 0.91 (s, 3H), 0.90 (s, 3H), 0.81 (m, 7H).

LC/MS: m/z=648.6 (M+H$^+$).

3β-O-(3',3'-Dimethylsuccinyl)-17β-acetylamino-21-oxolup-18-ene 19-1

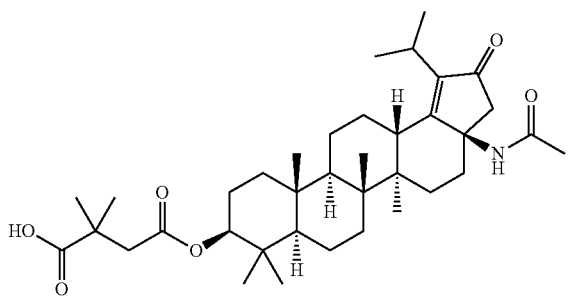

To a stirring solution of compound 15-1 (50 mg, 0.08 mmol) in THF (1 mL) is added TEA (23 μL, 0.18 mmol) and acetyl chloride (9 μL, 0.12 mmol). The mixture is stirred for 2 hours at room temperature, diluted with ethyl acetate, washed twice with water and brine, dried over sodium sulfate and concentrated to dryness. The residue is purified by flash column chromatography on silica gel (methanol/DCM 0% to 5%) to give the title compound 19-1 as a white solid (25 mg, 50%).

$^1$H NMR (400 MHz, CDCl$_3$): δ [ppm] 5.43 (s, 1H), 4.48 (d×d, 1H), 3.12 (m, 1H), 2.75 (t, 1H), 2.69 (d, 1H), 2.65 (d, 1H), 2.55 (d, 1H), 2.30 (m, 2H), 1.97 (s, 3H), 1.94-1.12 (m, 28H), 1.10 (s, 3H), 1.01 (m, 1H), 0.92 (s, 3H), 0.89 (s, 3H), 0.83 (s, 3H), 0.81 (s, 3H).

LC/MS: m/z=612.64 (M+H$^+$).

3β-O-(3',3'-Dimethylsuccinyl)-17β-nnethoxycarbonylamino-21-oxolup-18-ene 20-1

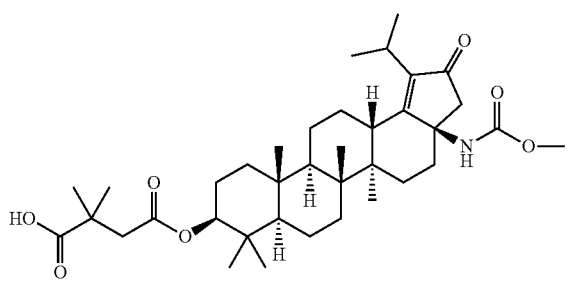

To a stirring suspension of compound 15-1 (51.6 mg, 0.085 mmol) in DCM (1 mL) is added TEA (24 μL, 0.19 mmol) and methylchloroformate (10 μL, 0.13 mmol). The mixture is stirred for 2 hours at room temperature, diluted with DCM, washed twice with water and brine, dried over sodium sulfate and concentrated to dryness. The residue is purified by flash column chromatography on silica gel (methanol/DCM 0% to 10%) and repurified by reverse-phase HPLC (55 to 85% CH$_3$CN in H$_2$O (3 mmol HCl) over 60 min at 244 nm) to give the title compound 20-1 as a white solid (1.5 mg, 3%).

$^1$H NMR (400 MHz, CDCl$_3$): δ [ppm] 4.73 (br s, 1H), 4.44 (d×d, 1H), 3.55 (s, 3H), 3.07 (m, 1H), 2.76 (t, 1H), 2.54 (m, 3H), 2.17 (m, 2H), 1.90-1.08 (m, 27H), 1.05 (s, 3H), 0.95 (m, 1H), 0.86 (s, 3H), 0.84 (s, 3H), 0.77 (s, 3H), 0.75 (s, 3H), 0.74 (m, 1H).

LC/MS: m/z=628.64 (M+H$^+$).

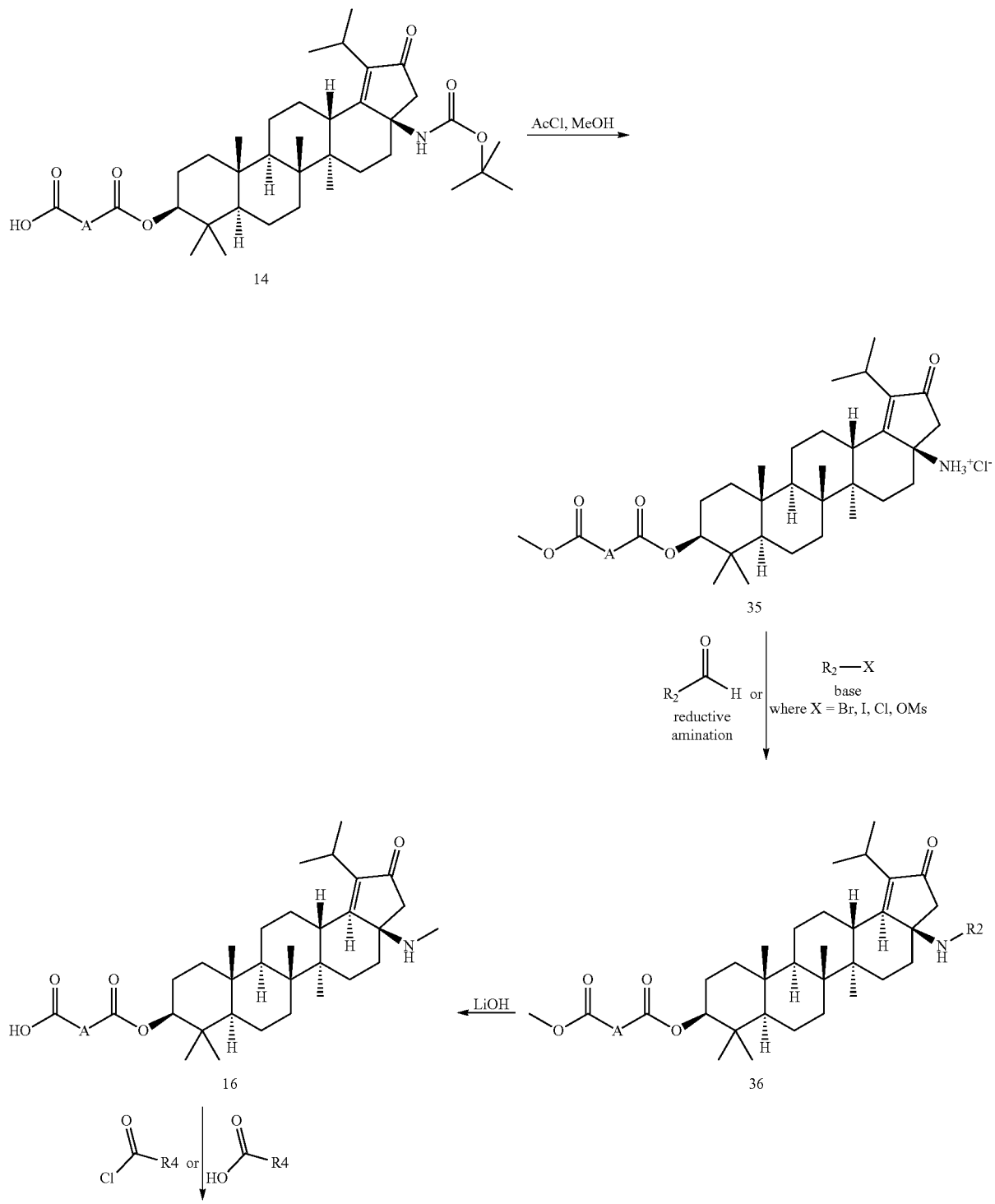

Scheme 5

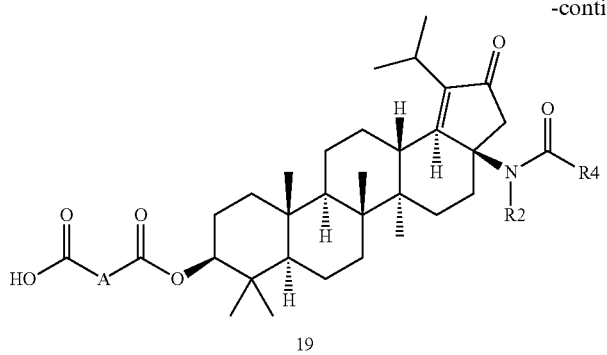

19

General Procedure for the Preparation of Compound 19:

Step 1: Compound 14 is treated with acetyl chloride in methanol and stirred at room temperature to give compound 35.

Step 2: An alkyl R₂ group is introduced to compound 35 by conventional reductive amination with an aldehyde or a ketone or by alkylation with an alkyl halide in presence of a base such as TEA, DIPEA or NaH in a solvent such as THF or DMF to give compound 36.

Step 3: The deprotection of the ester group occurs in solvents such as methanol, THF or dioxane using an aqueous solution of inorganic base such as lithium hydroxide or potassium hydroxide (3 to 10 eq.) at temperature ranging from 20 to 60° C.

Step 4: Amides 19 are prepared by coupling compound 16 with the appropriate acyl chloride (1 to 3 eq.), preactivated carboxylic acid, mixed anhydride or anhydride in solvents such as THF, DMF or DCM and in the presence of a base such as TEA or DIPEA.

3β-O-(3',3'-Dimethylsuccinyl)-17β-[methyl-(5-methyl-[1,3,4]oxadiazole-2-carbonyl)-amino]-21-oxo-lup-18-ene 19-69

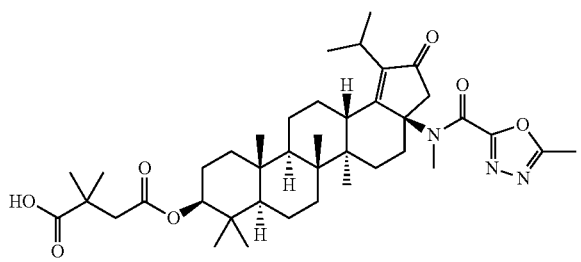

Step 1: To an ice-cold stirring suspension of 14-1 (146.8 mg, 0.22 mmol) in MeOH (2 mL) is added acetyl chloride (0.16 mL, 2.19 mmol). The mixture is stirred at room temperature overnight and the solvent is removed by evaporation. The residue is purified by flash column chromatography on silica gel (methanol/DCM 0% to 8%) to yield the title compound 3β-O-(3',3'-Dimethylsuccinyl-methyl-ester)-17β-amino-21-oxolup-18-ene hydrochloride 35-1 (118 mg, 86%).

1H NMR (400 MHz, CDCl₃): δ [ppm] 4.48 (d×d, 1H), 3.67 (s, 3H), 3.30 (m, 2H), 2.58 (q, 2H), 2.45 (q, 2H), 2.00-1.20 (m, 15H), 1.25 (s, 3H), 1.24 (s, 3H), 1.17 (d, 3H), 1.15 (d, 3H), 1.14 (s, 3H), 1.00 (m, 1H), 0.82 (s, 3H), 0.80 (s, 3H), 0.79 (m, 1H).

Step 2: To an ice-cold stirring solution of 35-1 (101 mg, 0.164 mmol) in dry THF (1.6 mL) is added sodium hydride (14 mg, 0.345 mmol, as a 60% dispersion in mineral oil). The mixture is stirred 15 minutes at 0° C. then methyl iodide (0.012 mL, 0.196 mmol) is added. The resulting mixture is stirred at 0° C. for 30 minutes then at room temperature overnight. The mixture is diluted with ethyl acetate, washed with aqueous ammonium chloride, water, aqueous sodium thiosulfate 5% and brine, dried over sodium sulfate. The residue is purified by flash column chromatography on silica gel (methanol/DCM 0% to 5%) to yield 3β-O-(3',3'-, Dimethylsuccinyl-methyl-ester)-17β-N-methyl-amino-21-oxo-lup-18-ene hydrochloride 36-1 (30 mg, 30%) as an oil.

1H NMR (400 MHz, CDCl₃): δ [ppm] 4.48 (d×d, 1H), 3.67 (s, 2H), 3.13 (sept., 1H), 2.62 (d, 1H), 2.55 (d, 1H), 2.37 (d, 1H), 2.11 (s, 3H), 1.98 (d, 1H), 1.97 (t×d, 1H), 1.87 (m, 3H), 1.72 (d×t, 1H), 1.68-0.70 (m, 14H), 1.26 (s, 3H), 1.25 (s, 3H), 1.19 (d, 3H), 1.17 (d, 3H), 1.13 (s, 3H), 0.90 (s, 3H), 0.89 (s, 3H), 0.82 (s, 3H), 0.80 (s, 3H).

LC/MS: m/z=598.45 (M+H+).

Step 3: To a stirring solution of 36-1 (80 mg, 0.134 mmol) in 1,4-dioxane (1 mL) and water (0.5 mL) is added LiOH 1N (0.401 mL, 0.401 mmol). The mixture is stirred overnight at room temperature, neutralized to pH 7 with HCl 1N, extracted with ethyl acetate (1×), DCM (containing few drops of methanol) (3×). The organic extracts are combined and dried over sodium sulfate. The residue is purified by flash column chromatography on silica gel (methanol/DCM 0% to 10%) to yield 16-2 (43 mg, 55%) as a white solid.

1H NMR (400 MHz, CD₃OD): δ [ppm] 4.46 (d×d, 1H), 3.25 (sept., 11-1), 2.89 (m, 1H), 2.58 (d, 1H), 2.53 (d, 1H), 2.38 (d, 1H), 2.12 (s, 3H), 2.07 (d, 1H), 2.01-1.93 (m, 4H), 1.79 (d×t, 1H), 1.70-1.27 (m, 11H), 1.24 (s, 3H), 1.23 (s, 3H), 1.20 (s, 3H), 1.18 (d, 3H), 1.17 (d, 3H), 1.14-0.98 (m, 2H), 0.96 (s, 6H), 0.86 (s, 3H), 0.85 (s, 3H), 0.84 (m, 1H).

LC/MS: m/z=584.52 (M+H+).

HPLC (D) RT=26.63 min.

Step 4: To an ice-cold stirring solution of potassium 5-methyl-[1,3,4]oxadiazole-2-carboxylate (13.4 mg, 0.081 mmol) in dry acetonitrile (1.0 mL) is added a catalytic amount of DMF followed by oxalyl chloride (0.037 mL, 0.074 mmol).

The mixture is stirred 50 minutes at 0° C., it is then added to an ice-cold stirring suspension of 16-2 (42.9 mg, 0.074 mmol) and TEA (0.021 mL, 0.147 mmol) in dry THF (1.3 mL). The resulting mixture is stirred 3.5 hours at room temperature, diluted with ethyl acetate, washed with water and brine, dried over sodium sulfate. The residue is purified by flash column chromatography on silica gel (methanol/DCM 0% to 10%) to yield the title compound 19-69 (8.2 mg, 16%) as white solid.

1H NMR (400 MHz, CDCl$_3$): δ [ppm] 4.48 (d×d, 1H), 3.89 (br s, 3H), 3.16 (sept., 1H), 2.64 (d, 2H), 2.59 (s, 3H), 2.54 (d, 1H), 2.44 (br s, 2H), 2.00-0.70 (m, 19H), 1.29 (s, 3H), 1.28 (s, 3H), 1.22 (t, 6H), 1.05 (s, 3H), 0.90 (s, 3H), 0.84 (s, 3H), 0.82 (s, 3H), 0.79 (s, 3H).

LC/MS: m/z=694.97 (M+H+).

HPLC (A) RT=24.93 min.

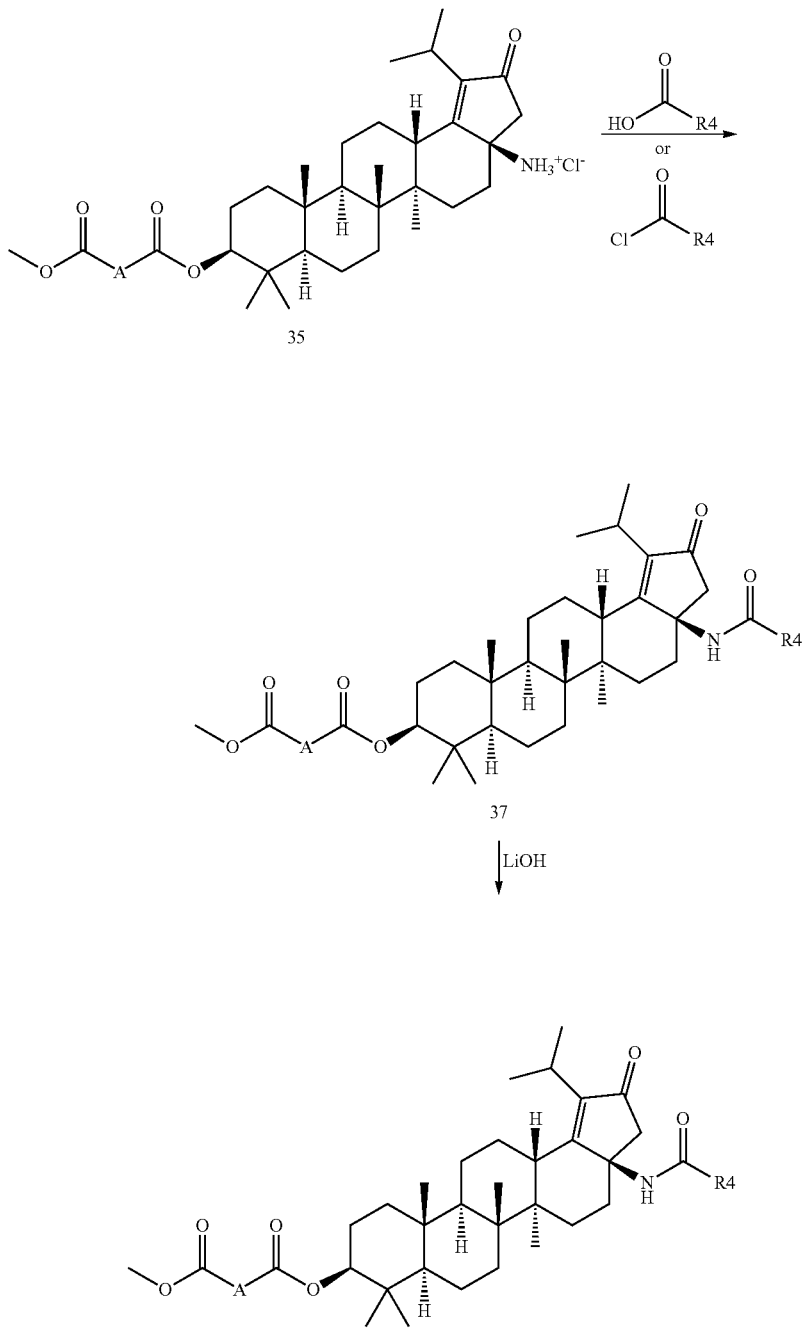

General Procedure

Step 1: Amides 19 are prepared by coupling compound 35 with the appropriate acyl chloride, preactivated carboxylic acid, mixed anhydride or anhydride in solvents such as THF, DCM or DMF and in the presence of a base such as TEA or DIPEA.

Step 2: The deprotection occurs in solvents such as methanol, THF or dioxane using an aqueous solution of inorganic base such as lithium hydroxide or potassium hydroxide (3 to 10 eq.) at temperature ranging from 20 to 60° C.

3β-O-(3',3'-Dimethylsuccinyl)-17β-(4-hydroxypyridine-3-yl)amido-21-oxolup-18-ene 19-50

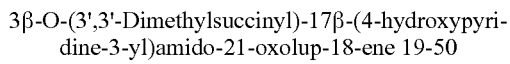

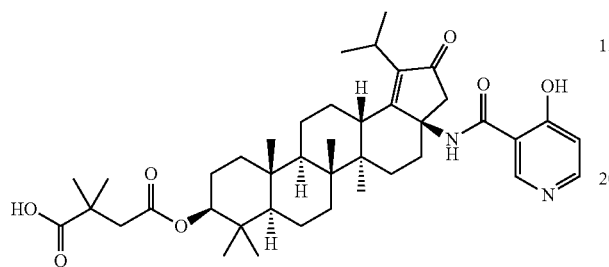

Step 1: To a stirring suspension of compound 35-1 (85.3 mg, 0.14 mmol) and 4-hydroxynicotinic acid (28.7 mg, 0.21 mmol) in DMF (1.5 mL) is added TEA (53 μL, 0.41 mmol) and HATU (78.4 mg, 0.21 mmol). The mixture is stirred for 2 hours at room temperature. Water is added slowly and the precipitate formed is collected by filtration and purified by flash column chromatography on silica gel (methanol/DCM 0% to 8%) to yield the title compound 3β-O-(3',3'-Dimethyl-succinyl-methyl-ester)-17β-(4-hydroxypyridine-3-yl)amido-21-oxolup-18-ene 37-1 (70 mg).

$^1$H NMR (400 MHz, CDCl$_3$): δ [ppm] 11.6 (br s, 1H), 10.92 (br s, 1H), 8.80 (s, 1H), 7.61 (d, 1H), 6.57 (m, 1H), 4.44 (d×d, 1H), 3.66 (s, 3H), 3.15 (m, 1H), 2.89 (t, 1H), 2.79 (d, 1H), 2.57 (q, 2H), 2.24 (m, 3H), 1.88 (m, 2H), 1.74-0.72 (m, 14H), 1.24 (s, 3H), 1.23 (s, 3H), 1.18 (d, 3H), 1.15 (d, 3H), 1.08 (s, 3H), 0.94 (s, 3H), 0.83 (s, 3H), 0.81 (s, 3H), 0.78 (s, 3H).

LC/MS: m/z=705.98 (M+H$^+$).

Step 2: To a stirring solution of 37-1 (70 mg, 0.10 mmol) in 1,4-dioxane (0.8 mL) and water (0.2 mL) is added LiOH.H$_2$O (12.5 mg, 0.30 mmol). The mixture is stirred overnight at room temperature, acidified to pH 3 with HCl 1N, and the precipitate formed is collected by filtration. The product is purified by flash column chromatography on silica gel (methanol/DCM 0% to 15%) to yield 19-50 (31 mg) as a white solid.

$^1$H NMR (400 MHz, CDCl$_3$): δ [ppm] 11.7 (br s, 1H), 10.80 (s, 1H), 8.42 (d×d, 1H), 7.38 (m, 1H), 6.52 (d×d, 1H), 4.42 (d×d, 1H), 3.12 (m, 1H), 2.93 (m, 1H), 2.80 (d, 1H), 2.54 (q, 2H), 2.40 (m, 1H), 2.29 (d, 1H), 2.07 (m, 5H), 1.88 (m, 2H), 1.70-0.70 (m, 10H), 1.22 (s, 3H), 1.21 (s, 3H), 1.18 (d, 3H), 1.16 (d, 3H), 1.03 (s, 3H), 0.90 (s, 3H), 0.80 (s, 3H), 0.78 (s, 3H), 0.76 (s, 3H).

LC/MS: m/z=691.86 (M+H$^+$).

Scheme 7

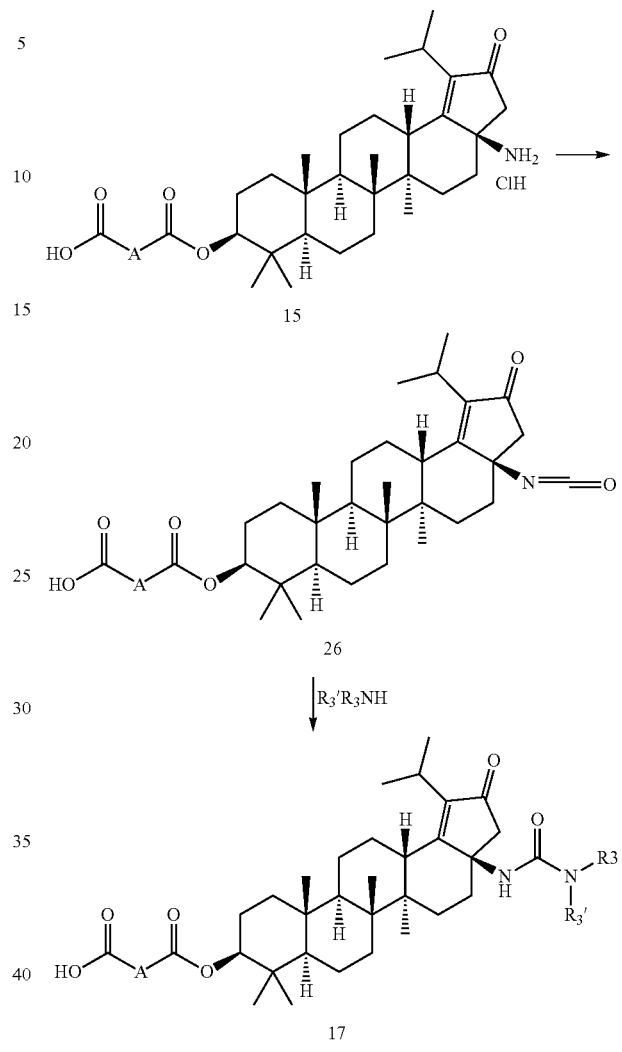

Isocyanates 26 are made, by treatment of compound 15 with phosgene or triphosgene. Ureas 17 are obtained by treatment of the isocyanates 26 with an amine in a solvent such as toluene or THF in the presence of a base such as TEA or DIPEA.

3β-O-(3',3'-Dimethylsuccinyl)-17β[N'-(1-tert-butyloxycarbonyl-piperidin-4-yl)-ureido]-21-oxolup-18-ene 17-9

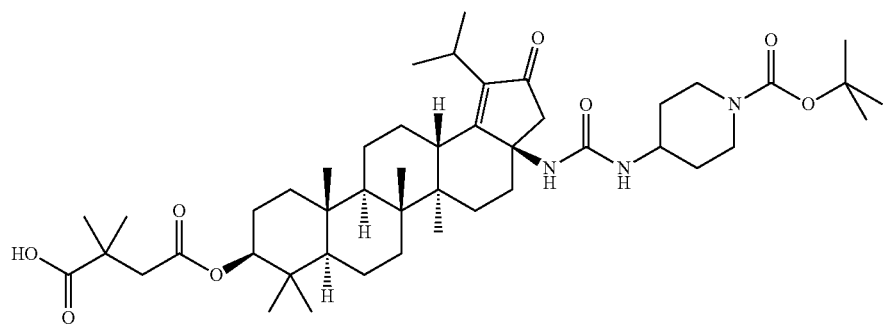

Step 1: To an ice-cold stirring solution of triphosgene (335 mg, 1.129 mmol) in dry THF (5 mL) is added drop wise over 10 minutes a solution of compound 15-1 (456 mg, 0.753 mmol) and DIPEA (0.33 mL, 1.881 mmol) in dry THF (6 mL). The resulting mixture is stirred at room temperature for 3 hours. Water is added drop wise at 0° C. and the mixture is diluted with ethyl acetate, washed with water and brine, dried over sodium sulfate. The residue is purified by flash column chromatography on silica gel (ethyl acetate/hexanes 0% to 80%) to yield 3β-O-(3',3'-dimethylsuccinyl)-21-oxolup-18-ene-17β-isocyanate 26-1 (419 mg) as a foam.

$^1$H NMR (400 MHz, CDCl$_3$): δ [ppm] 4.49 (d×d, 1H), 3.11 (sept., 1H), 2.99 (d×d, 1H), 2.67 (d, 1H), 2.59 (d, 1H), 2.54 (d, 1H), 2.41 (d, 1H), 2.10 (m, 1H), 2.04-1.80 (m, 3H), 1.75 (d×t, 1H), 1.70-1.46 (m, 6H), 1.39-1.24 (m, 5H), 1.30 (s, 3H), 1.28 (s, 3H), 1.18 (d, 3H), 1.17 (d, 3H), 1.16 (s, 3H), 1.01 (t×d, 1H), 0.91 (s, 3H), 0.89 (s, 3H), 0.83 (s, 3H), 0.81 (s, 3H), 0.78 (m, 1H).

IR (ν, cm$^{-1}$): 2257 (NCO).

Step 2: To a stirring solution of 3β-O-(3',3'-dimethylsuccinyl)-21-oxolup-18-ene-17β-isocyanate 26-1 (151 mg, 0.253 mmol) in dry toluene (6 mL) is added 4-amino-1-Boc-piperidine (203 mg, 1.014 mmol). The mixture is stirred 2 hours at 80° C., cooled down and diluted with ethyl acetate, washed with HCl 1N, water and brine, dried over sodium sulfate. The residue is purified by flash column chromatography on silica gel (methanol/DCM 0% to 10%) to yield the title compound 17-9 (173 mg) as a white solid.

$^1$H NMR (400 MHz, CDCl$_3$): δ [ppm] 5.40 (br s, 1H), 4.56 (br s, 1H), 4.47 (d×d, 1H), 3.97 (br s, 2H), 3.66 (br s, 1H), 3.16 (sept., 1H), 2.91 (d, 1H), 2.78 (t, 2H), 2.66 (d, 1H), 2.59 (d, 1H), 2.52 (d, 1H), 2.28 (d, 1H), 2.13 (d, 1H), 1.99 (m, 1H), 1.90-0.70 (m, 19H), 1.42 (s, 9H), 1.28 (s, 3H), 1.27 (s, 3H), 1.21 (d, 3H), 1.17 (d, 3H), 1.10 (s, 3H), 0.92 (s, 3H), 0.89 (s, 3H), 0.82 (s, 3H), 0.80 (s, 3H).

LC/MS: m/z=797.44 (M+H$^+$).

HPLC (Method A) RT=29.8 min.

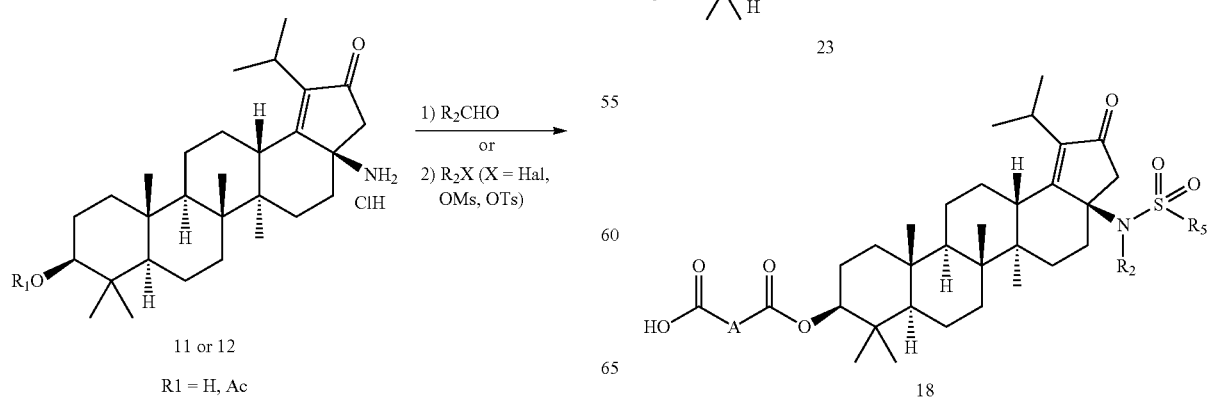

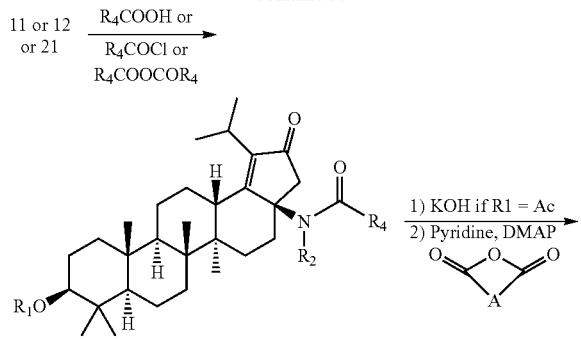

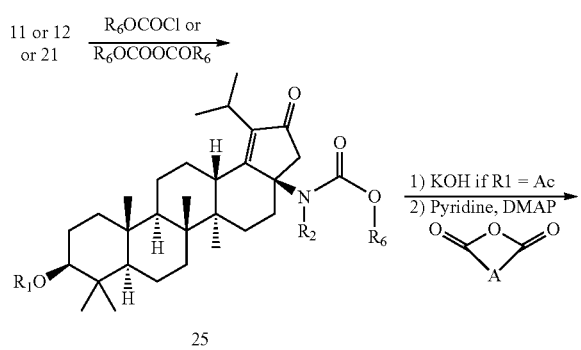

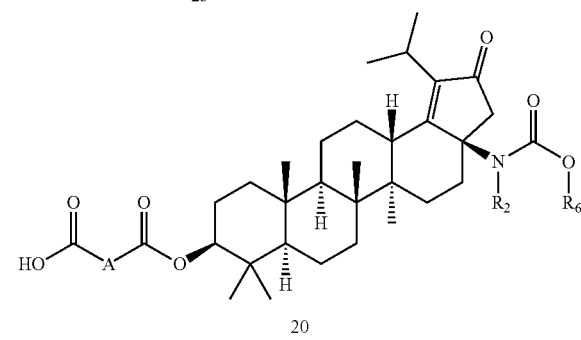

General Procedure for the Preparation of Compound 21:

An alkyl $R_2$ group is introduced to compound 11 or 12 by conventional reductive amination with an aldehyde (see A. F. Abdel-Magid, et al. *J. Org. Chem.* (1996), 61, 3849-3862) or by alkylation with an alkyl halide in presence of a base such as TEA, DIPEA or NaH in a solvent such as THF or DMF to give compound 21.

General Procedure for the Synthesis of Ureas 17

Step 1: A solution of compound 11, 12 or 21 and the appropriate isocyanate or carbamoyl chloride in solvents such as toluene, dichloromethane or chloroform is stirred for 4 to 20 hours at room temperature or under reflux. The residue obtained is purified by flash column chromatography.

If R1=Ac then deprotection occurs in solvents such as methanol, THF or dioxane using an aqueous solution of inorganic base such as sodium hydroxide or potassium hydroxide (10 to 20 eq.) at temperature ranging from 20 to 60° C. to give the alcohol 22 (R1=H).

Step 2: A solution of urea 22 (R1=H), a base such as DMAP, TEA, DABCO or DIPEA and the appropriate anhydride (2 to 10 equivalents) in solvents such as pyridine, TEA or toluene (0.2-1.0 M) is heated from 90 to 120° C. for 4 to 24 hours. The mixture is concentrated, washed with acid and purified by flash column chromatography on silica gel to yield compound 17.

General Procedure for the Synthesis of Sulfonamides 18

Step 1: A solution of compound 11, 12 or 21 and the appropriate sulfonyl chloride in solvents such as THF or DCM and in the presence of a base such as TEA or DIPEA is stirred for 4 to 20 hours at room temperature or under reflux. The residue obtained is purified by flash chromatography on silica gel to afford the desired amide 23, If R1=Ac then deprotection occurs in solvents such as methanol, THF or dioxane using an aqueous solution of inorganic base such as sodium hydroxide or potassium hydroxide (10 to 20 eq.) at temperature ranging from 20 to 60° C. to give the alcohol 23 (R1=H).

Step 2: A solution of sulfonamide 23 (R1=H), a base such as DMAP, TEA, DABCO or DIPEA and the appropriate anhydride (2 to 10 equivalents) in solvents such as pyridine, TEA or toluene (0.2-1.0 M) is heated from 90 to 120° C. for 4 to 24 hours. The mixture is concentrated, washed with acid and purified by flash column chromatography on silica gel to yield compound 18.

General Procedure for the Synthesis of Amides 19

Step 1: A solution of compound 11, 12 or 21 and the appropriate acyl chloride or anhydride in solvents such as THF or DCM and in the presence of a base such as TEA or DIPEA is stirred for 4 to 20 hours at room temperature or under reflux. The residue obtained is purified by flash chromatography on silica gel to afford the desired amide 24.

If R1=Ac then deprotection occurs in solvents such as methanol, THF or dioxane using an aqueous solution of inorganic base such as sodium hydroxide or potassium hydroxide (10 to 20 eq.) at temperature ranging from 20 to 60° C. to give the alcohol 24 (R1=H).

Step 2: A solution of amide 24 (R1=H), a base such as DMAP, TEA, DABCO or DIPEA and the appropriate anhydride (2 to 10 equivalents) in solvents such as pyridine, TEA or toluene (0.2-1.0 M) is heated from 90 to 120° C. for 4 to 24 hours. The mixture is concentrated, washed with acid and purified by flash column chromatography on silica gel to yield compound 19.

General Procedure for the Synthesis of Carbamates 20

Step 1: To a stirring solution of compound 11, 12 or 21 in toluene or benzene is added the desired chloroformate or anhydride (3 equivalents). The resulting mixture is stirred 2 to 4 hours under reflux. After standard acidic workup, the residue obtained is purified by flash chromatography on silica gel to afford the desired carbamate 25.

If R1=Ac then deprotection occurs in solvents such as methanol, THF or dioxane using an aqueous solution of inorganic base such as sodium hydroxide or potassium hydroxide (10 to 20 eq.) at temperature ranging from 20 to 60° C. to give the alcohol 25 (R1=H).

Step 2: A stirring solution of carbamate 25 (R1=H), a base such as DMAP, TEA, DABCO or DIPEA and the appropriate anhydride (2 to 10 equivalents) in solvents such as pyridine, TEA or toluene (0.2-1.0 M) is heated from 90 to 120° C. for 4 to 24 hours. The mixture is concentrated, washed with acid and purified by flash column chromatography on silica gel to yield compound 20.

17β-Benzamido-3β-hydroxy-21-oxolup-18-ene 24-1

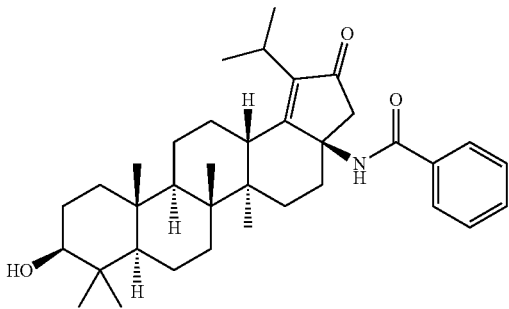

To a stirring suspension of compound 12 (62.7 mg, 0.13 mmol) in THF (1.3 mL) is added TEA (37 μL, 0.28 mmol) and benzoyl chloride (23 μL, 0.20 mmol). The mixture is stirred for 3 hours at room temperature, diluted with ethyl acetate, washed twice with 1N HCl, water and brine, dried over sodium sulfate and concentrated to dryness. The residue is purified by flash column chromatography on silica gel (methanol/DCM 0% to 4%) to give the title compound 24-1 as a white solid (55 mg, 77%).

$^1$H NMR (400 MHz, CDCl$_3$): δ [ppm] 7.73 (m, 2H), 7.50 (m, 1H), 7.43 (m, 2H), 6.13 (s, 1H), 3.19 (m, 2H), 2.90 (m, 1H), 2.87 (d, 1H), 2.40 (m, 1H), 2.35 (d, 1H), 1.94 (m, 2H), 1.80-1.20 (m, 20H), 1.14 (s, 3H), 0.96 (m, 6H), 0.86 (m, 3H), 0.75 (s, 3H), 0.70 (m, 1H).

3β-O-(3',3% Dimethylsuccinyl)-17β-benzamido-21-oxolup-18-ene 19-2

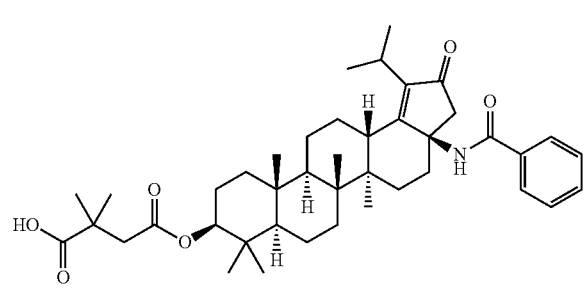

A stirring solution of compound 24-1 (55 mg, 0.10 mmol), DMAP (14.8 mg, 0.12 mmol) and 2,2-dimethylsuccinic anhydride (38.7 mg, 0.30 mmol) in dry pyridine (1.0 mL) is heated at 120° C. for 4 hours. Another 0.30 mmol of 2,2-dimethylsuccinic anhydride is added and heating at 120° C. is continued for 24 hours. The mixture is cooled down to room temperature and concentrated to dryness. The residue is diluted in ethyl acetate, washed twice with HCl 1N, water and brine, dried over sodium sulfate and concentrated to dryness. The residue is purified by flash column chromatography on silica gel (methanol/DCM 0% to 10%) to yield the title compound 19-2 as a white solid (48 mg, 71%).

$^1$H NMR (400 MHz, CDCl$_3$): δ [ppm] 7.71 (m, 2H), 7.50 (m, 1H), 7.42 (m, 2H), 6.11 (s, 1H), 4.48 (d×d, 1H), 3.17 (m, 1H), 2.90 (d, 1H), 2.83 (d, 1H), 2.66 (d, 1H), 2.55 (d, 1H), 2.41 (d, 1H), 2.36 (d, 1H), 1.95 (m, 3H), 1.76-1.16 (m, 26H), 1.13 (s, 3H), 0.97 (s, 3H), 0.87 (s, 3H), 0.83 (s, 3H), 0.79 (s, 3H).

LC/MS: m/z=674.70 (M+H*).

17β-(pyridin-2-yl)amido-3β-hydroxy-21-oxolup-18-ene 24-2

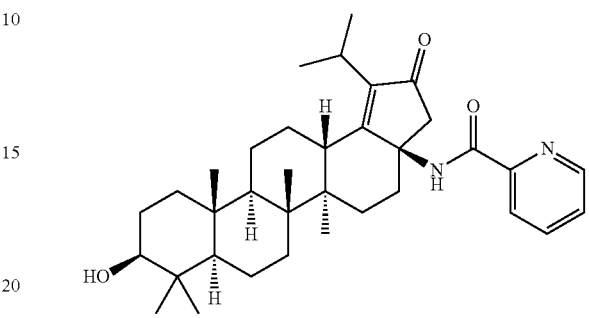

To a stirring suspension of compound 12 (107.7 mg, 0.22 mmol) and picolinic acid (41.3 mg, 0.34 mmol) in DMF (2.2 mL) is added TEA (71 μL, 0.56 mmol) and HATU (127.6 mg, 0.34 mmol). The mixture is stirred for 2 hours at room temperature. Water is added slowly and the precipitate formed is collected by filtration to give the title compound 24-2 as an off-white solid (120 mg).

$^1$H NMR (400 MHz, CDCl$_3$): δ [ppm] 8.54 (m, 1H), 8.33 (br s, 1H), 8.13 (m, 1H), 7.83 (t×d, 1H), 7.43 (d×d, 1H), 3.19 (m, 2H), 2.86 (t, 2H), 2.47 (m, 1H), 2.37 (d, 1H), 1.96 (m, 3H), 1.76-1.16 (m, 18H), 1.04-0.86 (m, 10H), 0.83 (s, 3H), 0.78-0.66 (m, 4H).

3β-O-(3',3'-Dimethylsuccinyl)-17β-(Pyridin-2-yl)amido-21-oxolup-18-ene hydrochloride 19-15

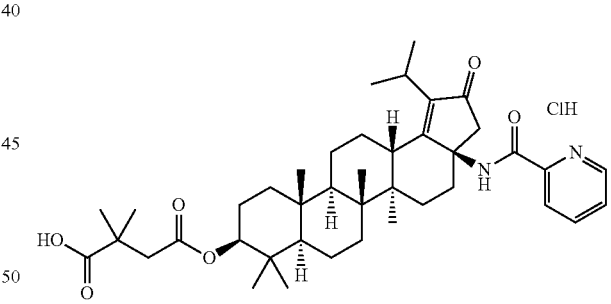

A stirring solution of compound 24-2 (113 mg, 0.21 mmol), DMAP (30.3 mg, 0.25 mmol) and 2,2-dimethylsuccinic anhydride (105.9 mg, 0.83 mmol) in dry pyridine (2.0 mL) is heated at 130° C. for 4 hours. Another 0.42 mmol of 2,2-dimethylsuccinic anhydride is added and heating at 130° C. is continued for 24 hours. The mixture is cooled down to room temperature and concentrated to dryness. The residue is diluted in ethyl acetate, washed twice with HCl 1N, water and brine, dried over sodium sulfate and concentrated to dryness. The residue is purified by flash column chromatography on silica gel (methanol/DCM 0% to 10%) to yield the title compound 19-15 as a pale yellow solid (137.6 mg).

$^1$H NMR (400 MHz, CDCl$_3$): δ [ppm] 8.52 (m, 1H), 8.32 (br s, 1H), 8.12 (m, 1H), 7.82 (t×d, 1H), 7.42 (d×d, 1H), 4.46 (d×d, 1H), 3.17 (m, 1H), 2.85 (m, 2H), 2.60 (q, 2H), 2.47 (m, 1H), 2.37 (d, 1H), 1.96 (m, 3H), 1.74-1.16 (m, 24H), 1.02-0.98 (m, 4H), 0.95 (s, 3H), 0.84-0.72 (m, 10H).

LC/MS: m/z=675.7 (M+H⁺).

Ureas 17 and carbamates 20 can also be prepared from the isocyanate 8 as described in scheme 9.

dride (2 to 10 equivalents) in solvents such as pyridine, TEA or toluene (0.2-1.0 M) is heated from 90 to 120° C. for 10 to 24 hours. The mixture is concentrated, washed with acid and purified by flash column chromatography on silica gel to yield compound 17.

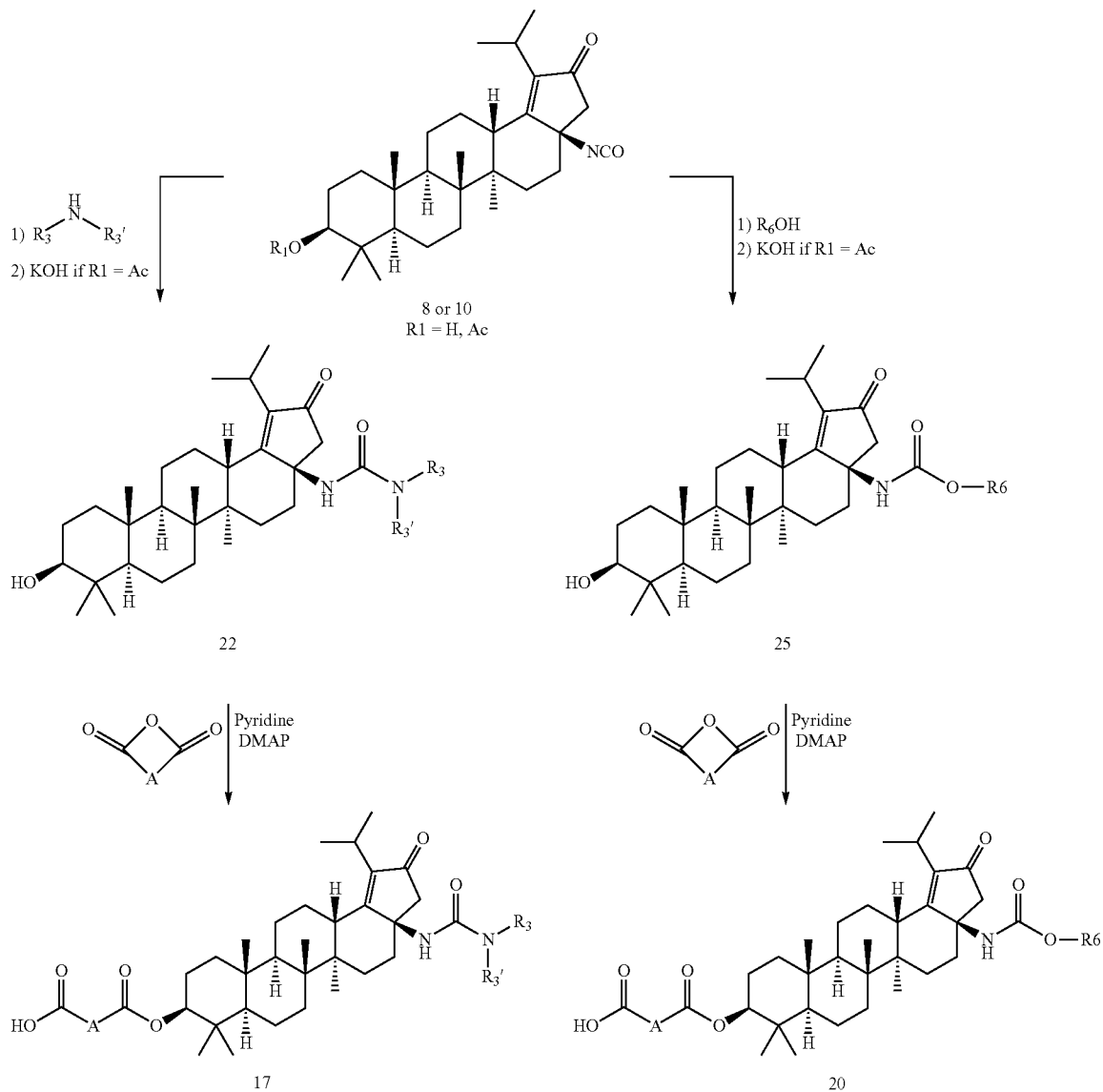

Scheme 9

General Procedure for the Synthesis of Ureas 17

Step 1: A solution of isocyanate 8 or 10 and the desired amine R₃'R₃NH in solvents such as benzene, toluene or chloroform is stirred for 4 to 20 hours at room temperature or under reflux. The residue obtained is purified by flash chromatography on silica gel to afford the desired urea intermediate 22.

If R1=Ac then deprotection occurs in solvents such as methanol, THF or dioxane using an aqueous solution of inorganic base such as sodium hydroxide or potassium hydroxide (10 to 20 eq.) at temperature ranging from 20 to 60° C. to give the alcohol 22 (R1=H).

Step 2: A solution of urea 22 (R1=H), a base such as DMAP, TEA, DABCO or DIPEA and the appropriate anhy- General Procedure for the Synthesis of Carbamates 20

Step 1: To a stirring solution of isocyanate 8 or 10 in toluene or benzene is added the desired alcohol (3 to 10 equivalents) and a catalyst such as titanium (IV) tea-butoxide: The resulting mixture is stirred 2 to 4 hours at room temperature. After standard workup, the residue obtained is purified by flash chromatography on silica gel to afford the desired carbamate intermediate 25.

If R1=Ac then deprotection occurs in solvents such as methanol, THF or dioxane using an aqueous solution of inorganic base such as sodium hydroxide or potassium hydroxide (10 to 20 eq.) at temperature ranging from 20 to 60° C. to give the alcohol 25 (R1=H).

Step 2: A stirring solution of carbamate 25 (R1=H), a base such as DMAP, TEA, DABCO or DIPEA and the appropriate anhydride (2 to 10 equivalents) in solvents such as pyridine, TEA or toluene (0.2-1.0 M) is heated from 90 to 120° C. for 10 to 24 hours. The mixture is concentrated, washed with acid and purified by flash column chromatography on silica gel to yield compound 20.

17β-(isopropylcarbonylamino)-3β-hydroxy-21-oxo-lup-18-ene 25-1

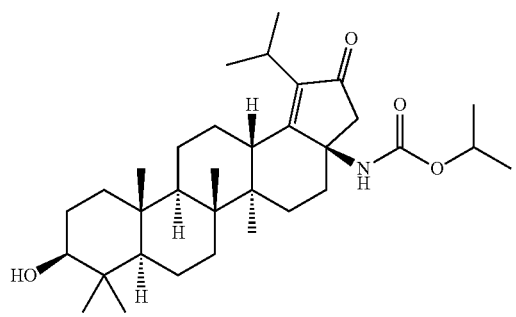

Step 1: To a stirring solution of compound 10 (300 mg, 0.59 mmol) in toluene (3 mL) is added isopropanol (68 μL, 0.88 mmol) and titanium (IV) tert-butoxide (23 μL, 0.06 mmol). The mixture is stirred for 1 hour at room temperature. A saturated solution of ammonium chloride and ethyl acetate are added and the organic layer is dried over sodium sulfate and concentrated to dryness. The residue is purified by flash column chromatography on silica gel (ethyl acetate/hexanes 0% to 50%) to yield the 17β-(isopropylcarbonylamino)-3β-acetoxy-21-oxolup-18-ene as white foam (349 mg).

$^1$H NMR (400 MHz, CDCl$_3$): δ [ppm] 4.85 (m, 1H), 4.73 (br s, 1H) 4.45 (dxd, 1H), 3.12 (m, 1H), 2.83 (m, 1H), 2.59 (m, 1H), 2.23 (d, 1H), 2.02 (s, 3H), 1.88 (m, 3H), 1.78-1.13 (m, 25H), 1.11 (s, 3H), 1.03 (m, 1H), 0.91 (s, 3H), 0.90 (s, 3H), 0.83 (s, 3H), 0.82 (s, 3H), 0.79 (m, 1H).

Step 2: To a solution of 17β-(isopropylcarbonylamino)-3β-acetoxy-21-oxolup-18-ene (349 mg, 0.6 mmol) in 2 mL of methanol and 6 mL of THF is added an aqueous 4N solution of potassium hydroxide (1.5 mL, 6 mmol). The reaction mixture is stirred for 24 hours at room temperature, acidified with 4N HCl and extracted with ethyl acetate. The organic layer is dried over sodium sulfate and concentrated to dryness to yield the title compound 25-1 (330 mg).

$^1$H NMR (400 MHz, CDCl$_3$): δ [ppm] 4.80 (br s, 1H), 4.65 (br s, 1H) 3.15 (dxd, 1H), 3.05 (m, 1H), 2.80 (m, 1H), 2.55 (m, 1H), 2.20 (d, 1H), 1.85 (m, 4H), 1.60-1.08 (m, 27H), 1.06 (s, 3H), 0.94 (m, 1H), 0.91 (s, 3H), 0.88 (s, 3H), 0.83 (s, 3H), 0.70 (s, 3H), 0.65 (m, 1H).

3β-O-(3',3'-Dimethylsuccinyl)-17β-(isopropylcarbonylamino)-21-oxolup-18-ene 20-2

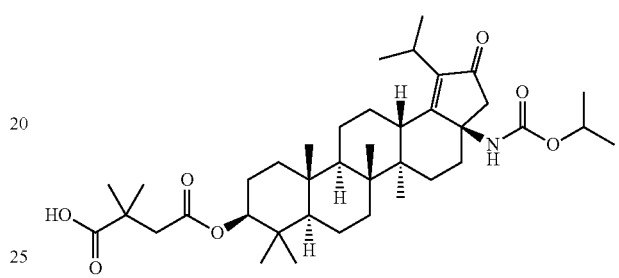

A stirring solution of compound 25-1 (327 mg, 0.6 mmol), DMAP (91 mg, 0.74 mmol) and 2,2-dimethylsuccinic anhydride (476 mg, 3.7 mmol) in dry pyridine (6.0 mL) is heated at 130° C. for 24 hours. The mixture is cooled down to room temperature and concentrated to dryness. The residue is diluted in ethyl acetate, washed twice with HCl 1N, water and brine, dried over sodium sulfate and concentrated to dryness. The residue is purified by flash column chromatography on silica gel (methanol/DCM 0% to 10%) and crystallized in water/methanol to yield the title compound 20-2 as a white solid (286 mg).

$^1$H NMR (400 MHz, CDCl$_3$): δ [ppm] 4.87 (br s, 1H), 4.70 (br s, 1H), 4.48 (dxd, 1H), 3.12 (m, 1H), 2.83 (m, 1H), 2.60 (m, 3H), 2.25 (m, 1H), 1.89 (m, 3H), 1.76-0.94 (m, 39H), 0.92 (s, 3H), 0.89 (s, 3H), 0.85-0.75 (m, 7H).

LC/MS: m/z=656.7 (M+H$^+$).

Table 1 illustrates some intermediates which are synthesized using the procedures described herein.

| Cpd# | Structure | Name | Analytical data |
|---|---|---|---|
| 11 | ![structure] | 3β-O-acetyl-17β-amino-21-oxolup-18-ene hydrochloride | LC/MS (M$^+$/M + H$^+$): 485.56 |

-continued

| Cpd# | Structure | Name | Analytical data |
|---|---|---|---|
| 12 | 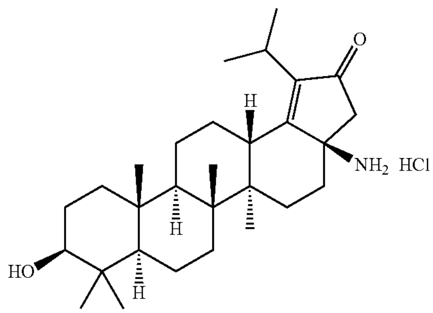 | 3β-hydroxy-17β-amino-21-oxolup-18-ene hydrochloride | LC/MS (M$^+$/M + H$^+$): 442.56 |
| 22-1 | 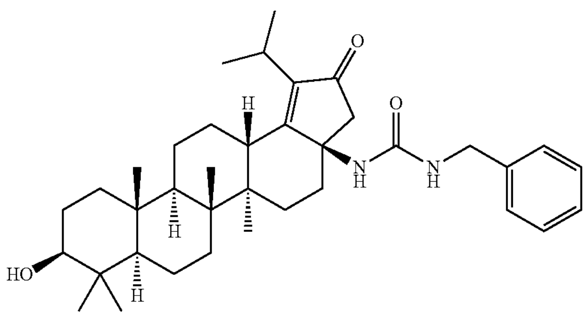 | 3β-hydroxy-17β-[N'-(benzyl)ureido]-21-oxolup-18-ene | LC/MS (M$^+$/M + H$^+$): 575.66 |
| 22-2 | 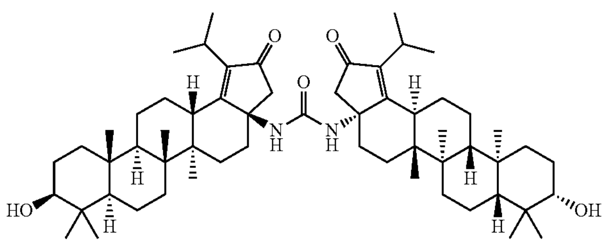 | 3β-hydroxy-17β-[N'-3β-hydroxy-oxolup-18-ene 17β-ureido]-21-oxolup-18-ene | LC/MS (M$^+$/M + H$^+$): 911.39 |
| 24-1 | 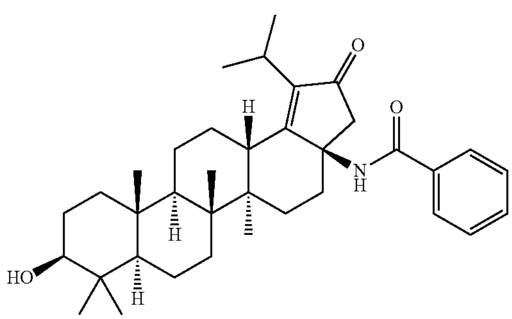 | 3β-hydroxy-17β-benzamido-21-oxolup-18-ene | $^1$H NMR (400 MHz, CDCl$_3$): δ [ppm] 7.73 (m, 2H), 7.50 (m, 1H), 7.43 (m, 2H), 6.13 (s, 1H), 3.19 (m, 2H), 2.90 (m, 1H), 2.87 (d, 1H), 2.40 (m, 1H), 2.35 (d, 1H), 1.94 (m, 2H), 1.80-1.20 (m, 20H), 1.14 (s, 3H), 0.96 (m, 6H), 0.86 (m, 3H), 0.75 (s, 3H), 0.70 (m, 1H). |
| 24-2 | 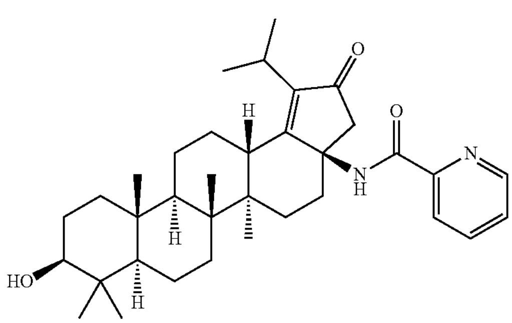 | 3β-hydroxy-17β-(pyridin-2-yl)amido-21-oxolup-18-ene | $^1$H NMR (400 MHz, CDCl$_3$): δ [ppm] 8.54 (m, 1H), 8.33(br s, 1H), 8.12 (m, 1H), 7.83 (m, 1H), 7.43 (m, 1H), 3.19 (m, 2H), 2.86 (m, 2H), 2.47 (m, 1H), 2.38 (d, 1H), 1.96 (m, 3H), 1.78-0.64 (m, 14H), 1.25 (d, 3H), 1.23 (d, 3H), 1.03 (s, 3H), 0.97 (s, 3H), 0.95 (s, 3H), 0.83 (s, 3H), 0.73 (s, 3H). |

| Cpd# | Structure | Name | Analytical data |
|---|---|---|---|
| 24-3 | 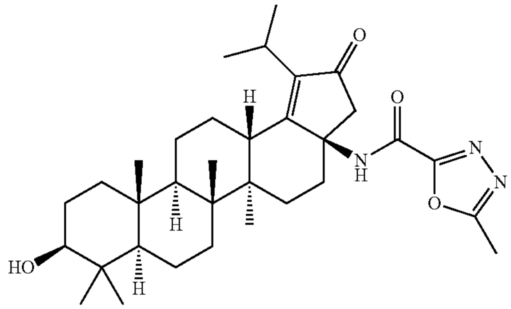 | 3β-hydroxy-17β-(5-methyl-[1,3,4]oxadiazole-2-amido)-21-oxolup-18-ene | HPLC: 24.98 Method (E) LC/MS (M$^+$/M + H$^+$): 552.34 |
| 24-4 | 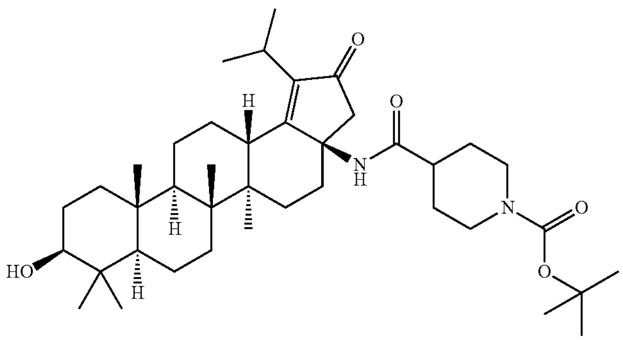 | 3β-hydroxy-17β-(1-tert-butyloxycarbonyl-piperidine-4-amido)-21-oxolup-18-ene | LC/MS (M$^+$/M + H$^+$): 553.61 (—Boc) |
| 24-5 | 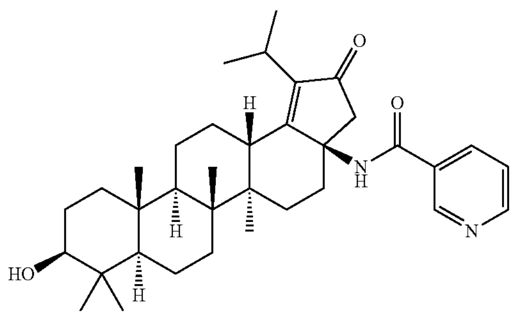 | 3β-hydroxy-17β-(pyridin-3-yl)amido-21-oxolup-18-ene | LC/MS (M$^+$/M + H$^+$): 547.50 |
| 26-6 | 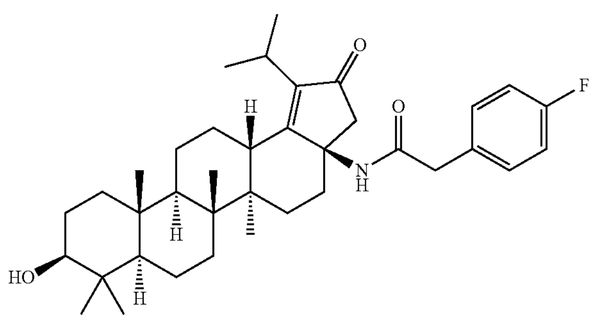 | 3β-hydroxy-17β-(4-fluorobenzyl)amido-21-oxolup-18-ene | LC/MS (M$^+$/M + H$^+$): 578.50 |
| 24-7 | 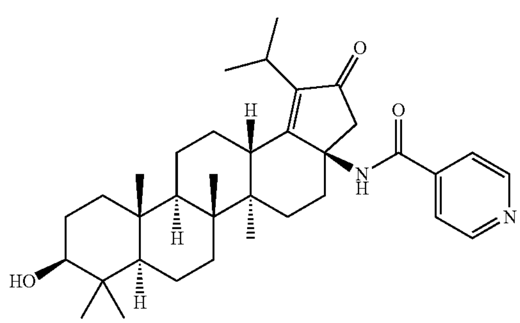 | 3β-hydroxy-17β-(pyridin-4-yl)amido-21-oxolup-18-ene | $^1$H NMR (400 MHz, CDCl$_3$): δ [ppm] 8.74 (m, 2H), 7.55 (m, 2H), 6.21 (br s, 1H), 3.18 (m, 2H), 2.86 (m, 2H), 2.40 (m, 2H), 1.94 (m, 3H), 1.79-0.68 (m, 14H), 1.23 (d, 3H), 1.21 (d, 3H), 1.13 (s, 3H), 0.98 (s, 3H), 0.96 (s, 3H), 0.86 (s, 3H), 0.75 (s, 3H). |

| Cpd# | Structure | Name | Analytical data |
|---|---|---|---|
| 24-8 | 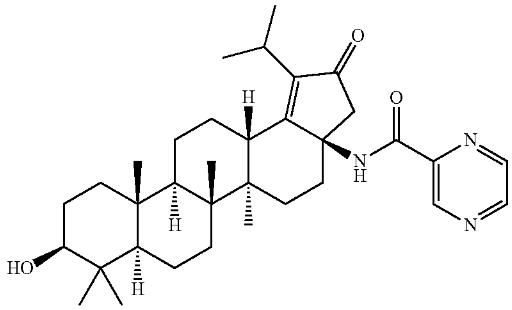 | 3β-hydroxy-17β-(pyrazin-2-yl)amido-21-oxolup-18-ene | ¹H NMR (400 MHz, CDCl₃): δ [ppm] 9.35 (d, 1H), 8.75 (d, 1H), 7.52 (d × d, 1H), 3.18 (m, 2H), 2.83 (m, 2H), 2.46 (m, 1H), 2.38 (d, 1H), 1.94 (m, 3H), 1.78-0.68 (m, 14H), 1.25 (d, 3H), 1.23 (d, 3H), 1.02 (s, 3H), 0.98 (s, 3H), 0.95 (s, 3H), 0.83 (s, 3H), 0.74 (s, 3H). |
| 24-9 | 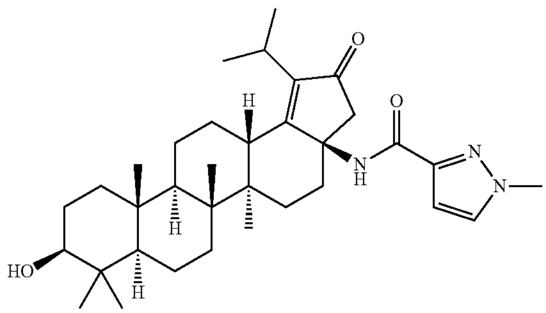 | 3β-hydroxy-17β-(1-methyl-1H-pyrazole-3-amido)-21-oxolup-18-ene | ¹H NMR (400 MHz, CDCl₃): δ [ppm] 7.33(br s, 1H), 6.95 (br s, 1H), 6.73 (br s, 1H), 3.90 (s, 3H), 3.16 (m, 3H), 2.83 (m, 2H), 2.38 (m, 2H), 1.94 (m, 3H), 1.78-0.66 (m, 13H), 1.23 (d, 3H), 1.21 (d, 3H), 1.06 (s, 3H), 0.95 (s, 6H), 0.84 (s, 3H), 0.74 (s, 3H). |
| 24-10 | 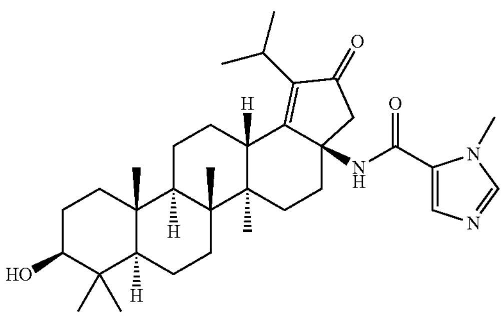 | 3β-hydroxy-17β-(1-methyl-1H-imidazole-5-amido)-21-oxolup-18-ene | ¹H NMR (400 MHz, CDCl₃): δ [ppm] 7.48 (br s, 1H), 7.41 (br s, 1H), 5.92 (br s, 1H), 3.85 (s, 3H), 3.17 (m, 2H), 2.83 (m, 2H), 2.38 (m, 2H), 1.92 (m, 3H), 1.78-0.68 (m, 14H), 1.22 (d, 3H), 1.21 (d, 3H), 1.12 (s, 3H), 0.95 (s, 6H), 0.86 (s, 3H), 0.75 (s, 3H). |
| 24-11 | 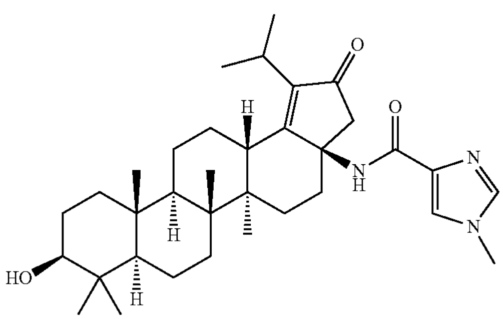 | 3β-hydroxy-17β-(1-methyl-1H-imidazole-4-amido)-21-oxolup-18-ene hydrochlorine | ¹H NMR (400 MHz, CDCl₃): δ [ppm] 7.45 (br s, 1H), 7.33 (br s, 1H), 7.18 (br s, 1H), 3.70 (s, 3H), 3.16 (m, 2H), 2.83 (m, 2H), 2.38 (m, 2H), 1.93 (m, 3H), 1.78-0.68 (m, 14H), 1.22 (br s, 6H), 1.04 (s, 3H), 0.94 (s, 6H), 0.82 (s, 3H), 0.73 (s, 3H). |
| 24-12 | 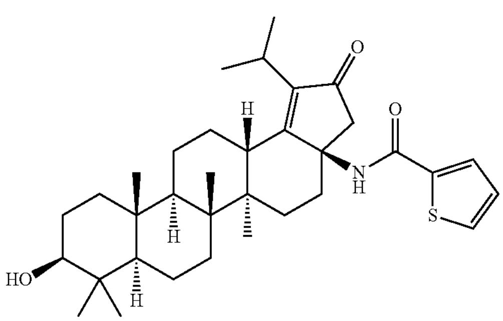 | 3β-hydroxy-17β-(2-thiophene)amido-21-oxolup-18-ene | ¹H NMR (400 MHz, CDCl₃): δ [ppm] 7.48 (m, 1H), 7.46 (m, 1H), 7.06 (d × d, 1H), 5.97 (br s, 1H), 3.17 (m, 2H), 2.85 (m, 2H), 2.36 (m, 2H), 1.95 (m, 3H), 1.78-0.67 (m, 14H), 1.23 (s, 3H), 1.21 (s, 3H), 1.11 (s, 3H), 0.96 (s, 3H), 0.95 (s, 3H), 0.85 (s, 3H), 0.74 (s, 3H). |

-continued

| Cpd# | Structure | Name | Analytical data |
|---|---|---|---|
| 24-13 | 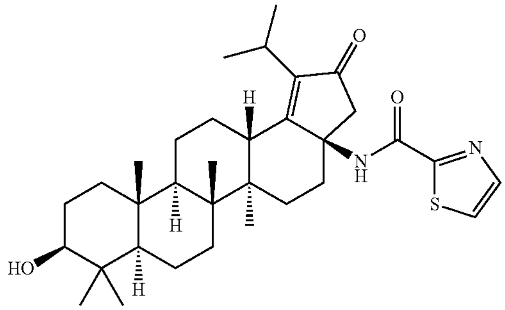 | 3β-hydroxy-17β-(1,3-thiazole-2-amido)-21-oxolup-18-ene | $^1$H NMR (400 MHz, CDCl$_3$): δ [ppm] 7.84 (d, 1H), 7.56 (d, 1H), 7.41 (br s, 1H), 3.17 (m, 2H), 2.85 (m, 2H), 2.40 (m, 2H), 1.95 (m, 3H), 1.80-0.67 (m, 14H), 1.23 (s, 3H), 1.21 (s, 3H), 1.12 (s, 3H), 0.98 (s, 3H), 0.94 (s, 3H), 0.83 (s, 3H), 0.73 (s, 3H). |
| 24-14 | 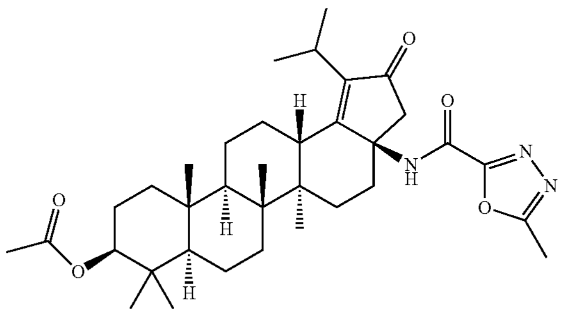 | 3β-O-acetyl-17β-(5-methyl-[1,3,4]oxadiazole-2-amido)-21-oxolup-18-ene | HPLC: 39.41 Method (E) LC/MS (M$^+$/M+H$^+$): 594.33 |
| 24-15 | 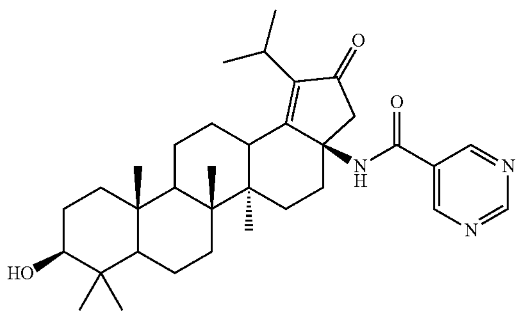 | 3β-hydroxy-17β-(pyrimidine-5-amido)-21-oxolup-18-ene | $^1$H NMR (400 MHz, CDCl$_3$): δ [ppm] 9.33 (s, 1H), 9.06 (S, 2H), 6.13 (br s, 1H), 3.17 (m, 2H), 2.80 (m, 2H), 2.41 (m, 2H), 1.95 (m, 2H), 1.78-0.66 (m, 15H), 1.23 (s, 3H), 1.21 (s, 3H), 1.05 (s, 3H), 0.98 (s, 3H), 0.96 (s, 3H), 0.86 (s, 3H), 0.75 (s, 3H). |
| 24-16 | 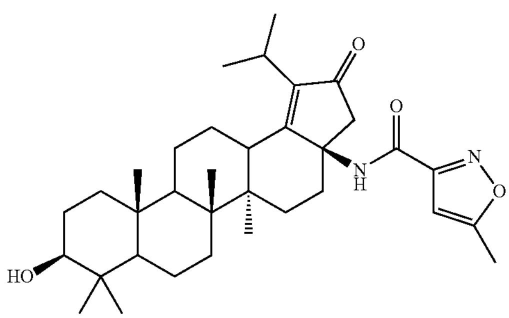 | 3β-hydroxy-17β-(5-methylisoxazole-3-amido)-21-oxolup-18-ene | $^1$H NMR (400 MHz, CDCl$_3$): δ [ppm] 6.86 (br s, 1H), 6.38 (d, 1H), 3.17 (m, 2H), 2.81 (m, 2H), 2.46 (s, 3H), 2.38 (m, 2H), 1.92 (m, 2H), 1.78-0.66 (m, 14H), 1.23 (s, 3H), 1.20 (s, 3H), 1.07 (s, 3H), 0.95 (s, 6H), 0.84 (s, 3H), 0.74 (s, 3H). |
| 24-17 | 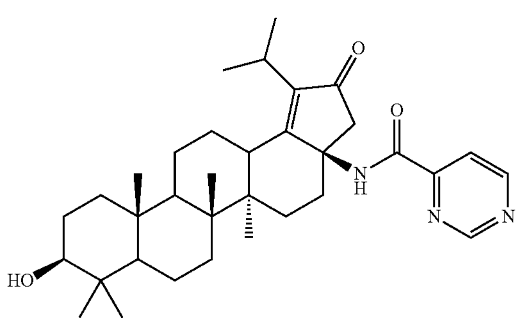 | 3β-hydroxy-17β-(pyrimidine-4-amido)-21-oxolup-18-ene | $^1$H NMR (400 MHz, CDCl$_3$): δ [ppm] 9.24 (d, 1H), 8.96 (d, 1H), 8.22 (br s, 1H), 8.05 (d × d, 1H), 3.18 (m, 2H), 2.83 (m, 2H), 2.41(m, 2H), 1.95 (m, 2H), 1.80-0.66 (m, 15H), 1.24 (s, 3H), 1.22 (s, 3H), 1.03 (s, 3H), 0.97 (s, 3H), 0.95 (s, 3H), 0.83 (s, 3H), 0.74 (s, 3H). |

| Cpd# | Structure | Name | Analytical data |
|---|---|---|---|
| 24-18 | 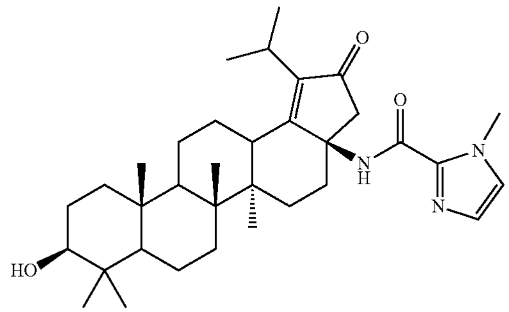 | 3β-hydroxy-17β-(1-methyl-1H-imidazole-2-amido)-21-oxolup-18-ene | $^1$H NMR (400 MHz, CDCl$_3$): δ [ppm] 7.53 (br s, 1H), 6.96 (d, 1H), 6.93 (d, 1H), 4.00 (s, 3H), 3.16 (m, 2H), 2.89 (m, 1H), 2.80 (d, 1H), 2.53 (m, 1H), 2.38 (d, 1H), 1.94 (m, 3H), 1.78-0.68 (m, 14H), 1.22 (d, 3H), 1.20 (d, 3H), 1.09 (s, 3H), 0.95 (s, 6H), 0.85 (s, 3H), 0.74 (s, 3H). |
| 24-19 | 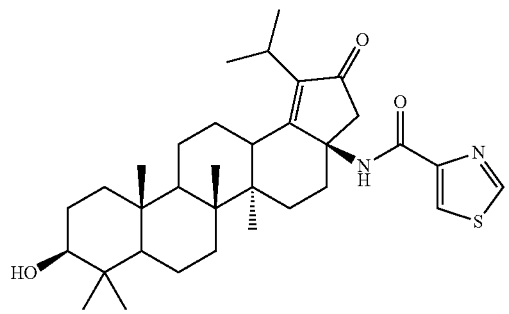 | 3β-hydroxy-17β-(1,3-thiazole-4-amido)-21-oxolup-18-ene | $^1$H NMR (400 MHz, CDCl$_3$): δ [ppm] 8.73 (d, 1H), 8.11 (d, 1H), 7.56 (br s, 1H), 3.17 (m, 2H), 2.83 (m, 2H), 2.39 (m, 2H), 1.95 (m, 3H), 1.79-0.66 (m, 14H), 1.24 (s, 3H), 1.22 (s, 3H), 1.04 (s, 3H), 0.96 (s, 3H), 0.95 (s, 3H), 0.83 (s, 3H), 0.74 (s, 3H). |
| 24-20 | 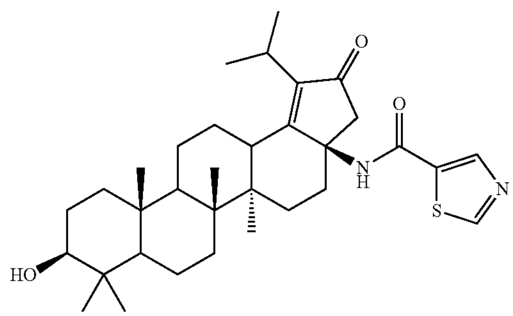 | 3β-hydroxy-17β-(1,3-thiazole-5-amido)-21-oxolup-18-ene | $^1$H NMR (400 MHz, CDCl$_3$): δ [ppm] 8.87 (s, 1H), 8.21 (s, 1H), 6.04 (br s, 1H), 3.17 (m, 2H), 2.83 (m, 2H), 2.38 (m, 2H), 1.95 (m, 3H), 1.79-0.66 (m, 14H), 1.23 (s, 3H), 1.21 (s, 3H), 1.10 (s, 3H), 0.97 (s, 3H), 0.95 (s, 3H), 0.85 (s, 3H), 0.74 (s, 3H). |
| 24-21 | 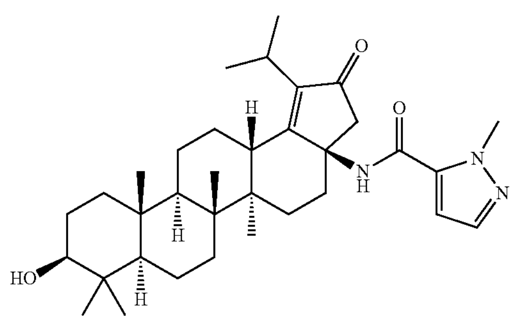 | 3β-hydroxy-17β-(1-methyl-1H-pyrazole-5-amido)-21-oxolup-18-ene | $^1$H NMR (400 MHz, CDCl$_3$): δ [ppm] 7.43 (d, 1H), 6.46 (d, 1H), 5.97 (br s, 1H), 4.10 (s, 3H), 3.18 (m, 3H), 2.83 (m, 2H), 2.38 (m, 2H), 1.94 (m, 3H), 1.78-0.66 (m, 14H), 1.23 (d, 3H), 1.21 (d, 3H), 1.13 (s, 3H), 0.96 (s, 3H), 0.95 (s, 3H), 0.87 (s, 3H), 0.75 (s, 3H). |
| 24-22 | 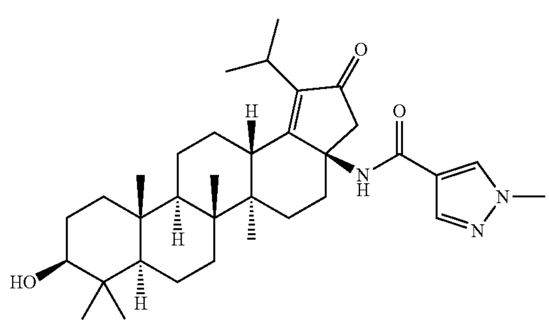 | 3β-hydroxy-17β-(1-methyl-1H-pyrazole-4-amido)-21-oxolup-18-ene | $^1$H NMR (400 MHz, CDCl$_3$): δ [ppm] 7.78 (s, 1H), 7.66 (d, 1H), 5.73 (br s, 1H), 3.90 (s, 3H), 3.17 (m, 2H), 2.83 (m, 2H), 2.34 (m, 2H), 1.93 (m, 3H), 1.78-0.66 (m, 14H), 1.23 (d, 3H), 1.21 (d, 3H), 1.07 (s, 3H), 0.95 (s, 6H), 0.84 (s, 3H), 0.74 (s, 3H) |

-continued

| Cpd# | Structure | Name | Analytical data |
|---|---|---|---|
| 24-23 | 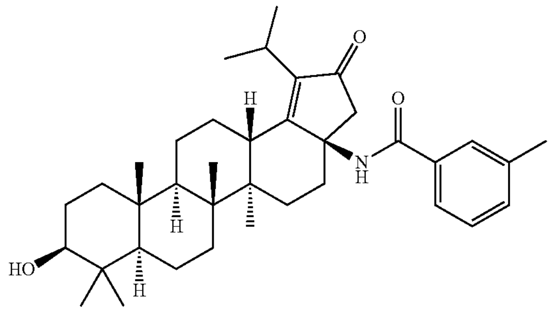 | 3β-hydroxy-17β-(3-methylbenzamido)-21-oxolup-18-ene | HPLC: 36.91 Method (E) LC/MS (M+/M + H+): 560.32 |
| 24-24 | 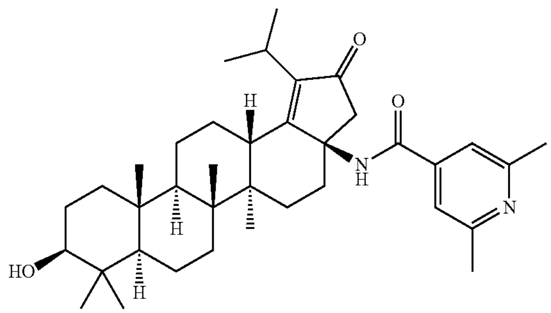 | 3β-hydroxy-17β-(2,6-dimethylpyridin-4-yl)amido-21-oxolup-18-ene | HPLC: 16.51 Method (C) LC/MS (M+/M + H+): 575.49 |
| 24-25 | 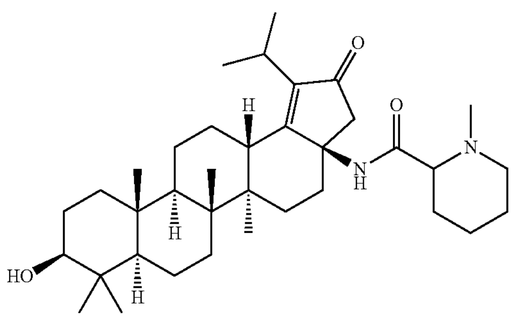 | 3β-hydroxy-17β-((RS)1-methylpiperidine-2-amido)-21-oxolup-18-ene | HPLC: 21.51; 22.02(1:1) Method (D) LC/MS (M+/M + H+): 567.51 |
| 24-26 | 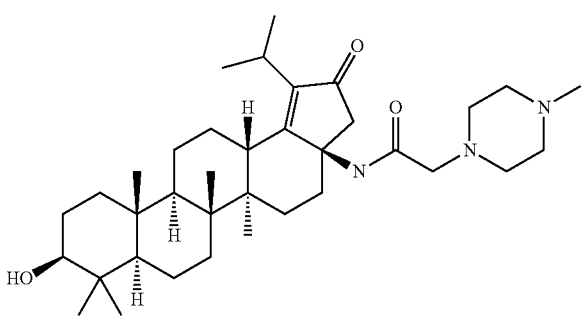 | 3β-hydroxy-17β-[2-(4-methylpiperazin-1-yl)-acetamido]-21-oxolup-18-ene | $^1$H NMR (400 MHz, CDCl$_3$): δ [ppm] 7.21 (s, 1H), 3.18 (m, 2H), 2.93 (d, 2H), 2.70 (m, 2H), 2.60 (m, 4H), 2.45 (m, 3H), 2.30 (s, 3H), 2.25 (m, 2H), 2.00-0.68 (m, 18H), 1.21 (d, 3H), 1.20 (d, 3H), 1.05 (s, 3H), 0.96 (s, 3H), 0.93 (s, 3H), 0.87 (s, 3H), 0.75 (s, 3H). |
| 24-27 | 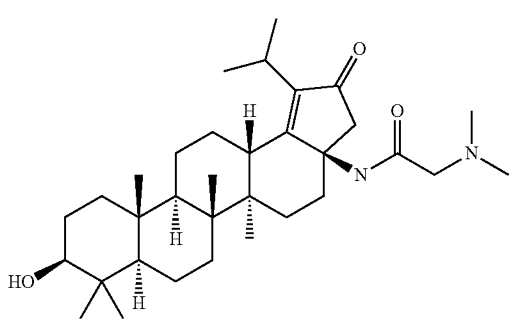 | 3β-hydroxy-17β-(2-dimethylamino-acetamido)-21-oxolup-18-ene | $^1$H NMR (400 MHz, CDCl$_3$): δ [ppm] 7.24 (s, 1H), 3,18 (m, 2H), 2.88 (d, 2H), 2.78 (m, 1H), 2.70 (d, 1H), 2.35 (m, 2H), 2.31 (s, 6H), 2.00-0.68 (m, 17H), 1.21 (d, 3H), 1.20 (d, 3H), 1.09 (s, 3H), 0.96 (s, 3H), 0.93 (s, 3H), 0.87 (s, 3H), 0.75 (s, 3H). |

| Cpd# | Structure | Name | Analytical data |
|---|---|---|---|
| 24-28 | 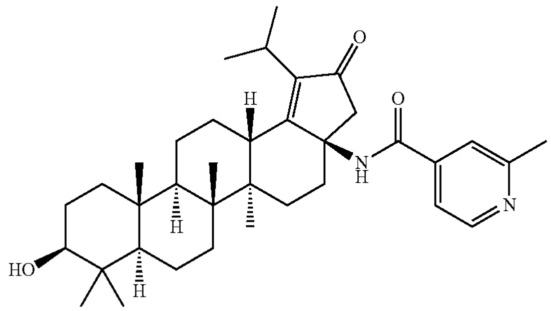 | 3β-hydroxy-17β-(2-methylpyridin-4-yl)amido-21-oxolup-18-ene | HPLC: 20.69 Method (C) LC/MS (M+/M + H+): 561.44 |
| 24-29 | 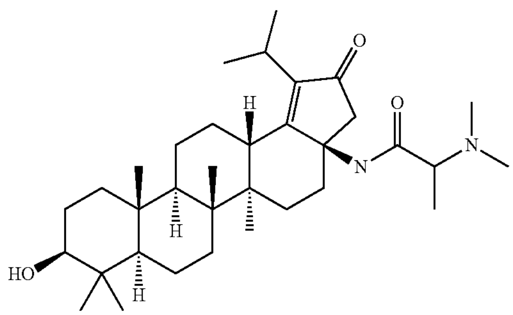 | 3β-hydroxy-17β-((RS)2-dimethylamino-propionamido)-21-oxolup-18-ene | HPLC: 11.19; 11.54 Method (C) LC/MS (M+/M + H+): 541.40 |
| 24-30 | 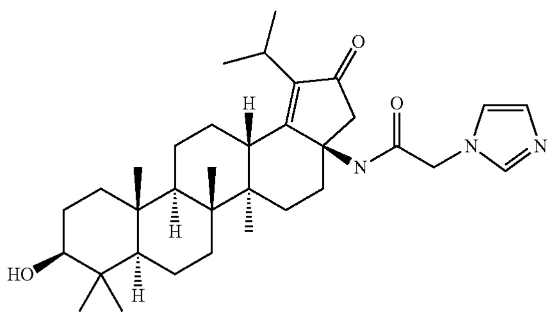 | 3β-hydroxy-17β-(2-imidazol-1-yl-acetamido)-21-oxolup-18-ene | HPLC: 11.44 Method (C) LC/MS (M+/M + H+): 550.39 |
| 24-31 | 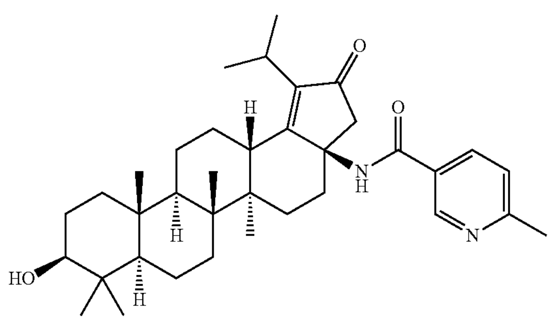 | 3β-hydroxy-17β-(6-methylpyridin-3-yl)amido-21-oxolup-18-ene | HPLC: 13.96 Method (E) LC/MS (M+/M + H+): 561.32 |
| 24-32 | 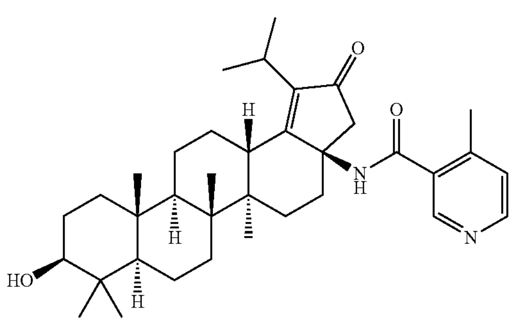 | 3β-hydroxy-17β-(4-methylpyridin-3-yl)amido-21-oxolup-18-ene | HPLC: 12.53 Method (E) LC/MS (M+/M + H+): 561.32 |

-continued

| Cpd# | Structure | Name | Analytical data |
|---|---|---|---|
| 24-33 | 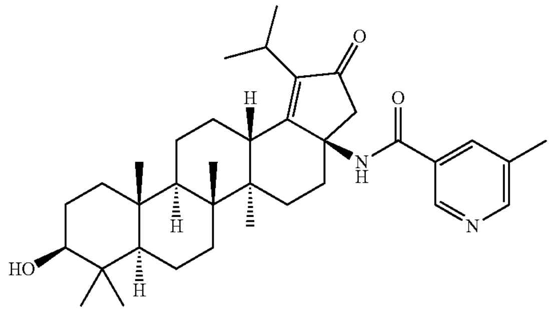 | 3β-hydroxy-17β-(5-methylpyridin-3-yl)amido-21-oxolup-18-ene | HPLC: 17.94 Method (E) LC/MS (M⁺/M + H⁺): 561.31 |
| 24-34 | 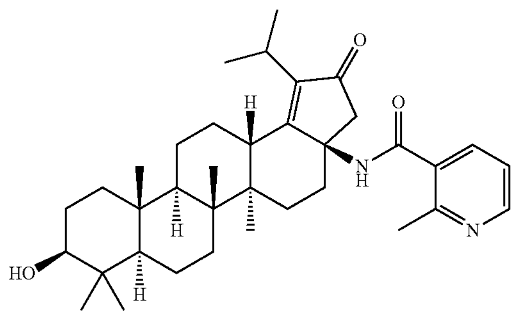 | 3β-hydroxy-17β-(2-methylpyridin-3-yl)amido-21-oxolup-18-ene | HPLC: 10.57 Method (E) LC/MS (M⁺/M + H⁺): 561.31 |
| 24-35 | 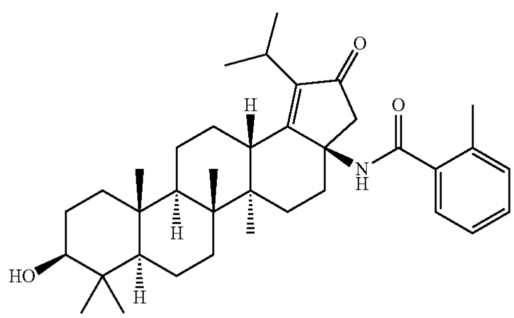 | 3β-hydroxy-17β-(2-methylbenzamido)21-oxolup-18-ene | HPLC: 35.40 Method (E) LC/MS (M⁺/M + H⁺): 560.30 |
| 24-36 | 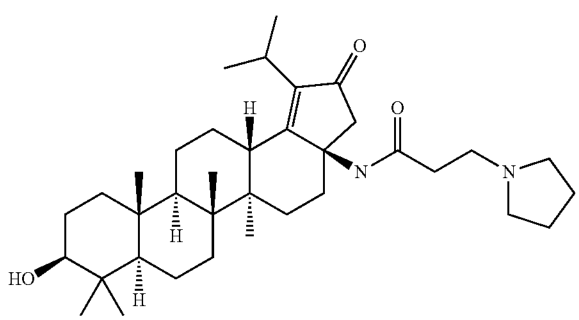 | 3β-hydroxy-17β-(3-pyrrolidin-1-yl-propionamido)-21-oxolup-18-ene | $^1$H NMR (400 MHz, CDCl$_3$): δ [ppm] 9.30 (br s, 1H), 3.18 (d × d, 1H), 3.12 (m, 1H), 2.73 (m, 3H), 2.55 (m, 3H), 2.32 (m, 3H), 2.28 (m, 4H), 2.05 (s, 3H), 1.94-0.66 (m, 24H), 1.20 (d, 3H), 1.17 (d, 3H), 1.10 (s, 3H), 0.96 (s, 3H), 0.91 (s, 3H), 0.87 (s, 3H), 0.75 (s, 3H). |
| 24-37 | 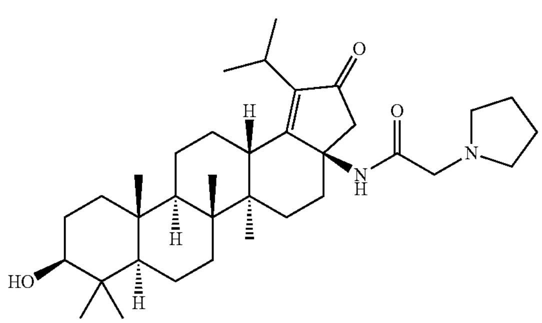 | 3β-hydroxy-17β-(2-pyrrolidin-1-yl-acetamido)-21-oxolup-18-ene | $^1$H NMR (400 MHz, CDCl$_3$): δ [ppm] 7.30 (br s, 1H), 3.19 (m, 2H), 3.02 (d, 2H), 2.69 (m, 2H), 2.58 (m, 4H), 2.26 (m, 2H), 1.95-0.62 (m, 42H). |

-continued

| Cpd# | Structure | Name | Analytical data |
|---|---|---|---|
| 24-38 | 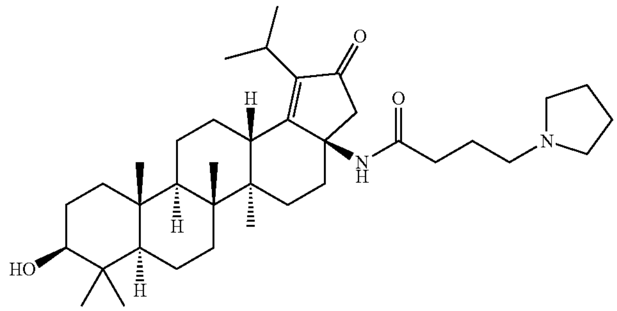 | 3β-hydroxy-17β-(4-pyrrolidin-1-yl-butyramido)-21-oxolup-18-ene | $^1$H NMR (400 MHz, CDCl$_3$): δ [ppm] 6.83 (br s, 1H), 3.19 (m, 1H), 3.11 (m, 1H), 2.77 (m, 1H), 2.66 (d, 1H), 2.48 (m, 5H), 2.28 (m, 3H), 2.05 (s, 3H), 2.00-0.66 (m, 46H). |
| 24-39 | 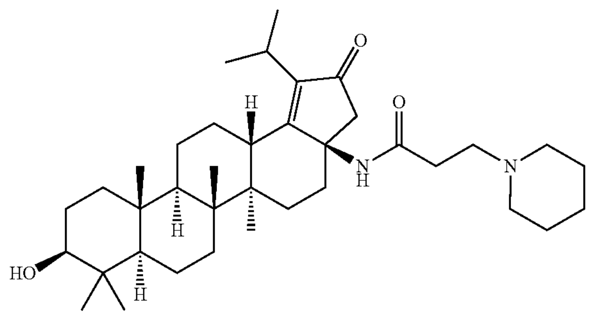 | 3β-hydroxy-17β-(3-piperidin-1-yl-propionamido)-21-oxolup-18-ene | $^1$H NMR (400 MHz, CDCl$_3$): δ [ppm] 9.30 (br s, 1H), 3.15 (m, 2H), 2.84 (m, 1H), 2.70-2.26 (m, 10H), 1.92 (m, 3H), 1.78-0.66 (m, 21H), 1.20 (d, 3H), 1.18 (d, 3H), 1.09 (s, 3H), 0.96 (s, 3H), 0.92 (s, 3H), 0.87 (s, 3H), 0.75 (s, 3H). |
| 24-40 | 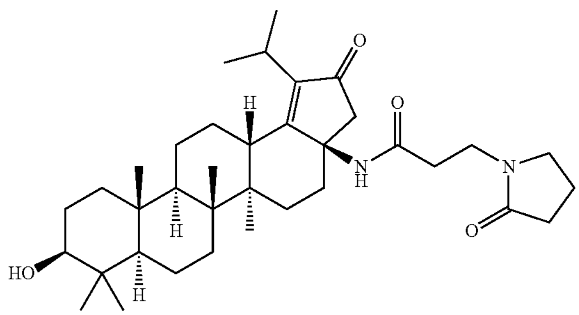 | 3β-hydroxy-17β-[3-(2-oxo-pyrrolidin-1-yl)-propionamido]-21-oxolup-18-ene | $^1$H NMR (400 MHz, CDCl$_3$): δ [ppm] 6.63 (br s, 1H), 3.62-3.38 (m, 4H), 3.18 (m, 5H), 2.60 (d, 1H), 2.48 (m, 2H), 2.32 (m, 3H), 1.94-0.66 (m, 18H), 1.19 (d, 3H), 1.17 (d, 3H), 1.09 (s, 3H), 0.95 (s, 3H), 0.91 (s, 3H), 0.87 (s, 3H), 0.75 (s, 3H). |
| 24-41 | 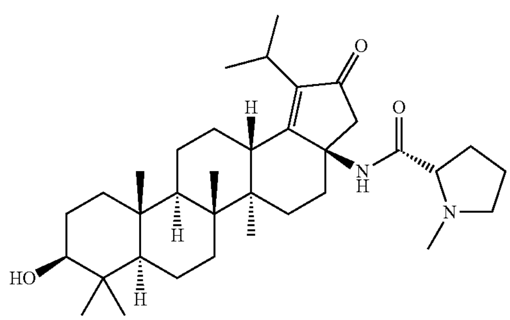 | 3β-hydroxy-17β-[(S)-1-methyl-pyrrolidine-2-amido]-21-oxolup-18-ene | LC/MS (M$^+$/M + H$^+$): 553.27 |
| 24-42 | 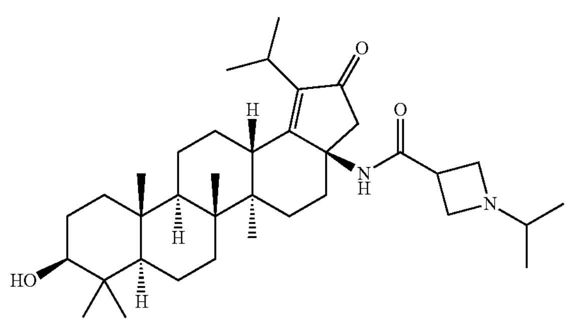 | 3β-hydroxy-17β-(1-isopropylazetidine-3-amido)-21-oxolup-18-ene | LC/MS (M$^+$/M + H$^+$): 567.30 |

| Cpd# | Structure | Name | Analytical data |
|------|-----------|------|-----------------|
| 24-43 | 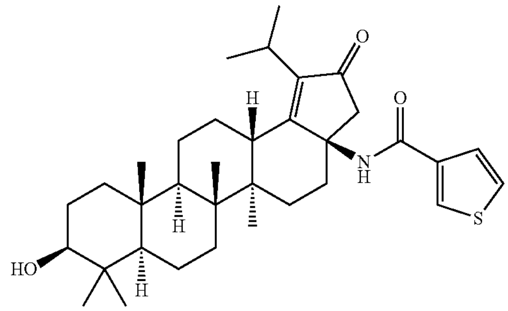 | 3β-hydroxy-17β-(3 thiophene)amido-21-oxolup-18-ene | LC/MS (M+/M + H+): 552.41 |
| 24-44 | 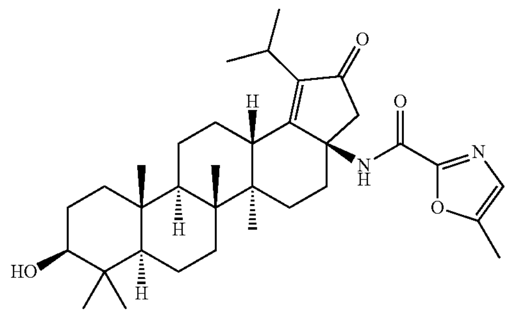 | 3β-hydroxy-17β-(5-methyl-[1,3]-oxazole-2-amido)-21-oxolup-18-ene | HPLC: 30.83 Method (E) LC/MS (M+/M + H+): 551.41 |
| 25-1 | 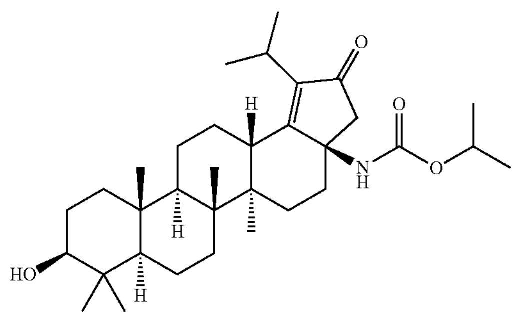 | 3β-hydroxy-17β-isopropyloxycarbonylamino-21-oxolup-18-ene | HPLC: 11.62 Method (J) LC/MS (M+/M + H+): 528.26 |
| 25-2 | 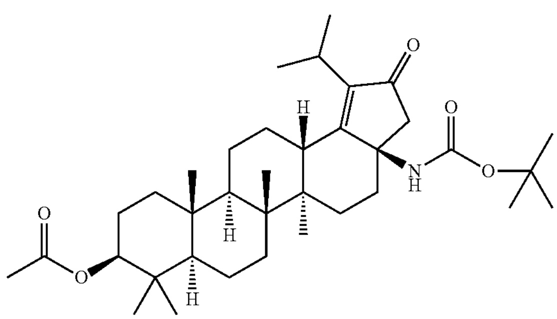 | 3β-O-acetyl-17β-tert-butyloxycarbonyl-amino]-21-oxolup-18-ene | LC/MS (M+/M + H+): 584.68 |
| 25-3 | 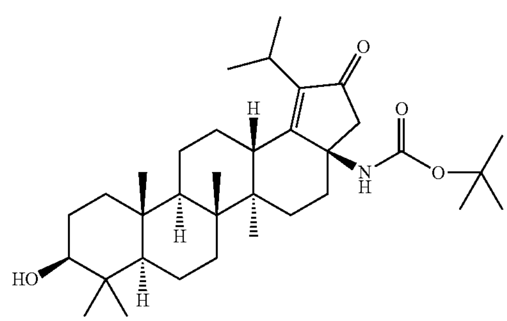 | 3β-hydroxy-17β-tert-butyloxycarbonyl-amino]-21-oxolup-18-ene | LC/MS (M+/M + H+): 542.61 |

-continued

| Cpd# | Structure | Name | Analytical data |
|---|---|---|---|
| 25-4 | 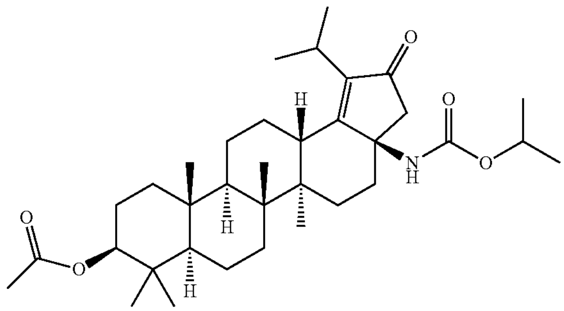 | 3β-O-acetyl-17β-isopropyloxycarbonylamino-21-oxolup-18-ene | LC/MS (M⁺/M + H⁺): 584.54 |
| 25-5 | 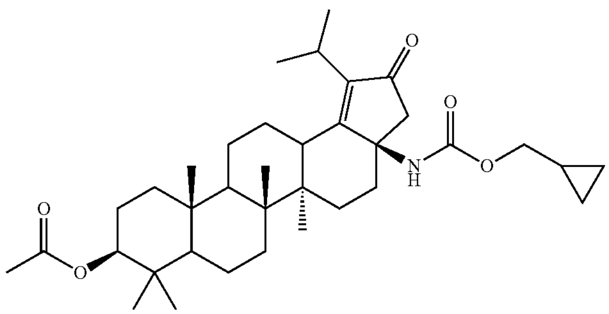 | 3β-O-acetyl-17β-cyclopropylmethoxycarbonylamino-21-oxolup-18-ene | $^1$H NMR (400 MHz, CDCl$_3$): δ [ppm] 4.83 (br s, 1H) 4.48 (d × d, 1H), 3.83 (d, 2H), 3.14 (m, 1H), 2.85 (m, 1H), 2.66 (d, 1H), 2.26 (d, 1H), 2.04 (s, 3H), 1.91-0.80 (m, 19H), 1.22 (s, 3H), 1.21 (s, 3H), 1.13 (s, 3H), 0.93 (s, 3H), 0.92 (s, 3H), 0.85 (s, 3H), 0.84 (s, 3H), 0.53 (d, 2H), 0.25 (d, 2H). |
| 25-6 | 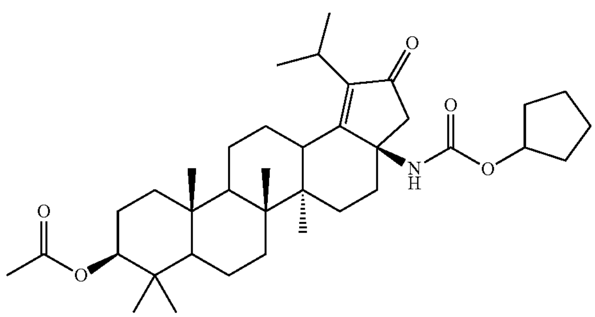 | 3β-O-acetyl-17β-cyclopentyloxycarbonylamino-21-oxolup-18-ene | $^1$H NMR (400 MHz, CDCl$_3$): δ [ppm] 5.04 (m, 1H), 4.74 (br s, 1H) 4.44 (d × d, 1H), 3.10 (m, 1H), 2.82 (m, 1H), 2.60 (d, 1H), 2.22 (d, 1H), 2.02 (s, 3H), 1.89-0.77 (m, 27H), 1.16 (s, 3H), 1.13 (s, 3H), 1.10 (s, 3H), 0.90 (s, 3H), 0.89 (s, 3H), 0.82 (s, 3H), 0.81 (s, 3H). |
| 25-7 | 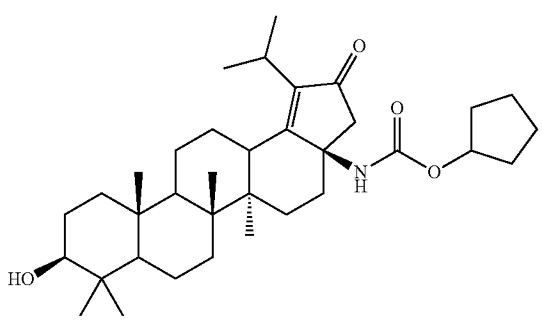 | 3β-hydroxy-17β-cyclopentyloxycarbonylamino-21-oxolup-18-ene | $^1$H NMR (400 MHz, CDCl$_3$): δ [ppm] 5.04 (m, 1H), 4.75 (br s, 1H), 3.15 (m, 2H), 2.84 (m, 1H), 2.60 (d, 1H), 2.22 (d, 1H), 1.89-0.77 (m, 26H), 1.18 (d, 3H), 1.16 (d, 3H), 1.10 (s, 3H), 0.90 (s, 3H), 0.89 (s, 3H), 0.82 (s, 3H), 0.81 (s, 3H), 0.70 (m, 1H). |
| 25-8 | 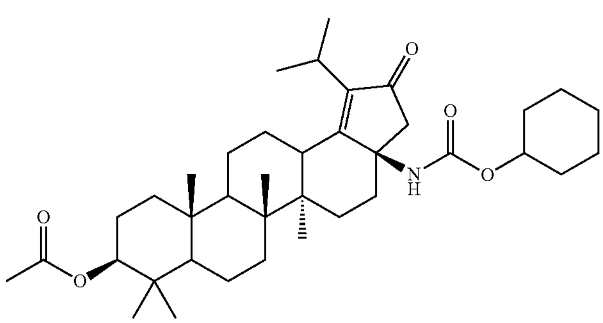 | 3β-O-acetyl-17β-cyclohexyloxycarbonylamino-21-oxolup-18-ene | $^1$H NMR (400 MHz, CDCl$_3$): δ [ppm] 4.72 (s, 1H), 4.60 (m, 1H) 4.45 (d × d, 1H), 3.11 (m, 1H), 2.82 (m, 1H), 2.62 (d, 1H), 2.23 (d, 1H), 2.02 (s, 3H), 1.90-0.77 (m, 29H), 1.20 (s, 3H), 1.19 (s, 3H), 1.10 (s, 3H), 0.91 (s, 3H), 0.89 (s, 3H), 0.83 (s, 3H), 0.82 (s, 3H). |

| Cpd# | Structure | Name | Analytical data |
|---|---|---|---|
| 25-9 | 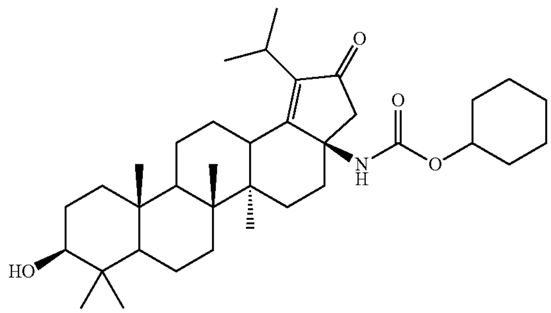 | 3β-hydroxy-17β-cyclohexyloxy-carbonylamino-21-oxolup-18-ene | ¹H NMR (400 MHz, CDCl₃): δ [ppm] 4.57 (b s, 1H), 3.17 (d × d, 1H), 3.11 (m, 1H), 2.83 (m, 1H), 2.62 (d, 1H), 2.22 (d, 1H), 2.02 (s, 3H), 1.88-1.20 (m, 29H), 1.18 (s, 3H), 1.16 (s, 3H), 1.09 (s, 3H), 0.94 (s, 3H), 0.91 (s, 3H), 0.86 (s, 3H), 0.74 (s, 3H). |
| 25-10 | 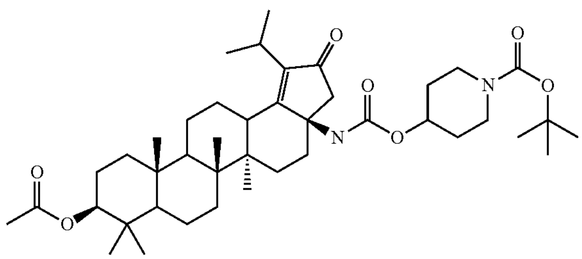 | 3β-O-acetyl-17β-(1-tert-butoxycarbonyl-piperidin-4-yloxycarbonylamino)-21-oxolup-18-ene | ¹H NMR (400 MHz, CDCl₃): δ [ppm] 4.76 (s, 1H), 4.74 (m, 1H) 4.45 (d × d, 1H), 3.72 (m, 2H), 3.13 (m, 1H), 3.12 (m, 2H), 2.80(m, 1H), 2.61 (d, 1H), 2.25 (d, 1H), 2.03 (s, 3H), 1.89-0.78 (m, 23H), 1.42 (s, 9H), 1.20 (s, 3H), 1.18 (s, 3H), 1.10 (s, 3H), 0.92 (s, 3H), 0.90 (s, 3H), 0.83 (s, 3H), 0.82 (s, 3H). |
| 25-11 | 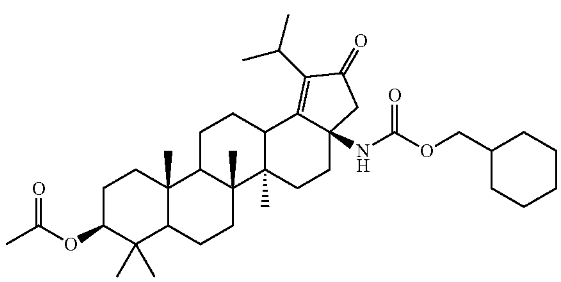 | 3β-O-acetyl-17β-cyclohexylmethoxy carbonylamino-21-oxolup-18-ene | ¹H NMR (400 MHz, CDCl₃): δ [ppm] 4.76 (s, 1H), 4.45 (d × d, 1H), 3.81 (d, 2H), 3.41 (d, 1H), 3.11 (m, 1H), 2.82(m, 1H), 2.62 (d, 1H), 2.24 (d, 1H), 2.01 (s, 3H), 1.89- 0.78 (m, 29H), 1.20 (s, 3H), 1.18 (s, 3H), 1.10 (s, 3H), 0.91 (s, 3H), 0.89 (s, 3H), 0.83 (s, 3H), 0.82 (s, 3H). |
| 25-12 | 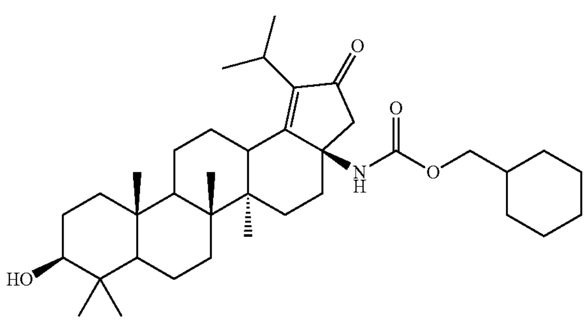 | 3β-hydroxy-17β-cyclohexylmethoxy carbonylamino-21-oxolup-18-ene | ¹H NMR (400 MHz, CDCl₃): δ [ppm] 4.82 (s, 1H), 3.81 (d, 2H), 3.40 (d, 1H), 3.18 (d × d, 1H), 3.10 (m, 1H), 2.82(m, 1H), 2.62 (d, 1H), 2.24 (d, 1H), 1.87-0.78 (m, 29H), 1.18 (s, 3H), 1.17 (s, 3H), 1.09 (s, 3H), 0.94 (s, 3H), 0.91 (s, 3H), 0.86 (s, 3H), 0.74 (s, 3H). |
| 25-13 | 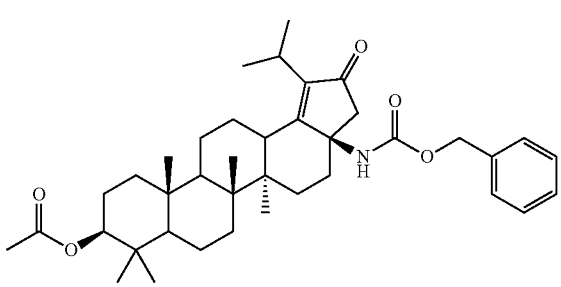 | 3β-O-acetyl-17β-benzyloxycarbonyl-amino-21-oxolup-18-ene | ¹H NMR (400 MHz, CDCl₃): δ [ppm] 7.32, (m, 5H), 5.03 (s, 2H), 4.84 (b s, 1H), 4.45 (d × d, 1H), 3.11 (m, 1H), 2.80 (m, 1H), 2.63 (d, 1H), 2.25 (d, 1H), 2.03 (s, 3H), 1.87-0.77 (m, 19H), 1.20 (s, 3H), 1.18 (s, 3H), 1.06 (s, 3H), 0.91 (s, 3H), 0.90 (s, 3H), 0.83 (s, 3H), 0.82 (s, 3H). |

| Cpd# | Structure | Name | Analytical data |
|---|---|---|---|
| 25-14 | 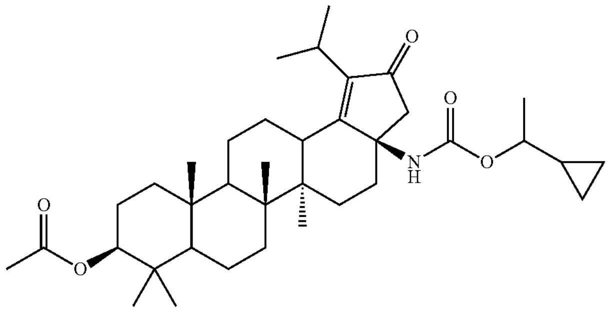 | 3β-O-acetyl-17β-cyclopropylmethoxy-carbonylamino-21-oxolup-18-ene | $^1$H NMR (400 MHz, CDCl$_3$): δ [ppm] 4.77 (br s, 1H) 4.48 (d × d, 1H), 4.15 (m, 1H), 3.15 (m, 1H), 2.86 (m, 1H), 2.66 (d, 1H), 2.26 (d, 1H), 2.05 (s, 3H), 1.94-0.81 (m, 19H), 1.63 (s, 3H), 1.23 (s, 3H), 1.22 (s, 3H), 1.14 (s, 3H), 0.95 (s, 3H), 0.93 (s, 3H), 0.86 (s, 3H), 0.85 (s, 3H), 0.39 (m, 3H), 0.21 (m, 1H). |
| 25-15 | 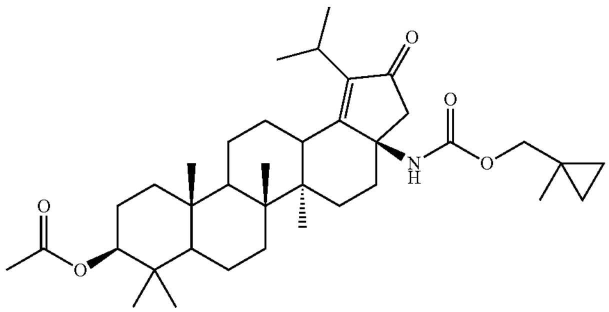 | 3β-O-acetyl-17β-cyclopropylmethoxy-carbonylamino-21-oxolup-18-ene | $^1$H NMR (400 MHz, CDCl$_3$): δ [ppm] 4.85 (br s, 1H) 4.48 (d × d, 1H), 3.83 (s, 2H), 3.15 (m, 1H), 2.82 (m, 1H), 2.69 (d, 1H), 2.28 (d, 1H), 2.04 (s, 3H), 1.93-0.80 (m, 18H), 1.23 (s, 3H), 1.21 (s, 3H), 1.14 (s,3H), 1.09 (s, 3H), 0.94 (s, 3H), 0.92 (s, 3H), 0.85 (s, 3H), 0.84 (s, 3H), 0.45 (d, 2H), 0.33 (d, 2H). |
| 25-16 | 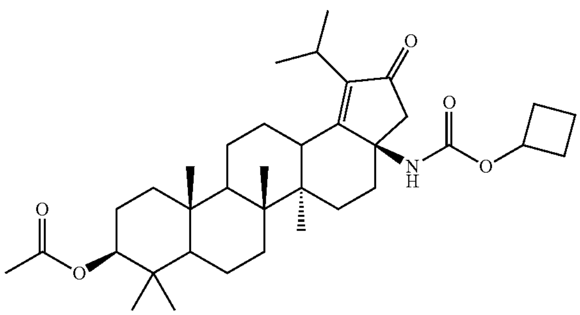 | 3β-acetoxy-17β-cyclobutyloxy-carbonylamino-21-oxolup-18-ene | $^1$H NMR (400 MHz, CDCl$_3$): δ [ppm] 4.87 (m, 1H), 4.78 (br s, 1H) 4.44 (d × d, 1H), 3.11 (m, 1H), 2.82(m, 1H), 2.62 (d, 1H), 2.22 (d, 1H), 2.01 (s, 3H), 2.00-0.77 (m, 25H), 1.14 (s, 3H), 1.11 (s, 3H), 1.10 (s, 3H), 0.90 (s, 3H), 0.89(s, 3H), 0.82 (s, 3H), 0.81 (s, 3H). |
| 25-17 | 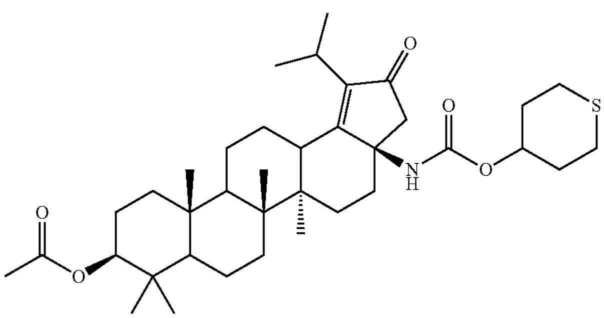 | 3β-acetoxy-17β-tetrahydro-thiopyran-4-yloxycarbonylamino-21-oxolup-18-ene | $^1$H NMR (400 MHz, CDCl$_3$): δ [ppm] 4.87 (s, 1H), 4.60 (m, 1H) 4.43 (d × d, 1H), 3.60 (m, 1H), 3.10 (m, 1H), 2.80 (m, 1H), 2.60 (m, 3H), 2.53 (d, 1H), 2.23 (d, 1H), 2.01 (s, 3H), 1.87-0.76 (m, 23H), 1.18 (s, 3H), 1.16 (s, 3H), 1.08 (s, 3H), 0.90 (s, 3H), 0.88 (s, 3H), 0.81 (s, 3H), 0.80 (s, 3H). |
| 25-18 | 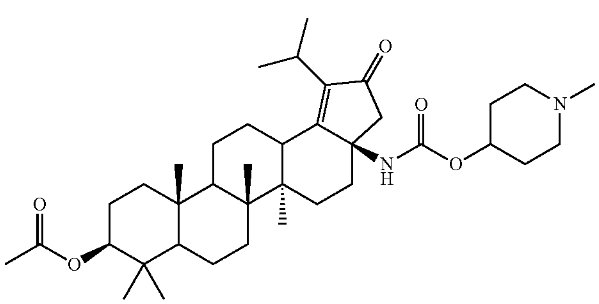 | 3β-acetoxy-17β-(1-methyl-piperidin-4-yloxycarbonylamino)-21-oxolup-18-ene | $^1$H NMR (400 MHz, CDCl$_3$): δ [ppm] 4.77 (s, 1H), 4.47 (m, 1H) 4.45 (d × d, 1H), 3.11(m, 1H), 2.81 (m, 1H), 2.64 (m, 1H), 2.59 (d, 1H), 2.26 (d, 1H), 2.24 (s, 3H), 2.14 (m, 2H), 2.02 (s, 3H), 1.88-0.77 (m, 23H), 1.20 (s, 3H), 1.18 (s, 3H), 1.10 (s, 3H), 0.91 (s, 3H), 0.89 (s, 3H), 0.82 (s, 3H), 0.81 (s, 3H). |

| Cpd# | Structure | Name | Analytical data |
|------|-----------|------|-----------------|
| 25-19 | 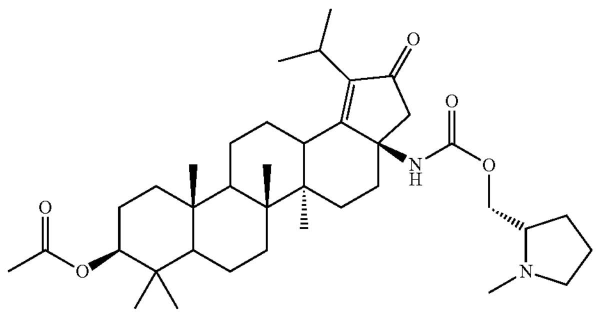 | 3β-acetoxy-17β-((S)-1-Methyl-pyrrolidin-2-yl)-methoxycarbonyl-amino-21-oxolup-18-ene | $^1$H NMR (400 MHz, CDCl$_3$): δ [ppm] 4.96 (br s, 1H), 4.44 (d × d, 1H) 4.10 (m, 1H), 3.95 (d × d, 1H), 3.13 (m, 2H), 2.80 (m, 1H), 2.60 (d, 1H), 2.35 (s, 4H), 2.11 (m, 2H), ), 2.01 (s, 3H), 1.90-0.77 (m, 21H), 1.19 (d, 3H), 1.17 (d, 3H), 1.08 (s, 3H), 0.90 (s, 3H), 0.89 (s, 3H) 0.82 (s, 3H), 0.81 (s, 3H). |
| 25-20 | 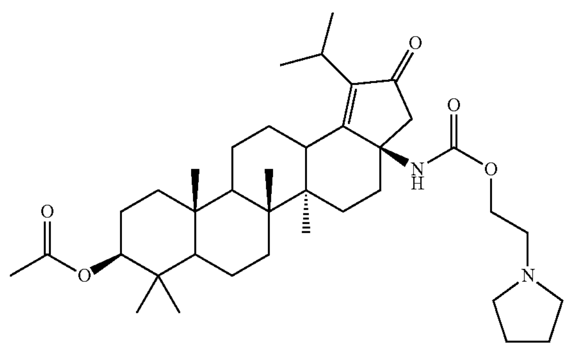 | 3β-acetoxy-17β-(2-pyrrolidin-1-ylethoxycarbonyl-amino)-21-oxolup-18-ene | $^1$H NMR (400 MHz, CDCl$_3$): δ [ppm] 5.20 (br s, 1H), 4.46 (d × d, 1H), 4.15 (br s, 2H), 3.14 (m, 1H), 2.85 (m, 1H), 2.65 (m, 7H), 2.28 (m, 4H), 2.05 (s, 3H), 1.88-0.80 (m, 19H), 1.22 (d, 3H), 1.20 (d, 3H), 1.11 (s, 3H), 0.93 (s, 3H), 0.92 (s, 3H), 0.85 (s, 3H), 0.84 (s, 3H). |
| 25-21 | 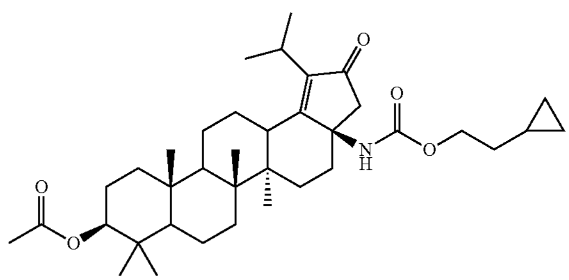 | 3β-acetoxy-17β-cyclopropylethoxy-carbonylamino-21-oxolup-18-ene | $^1$H NMR (400 MHz, CDCl$_3$): δ [ppm] 4.74 (s, 1H) 4.43 (d × d, 1H), 4.04 (d, 2H), 3.10 (m, 1H), 2.81 (m, 1H), 2.61 (d, 1H), 2.20 (d, 1H), 2.00 (s, 3H), 1.86-0.77 (m, 21H), 1.18 (s, 3H), 1.16 (s, 3H), 1.08 (s, 3H), 0.89 (s, 3H), 0.87 (s, 3H), 0.80 (s, 3H), 0.79 (s, 3H), 0.38 (m, 2H), 0.00 (m, 2H). |
| 25-22 | 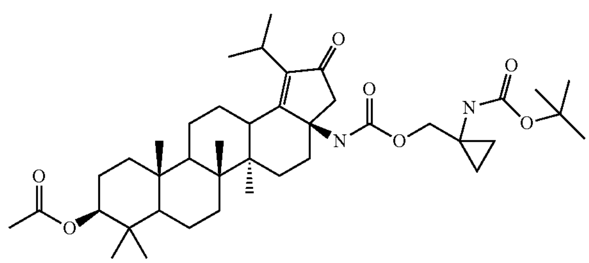 | 3β-O-acetyl-17β-(1-tert-butoxycarbonylamino-cyclopropylmethoxy-carbonylamino)-21-oxolup-18-ene | $^1$H NMR (400 MHz, CDCl$_3$): δ [ppm] 4.86 (br s, 1H) 4.45 (d × d, 1H), 3.55 (d, 2H), 3.12 (m, 1H), 2.82 (m, 1H), 2.64 (d, 1H), 2.25 (d, 1H), 2.02 (s, 3H), 1.89-1.16 (m, 18H), 1.41 (s, 9H) 1.20 (s, 3H), 1.18 (s, 3H), 1.11 (s, 3H), , 0.92 (s, 3H), 0.89 (s, 3H), 0.83 (s, 3H), 0.82 (s, 3H), 0.80 (m, 4H). |
| 25-23 | 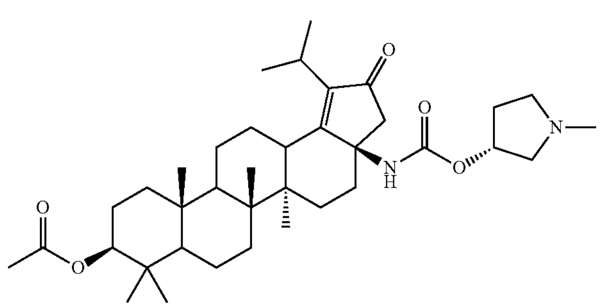 | 3β-acetoxy-17β-(1-methyl-pyrrolidin-3-yloxycarbonylamino)-21-oxolup-18-ene | $^1$H NMR (400 MHz, CDCl$_3$): δ [ppm] 5.26 (m, 1H), 5.10 (br s, 1H), 4.89 (d × d, 1H), 3.11 (m, 1H), 2.85 (m, 2H), 2.60 (d, 1H), 2.45-2.20 (m, 8H), 2.02 (s, 3H), 1.92-0.72 (m, 22H), 1.19 (s, 3H), 1.17 (s, 3H), 1.08 (s, 3H), 0.90 (s, 3H), 0.89 (s, 3H), 0.82 (s, 3H), 0.81 (s, 3H). |

| Cpd# | Structure | Name | Analytical data |
|---|---|---|---|
| 25-24 | 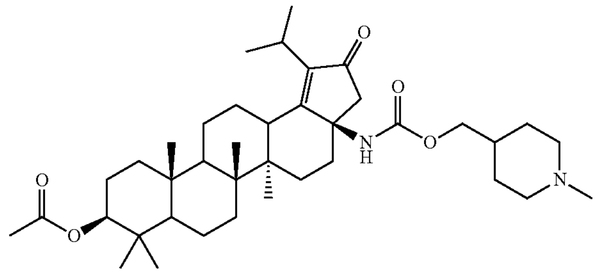 | 3β-O-acetyl-17β-(1-methylpiperidin-4-ylmethoxycarbonyl amino)-21-oxolup-18-ene | $^1$H NMR (400 MHz, CDCl$_3$): δ [ppm] 4.83 (br s, 1H), 4.48 (d × d, 1H), 3.88 (m, 2H), 3.12 (m, 1H), 2.85 (m, 3H), 2.60 (d, 1H), 2.28 (s, 3H), 2.20 (m, 2H), 2.02 (s, 3H), 1.99-0.77 (m, 24H), 1.19 (d, 3H), 1.17 (d, 3H), 1.09 (s, 3H), 0.90 (s, 3H), 0.89 (s, 3H), 0.82 (s, 3H), 0.81 (s, 3H). |
| 25-25 | 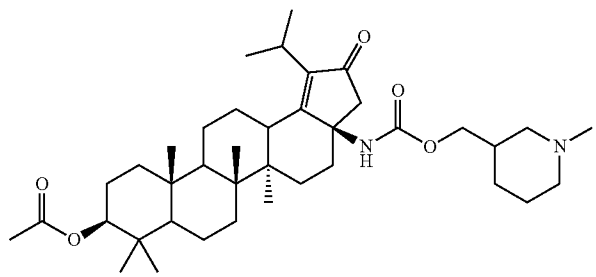 | 3β-O-acetyl-17β-(1-methylpiperidin-3-ylmethoxycarbonyl amino)-21-oxolup-18-ene | $^1$H NMR (400 MHz, CDCl$_3$): δ [ppm] 4.88 (br s, 1H), 4.45 (d × d, 1H), 3.92 (m, 1H), 3.82 (m, 1H), 3.10 (m, 1H), 2.80 (m, 3H), 2.60 (d, 1H), 2.28 (s, 3H), 2.20 (m, 2H), 2.02 (s, 3H), 1.99-0.75 (m, 24H), 1.19 (d, 3H), 1.17 (d, 3H), 1.10 (s, 3H), 0.90 (s, 3H), 0.88 (s, 3H), 0.82 (s, 3H), 0.81 (s, 3H). |
| 25-26 | 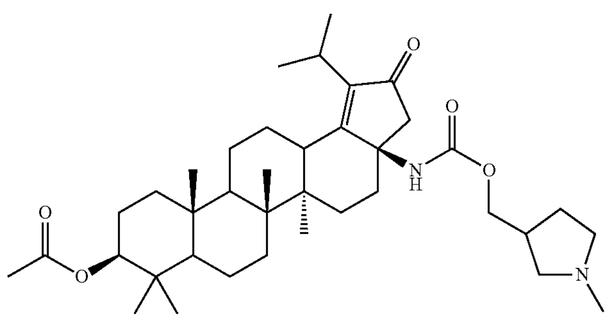 | 3β-acetoxy-17β-(1-Methyl-pyrrolidin-3-yl)-methoxycarbonyl-amino-21-oxolup-18-ene | $^1$H NMR (400 MHz, CDCl$_3$): δ [ppm] 5.75 (br s, 1H), 4.45 (d × d, 1H), 3.90 (m, 2H) 3.20 (m, 1H), 2.85 (m, 1H), 2.75-2.40 (m, 7H), 2.35 (s, 3H), 2.20 (m, 4H), 2.00 (s, 3H), 1.99-0.76 (m, 16H), 1.18 (s, 3H), 1.16 (s, 3H), 1.09 (s, 3H), 0.89 (s, 3H), 0.88 (s, 3H), 0.81 (s, 3H), 0.80 (s, 3H). |
| 25-27 | 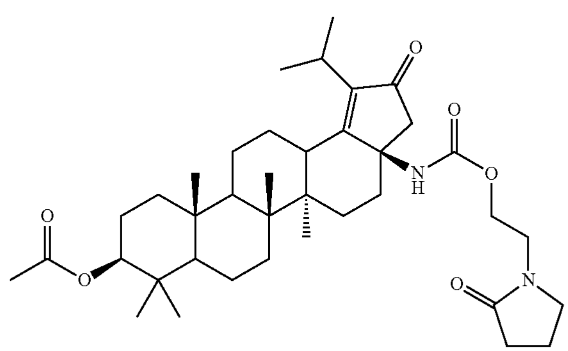 | 3β-acetoxy-17β-[3-(2-oxo-pyrrolidin-1-yl)-propionamido]-21-oxolup-18-ene | $^1$H NMR (400 MHz, CDCl$_3$): δ [ppm] 4.86 (br s, 1H), 4.45 (d × d, 1H), 4.15 (m, 2H) 3.43 (m, 4H), 3.12 (m, 1H), 2.80 (m, 1H), 2.60 (d, 1H), 2.34 (m, 1H), 2.25 (m, 2H), 2.02 (s, 3H), 2.00-0.77 (m, 20H), 1.20 (s, 3H), 1.18 (s, 3H), 1.10 (S, 3H), 0.90 (s, 3H), 0.89 (s, 3H), 0.83 (s, 3H), 0.82 (s, 3H). |

Scheme 10

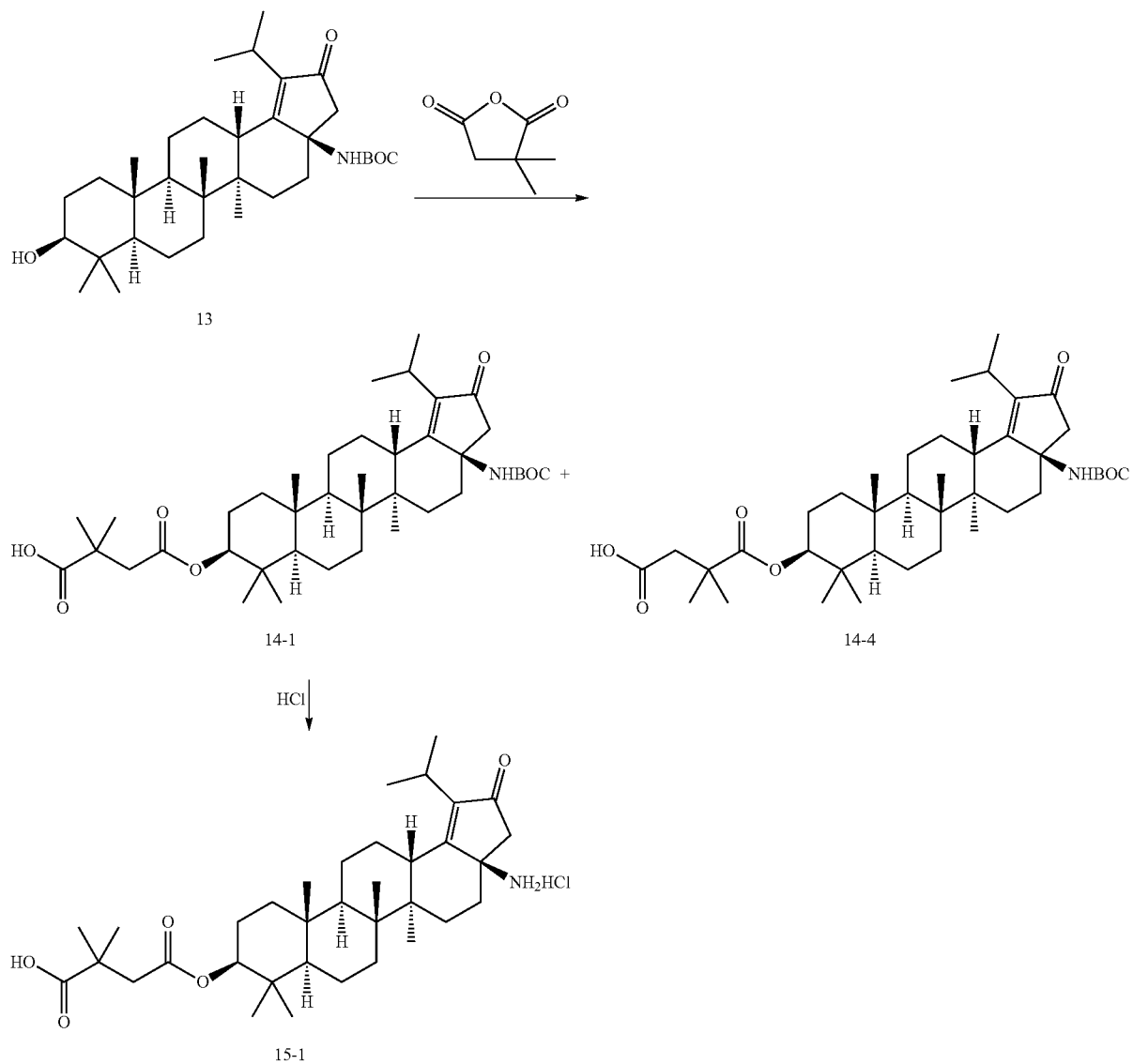

3β-O-(3',3'-Dimethylsuccinyl)-17β-tert-butyloxycarbonylamino-21-oxolup-18-ene

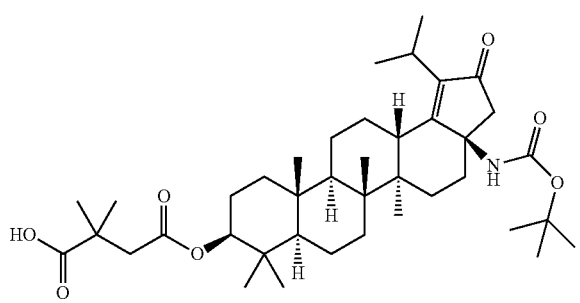

To a stirring mixture of compound 13 (43 g, 0.079 mot), DMAP (11.7 g, 0.095 mot) in TEA (396 mL) is added 2,2-dimethylsuccinic anhydride (25.4 g, 0.198 mot). The reaction mixture is heated at 95° C. overnight. The mixture is cooled down to room temperature and concentrated to dryness. The residue is dissolved in ethyl acetate (400 mL) and washed twice with a saturated solution of NaHCO$_3$ (100 mL). The mixture is diluted with 100 mL of EtOAc and 1N HCl (100 mL) is added while stirring. The mixture is cooled in an ice-bath and stirred for 30 min. The precipitate formed is collected by filtration to yield the title compound 14-1 as a white solid (39 g) in a ratio of 97:3 of 14-1:14-4 respectively. The organic layer of the filtrate is dried over sodium sulfate and concentrated to dryness. The solid obtained (16 g) is recrystallized twice with ethyl methyl ketone to give the title compound 14-1 (3.6 g) in a ratio of 98:2 of 14-1:14-4 respectively.

HPLC analysis: 14-1 RT: 13.4 min, 14-4 RT: 14.1 min using method (J)

3β-O-(3',3'-Dimethylsuccinyl)-17β-amino-21-oxo-lup-18-ene hydrochloride 15-1

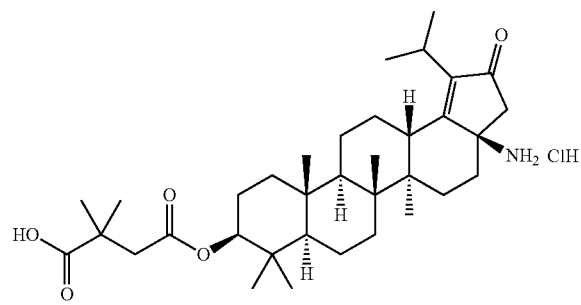

A solution of compound 14-1 (53.6 g, 0.08 mol) in 4N HCl in dioxane (536 mL) is stirred at room temperature overnight. The mixture is concentrated to dryness and triturated with hexanes to give the title compound 15-1 (46 g, 95%) as a white solid.

$^1$H NMR (400 MHz, DMSO-d$_6$): δ [ppm] 4.36 (d×d, 1H), 3.18 (d×d, 1H), 3.05 (m, 1H), 2.48 (m, 2H), 2.13 (d, 2H), 2.0-1.18 (m, 16H), 1.17-0.94 (m, 17H), 0.84 (s, 3H), 0.82 (s, 3H), 0.76 (s, 6H).

The compounds of the present invention wherein Y is C(O) can be prepared as generally described in schemes 11, 12, 13 or 14.

-continued

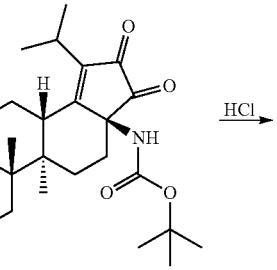

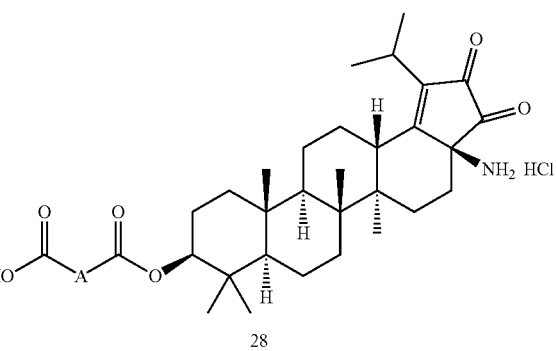

General Procedure:

Step 1: Selenium dioxide (4 to 6 eq.) is added to a solution of compound 14 previously dissolved in dioxane, acetic acid and acetic anhydride. The reaction mixture is refluxed overnight, then cooled to room temperature and filtered through Celite. The residue is dissolved in DCM, washed with water, brine, dried over sodium sulfate and evaporated to dryness. The crude material is purified by flash chromatography on silica gel to yield the compound 27.

Step 2: The compound 27 is deprotected in solvents such as THF or dioxane and 4N HCl. The mixture is stirred for 12 to 24 hours at room temperature then concentrated to dryness to give 28.

Scheme 11

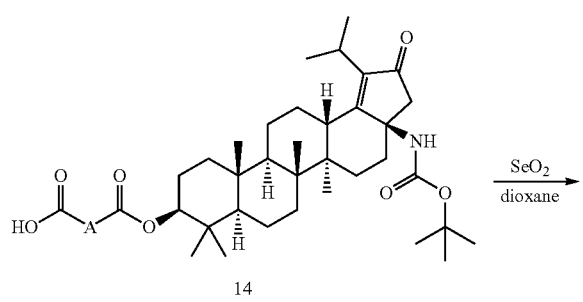

Scheme 12

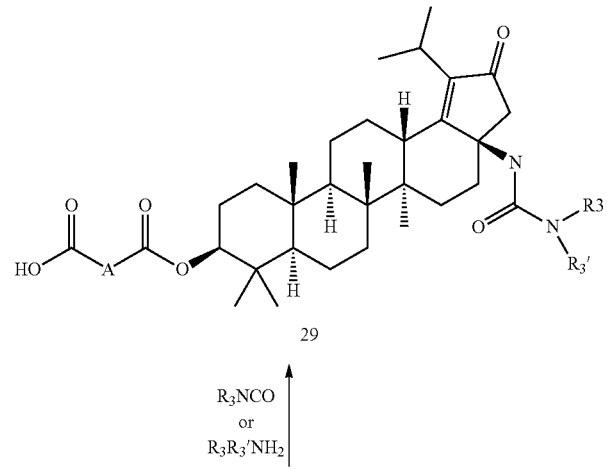

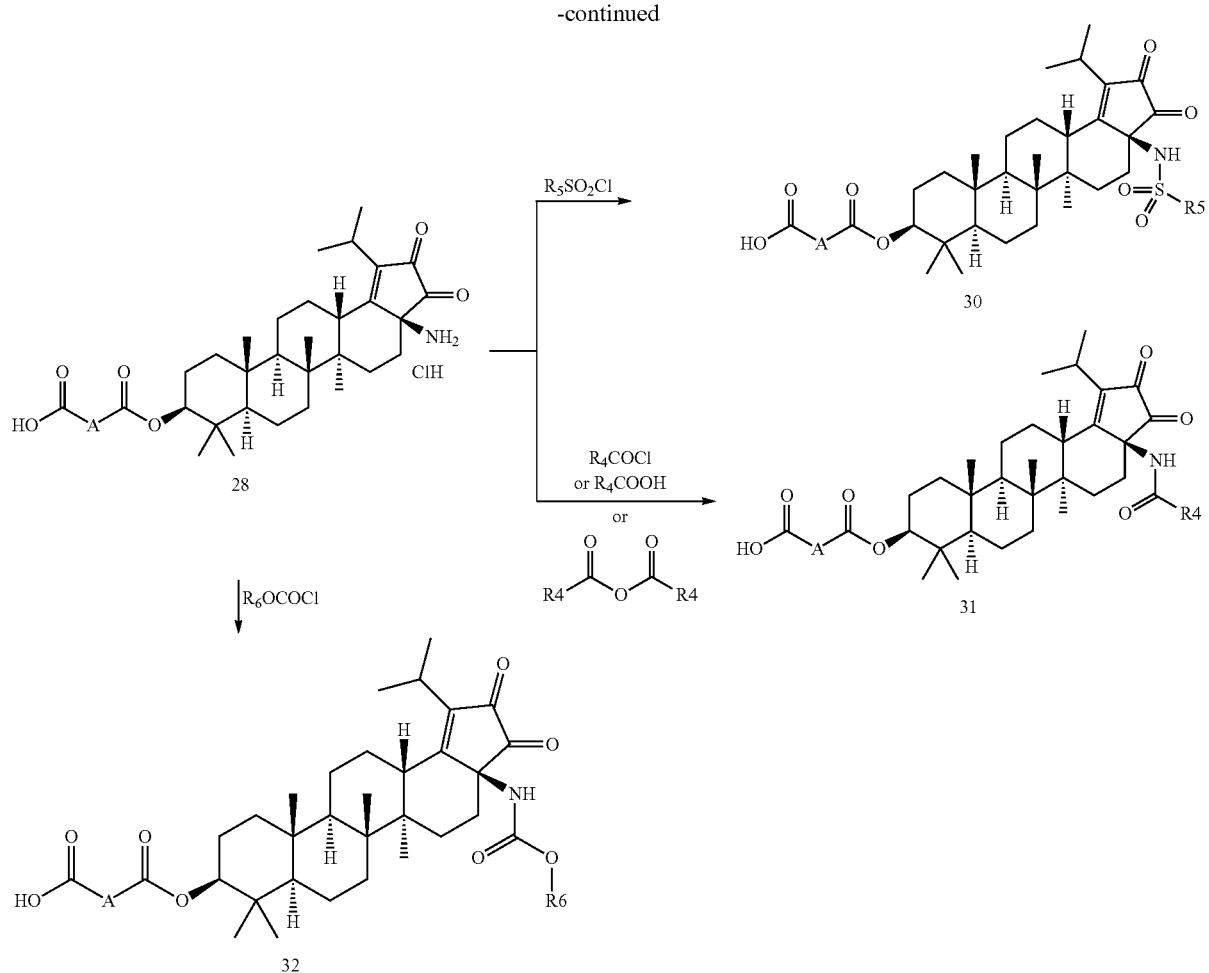

General Procedures:

Ureas 29 are made by treatment of compound 28 with an isocyanate (1 to 3 eq.) or phosgene or triphosgene followed by an amine ($R_3R_3'NH_2$) in a solvent such as toluene or THF.

Sulfonamides 30 are obtained by coupling compound 28 with the appropriate sulfonyl chloride (1 to 3 eq.) in solvents such as THF or DCM and in the presence of a base such as TEA or DIPEA.

Amides 31 are prepared by coupling compound 28 with the appropriate acyl chloride (1 to 3 eq.), preactivated carboxylic acid, mixed anhydride or anhydride in solvents such as THF or DCM and in the presence of a base such as TEA or DIPEA.

Carbamates 32 are obtained by reacting compound 28 with the appropriate chloroformate (1 to 3 eq.) in solvents such as THF or DCM and in the presence of a base such as TEA or DIPEA.

Scheme 13

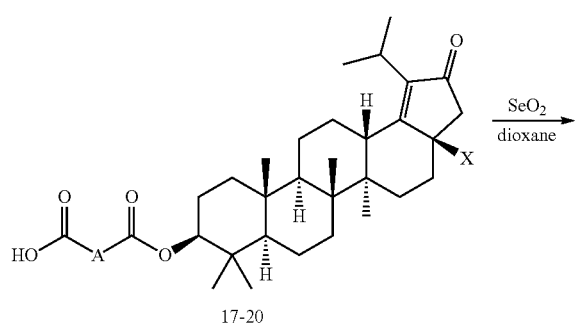

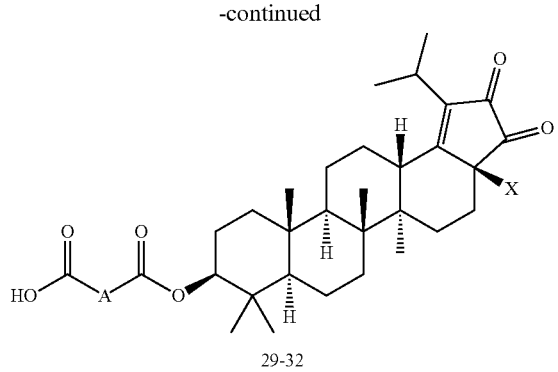

General Procedure:

Selenium dioxide (4 to 6 eq.) is added to a solution of compound 17, 18, 19 or 20 previously dissolved in dioxane, acetic acid and acetic anhydride. The reaction mixture is refluxed overnight, then cooled to room temperature and filtered through Celite. The residue is dissolved in DCM, washed with water, brine, dried over sodium sulfate and evaporated to dryness. The crude material is purified by flash chromatography on silica gel to yield the compound 29, 30, 31 or 32, respectively.

Scheme 14

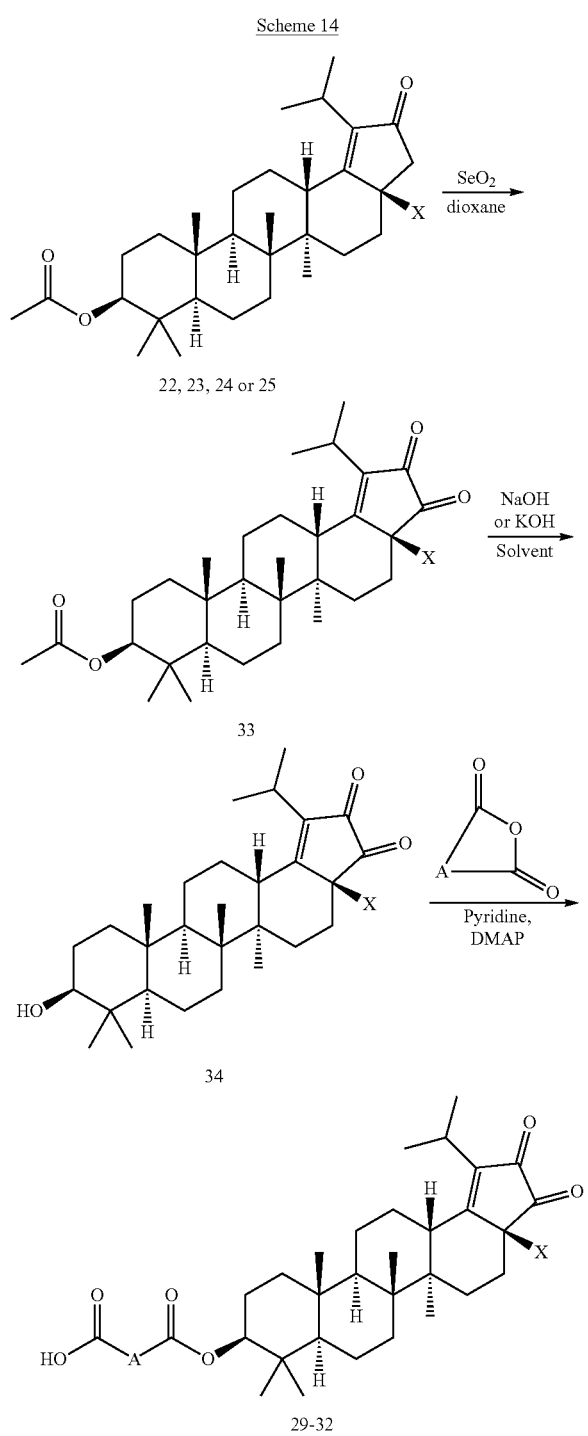

General Procedure:

Step 1: Selenium dioxide (4 to 6 eq.) is added to a solution of compound 22, 23, 24 or 25 previously dissolved in dioxane, acetic acid and acetic anhydride. The reaction mixture is refluxed overnight, then cooled to room temperature and filtered through Celite. The residue is dissolved in DCM, washed with water, brine, dried over sodium sulfate and evaporated to dryness. The crude material is purified by flash chromatography on silica gel to yield the compound 33.

Step 2: The ester 33 is deprotected in solvents such as methanol, THF or dioxane using an aqueous solution of inorganic base such as sodium hydroxide or potassium hydroxide (10 to 20 eq.) at temperature ranging from 20 to 60° C. to give the alcohol 34.

Step 3: To the alcohol 34 in solvents such as pyridine, TEA or toluene (0.2-1.0 M) is added a cyclic anhydride (2 to 10 eq.) and base such as DMAP, TEA, DABCO or DIPEA (1.1 to 2 eq.). The reaction mixture is heated at temperature ranging from 90 to 140° C. until completion to yield after standard acidic aqueous work up and purification by flash chromatography on silica gel the acid 29, 30, 31 or 32.

HIV Replication Activity

HIV-1 Replication in MT2 cell line with and without 30% human serum: The cells are infected at a Multiciplicity of Infection (MOI) of 0.5 for 3 h and then washed twice with complete media to remove residual virus. Cells are then resuspended at $0.5 \times 10^6$/ml in complete medium (RPMI, 10% FBS, 1% sodium pyruvate), and seeded into 96-well plates ($6.25 \times 10^4$/well). The cells are cultured in the presence or absence of various concentrations of test compounds in serial dilutions for 3 days at 37° C. The test compounds are serially diluted in complete medium supplemented or not with 30% human serum. After 3 days, 100 μL of cultured medium with cells are replaced with 120 μL of freshly diluted test compounds in complete medium containing or not 30% Human serum. The level of HIV-1 replication is determined at days 5 after infection by the presence of viral RT activity in harvested supernatant fluid. The $IC_{50}$ and $IC_{90}$ values for the virus replication are determined by using GRAPHPAD PRISM software.

PBMCs are separated from healthy donors' blood by standard density gradient centrifugation, resuspended at a cell density of $1.5 \times 10^6$ cells/ml in culture medium containing 2 μg/mL of phytohaemagglutinin (PHA), and thereafter incubated for 3 days at 37° C. in a humidified 5% $CO_2$ atmosphere. The PHA-stimulated PBMCs are adjusted at a concentration of $5 \times 10^6$/mL and then infected with HIV-1$_{IIIB}$ at a MOI of 5.0 for 3 hours at 37° C. in a humidified 5% $CO_2$ atmosphere and then washed to remove any residual virus. Thereafter, cells are resuspended in culture medium supplemented with interleukin-2 (IL-2) at a concentration of 50 units/mL (2x) and seeded at a density of $0.2 \times 10^6$ cells/well into 96-well plates in the absence or presence of various concentrations of the test compound. Then, infected-cells are cultured for 4 days at 37° C. in a humidified 5% $CO_2$ atmosphere in the absence or presence of 30% human serum after which an aliquot of cultured medium supernatant is replaced with fresh medium supplemented with human serum (when necessary) containing the serially diluted test compound. The $IC_{50}$ and $IC_{90}$ values for the virus replication are determined at day 6 post-infection by measuring the reverse transcriptase activity in the harvested supernatant by using GRAPHPAD PRISM software.

The IC50 of the compounds tested in accordance with the HIV replication activity assay MT2 (HIV$_{IIIB}$) are represented in Table 1.

Table 2 of compounds illustrates some of the compounds of the present invention which are synthesized and tested using the procedures described herein.

Retention time ($t_R$) for each compound are measured using the standard analytical HPLC methods described above.

TABLE 2

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 14-1 | 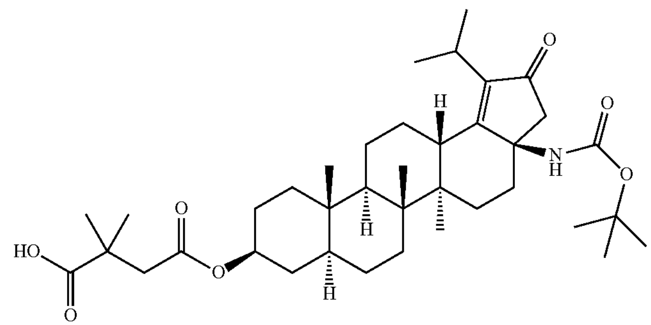 | +++ | +++ | | 670.69 |
| 14-2 | 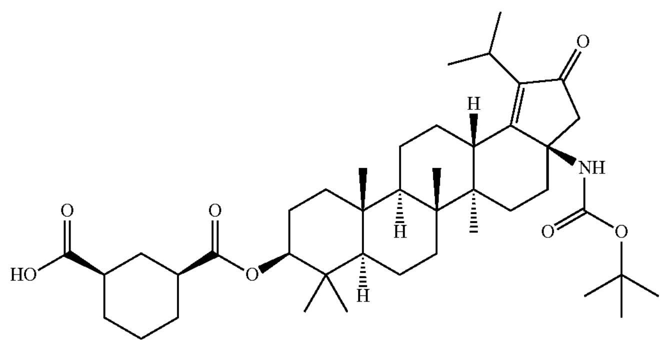 | | + | $^1$H NMR (400 MHz, CH$_3$OD): δ [ppm] 6.90 (br s, 1H), 4.46 (d × d, 1H), 3.17 (sept., 1H), 2.96 (d × d, 1H), 2.50 (d, 1H), 2.37 (m, 1H), 2.18 (d, 1H), 2.17 (br s, 2H), 2.04-1.81 (m, 5H), 1.78 (d × t, 1H), 1.74-0.80 (m, 19H), 1.40 (s, 9H), 1.18 (t, 9H), 0.99 (s, 3H), 0.96 (s, 3H), 0.88 (s, 3H), 0.85 (s, 3H). | |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 14-3 | 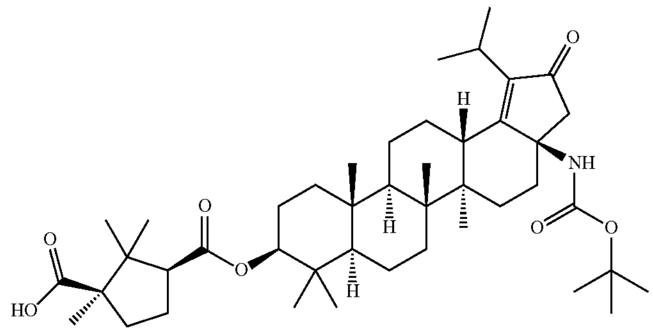 | | +++ | 34.99 (B) | 725.16 |
| 15-1 | 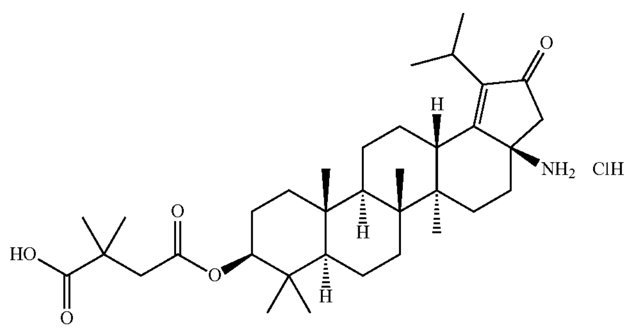 | +++ | +++ | | 570.59 |
| 15-2 | 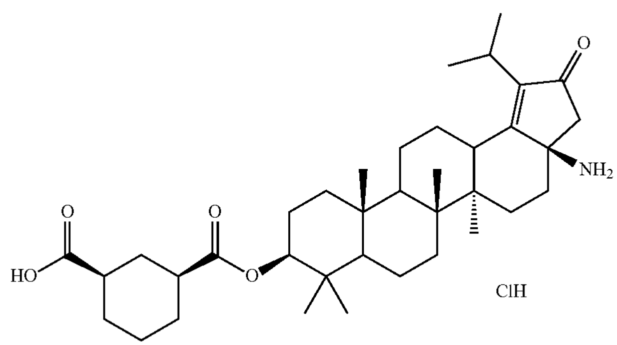 | | + | — | 579.42 (M − NH2) |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 15-3 | 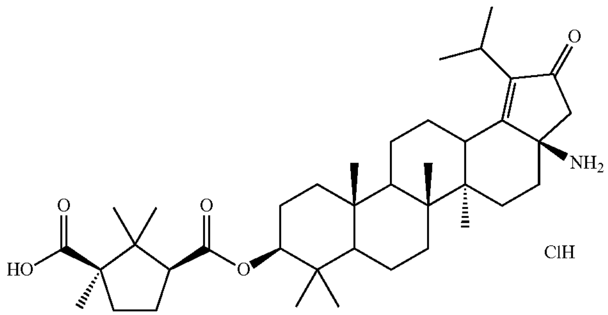 | | +++ | 20.56 (C) | 625.55 |
| 16-1 | 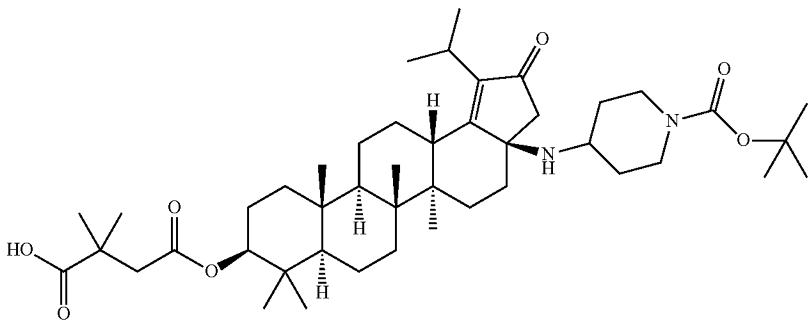 | +++ | +++ | | 753.7 |
| 16-2 | 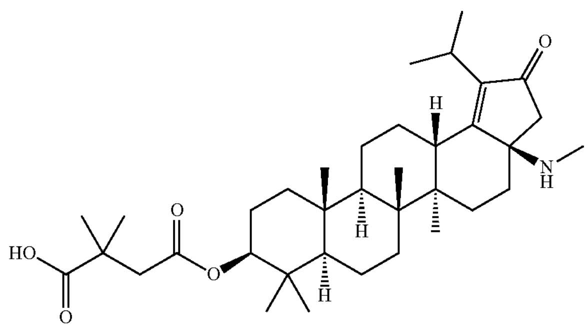 | | +++ | 26.63 (D) | 584.5 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-1 | 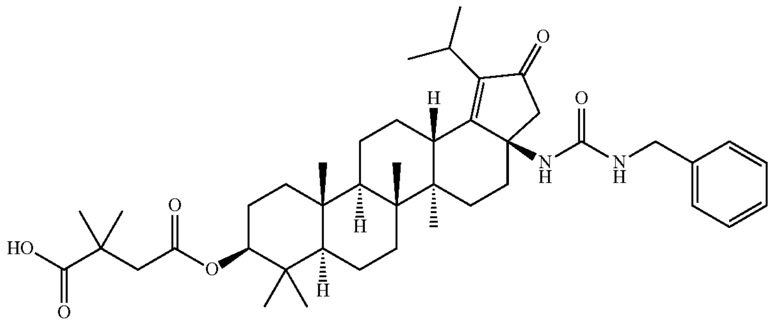 | +++ | +++ | | 703.68 |
| 17-2 | 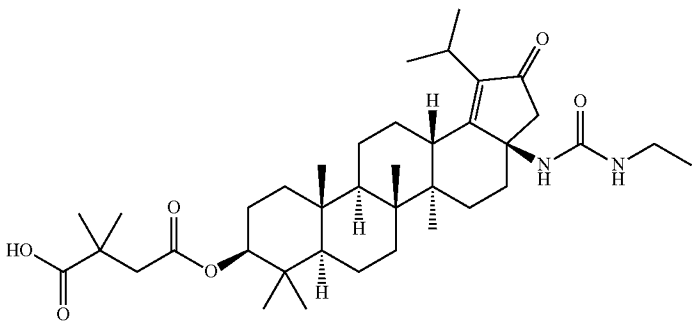 | +++ | +++ | 21.6 (A) | 641.6 |
| 17-3 | 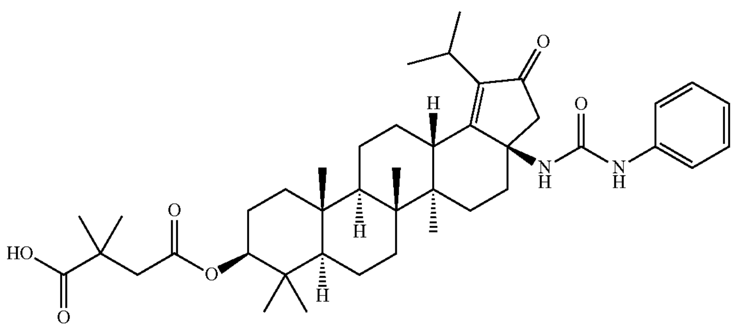 | +++ | +++ | 30.9 (A) | 689.6 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-4 | 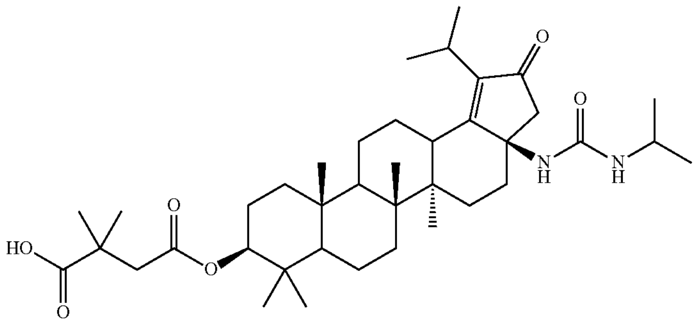 | +++ | +++ | 7.63 (F) | 655.7 |
| 17-5 | 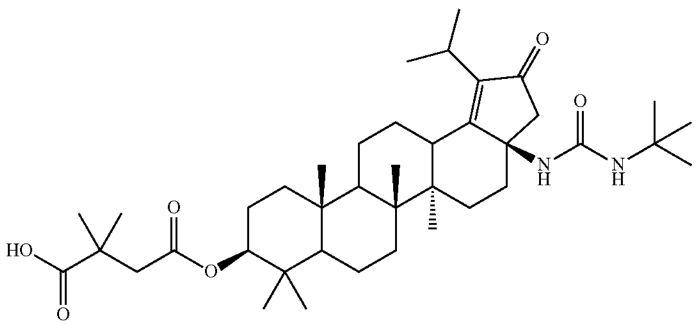 | +++ | +++ | 9.12 (F) | 671.9 |
| 17-6 | 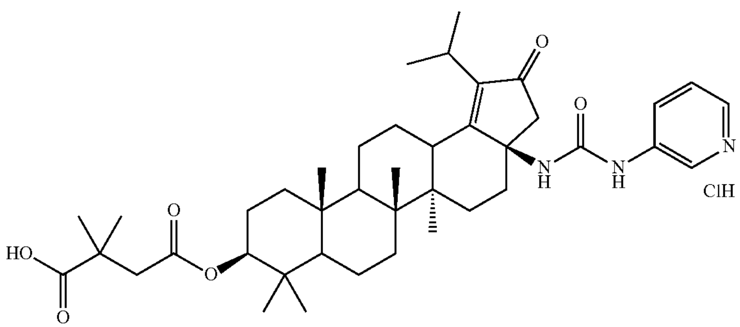 | +++ | +++ | 13.6 (G) | 691.9 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-7 | 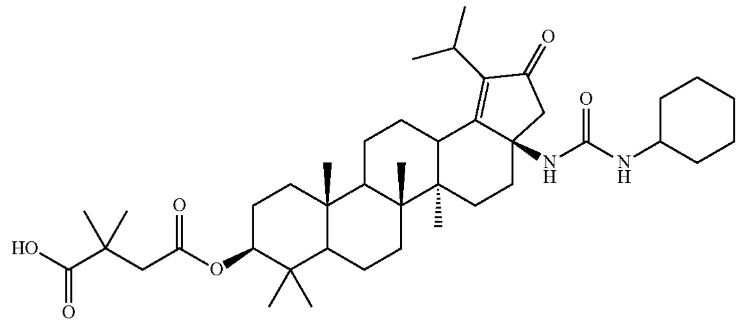 | | +++ | 9.81 (F) | 695.9 |
| 17-8 | 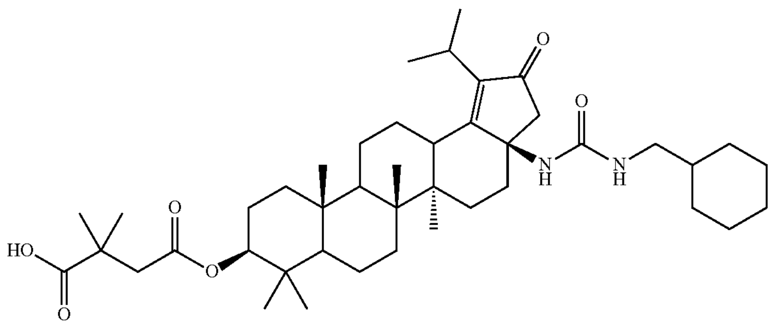 | | +++ | 10.64 (F) | 709.9 |
| 17-9 | 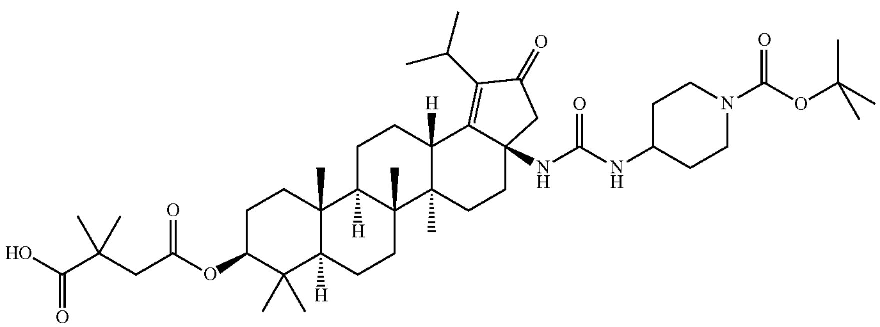 | | +++ | | 797.44 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-10 | 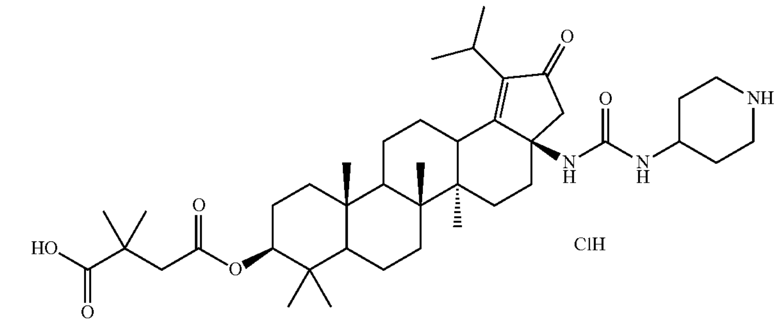 | | + | 26.69 (D) | 696.73 |
| 17-11 | 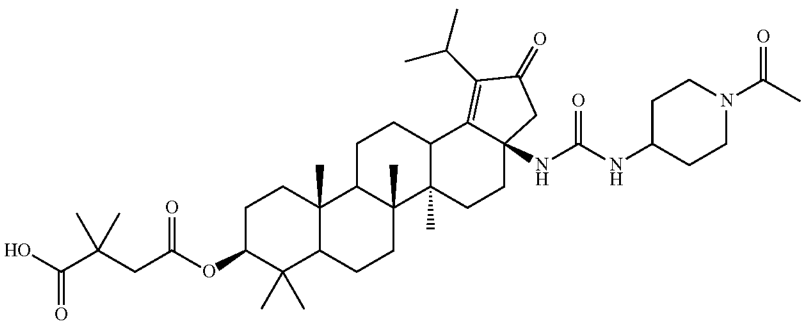 | | +++ | 33.92 (C) | 739.06 |
| 17-12 | 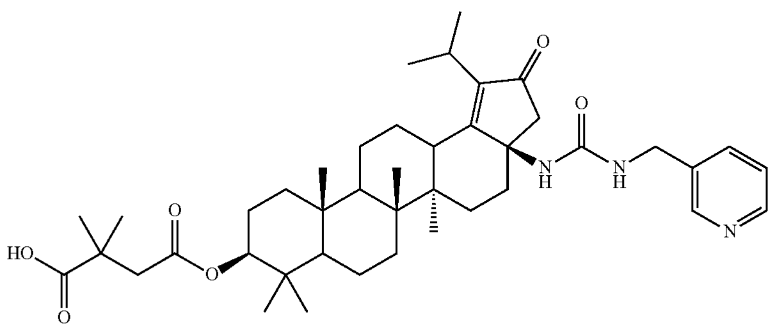 | | +++ | 4.75 (A) | 704.88 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-13 | 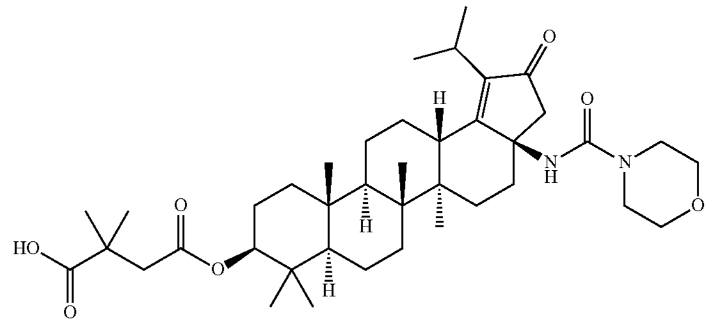 | +++ | +++ | 20.92 (A) | 683.81 |
| 17-14 | 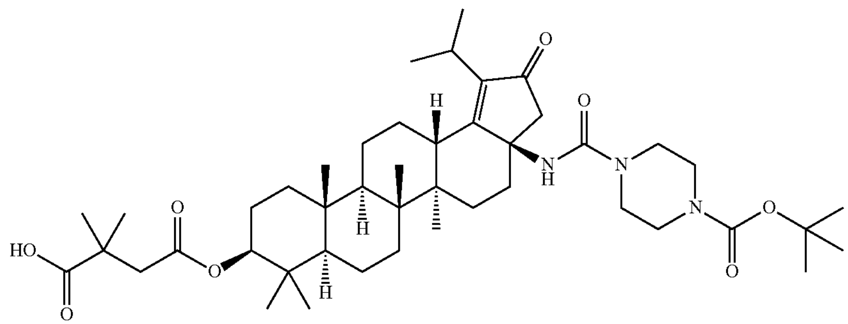 | +++ | +++ | 30.77 (A) | 783.74 |
| 17-15 | 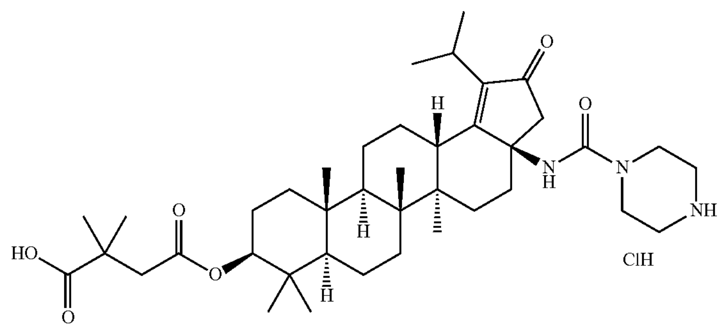 | +++ | +++ | 26.29 (D) | 682.83 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-16 | 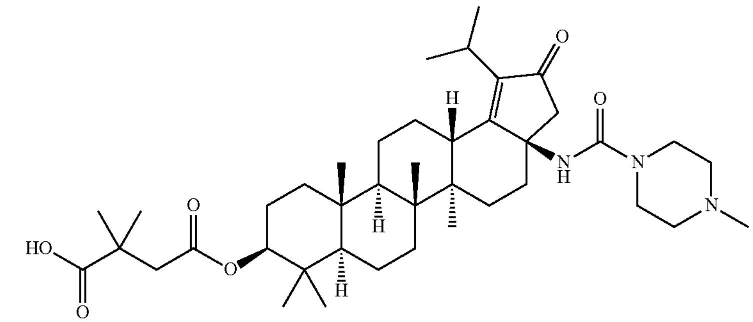 | | +++ | 26.50 (D) | 696.86 |
| 17-17 | 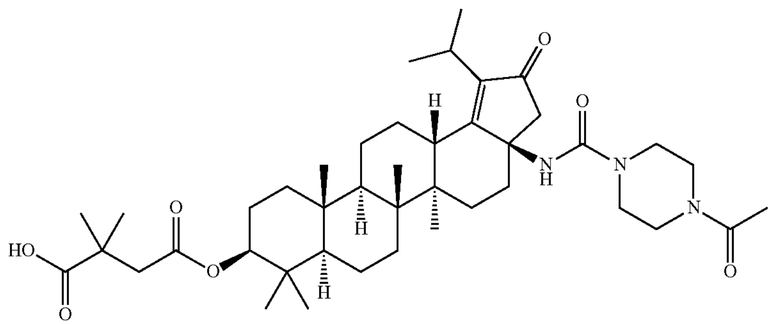 | | +++ | 15.44 (A) | 725.02 |
| 17-18 | 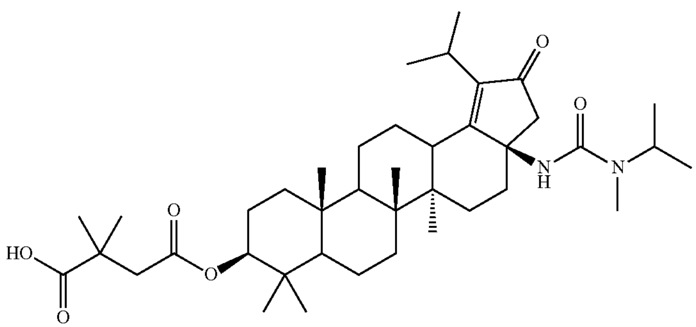 | | +++ | 29.84 (A) | 669.63 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-19 | 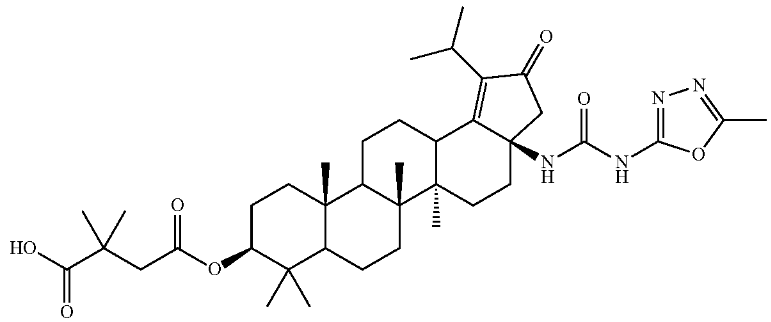 | | +++ | 31.01 (E) | 695.75 |
| 17-20 | 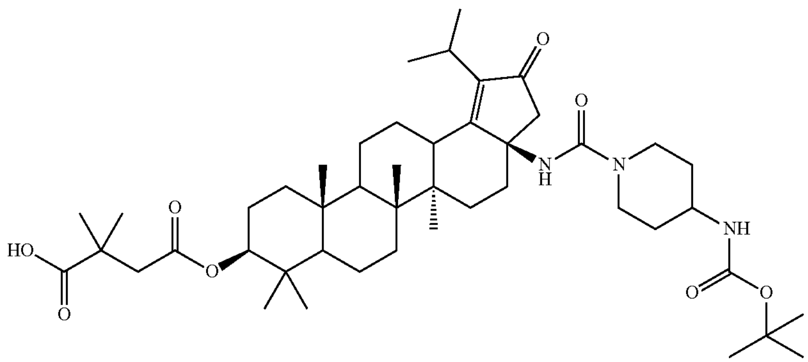 | | +++ | 19.49 (B) | 797.43 |
| 17-21 | 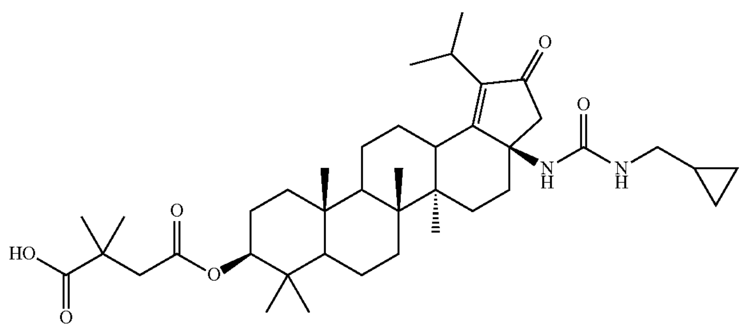 | | ++ | 17.12 (B) | 667.68 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-22 | 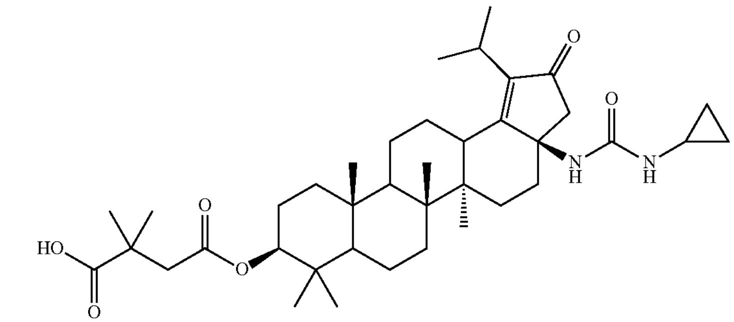 | | +++ | 15.72 (B) | 653.60 |
| 17-23 | TFA | | ++ | 26.15 (D) | 696.83 |
| 17-24 | ClH | | ++ | 12.53 (G) | 696.96 |

TABLE 2-continued
| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-25 | 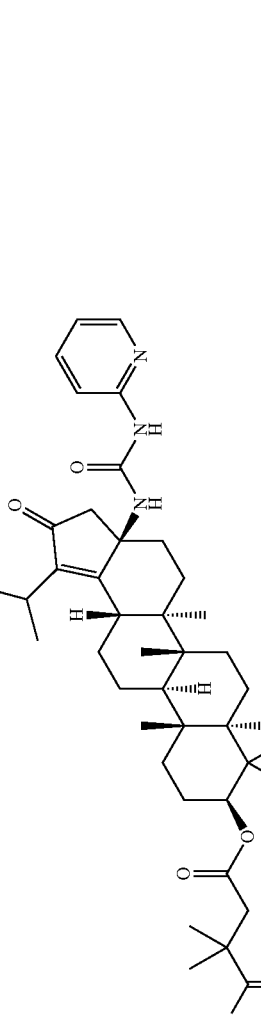 | | +++ | 30.31 (E) | 690.81 |
| 17-26 | 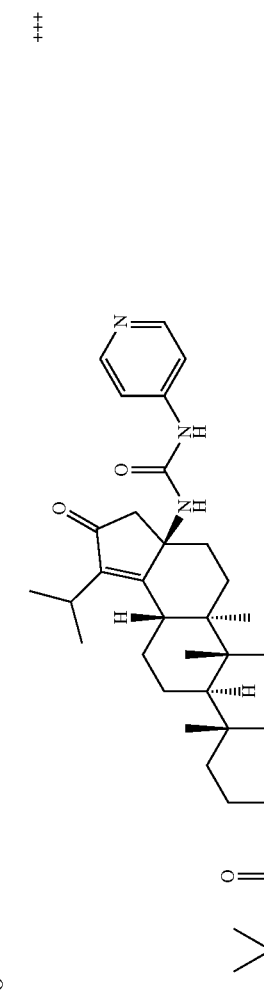 | | +++ | 20.22 (C) | 690.4 |
| 17-27 | 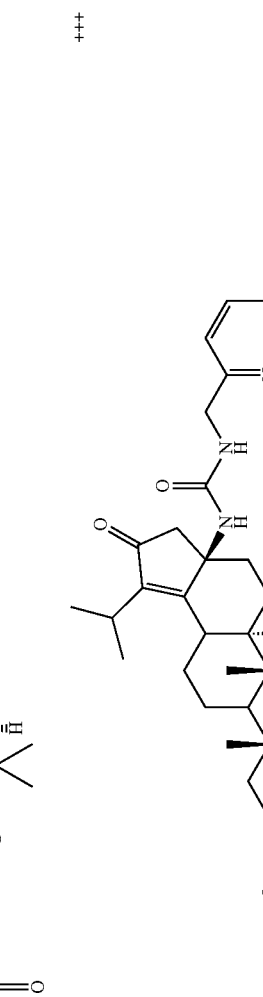 | | +++ | 21.45 (C) | 704.4 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-28 | 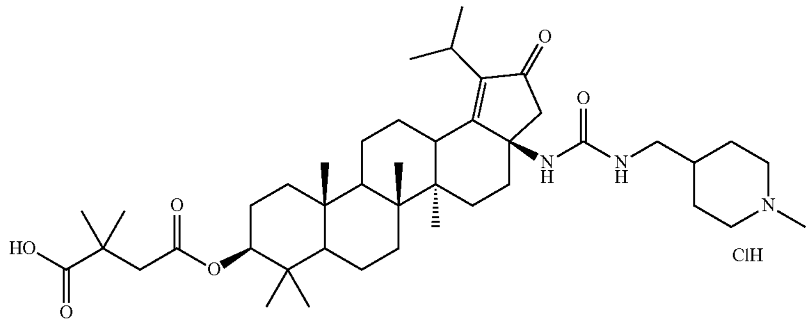 | | + | 11.95 (G) | 724.97 |
| 17-29 | 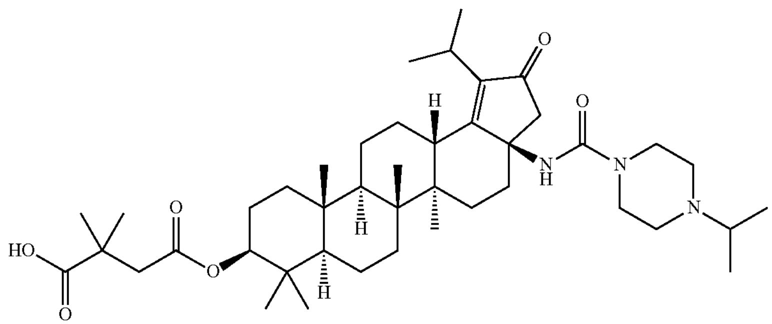 | | +++ | 18.32 (C) | 724.5 |
| 17-30 | 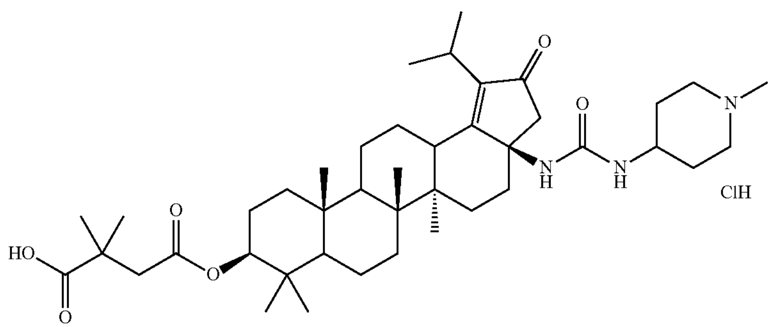 | | +++ | 11.76 (G) | 710.97 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-31 | 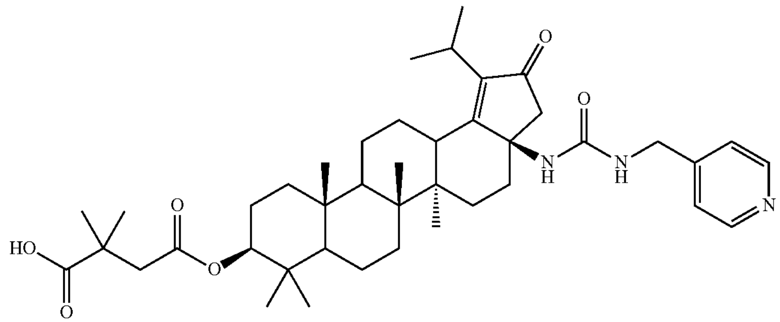 | | +++ | 18.26 (C) | 704.88 |
| 17-32 | 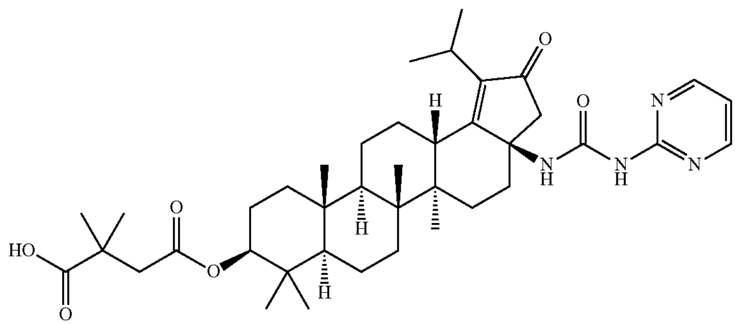 | | +++ | 25.18 (A) | 691.79 |
| 17-33 | 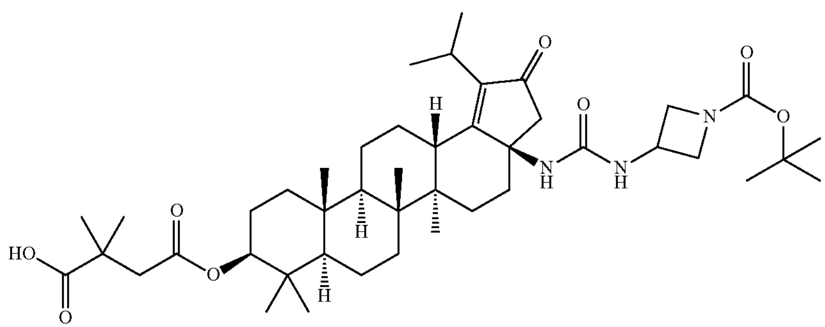 | | +++ | 25.95 (A) | 769.38 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-34 | 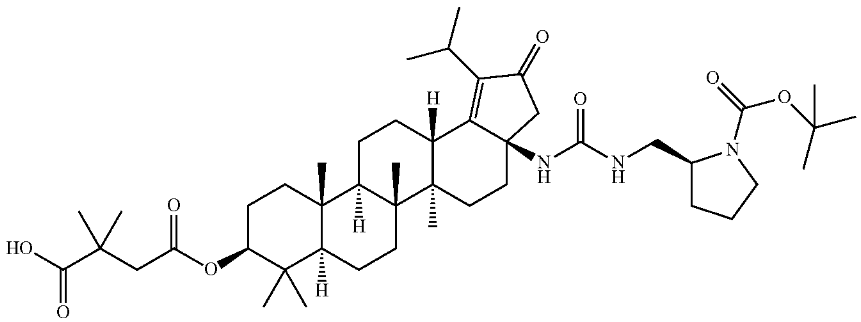 | +++ | +++ | 23.89 (B) | 797.64 |
| 17-35 | 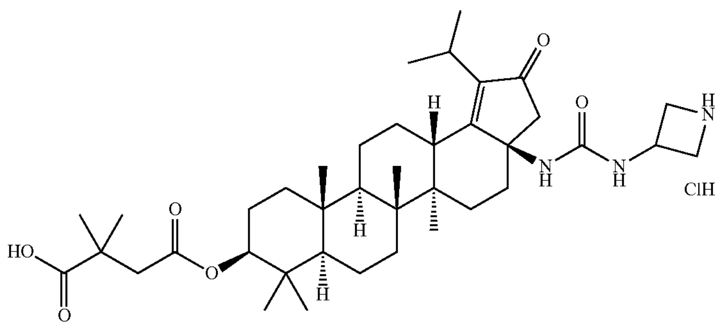 | | ++ | 19.12 (D) | 668.85 |
| 17-36 | 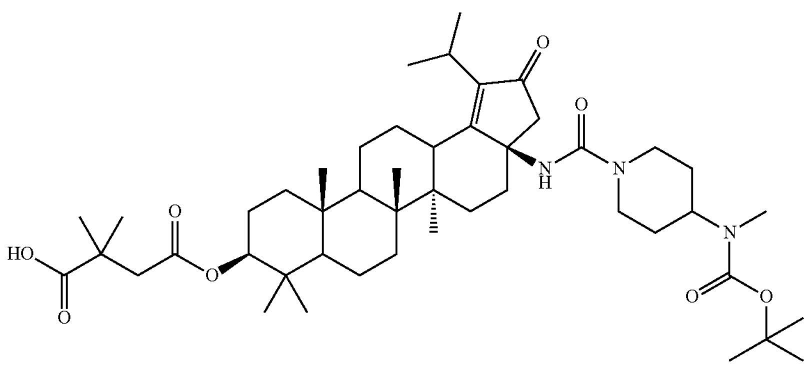 | +++ | +++ | 23.59 (B) | 811.73 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M+/M + H+ |
|---|---|---|---|---|---|
| 17-37 | 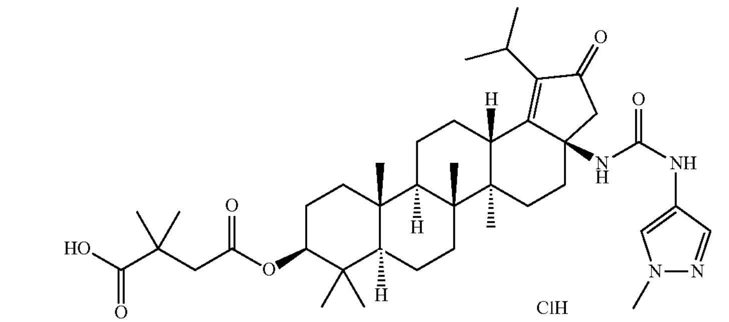 | | +++ | 12.85 (H) | 693.91 |
| 17-38 | 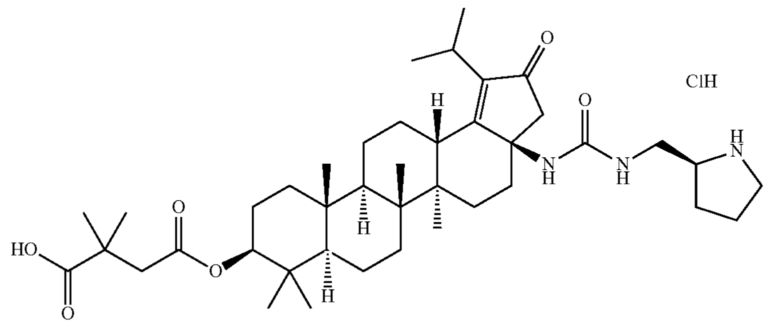 | | +++ | 28.20 (B) | 697.05 |
| 17-39 | 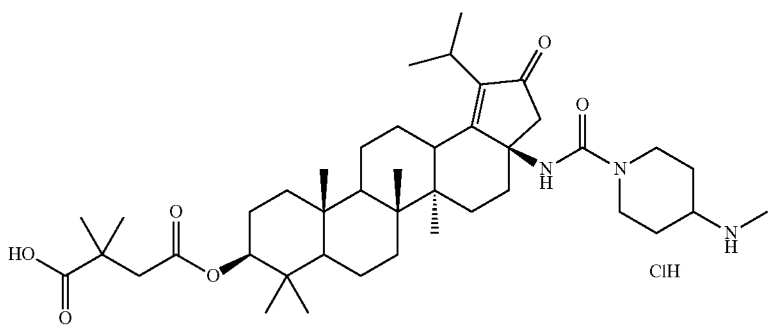 | | ++ | 16.15 (C) | 711.13 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-40 | 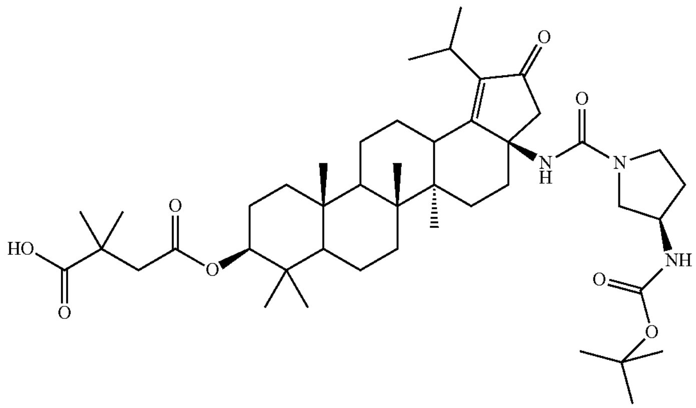 | | +++ | 26.03 (A) | 783.57 |
| 17-41 | 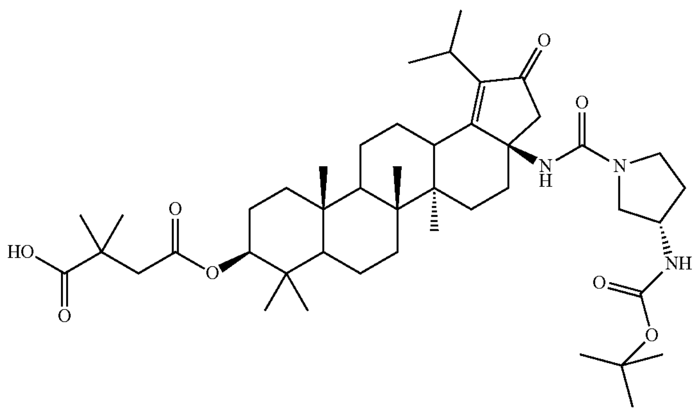 | | +++ | 26.28 (A) | 783.58 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-42 | 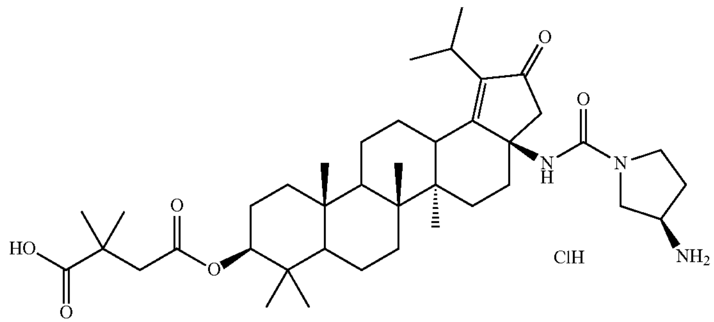 | | ++ | 15.39 (C) | 682.95 |
| 17-43 | 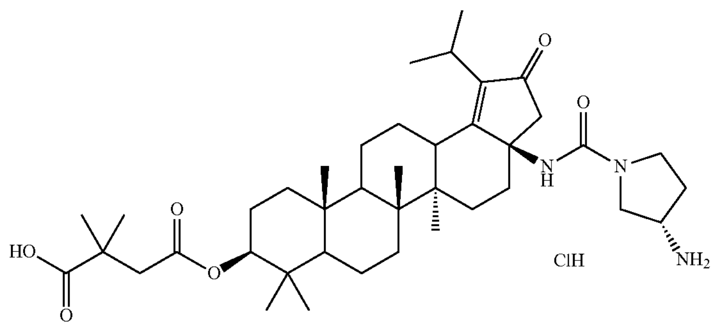 | | +++ | 15.57 (C) | 682.93 |
| 17-44 | 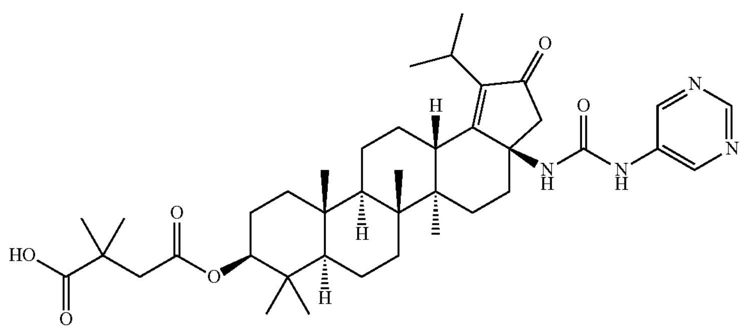 | | +++ | 6.00 (F) | 691.96 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-45 | 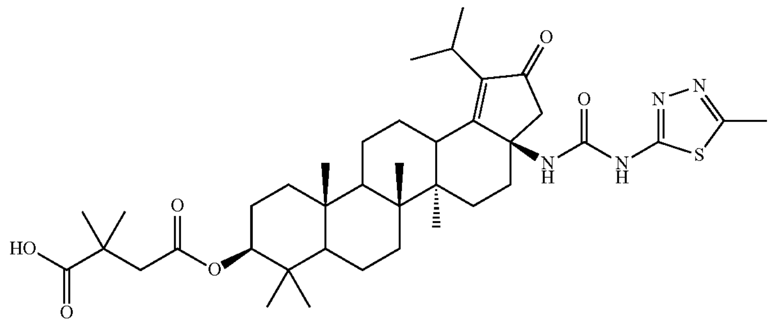 | | +++ | 30.73 (E) | 712.09 |
| 17-46 | ClH | | +++ | 13.25 (H) | 692.03 |
| 17-47 | ClH | | +++ | 8.85 (H) | 705.08 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-48 | 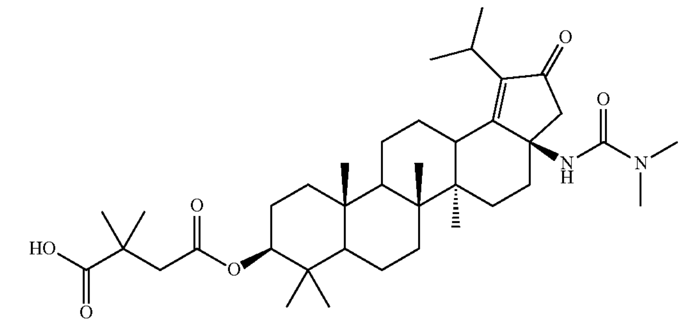 | | +++ | 8.11 (F) | 641.78 |
| 17-50 | 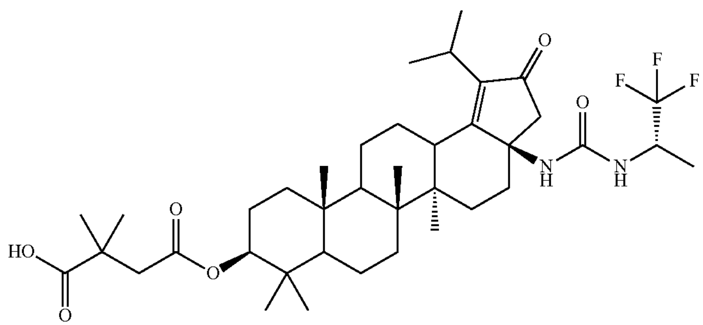 | | +++ | 9.39 (F) | 710.06 |
| 17-51 | 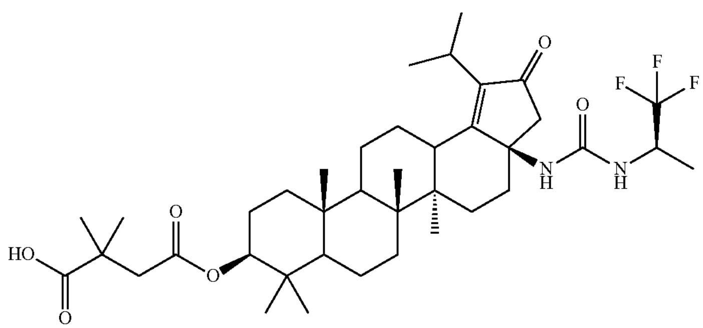 | | +++ | 9.73 (F) | 710.06 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-52 | 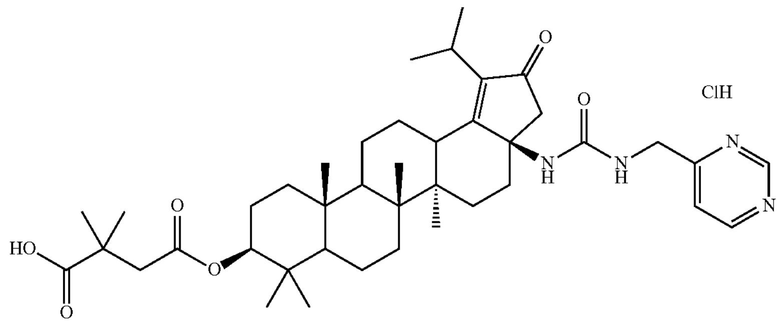 | | +++ | 24.08 (E) | 706.07 |
| 17-53 | 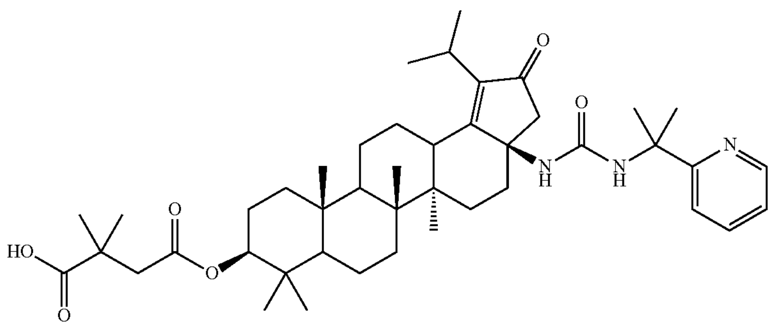 | | +++ | 24.08 (E) | 706.07 |
| 17-54 | 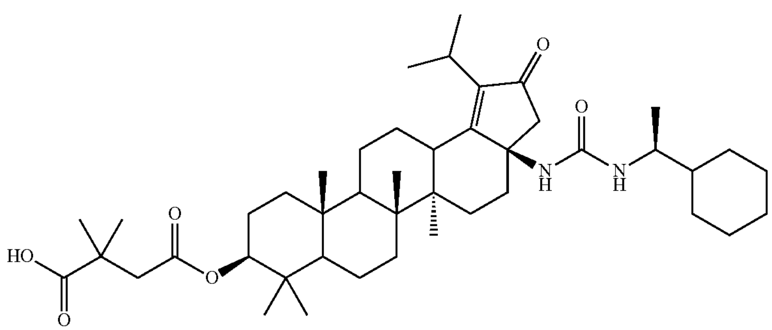 | | +++ | 28.20 (B) | 724.22 |

TABLE 2-continued

| Cpd# | Structure | MT2 (HIV_IIIB) IC50 range | MT2 (HIV_IIIB) with HS 30% IC50 range | $t_R$ (min) (Method) | M+/M + H+ |
|---|---|---|---|---|---|
| 17-55 | 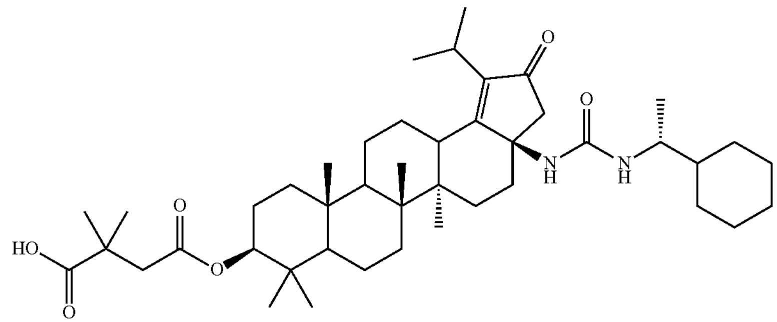 | +++ | | 26.47 (B) | 724.23 |
| 17-56 | 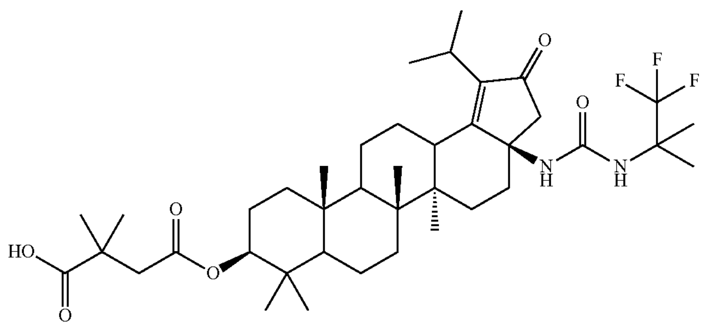 | | +++ | 10.80 (F) | 724.19 |
| 17-57 | 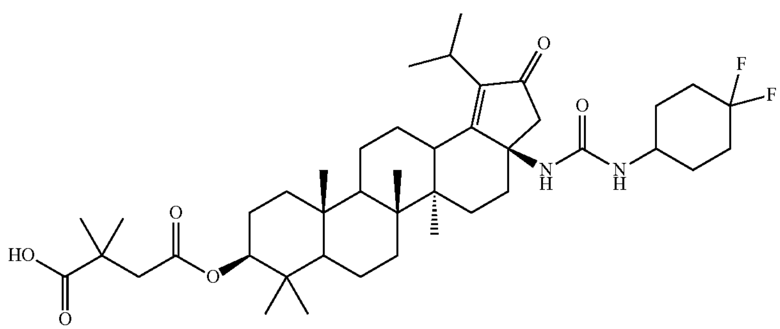 | | +++ | 9.55 (F) | 732.27 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-58 | 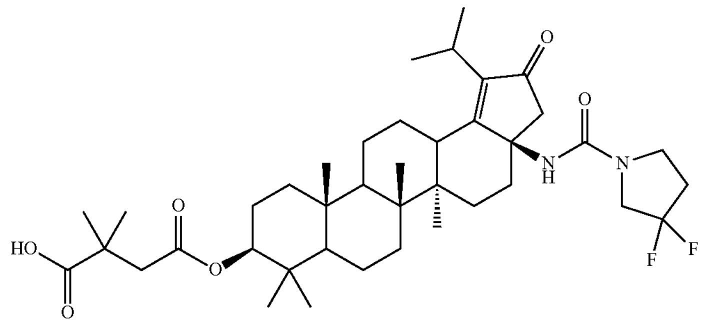 | | +++ | 9.20 (F) | 704.08 |
| 17-59 | 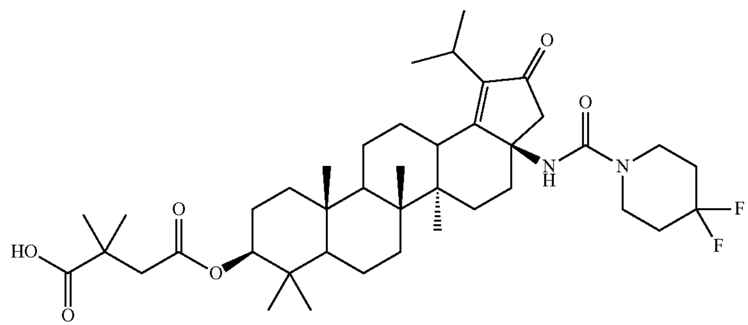 | | +++ | 28.13 (A) | 718.14 |
| 17-60 | 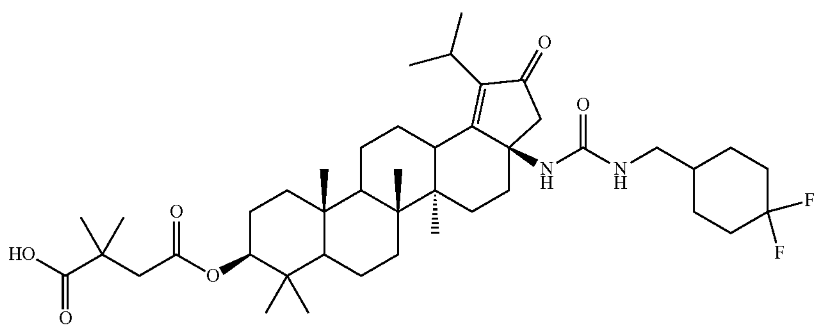 | | +++ | 27.66 (A) | 746.33 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-61 | 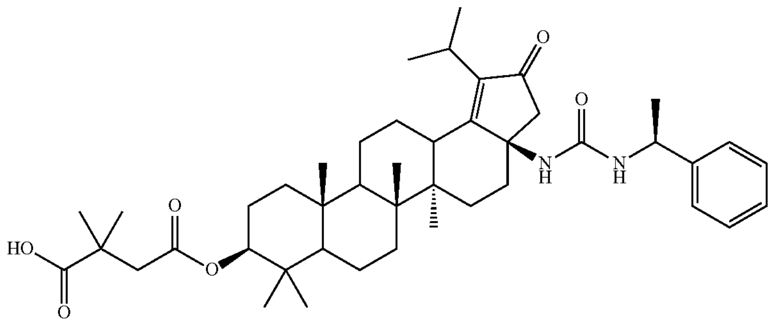 | | +++ | 10.48 (F) | 718.19 |
| 17-62 | 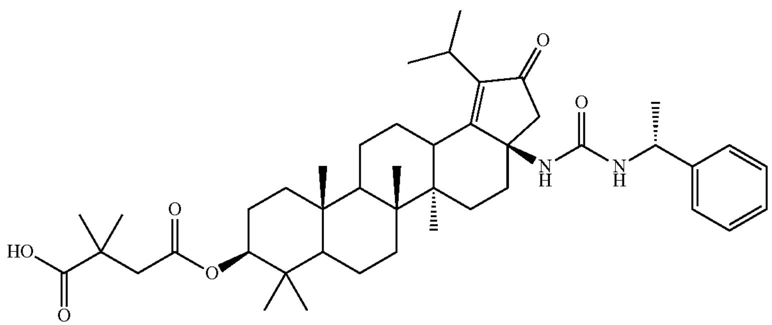 | | +++ | 10.03 (F) | 718.19 |
| 17-63 | 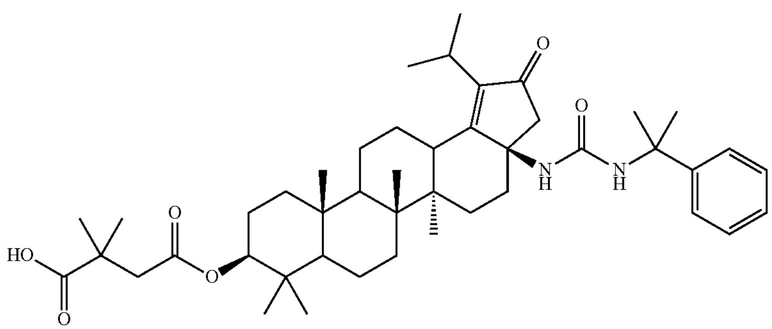 | | +++ | 11.44 (F) | 732.29 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-64 | 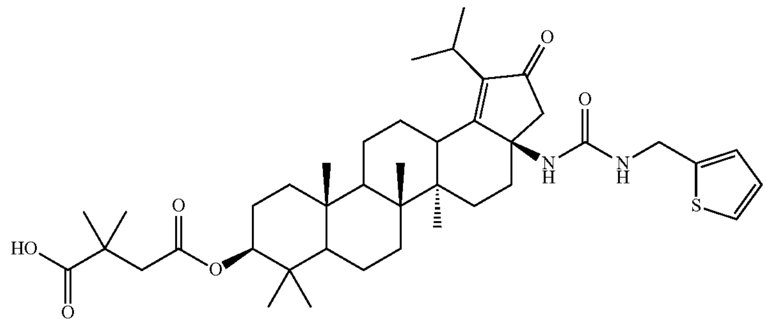 | | +++ | 9.17 (F) | 710.09 |
| 17-65 | 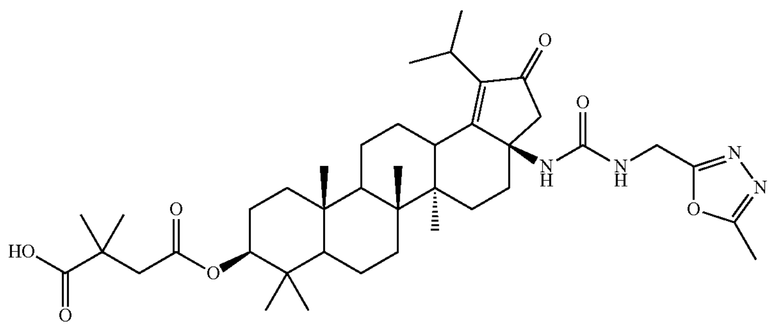 | | +++ | 15.39 (A) | 710.13 |
| 17-66 | 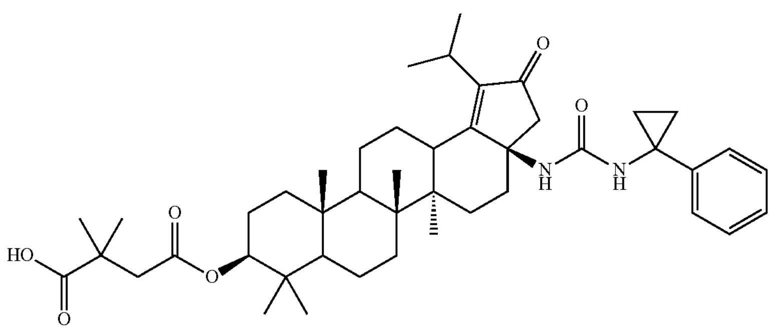 | | +++ | 10.69 (F) | 730.27 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-67 | 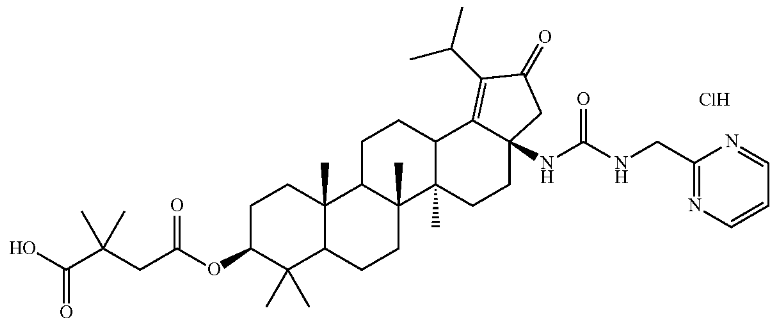 | | +++ | 5.52 (F) | 706.11 |
| 17-68 | 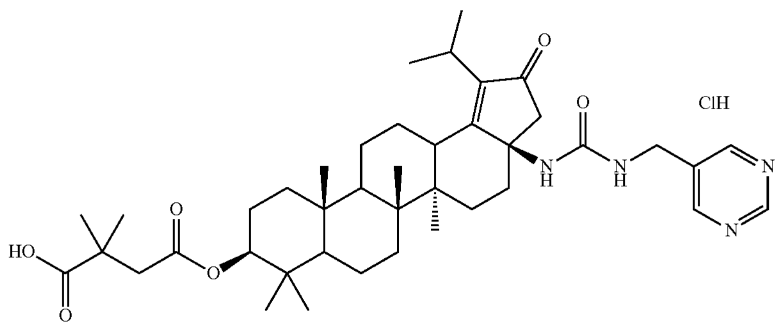 | | +++ | 23.59 (E) | 706.04 |
| 17-69 | 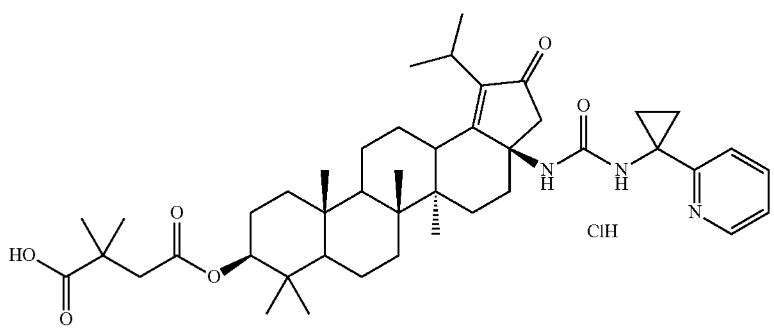 | | +++ | 17.10 (E) | 731.26 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 17-70 | 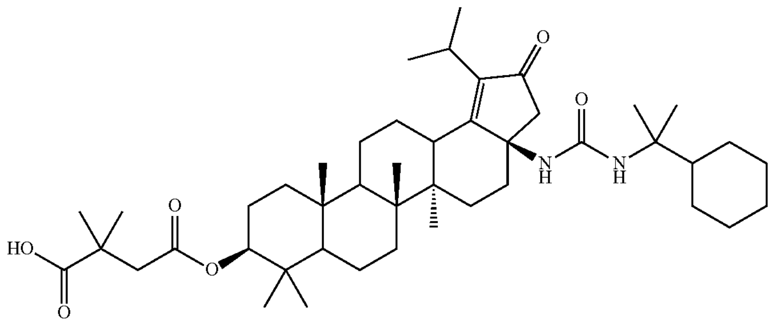 | | + | 31.66 (B) | 738.28 |
| 17-72 | 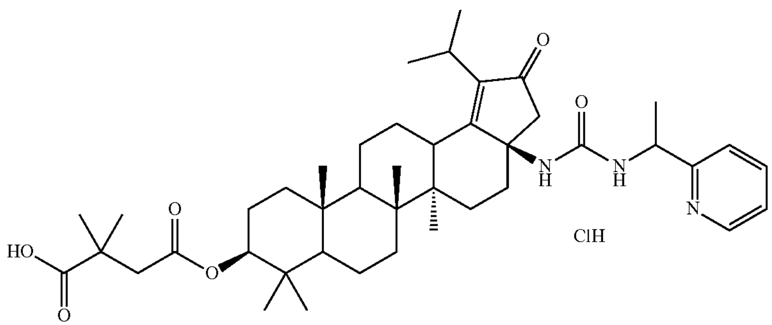 | | +++ | 10.00 (H) | 719.18 |
| 17-73 | 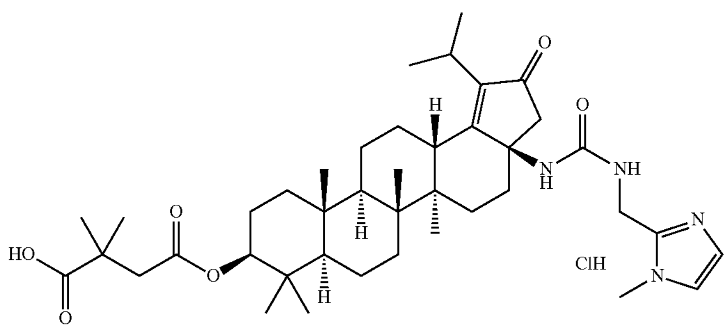 | | +++ | 12.45 (I) | 708.07 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 17-74 | 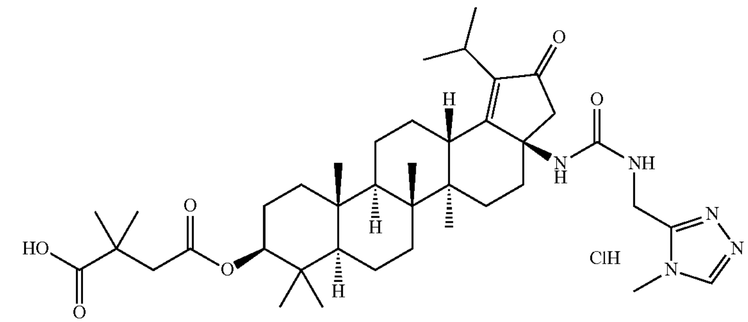 | | + | 10.03 (H) | 709.07 |
| 17-75 | 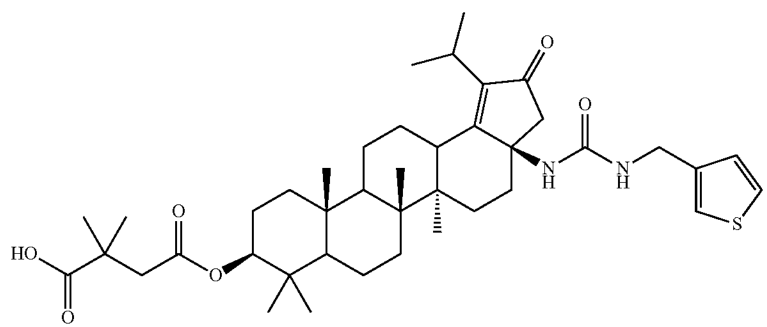 | | +++ | 9.04 (G) | 710.01 |
| 17-76 | 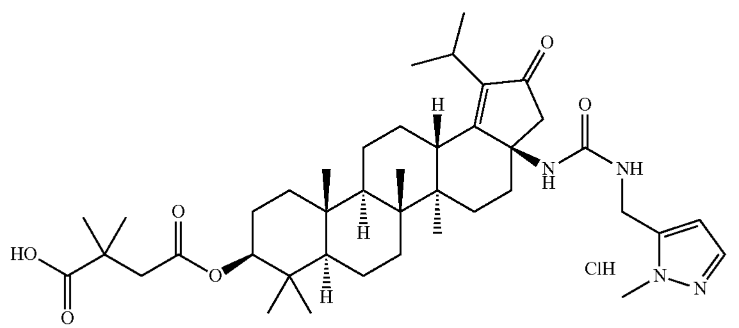 | | +++ | 5.76 (G) | 708.08 |

TABLE 2-continued
| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 18-1 | 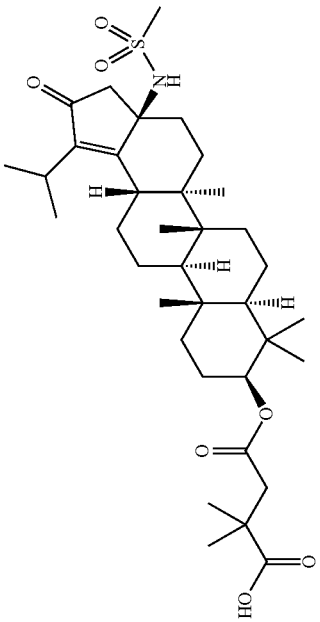 | +++ | +++ | | 648.6 |
| 19-1 | 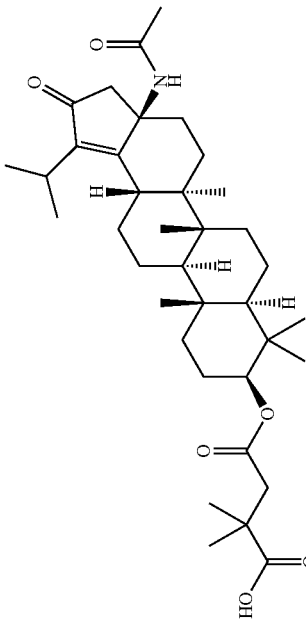 | +++ | +++ | | 612.64 |
| 19-2 | 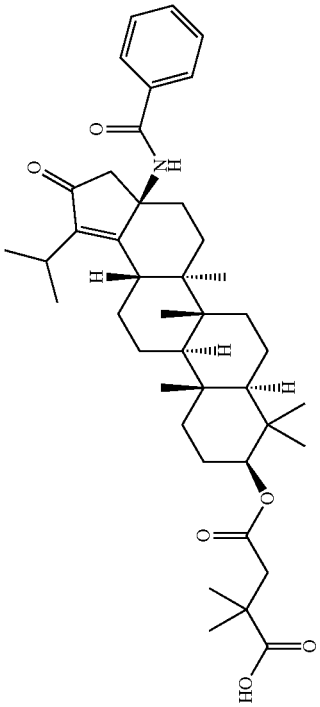 | +++ | +++ | | 674.70 |

TABLE 2-continued

| Cpd# | Structure | MT2 (HIV_IIIB) IC50 range | MT2 (HIV_IIIB) with HS 30% IC50 range | t_R (min) (Method) | M+/M + H+ |
|---|---|---|---|---|---|
| 19-3 | 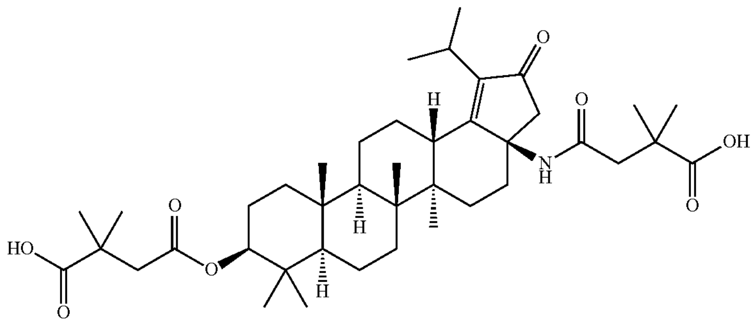 | +++ | | 21.8 (A) | 698.8 |
| 19-4 | 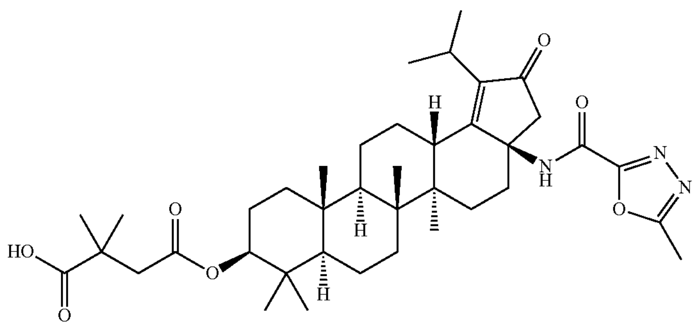 | +++ | +++ | 32.5 (E) | 680.6 |
| 19-5 | 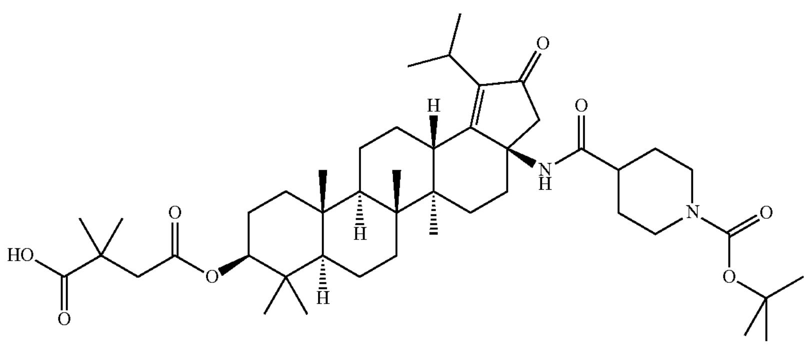 | +++ | +++ | 31.8 (A) | 681.7 (M − Boc) |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-6 | 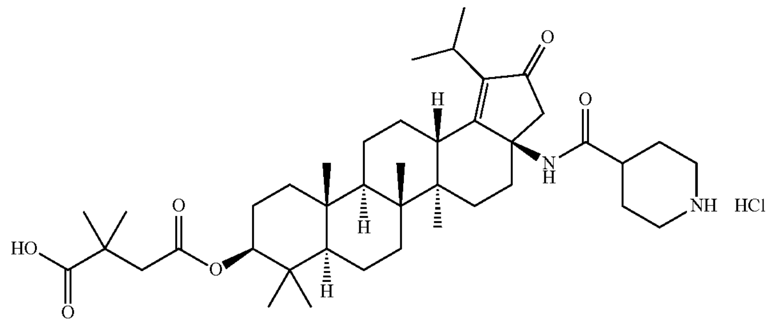 | +++ | + | 26.4 (D) | 681.6 |
| 19-7 | 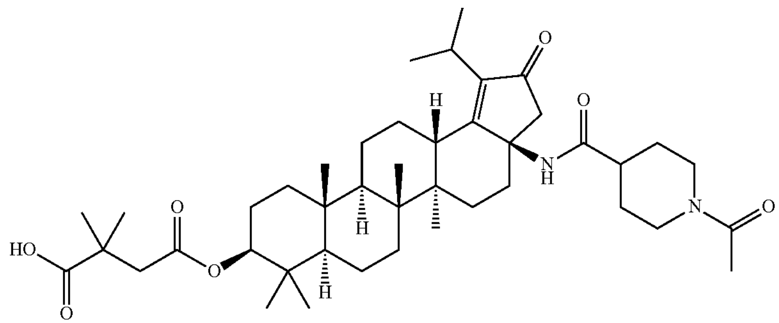 | +++ | +++ | 24.9 (E) | 723.6 |
| 19-8 | 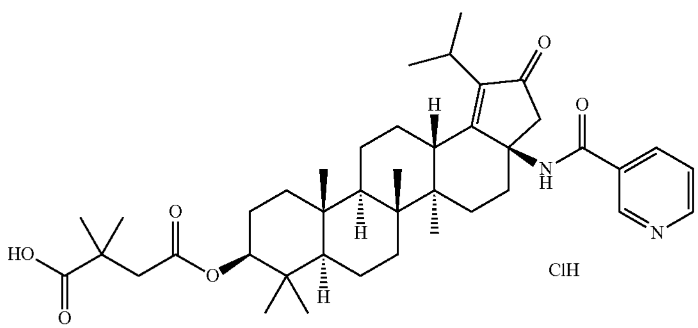 | +++ | +++ | 26.5 (E) | 675.6 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-9 | 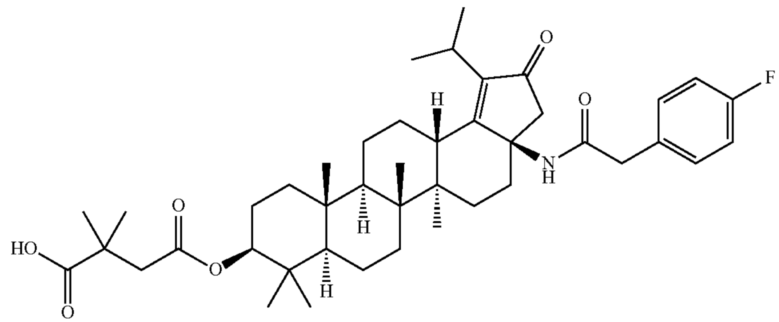 | +++ | +++ | 29.9 (A) | 706.6 |
| 19-10 | 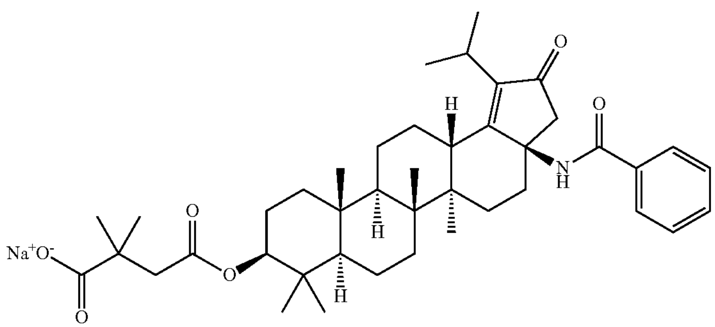 | +++ | +++ | ND | ND |
| 19-11 | 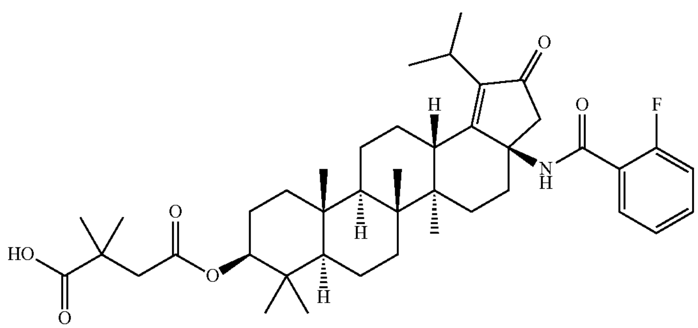 | +++ | +++ | 33.6 (A) | 691.0 (M+) |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-12 | 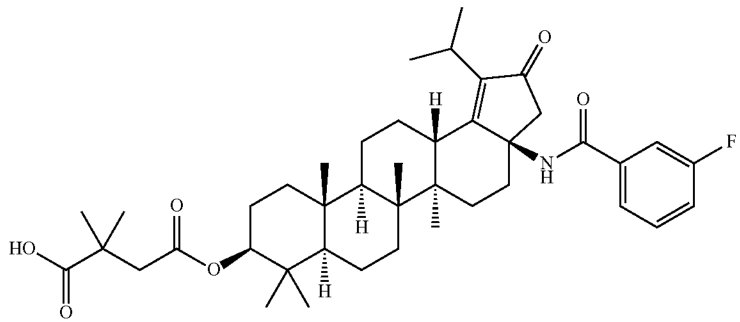 | | +++ | 32.4 (A) | 692.8 |
| 19-13 | 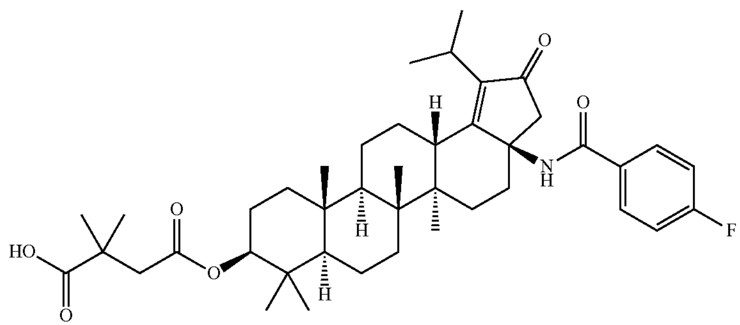 | +++ | +++ | 31.8 (A) | 691.0 (M+) |
| 19-14 | 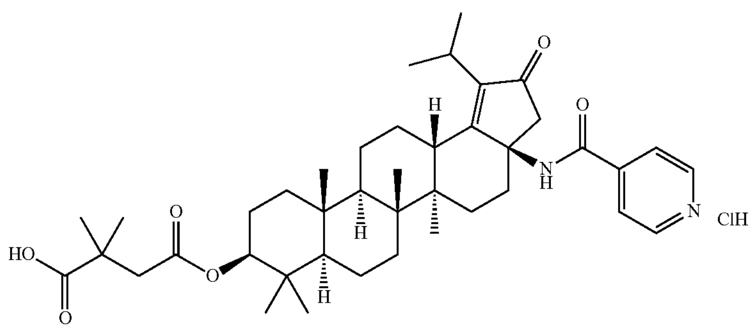 | | +++ | 24.4 (E) | 675.7 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M+/M + H+ |
|---|---|---|---|---|---|
| 19-15 | 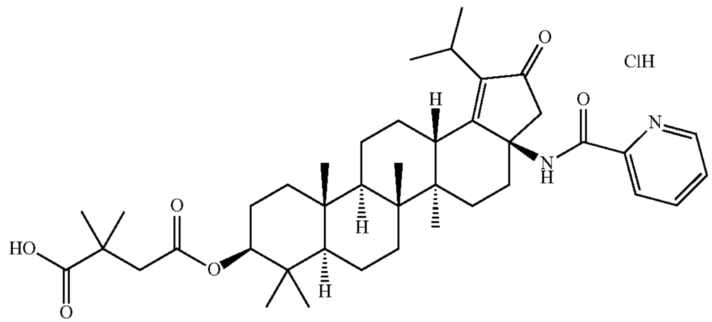 | | +++ | | 675.7 |
| 19-16 | 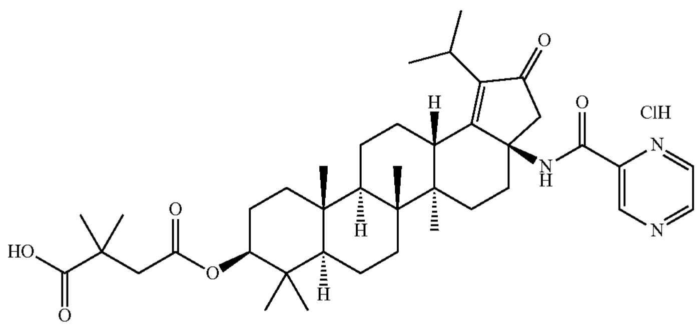 | | +++ | 38.1 (E) | 676.7 |
| 19-17 | 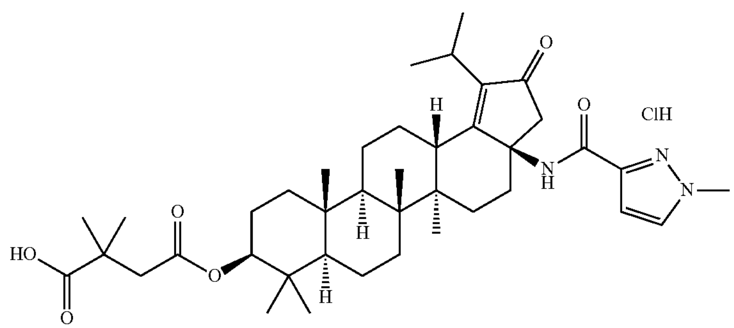 | | +++ | 25.9 (A) | 678.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-18 | 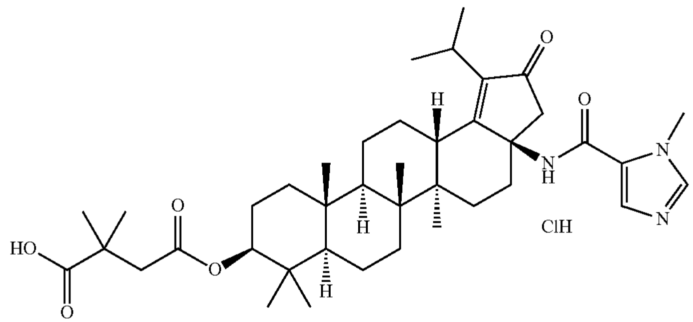 | | +++ | 7.1 (H) | 678.7 |
| 19-19 | 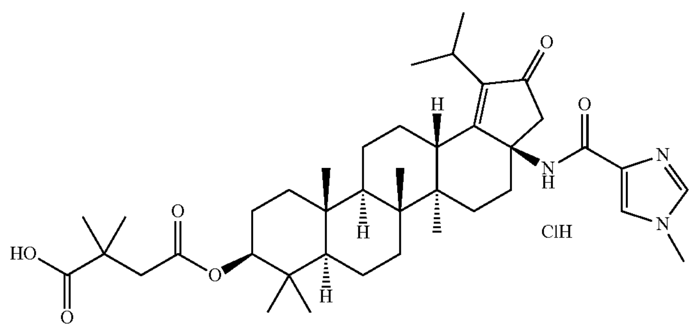 | | +++ | 10.9 (H) | 678.7 |
| 19-20 | 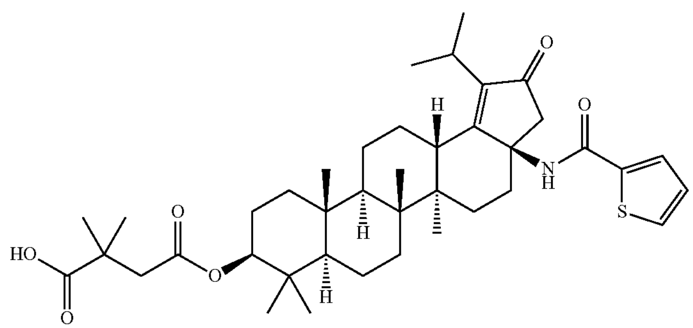 | | +++ | 30.2 (A) | 680.7 |

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-21 | 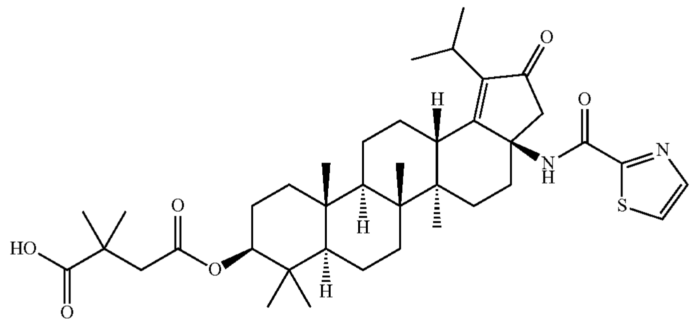 | +++ | +++ | 32.7 (A) | 681.7 |
| 19-22 | ClH | | +++ | 32.2 (E) | 676.7 |
| 19-23 | 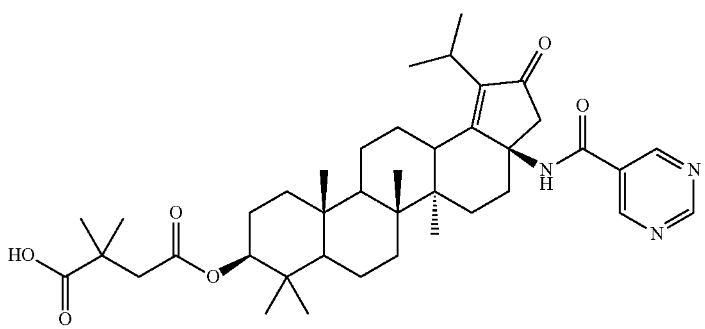 | | +++ | 30.0 (E) | 676.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-24 | 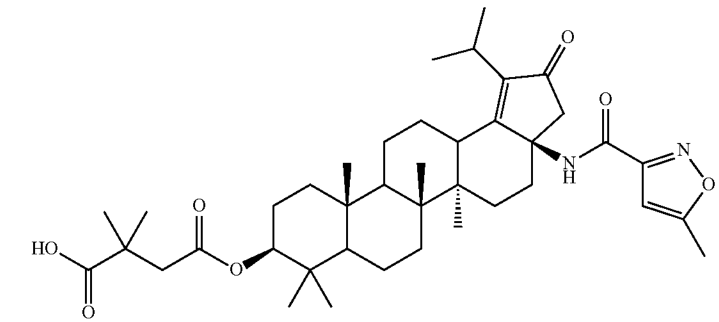 | +++ | +++ | 31.5 (A) | 679.8 |
| 19-25 | 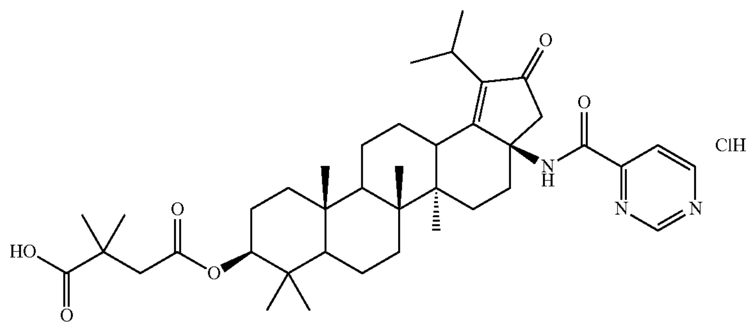 | | +++ | 38.6 (E) | 676.8 |
| 19-26 | 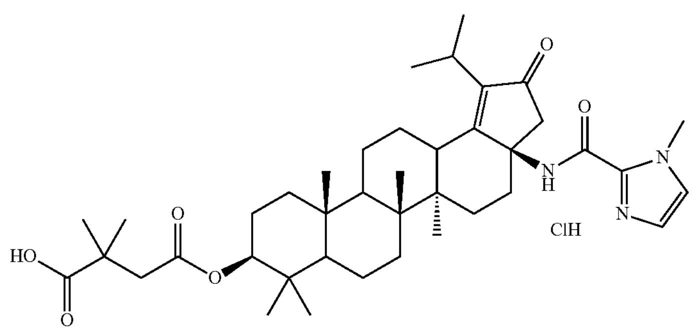 | | +++ | 35.5 (E) | 678.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-27 | 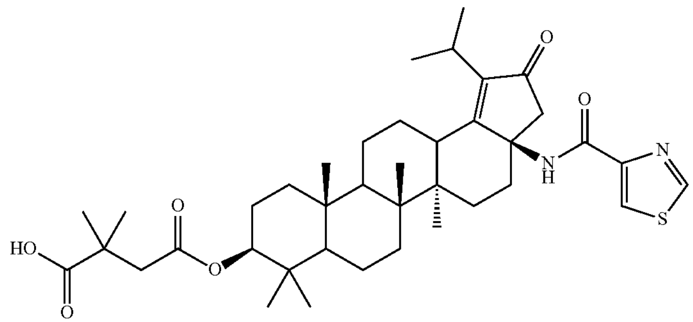 | | +++ | 30.6 (A) | 681.7 |
| 19-28 | 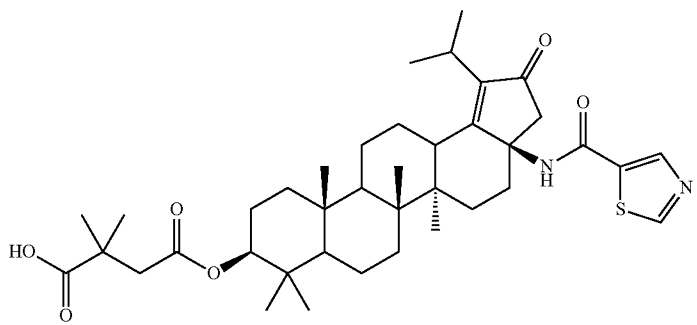 | | +++ | 23.9 (A) | 681.7 |
| 19-29 | 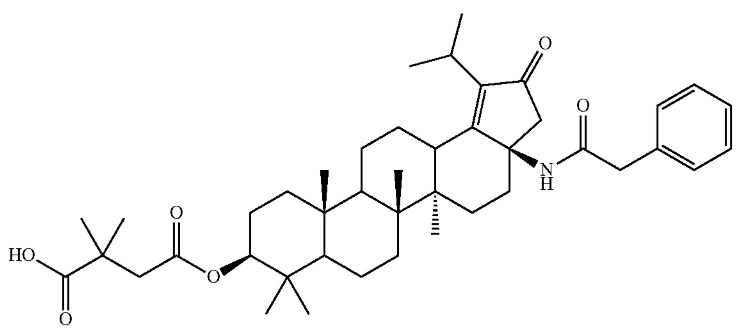 | | +++ | 30.8 (A) | 688.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-30 | 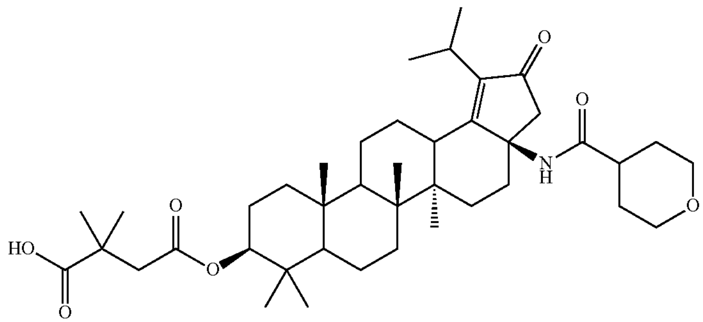 | | +++ | — | 682.84 |
| 19-31 | 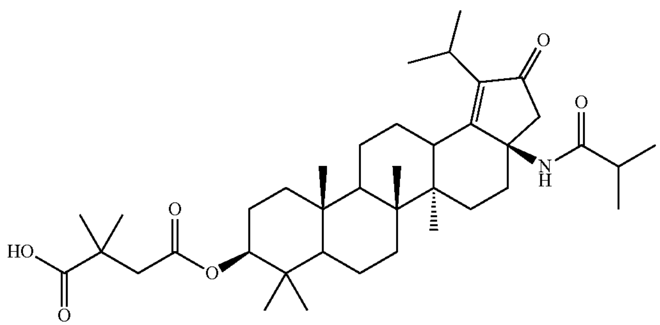 | | +++ | 8.32 (F) | 640.5 |
| 19-32 | 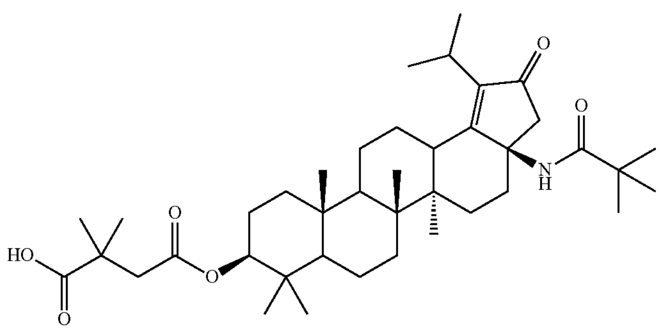 | | +++ | 9.47 (F) | 654.2 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M+/M + H+ |
|---|---|---|---|---|---|
| 19-33 | 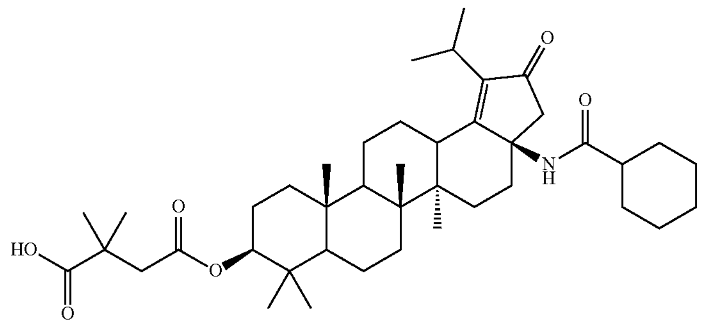 | +++ | +++ | 10.37 (F) | 680.75 |
| 19-34 | 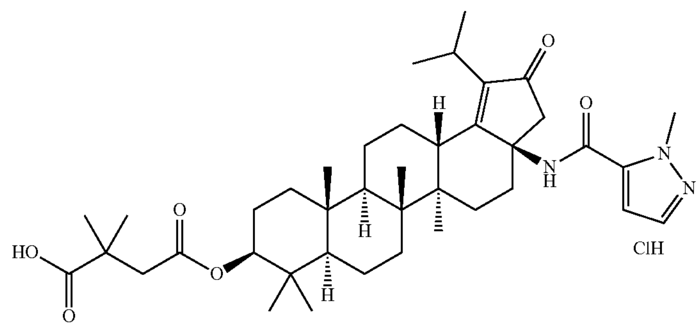 | +++ | +++ | 35.3 (E) | 678.7 |
| 19-35 | 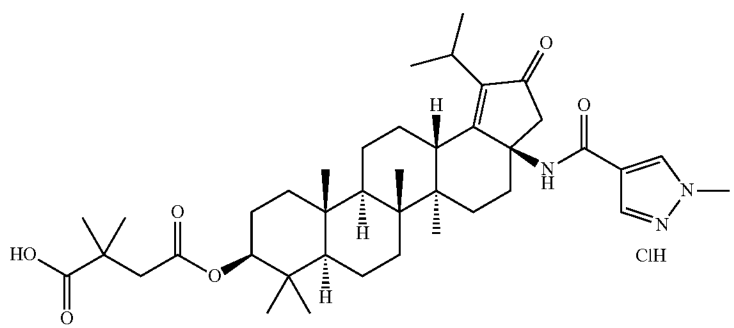 | +++ | +++ | 28.3 (E) | 678.7 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-36 | 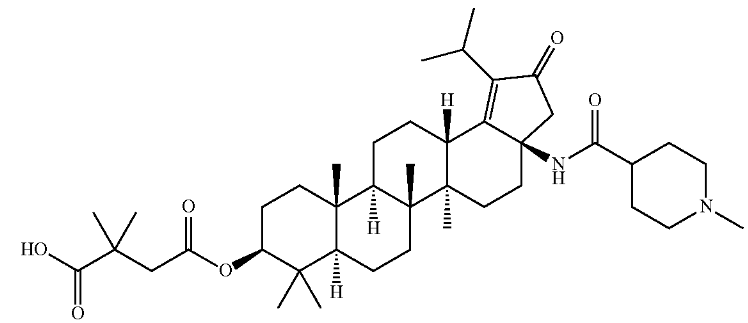 | | +++ | 27.2 (D) | 695.8 |
| 19-37 | 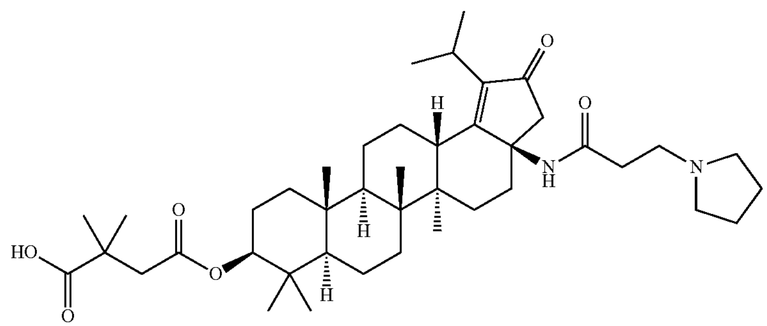 | | +++ | 28.7 (D) | 695.8 |
| 19-38 | 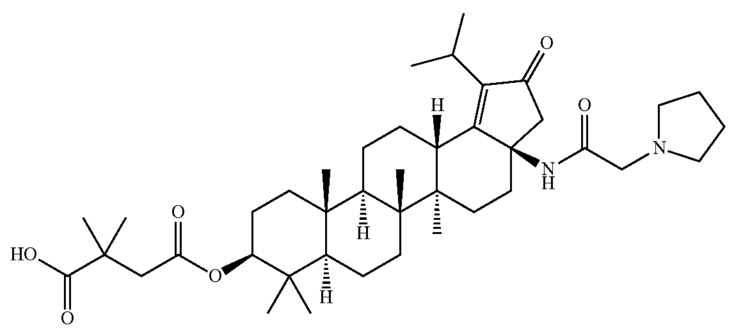 | | +++ | 19.0 (C) | 681.7 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-39 | 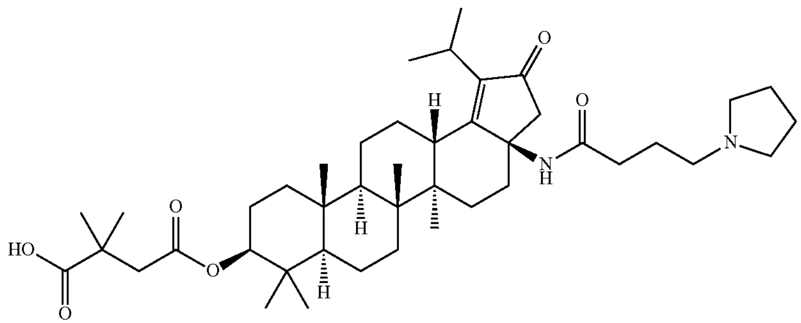 | | +++ | 19.2 (C) | 709.9 |
| 19-40 | 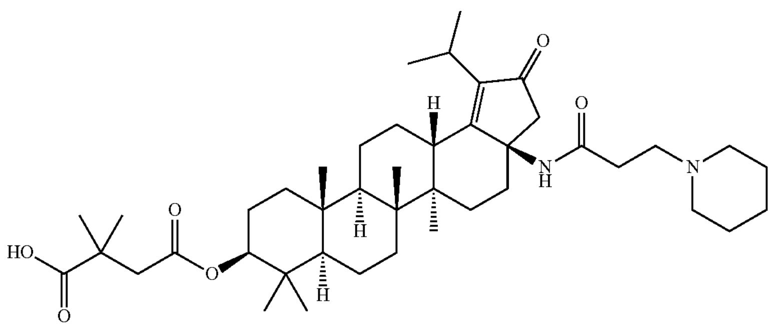 | | +++ | 20.2 (C) | 709.9 |
| 19-41 | 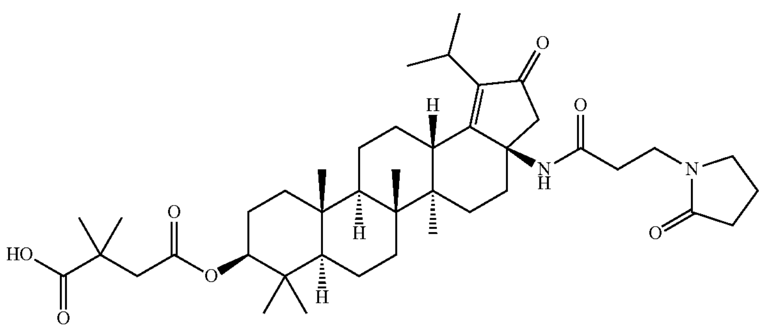 | | +++ | 11.2 (H) | 709.9 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-42 | 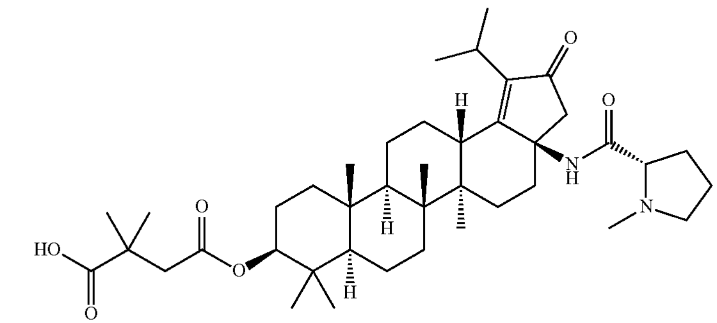 | | +++ | 18.0 (C) | 681.7 |
| 19-43 | 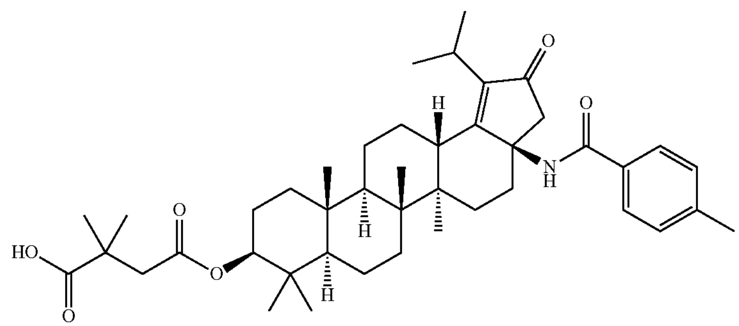 | | +++ | 33.7 (A) | 688.4 |
| 19-44 | 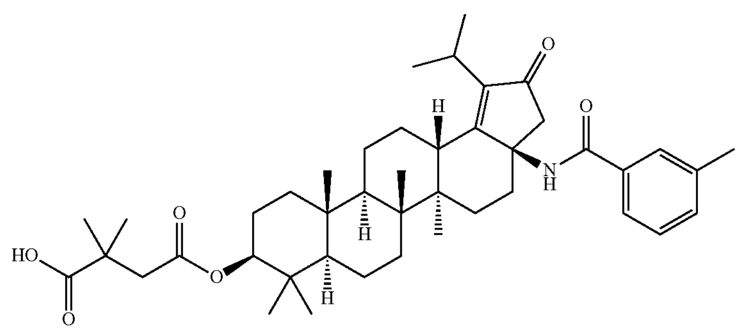 | | +++ | 24.6 (B) | 688.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-45 | 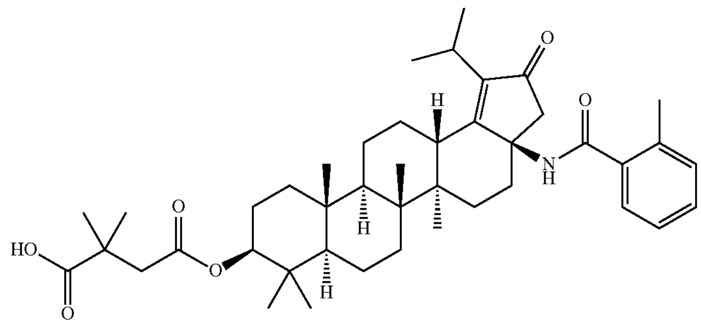 | | +++ | 32.4 (A) | 688.8 |
| 19-46 | 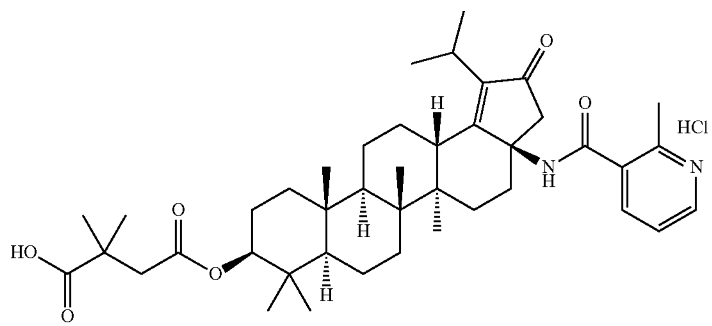 | | +++ | 9.2 (A) | 689.8 |
| 19-47 | 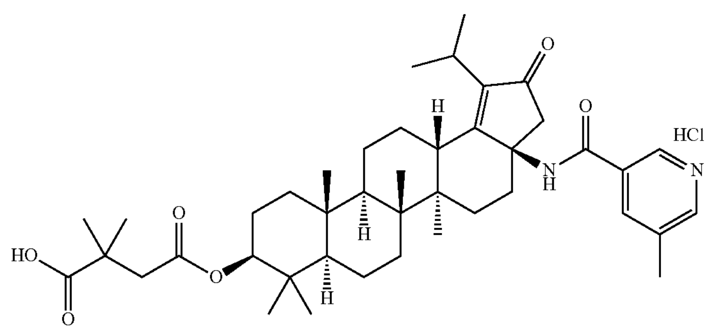 | | +++ | 25.4 (E) | 689.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M+/M + H+ |
|---|---|---|---|---|---|
| 19-48 | 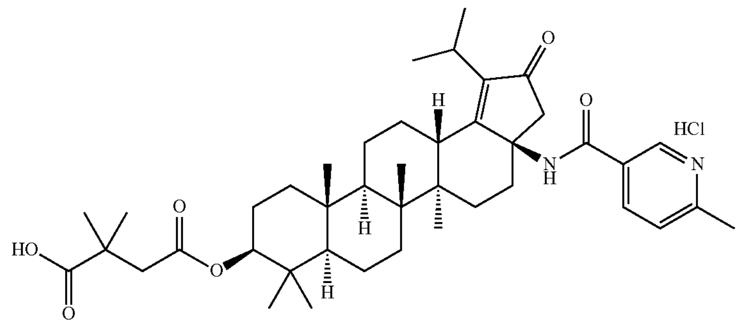 | | +++ | 21.4 (E) | 689.7 |
| 19-49 | 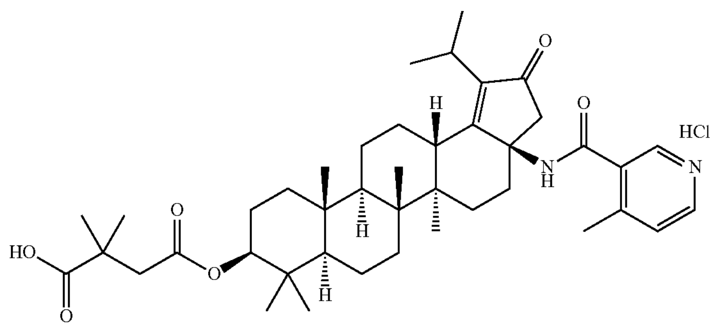 | | +++ | 19.6 (E) | 689.9 |
| 19-50 | 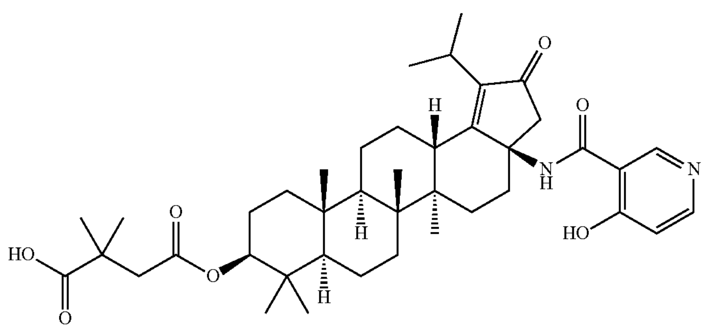 | | +++ | 25.4 (E) | 691.9 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 19-51 | 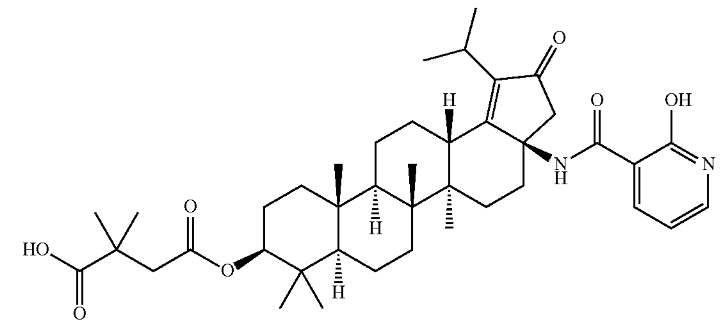 | | +++ | 29.0 (E) | 691.9 |
| 19-52 | 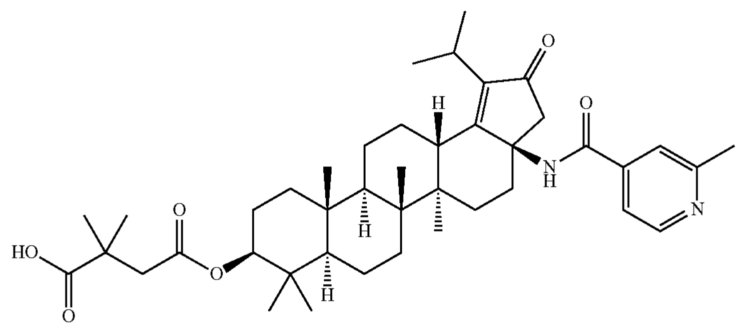 | | +++ | 18.4 (E) | 689.9 |
| 19-53 | 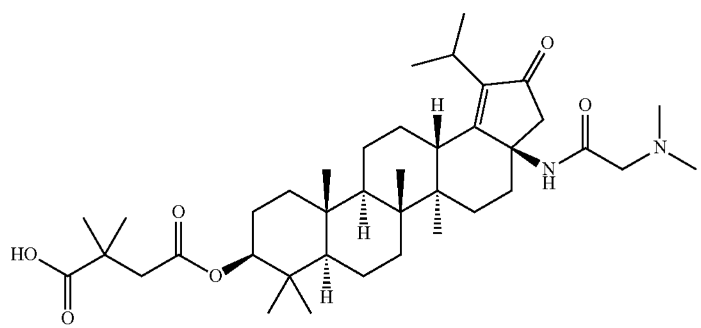 | | +++ | 27.1 (D) | 655.8 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-54 | 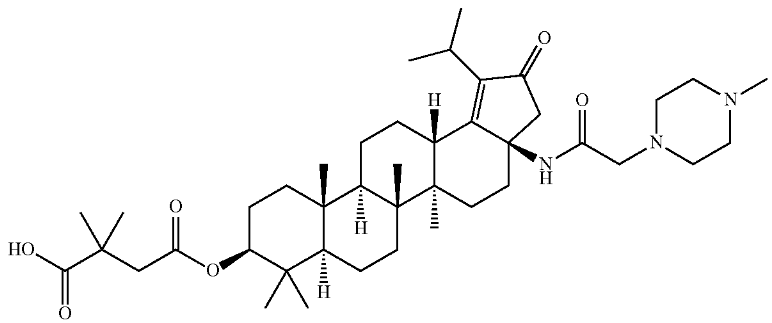 | | +++ | 26.5 (D) | 711.1 |
| 19-55 | 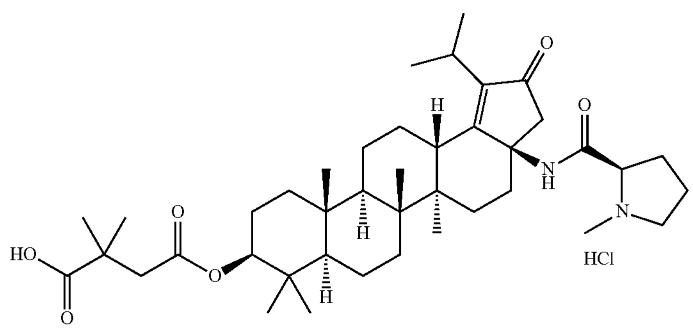 | | +++ | 8.2 (H) | 681.9 |
| 19-56 | 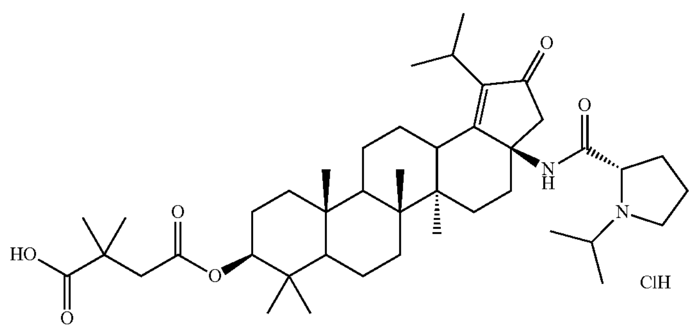 | | +++ | 7.92 (H) | 701.09 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-57 | 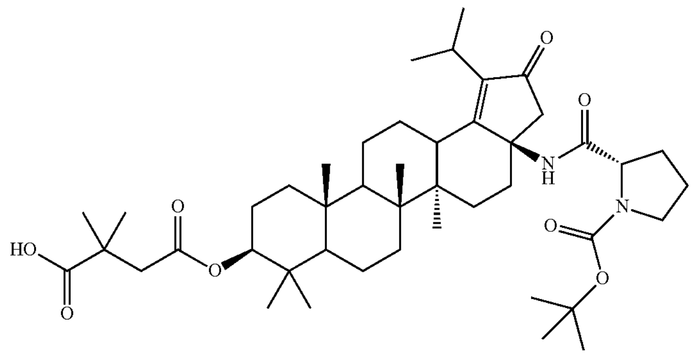 | | +++ | 32.08 (A) | 667.71 (M − Boc) |
| 19-58 | 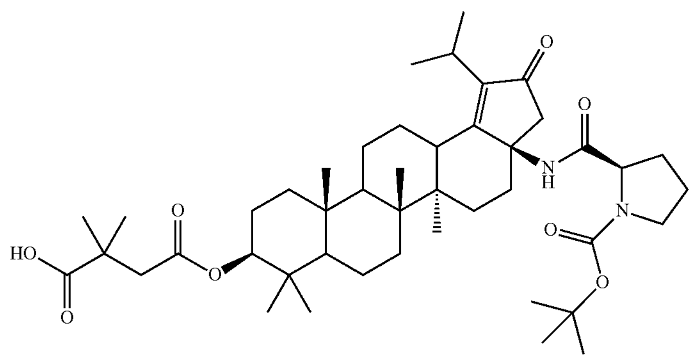 | | +++ | 33.66 (A) | 667.75 (M − Boc) |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 19-59 | 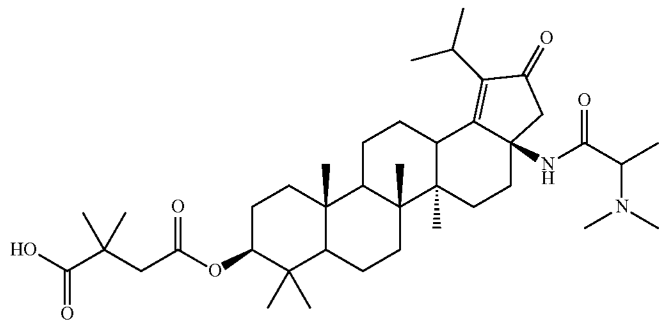 | | +++ | 17.64 and 18.01 (C) | 669.86 |
| 19-60 | 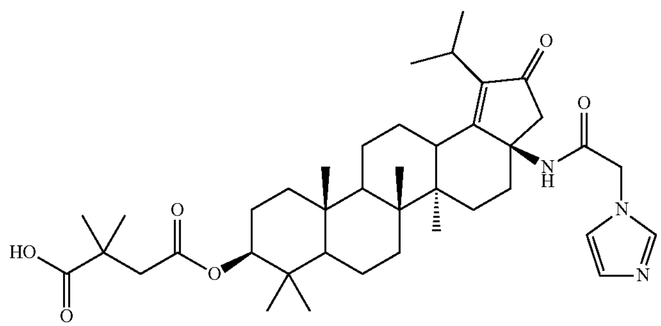 | | +++ | 17.92 (C) | 678.87 |
| 19-61 | 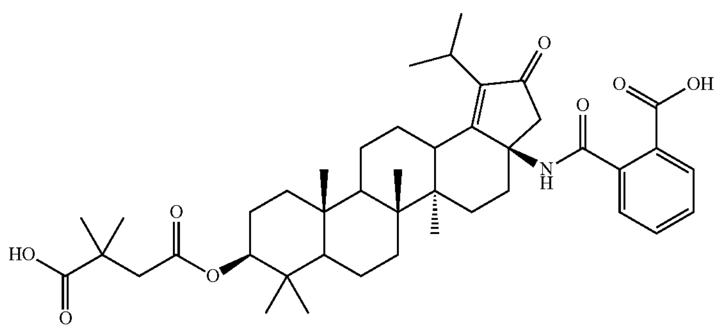 | | +++ | — | 718.98 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-62 | 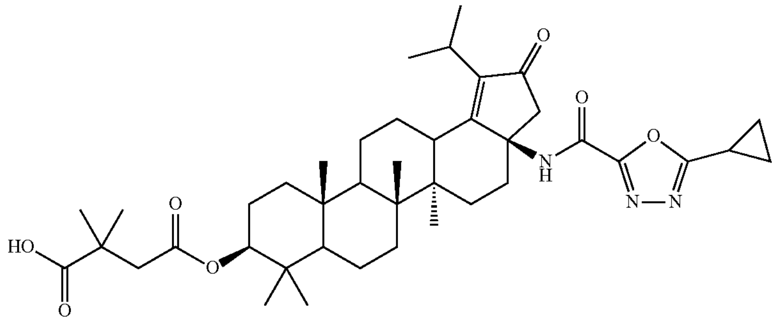 | | +++ | — | 707.09 |
| 19-63 | 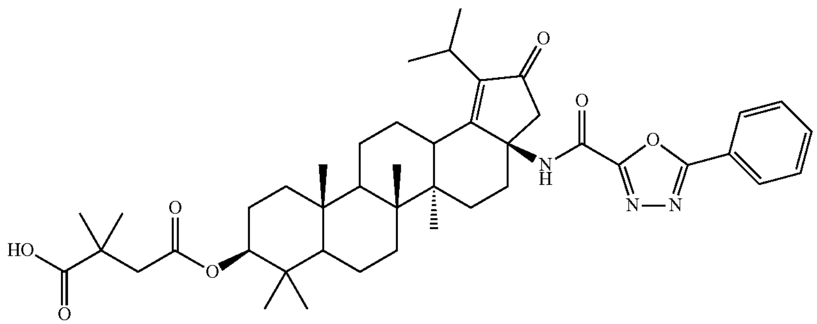 | | +++ | — | 743.31 |
| 19-64 | 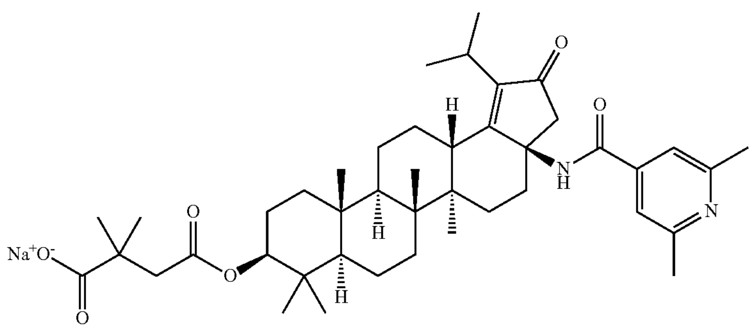 | | +++ | 23.49 (C) | 704.06 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 19-65 | 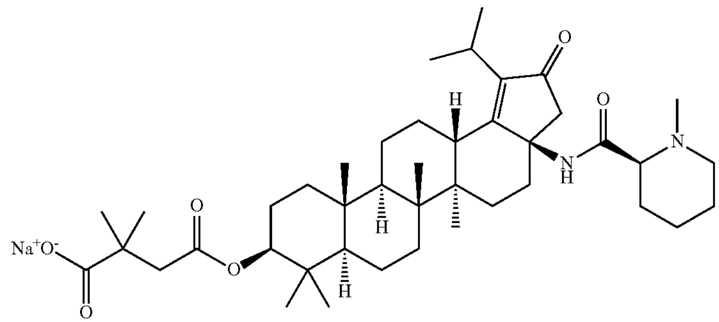 | | +++ | 28.56 (D) | 696.06 |
| 19-66 | 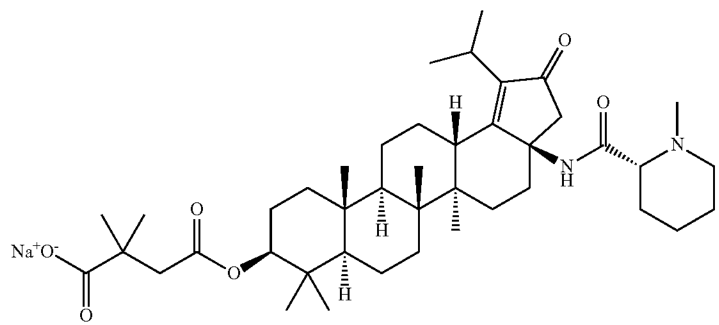 | | +++ | 27.96 (D) | 696.06 |
| 19-67 | 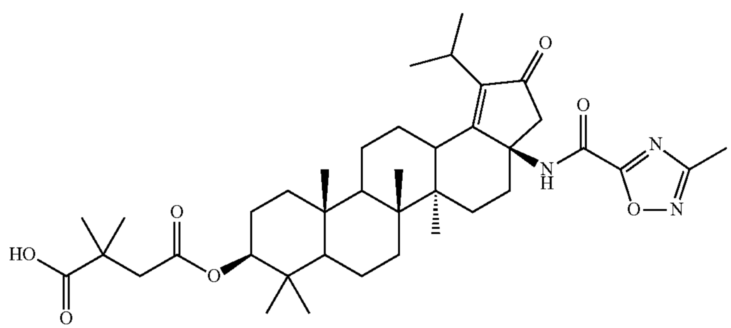 | | +++ | 27.57 (A) | 680.9 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M+/M + H+ |
|---|---|---|---|---|---|
| 19-68 | 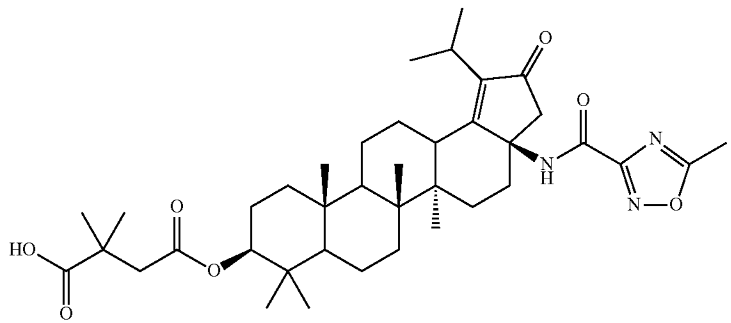 | | +++ | 25.38 (A) | 680.9 |
| 19-69 | 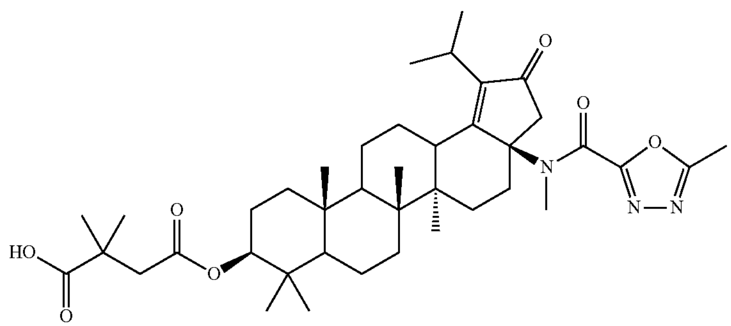 | | +++ | 24.93 (A) | 694.9 |
| 19-70 | 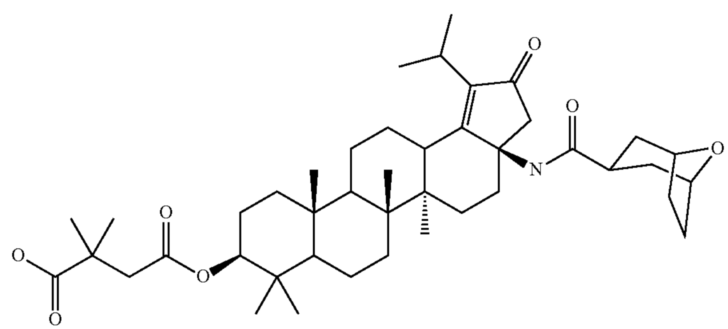 | | +++ | 26.87 (A) | 709.15 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 19-71 | 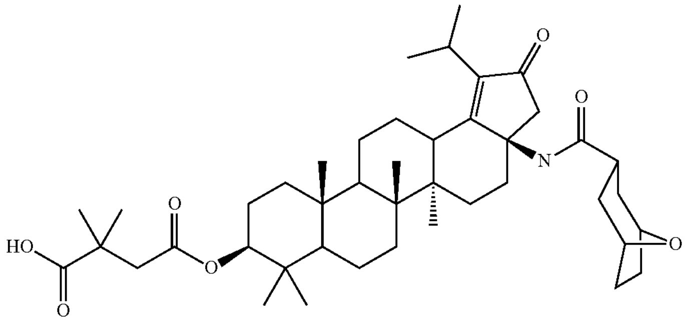 | | +++ | 26.06 (A) | 709.15 |
| 19-72 | 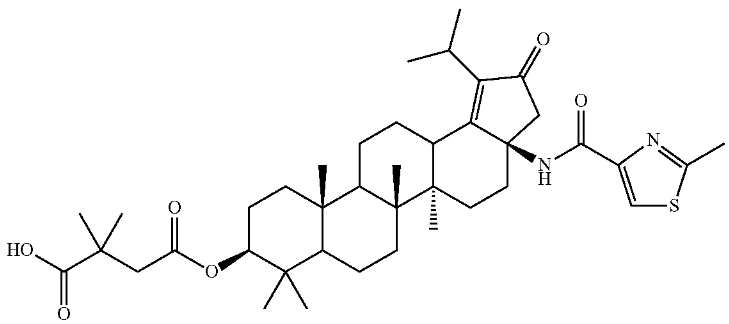 | | +++ | 34.2 (A) | 696.0 |
| 19-73 | HCl | | +++ | 17.28 (C) | 667.93 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 19-74 | 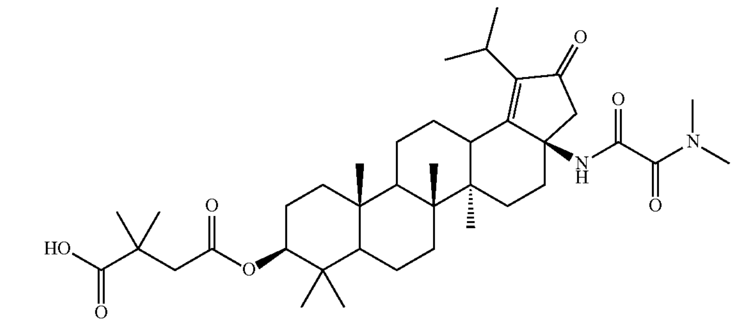 | +++ | | 20.9 (A) | 669.9 |
| 19-75 | 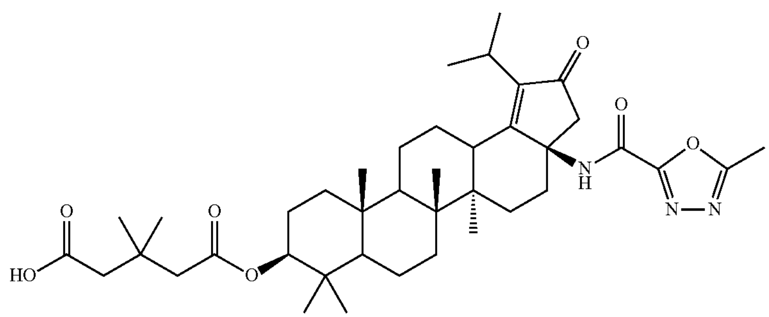 | +++ | | 25.0 (A) | 695.0 |
| 19-76 | 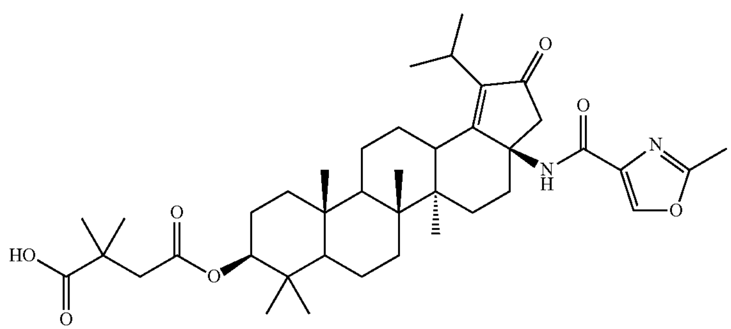 | +++ | | 9.68 (F) | 679.9 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M+/M + H+ |
|---|---|---|---|---|---|
| 19-77 | 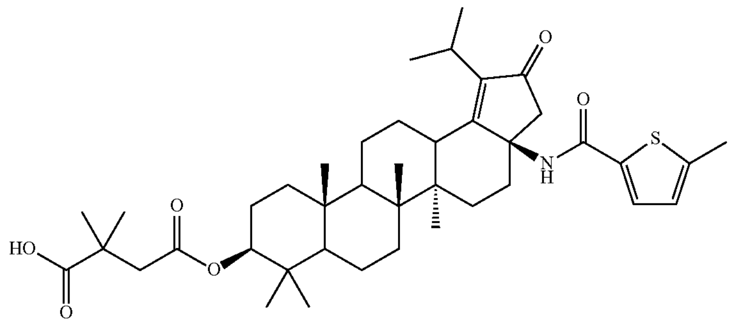 | | +++ | 9.07 (F) | 695.0 |
| 19-78 | 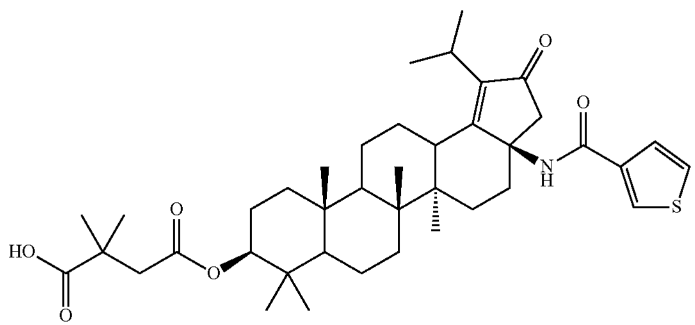 | | +++ | 29.3 (A) | 680.9 |
| 19-79 | 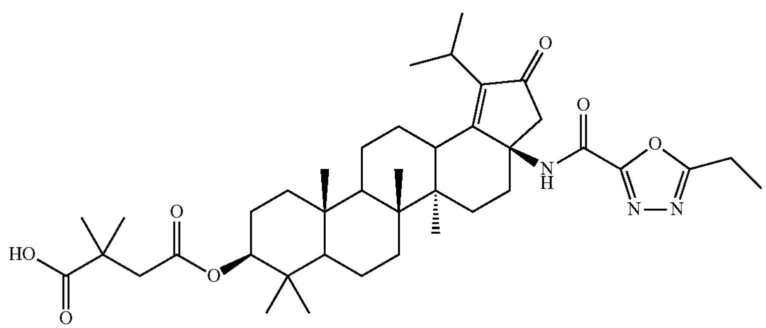 | | +++ | 25.9 (A) | 695.0 |

TABLE 2-continued

| Cpd# | Structure | MT2 (HIV_IIIB) IC50 range | MT2 (HIV_IIIB) with HS 30% IC50 range | t_R (min) (Method) | M+/M + H+ |
|---|---|---|---|---|---|
| 19-80 | 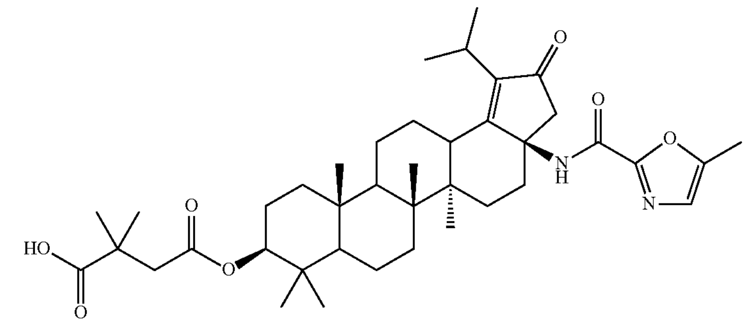 | | +++ | 38.1 (E) | 679.9 |
| 19-81 | 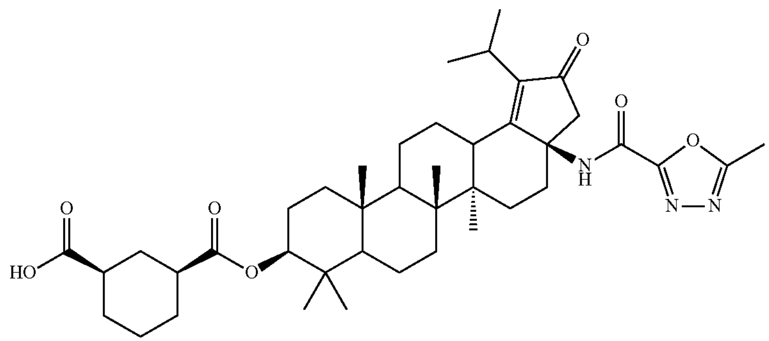 | | ++ | — | 706.96 |
| 19-82 | 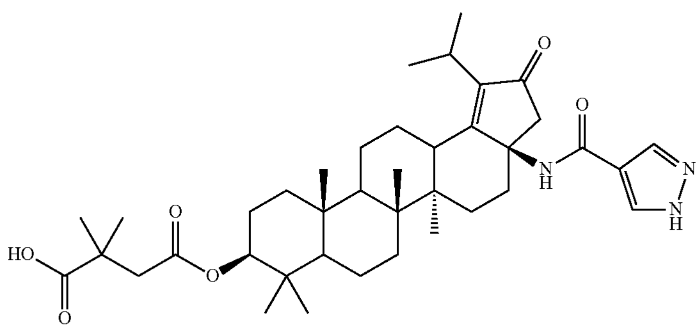 | | +++ | 24.12 (E) | 664.82 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 19-84 | 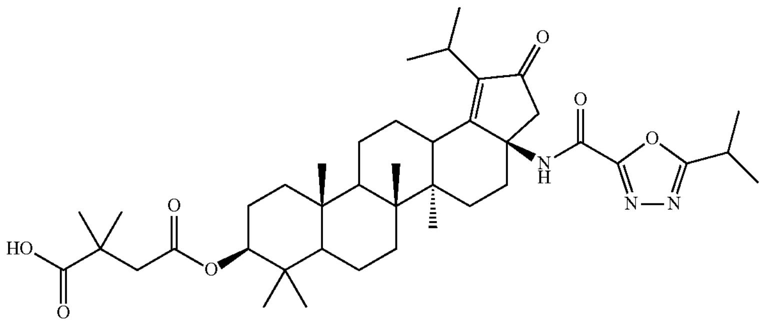 | | +++ | 10.40 (F) | 709.07 |
| 20-1 | 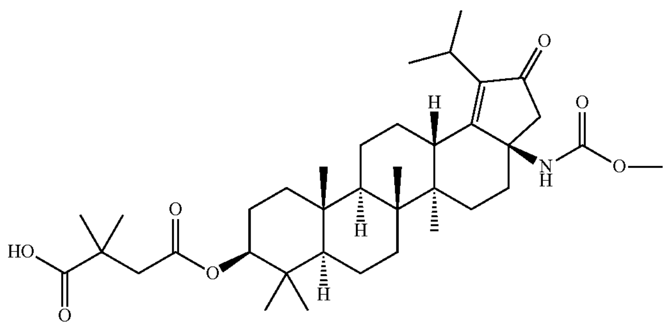 | +++ | +++ | | 628.64 |
| 20-2 | 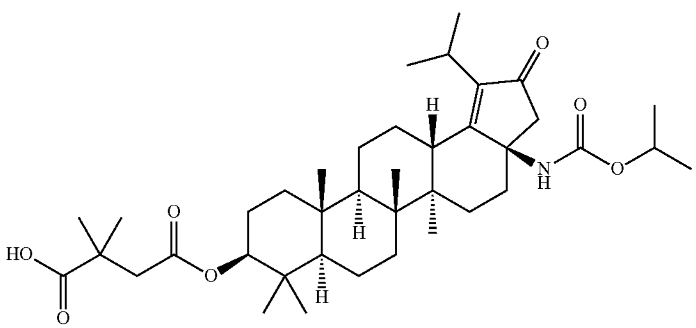 | +++ | +++ | 33.3 (A) | 656.6 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 20-3 | 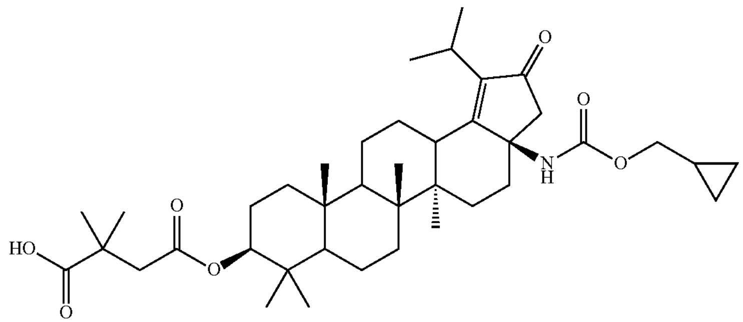 | +++ | +++ | | 668.73 |
| 20-4 | 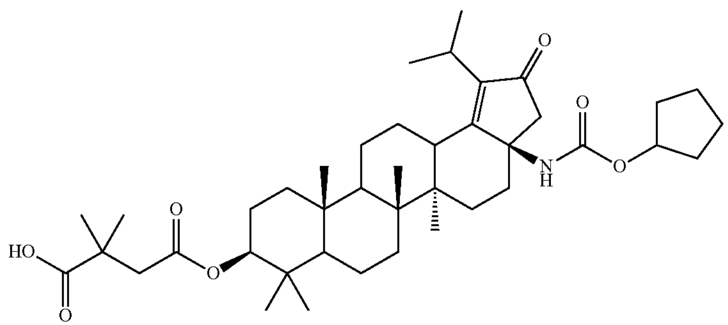 | | +++ | | 682.83 |
| 20-5 | 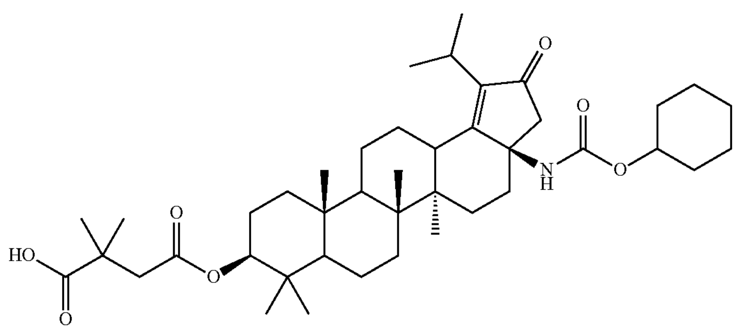 | | +++ | | 696.93 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 20-6 | 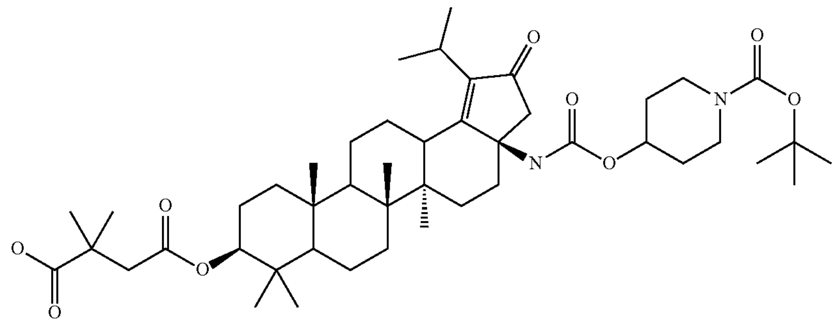 | +++ | +++ | | 798.50 |
| 20-7 | 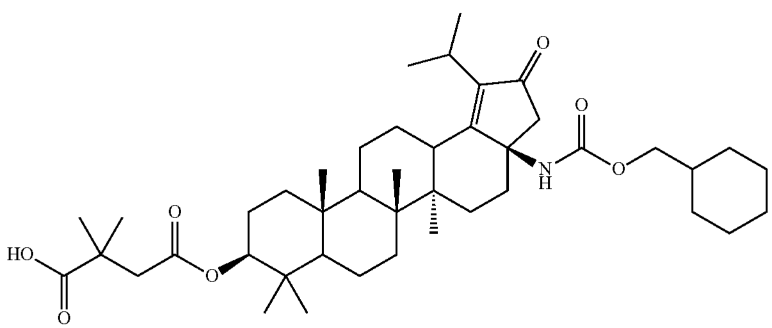 | +++ | +++ | | 711.03 |
| 20-8 | 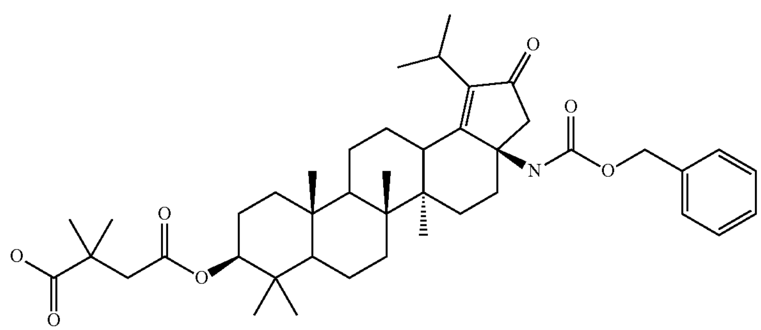 | +++ | +++ | | 704.92 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 20-9 | 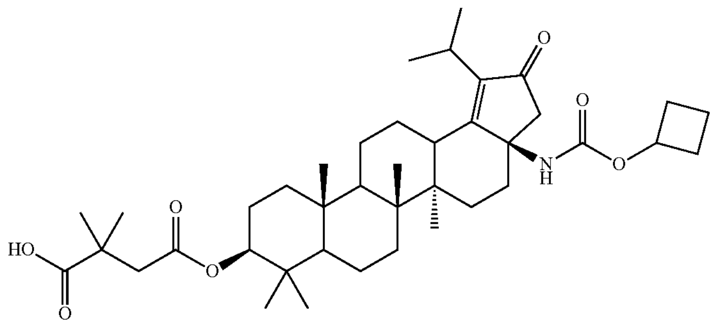 | | +++ | — | 668.65 |
| 20-10 | 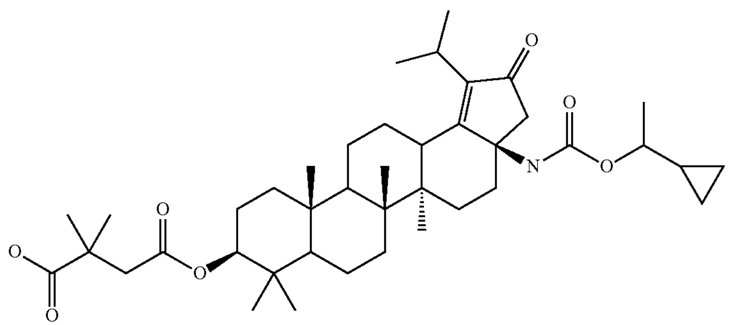 | | +++ | 13.84 (I) | 682.5 |
| 20-11 | 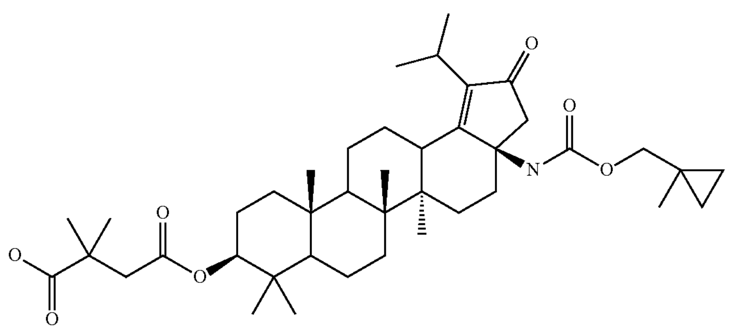 | | +++ | — | 682.79 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 20-12 | 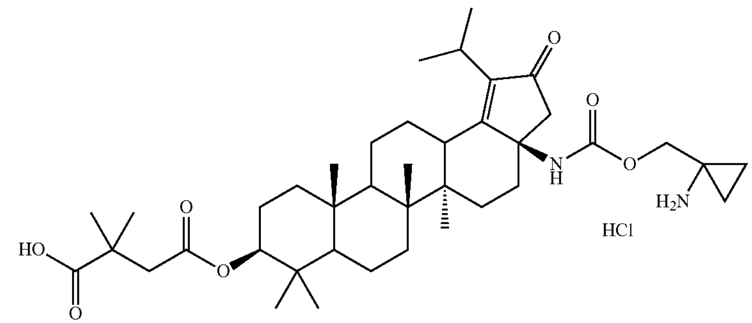 | +++ | +++ | 12.32 (G) | 683-5 |
| 20-13 | 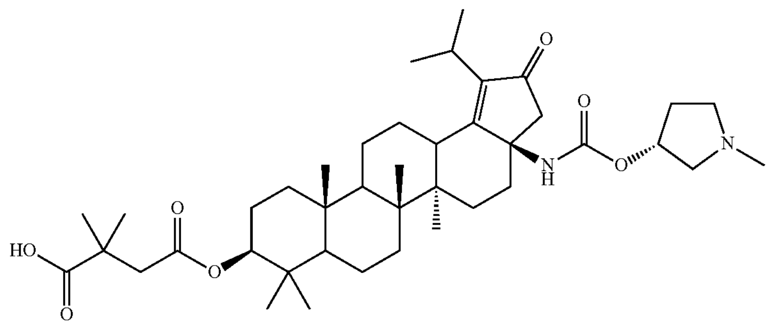 | +++ | +++ | 29.0 (E) | 697.91 |
| 20-14 | 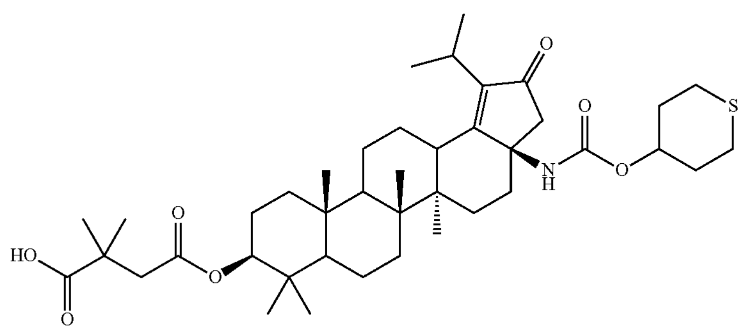 | +++ | +++ | — | 714.87 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 20-15 | 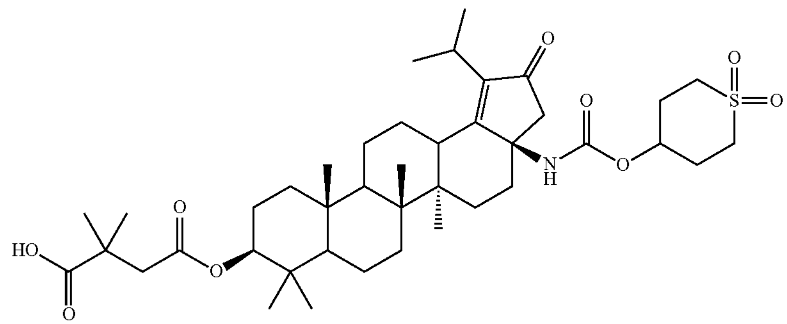 | | +++ | 6.53 (F) | 747.17 |
| 20-16 | 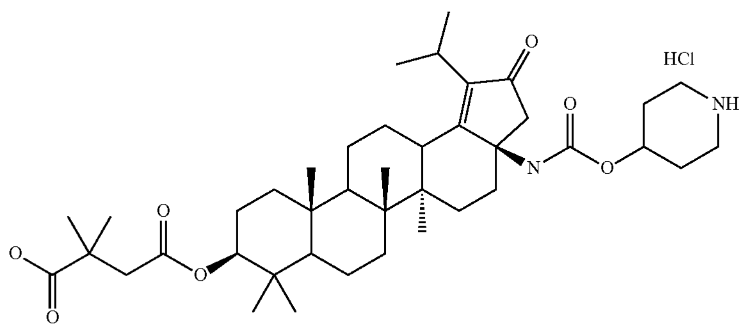 | | +++ | 12.03 (G) | 697.8 |
| 20-17 | 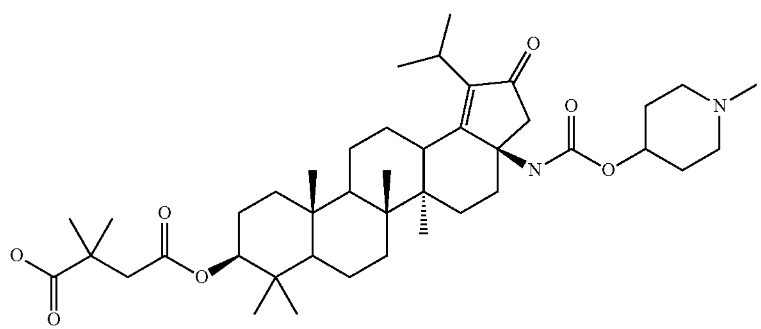 | | +++ | 12.32 (G) | 711.93 |

TABLE 2-continued

| Cpd# | Structure | MT2 (HIV$_{IIIB}$) IC50 range | MT2 (HIV$_{IIIB}$) with HS 30% IC50 range | $t_R$ (min) (Method) | M$^+$/M + H$^+$ |
|---|---|---|---|---|---|
| 20-18 | 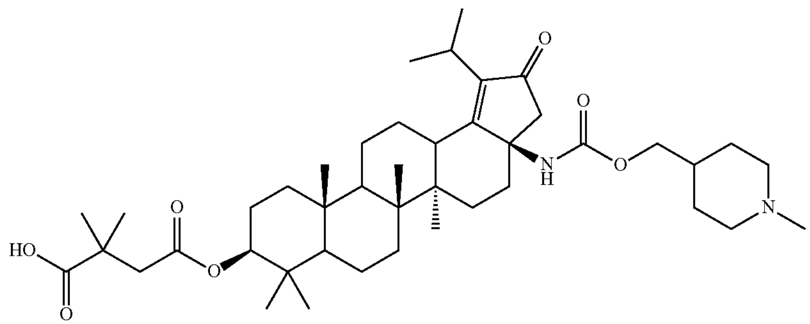 | | +++ | 19.87 (C) | 726.13 |
| 20-19 | 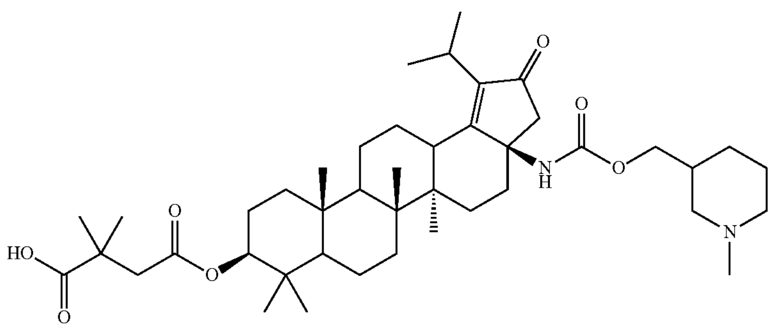 | | +++ | 19.43 (C) | 726.12 |
| 20-20 | 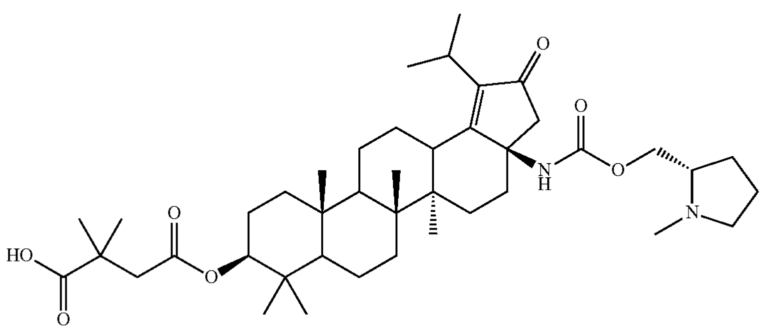 | | +++ | 29.73 (D) | 711.93 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 20-21 | 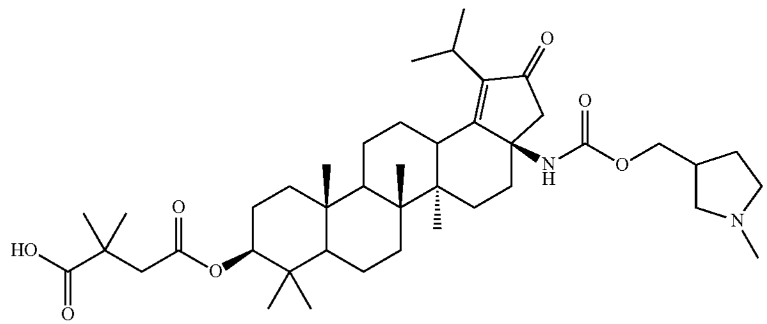 | | +++ | — | 712.04 |
| 20-22 | 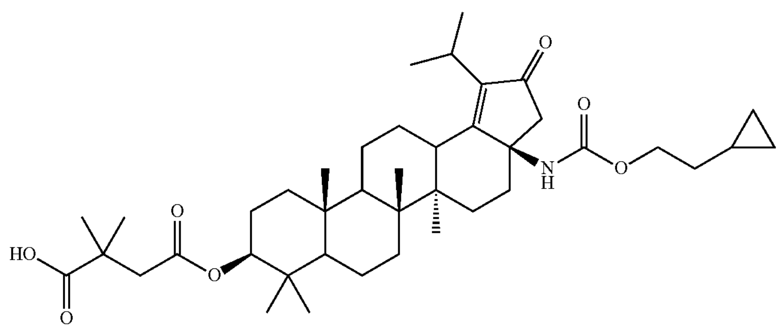 | | +++ | — | 682.73 |

TABLE 2-continued

| Cpd# | Structure | MT2 (HIV$_{IIIB}$) IC50 range | MT2 (HIV$_{IIIB}$) with HS 30% IC50 range | t$_R$ (min) (Method) | M$^+$/M + H$^+$ |
|---|---|---|---|---|---|
| 20-23 | 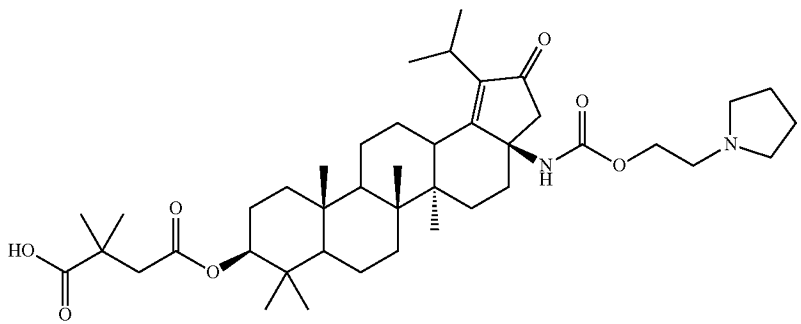 | | +++ | 29.66 (D) | 711.84 |
| 20-24 | 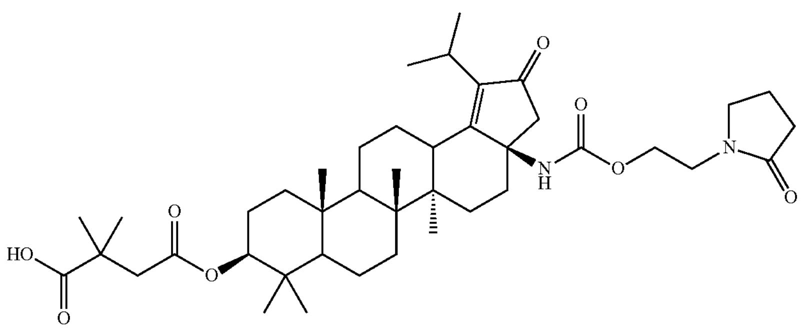 | | +++ | 6.19 (F) | 726.06 |

When the compounds are tested more than once, the average IC50 is provided.

MT2(HIV$_{IIIB}$) IC50 with or without HS
+>1000 nM
++200-999 nM
+++<199 nM

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

We claim
1. A compound of formula (I):

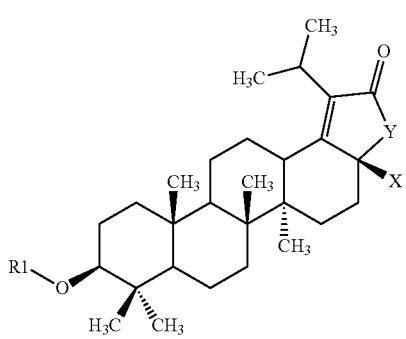

wherein
R$^1$ is

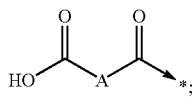

A is C$_{1-8}$ alkyl, C$_{2-8}$ alkenyl, or —(CH$_2$)$_{1-2}$O(CH$_2$)$_{1-2}$—;
Y is C=O or C—R$_{y1}$R$_{y2}$;
R$_{y1}$ and R$_{y2}$ are each independently H or —CH$_3$;
X is NR$_2$R$_3$;

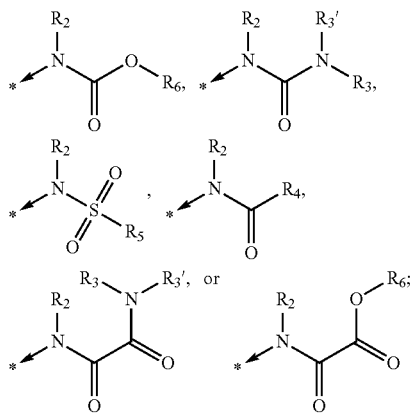

R$_2$ is H, C$_{1-12}$ alkyl which is unsubstituted or substituted one or more times by R$^{10}$, C$_{2-12}$ alkenyl which is unsubstituted or substituted one or more times by R$^{10}$, or C$_{2-12}$ alkynyl which is unsubstituted or substituted one or more times by R$^{10}$;

R$_3$ and R$_3$' are each independently H, C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;

R$_3$ and R$_3$' can also be taken together to form 5-12 member heteroaryl which is unsubstituted or substituted one or more times by R$^{11}$, or a 3-12 member heterocycle which is unsubstituted or substituted one or more times by R$^{12}$;

R$_4$ is C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;

R$_5$ and R$_6$ are each independently C$_{1-12}$ alkyl which is unsubstituted or substituted one or more times by R$^{10}$, C$_{2-12}$ alkenyl which is unsubstituted or substituted one or more times by R$^{10}$, C$_{2-12}$ alkynyl which is unsubstituted or substituted one or more times by R$^{10}$, C$_{6-14}$ aryl which is unsubstituted or substituted one or more times by R$^{11}$, C$_{7-16}$ aralkyl which is unsubstituted or substituted one or more times by R$^{11}$, 5-12 member heteroaryl which is unsubstituted or substituted one or more times by R$^{11}$, 6-18 member heteroaralkyl which is unsubstituted or substituted one or more times by R$^{11}$, 3-12 member heterocycle which is unsubstituted or substituted one or more times by R$^{12}$, or 4-18 member heterocycle-alkyl which is unsubstituted or substituted one or more times by R$^{12}$;

R$^{10}$ is halogen, oxo, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$ alkyl, —NHC(O)OC$_{1-4}$ alkyl, —N(C$_{1-4}$ alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$ alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl)C$_{1-4}$ alkyl, —C(NOC$_{1-4}$ alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(C)(OC$_{1-4}$alkyl)OH, —P(O)(OC$_{1-4}$alkyl)$_2$, amidino, or guanidino;

R$^{11}$ is halogen, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$alkyl, —NHC(O)OC$_{1-4}$alkyl, —N(C$_{1-4}$alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl)C$_{1-4}$ alkyl, —C(NOC$_{1-4}$alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino; and R$^{12}$ is halogen, oxo, C$_{1-6}$ alkyl, halogenated C$_{1-6}$ alkyl, C$_{2-6}$ alkenyl, C$_{2-6}$ alkynyl, C$_{1-6}$ alkoxy, —NH$_2$, —NH(C$_{1-4}$ alkyl), —N(C$_{1-4}$ alkyl)$_2$, —C(O)NH$_2$, —C(O)NH(C$_{1-4}$ alkyl), —C(O)N(C$_{1-4}$ alkyl)$_2$, —NHC(O)H, —N(C$_{1-4}$ alkyl)C(O)H, —N(C$_{1-4}$ alkyl)C(O)C$_{1-4}$ alkyl, —NHC(O)C$_{1-4}$alkyl, —NHC(O)OC$_{1-4}$alkyl, —N(C$_{1-4}$alkyl)C(O)OC$_{1-4}$ alkyl, —NHC(O)NH$_2$, —N(C$_{1-4}$ alkyl)C(O)NH$_2$, —NHC(O)NHC$_{1-4}$ alkyl, —N(C$_{1-4}$ alkyl)C(O)NHC$_{1-4}$ alkyl, —N(C$_{1-4}$ alkyl)C(O)N(C$_{1-4}$ alkyl)$_2$, —NHC(O)N(C$_{1-4}$alkyl)$_2$, —C(O)H, —C(O)C$_{1-4}$ alkyl, C(O)OH, —C(O)OC$_{1-4}$ alkyl, —OC(O)C$_{1-4}$ alkyl, —OC(O)NH(C$_{1-4}$ alkyl), —OC(O)N(C$_{1-4}$ alkyl)$_2$, —C(NOH)C$_{1-4}$ alkyl, —C(NOH)H, —C(NOC$_{1-4}$ alkyl) C$_{1-4}$ alkyl, —C(NOC$_{1-4}$alkyl)H, hydroxyl, nitro, azido, cyano, —S(O)$_{0-3}$H, —S(O)$_{0-3}$C$_{1-4}$ alkyl, —SO$_2$NH$_2$, —SO$_2$NH(C$_{1-4}$ alkyl), —SO$_2$N(C$_{1-4}$ alkyl)$_2$, —N(C$_{1-4}$ alkyl)SO$_2$C$_{1-4}$ alkyl, —NHSO$_2$C$_{1-4}$ alkyl, —P(O)(OH)$_2$, —P(O)(OC$_{1-4}$alkyl)OH, —P(O)(OC$_{1-4}$alkyl)$_2$, amidino, or guanidino;

or a pharmaceutically acceptable salt thereof.

2. A compound according to claim 1, wherein Y is —CH$_2$—.

3. A compound according to claim 2, wherein R$_1$ is 3',3'-dimethylsuccinyl.

4. A compound according to claim 3, wherein R$_2$ is H.

5. A compound according to claim 3, wherein said compound is defined by formula (II):

(II)

6. A compound according to claim 5, wherein R$_3$' is H.

7. A compound according to claim 5, wherein R$_3$ is 5-6 member heteroaryl selected from pyrazole, oxadiazole, pyridine, pyrimidine, imidazole, or thiadiazole which is unsubstituted or substituted one or more times by one or more times by halogen, C$_{1-3}$ alkyl, C$_{1-3}$ alkoxy, or halogenated C$_{1-3}$ alkyl.

8. A compound according to claim 6, wherein R$_3$ is piperidine which is unsubstituted or substituted one or more times by halogen, C$_{1-3}$ alkyl, C$_{1-3}$ alkoxy, or halogenated C$_{1-3}$ alkyl.

9. A compound according to claim 6, wherein R$_3$ is cyclohexyl.

10. A compound according to claim 6, wherein R$_3$ is difluorocyclohexyl.

11. A compound according to claim 3, wherein said compound is defined by formula (III):

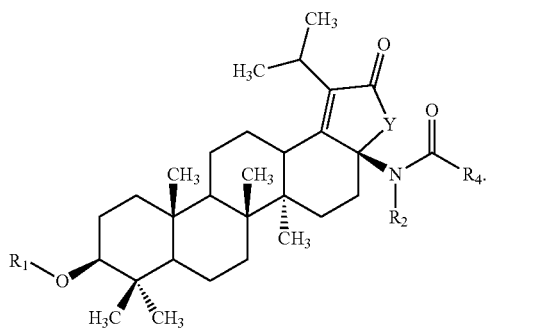

(III)

12. A compound according to claim 11, wherein R$_4$ is 5-6 member heteroaryl selected from pyridine, pyrimidine, pyrazole, thaizole, oxadiazole, or imidazole which is unsubstituted or substituted one or more times by halogen, C$_{1-3}$ alkyl, C$_{1-3}$ alkoxy, or halogenated C$_{1-3}$ alkyl.

13. A compound according to claim 11, wherein R$_4$ is piperidine which is unsubstituted or substituted one or more times by halogen, C$_{1-3}$ alkyl, C$_{1-3}$ alkoxy, or halogenated C$_{1-3}$ alkyl.

14. A compound according to claim 11, wherein R$_4$ is cyclohexyl which is unsubstituted or substituted one or more times by halogen, C$_{1-3}$ alkyl, C$_{1-3}$ alkoxy, or halogenated C$_{1-3}$ alkyl.

15. A compound according to claim 3, wherein said compound is defined formula (IV):

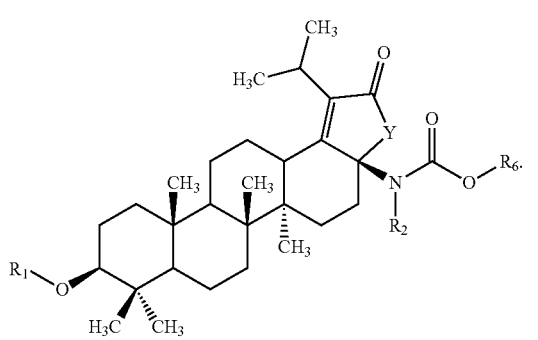

(IV)

16. A compound selected from:
3β-O-(3',3'-Dimethylsuccinyl)-17β-tert-butyloxycarbonylamino-21-oxolup-18-ene;
3β-O-(3',3'-Dimethylsuccinyl)-17β-amino-21-oxolup-18-ene;

3β-O-(cis-Cyclohexane-3'-carboxylic acid-1'-carboxyl)-17β-amino-21-oxolup-18-ene;
3β-O-[(1'R,3'S)-1',2',2'-Trimethyl-cyclopentane-3'-carboxylic acid-1'-carboxyl]-17β-amino-21-oxolup-18-ene;
3β-O-(3',3'-Dimethylsuccinyl)-17β-(1-tert-butyloxycarbonylpiperidine-4-amino]-21-oxolup-18-ene;
3β-O-(3',3'-Dimethylsuccinyl)-17β-(methylamino)-21-oxolup-18-ene;
3β-O-(3',3'-Dimethylsuccinyl)-17β-[N'-(benzyl)ureido]-21-oxolup-18-ene;
3β-O-(3',3'-Dimethylsuccinyl)-17β-[N'-(ethyl)ureido]-21-oxolup-18-ene;
3β-O-(3',3'-Dimethylsuccinyl)-17β[N'-(phenyl)ureido]-21-oxolup-18-ene;
3β-O-(3',3'-Dimethylsuccinyl)-17β[N'-(isopropyl)ureido]-21-oxolup-18-ene;
3β-O-(3',3'-Dimethylsuccinyl)-17β[N'-(tert-butyl)ureido]-21-oxolup-18-ene;
3β-O-(3',3'-Dimethylsuccinyl)-17β[N'-(pyridin-3-yl)ureido]-21-oxolup-18-ene;
3β-O-(3',3'-Dimethylsuccinyl)-17β[N'-(cyclohexyl)ureido]-21-oxolup-18-ene;
3β-O-(3',3'-Dimethylsuccinyl)-17β[N'-(cyclohexylmethyl) ureido]-21-oxolup-18-ene;
3β-O-(3',3'-Dimethylsuccinyl)-17β[N'-(1-tert- butyloxycarbonyl -piperidin-4-yl)-ureido]-21-oxolup-18-ene;
3β-O-(3',3'-Dimethylsuccinyl)-17β-(N'-piperidin-4-yl-ureido)-21-oxolup-18-ene;
3β-O-(3',3'-Dimethylsuccinyl)-17β[N'-(1-acetyl-piperidin-4-yl)-ureido]-21-oxolup-18-ene;
3β-O-(3',3'-Dimethylsuccinyl)-17β[N'-(pyridin-3-ylmethyl)ureido]-21-oxolup-18-ene;
3β-O-(3',3'-Dimethylsuccinyl)-17β-[(morpholine-4-carbonyl)-amino]-21-oxolup-18-ene;
3β-O-(3',3'-Dimethylsuccinyl)-17β-[(4-tert-butyloxycarbonyl-piperazine-1-carbonyl)-amino]-21-oxolup-18-ene;
3β-O-(3',3'-Dimethylsuccinyl)-17β-[(piperazine-1-carbonyl)-amino]-21-oxolup-18-ene;
3β-O-(3',3'-Dimethylsuccinyl)-17β-[(4-methyl-piperazine-1-carbonyl)-amino]-21-oxolup-18-ene;
3β-O-(3',3'-Dimethylsuccinyl)-17β-[(4-acetyl-piperazine-1-carbonyl)-amino]-21-oxolup-18-ene;
3β-O-(3',3'-Dimethylsuccinyl)-17β[N'-isopropyl-N'-methyl-ureido]-21-oxolup-18-ene;
3β-O-(3',3'-Dimethylsuccinyl)-17β-(N'-5-methyl-[1,3,4]oxadiazol-2-yl-ureido)-21-oxolup-18-ene;
3β-O-(3',3'-Dimethylsuccinyl)-17β-[(4-tert-butoxycarbonylamino-piperidine-1-carbonyl)-amino]-21-oxolup-18-ene;
3β-O-(3',3'-Dimethylsuccinyl)-17β-(N'-cyclopropylmethyl-ureido)-21-oxolup-18-ene;
3β-O-(3',3'-Dimethylsuccinyl)-17β-(N'-cyclopropyl-ureido)-21-oxolup-18-ene;
3β-O-(3',3'-Dimethylsuccinyl)-17β-[(4-amino-piperidine-1-carbonyl)-amino]-21-oxolup-18-ene trifluoroacetate;
3β-O-(3',3'-Dimethylsuccinyl)-17β-[(4-amino-piperidine-1-carbonyl)-amino]-21-oxolup-18-ene;
3β-O-(3',3'-Dimethylsuccinyl)-17β-(N'-pyridin-2-yl-ureido)-21-oxolup-18-ene;
3β-O-(3',3'-Dimethylsuccinyl)-17β-(N'-pyridin-4-yl-ureido)-21-oxolup-18-ene;
3β-O-(3',3'-Dimethylsuccinyl)-17β-[N'-(pyridin-2-ylmethyl)ureido]-21-oxolup-18-ene;
3β-O-(3',3'-Dimethylsuccinyl)-17β'[N'-(1-methyl-piperidin-4-ylmethyl)-ureido]-21-oxolup-18-ene;
3β-O-(3',3'-Dimethylsuccinyl)-17β-[(4-isopropyl-piperazine-1-carbonyl)-amino]-21-oxolup-18-ene;
3β-O-(3',3'-Dimethylsuccinyl)-17β-[N'-(1-methyl-piperidin-4-yl)-ureido]-21-oxolup-18-ene;
3β-O-(3',3'-Dimethylsuccinyl)-17β-[N'-(pyridin-4-ylmethyl)ureido]-21-oxolup-18-ene;
3β-O-(3',3'-Dimethylsuccinyl)-17β-(N'-pyrimidin-2-yl-ureido)-21-oxolup-18-ene;
3β-O-(3',3'-Dimethylsuccinyl)-17β-[N'-(1-tert-butyloxycarbonyl-azetidin-3-yl)-ureido]-21-oxolup-18-ene;
3β-O-(3',3'-Dimethylsuccinyl)-17β-[(3-(S)-1-tert-butyloxycarbonyl-pyrrolidin-2-ylmethyl)-ureido]-21-oxolup-18-ene;
3β-O-(3',3'-Dimethylsuccinyl)-17β-[azetidin-3-yl-ureido)]-21-oxolup-18-ene;
3β-O-(3',3'-Dimethylsuccinyl)-17β-[(4-(tert-butyloxycarbonyl-methyl-amino)-piperidine-1-carbonyl)-amino]-21-oxolup-18-ene;
3β-O-(3',3'-Dimethylsuccinyl)-17β-[N'-(1-methyl-1H-pyrazol-4-yl)ureido]-21-oxolup-18-ene;
3β-O-(3',3'-Dimethylsuccinyl)-17β-(3-(S)-1-pyrrolidin-2-ylmethyl-ureido)-21-oxolup-18-ene;
3β-O-(3',3'-Dimethylsuccinyl)-17β-[(4-methylamino-piperidine-1-carbonyl)-amino]-21-oxolup-18-ene;
3β-O-(3',3'-Dimethylsuccinyl)-17β-[((R)-3-tert-butyloxycarbonyl amino-pyrrolidine-1-carbonyl)-amino]-21-oxolup-18-ene;
3β-O-(3',3'-Dimethylsuccinyl)-17β-[((S)-3-tert-butyloxycarbonyl amino-pyrrolidine-1-carbonyl)-amino]-21-oxolup-18-ene;
3β-O-(3',3'-Dimethylsuccinyl)-17β-[((R)-3-amino-pyrrolidine-1-carbonyl)-amino]-21-oxolup-18-ene;
3β-O-(3',3'-Dimethylsuccinyl)-17β-[((S)-3-amino-pyrrolidine-1-carbonyl)-amino]-21-oxolup-18-ene;
3β-O-(3',3'-Dimethylsuccinyl)-17β-(N'-pyrimidin-5-yl-ureido)-21-oxolup-18-ene;
3β-O-(3',3'-Dimethylsuccinyl)-17β-(N'-5-methyl-[1,3,4]thiadiazol-2-yl-ureido)-21-oxolup-18-ene;
3β-O-(3',3'-Dimethylsuccinyl)-17β-(N'-pyrimidin-4-yl-ureido)-21-oxolup-18-ene;
3β-O-(3',3'-Dimethylsuccinyl)-17β-(N'-2-methylpyridin-4-yl-ureido)-21-oxolup-18-ene;
3β-O-(3',3'-Dimethylsuccinyl)-17β-[N'N'-dimethyl-ureido]-21-oxolup-18-ene;
3β-O-(3',3'-Dimethylsuccinyl)-17β-[N'-((S)-2,2,2-trifluoro-1-methyl-ethyl)-ureido]-21-oxolup-18-ene;
3β-O-(3',3'-Dimethylsuccinyl)-17β-[N'-((R)-2,2,2-trifluoro-1-methyl-ethyl)-ureido]-21-oxolup-18-ene;
3β-O-(3',3'-Dimethylsuccinyl)-17β[N'-(pyrimidin-4-ylmethyl)ureido]-21-oxolup-18-ene;
3β-O-(3',3'-Dimethylsuccinyl)-17β-[N'-(1-methyl-1-pyridin-2-yl-ethyl)ureido]-21-oxolup-18-ene;
3β-O-(3',3'-Dimethylsuccinyl)-17β-[N'-((S)-1-cyclohexyl-ethyl)ureido]-21-oxolup-18-ene;
3β-O-(3',3'-Dimethylsuccinyl)-17β-[N'-((R)-1-cyclohexyl-ethyl)ureido]-21-oxolup-18-ene;
3β-O-(3',3'-Dimethylsuccinyl)-17β-[N'-(2,2,2-trifluoro-1,1-dimethyl-ethyl)ureido]-21-oxolup-18-ene;
3β-O-(3',3'-Dimethylsuccinyl)-17β-[N'-(4,4-difluorocyclohexyl)ureido]-21-oxolup-18-ene;
3β-O-(3',3'-Dimethylsuccinyl)-17β-(3,3-difluoro-pyrrolidine-1-carbonyl)-amino]-21-oxolup-18-ene;
3β-O-(3',3'-Dimethylsuccinyl)-17β-[(4,4-difluoro-piperidine-1-carbonyl)-amino]-21-oxolup-18-ene;

3β-O-(3',3'-Dimethylsuccinyl)-17β[N'-(4,4-difluoro-cyclohexyl-methyl)ureido]-21-oxolup-18-ene;
3β-O-(3',3'-Dimethylsuccinyl)-17β-[N'-((S)-1-phenyl-ethyl)-ureido]-21-oxolup-18-ene;
3β-O-(3',3'-Dimethylsuccinyl)-17β-[N'-((R)-1-phenyl-ethyl)-ureido]-21-oxolup-18-ene;
3β-O-(3',3'-Dimethylsuccinyl)-17β-[N'-(1-methyl-1-phenyl-ethyl)-ureido]-21-oxolup-18-ene;
3β-O-(3',3'-Dimethylsuccinyl)-17β-[N'-(thiophen-2-ylmethyl)-ureido]-21-oxolup-18-ene;
3β-O-(3',3'-Dimethylsuccinyl)-17β-[N'-(2-methyl-[1,3,4]oxadiazol-2-ylmethyl)-ureido]-21-oxolup-18-ene;
3β-O-(3',3'-Dimethylsuccinyl)-17β-[N'-(1-phenyl-cyclopropyl)-ureido]-21-oxolup-18-ene;
3β-O-(3',3'-Dimethylsuccinyl)-17β[N'-(pyrimidin-2-ylmethyl)ureido]-21-oxolup-18-ene;
3β-O-(3',3'-Dimethylsuccinyl)-17β-[N'-(pyrimidin-5-ylmethyl)ureido]-21-oxolup-18-ene;
3β-O-(3',3'-Dimethylsuccinyl)-17β-[N'-(1-pyridin-2-yl-cyclopropyl)-ureido]-21-oxolup-18-ene;
3β-O-(3',3'-Dimethylsuccinyl)-17β-[N'-(1-methyl-1-cyclohexyl-ethyl)-ureido]-21-oxolup-18-ene;
3β-O-(3',3'-Dimethylsuccinyl)-17β-[N'-(1-pyridin-2-yl-ethyl)-ureido]-21-oxolup-18-ene;
3β-O-(3',3'-Dimethylsuccinyl)-17β-[N'-(1-methyl-1H-imidazol-2-yl-methyl)-ureido]-21-oxolup-18-ene;
3β-O-(3',3'-Dimethylsuccinyl)-17β-[N'-(4-methyl-4H-[1,2,4]triazol-3-yl-methyl)-ureido]-21-oxolup-18-ene;
3β-O-(3',3'-Dimethylsuccinyl)-17β-[N'-(thiophen-3-ylmethyl)-ureido]-21-oxolup-18-ene;
3β-O-(3',3'-Dimethylsuccinyl)-17β-[N'-(2-methyl-2H-pyrazol-3-yl-methyl)-ureido]-21-oxolup-18-ene;
3β-O-(3',3'-Dimethylsuccinyl)-17β-methylsulfonylamino-21-oxolup-18-ene;
3β-O-(3',3'-Dimethylsuccinyl)-17β-acetylamino-21-oxolup-18-ene;
3β-O-(3',3'-Dimethylsuccinyl)-17β-benzamido-21-oxolup-18-ene;
3β-O,17β-N-bis(3',3'-dimethylsuccinyl)-21-oxolup-18-ene;
3β-O-(3',3'-Dimethylsuccinyl)-17β-(5-methyl-[1,3,4]oxadiazole-2-amido)-21-oxolup-18-ene;
3β-O-(3',3'-Dimethylsuccinyl)-17β-(1-tert-butyloxycarbonylpiperidine-4-amido)-21-oxolup-18-ene;
3β-O-(3',3'-Dimethylsuccinyl)-17β-(piperidine-4-amido)-21-oxolup-18-ene;
3β-O-(3',3'-Dimethylsuccinyl)-17β-(1-acetylpiperidine-4-amido)-21-oxolup-18-ene;
3β-O-(3',3'-Dimethylsuccinyl)-17β-(pyridin-3-yl)amido-21-oxolup-18-ene;
3β-O-(3',3'-Dimethylsuccinyl)-17β-(4-fluorobenzyl)amido-21-oxolup-18-ene;
3β-O-(3',3'-Dimethylsuccinyl)-17β-benzamido-21-oxolup-18-ene;
3β-O-(3',3'-Dimethylsuccinyl)-17β-(2-fluorobenzamido)-21-oxolup-18-ene;
3β-O-(3',3'-Dimethylsuccinyl)-17β-(3-fluorobenzamido)-21-oxolup-18-ene;
3β-O-(3',3'-Dimethylsuccinyl)-17β-(4-fluorobenzamido)-21-oxolup-18-ene;
3β-O-(3',3'-Dimethylsuccinyl)-17β-(pyridin-4-yl)amido-21-oxolup-18-ene;
3β-O-(3',3'-Dimethylsuccinyl)-17β-(pyridin-2-yl)amido-21-oxolup-18-ene;
3β-O-(3',3'-Dimethylsuccinyl)-17β-(pyrazin-2-yl)amido-21-oxolup-18-ene;
3β-O-(3',3'-Dimethylsuccinyl)-17β-(1-methyl-1H-pyrazole-3-amido)-21-oxolup-18-ene;
3β-O-(3',3'-Dimethylsuccinyl)-17β-(1-methyl-1H-imidazole-5-amido)-21-oxolup-18-ene;
3β-O-(3',3'-Dimethylsuccinyl)-17β-(1-methyl-1H-imidazole-4-amido)-21-oxolup-18-ene;
3β-O-(3',3'-Dimethylsuccinyl)-17β-(2-thiophene)amido-21-oxolup-18-ene;
3β-O-(3',3'-Dimethylsuccinyl)-17β-(1,3-thiazole-2-amido)-21-oxolup-18-ene;
3β-O-(3',3'-Dimethylsuccinyl)-17β-(pyrimidine-2-amido)-21-oxolup-18-ene;
3β-O-(3',3'-Dimethylsuccinyl)-17β-(pyrimidine-5-amido)-21-oxolup-18-ene;
3β-O-(3',3'-Dimethylsuccinyl)-17β-(5-methylisoxazole-3-amido)-21-oxolup-18-ene;
3β-O-(3',3'-Dimethylsuccinyl)-17β-(pyrimidine-4-amido)-21-oxolup-18-ene;
3β-O-(3',3'-Dimethylsuccinyl)-17β-(1-methyl-1H-imidazole-2-amido)-21-oxolup-18-ene;
3β-O-(3',3'-Dimethylsuccinyl)-17β-(1,3-thiazole-4-amido)-21-oxolup-18-ene;
3β-O-(3',3'-Dimethylsuccinyl)-17β-(1,3-thiazole-5-amido)-21-oxolup-18-ene;
3β-O-(3',3'-Dimethylsuccinyl)-17β-phenylacetamido-21-oxolup-18-ene;
3β-O-(3',3'-Dimethylsuccinyl)-17β-tetrahydro-pyran-4-carbonylamino-21-oxolup-18-ene;
3β-O-(3',3'-Dimethylsuccinyl)-17β-isopropylamido-21-oxolup-18-ene;
3β-O-(3',3'-Dimethylsuccinyl)-17β-tert-butylamido-21-oxolup-18-ene;
3β-O-(3',3'-Dimethylsuccinyl)-17β-cyclohexylamido-21-oxolup-18-ene;
3β-O-(3',3'-Dimethylsuccinyl)-17β-(1-methyl-1H-pyrazole-5-amido)-21-oxolup-18-ene;
3β-O-(3',3'-Dimethylsuccinyl)-17β-(1-methyl-1H-pyrazole-4-amido)-21-oxolup-18-ene;
3β-O-(3',3'-Dimethylsuccinyl)-17β-(1-methylpiperidine-4-amido)-21-oxolup-18-ene;
3β-O-(3',3'-Dimethylsuccinyl)-17β-(3-pyrrolidin-1-yl-propionamido)-21-oxolup-18-ene;
3β-O-(3',3'-Dimethylsuccinyl)-17β-(2-pyrrolidin-1-yl-acetamido)-21-oxolup-18-ene;
3β-O-(3',3'-Dimethylsuccinyl)-17β-(4-pyrrolidin-1-yl-butyramido)-21-oxolup-18-ene;
3β-O-(3',3'-Dimethylsuccinyl)-17β-(3-piperidin-1-yl-propionamido)-21-oxolup-18-ene;
3β-O-(3',3'-Dimethylsuccinyl)-17β-[3-(2-oxo-pyrrolidin-1-yl)-propionamido]-21-oxolup-18-ene;
3β-O-(3',3'-Dimethylsuccinyl)-17β-(S)-1-methyl-pyrrolidine-2-amido]-21-oxolup-18-ene;
3β-O-(3',3'-Dimethylsuccinyl)-17β-(4-methylbenzamido)-21-oxolup-18-ene;
3β-O-(3',3'-Dimethylsuccinyl)-17β-(3-methylbenzamido)-21-oxolup-18-ene;
3β-O-(3',3'-Dimethylsuccinyl)-17β-(2-methylbenzamido)-21-oxolup-18-ene;
3β-O-(3',3'-Dimethylsuccinyl)-17β-(2-methylpyridin-3-yl)amido-21-oxolup-18-ene;
3β-O-(3',3'-Dimethylsuccinyl)-17β-(5-methylpyridin-3-yl)amido-21-oxolup-18-ene;
3β-O-(3',3'-Dimethylsuccinyl)-17β-(6-methylpyridin-3-yl)amido-21-oxolup-18-ene;
3β-O-(3',3'-Dimethylsuccinyl)-17β-(4-methylpyridin-3-yl)amido-21-oxolup-18-ene;

3β-O-(3',3'-Dimethylsuccinyl)-17β-(4-hydroxypyridin-3-yl)amido-21-oxolup-18-ene;
3β-O-(3',3'-Dimethylsuccinyl)-17β-(2-hydroxypyridin-3-yl)amido-21-oxolup-18-ene;
3β-O-(3',3'-Dimethylsuccinyl)-17β-(2-methylpyridin-4-yl)amido-21-oxolup-18-ene;
3β-O-(3',3'-Dimethylsuccinyl)-17β-(2-dimethylamino-acetamido)-21-oxolup-18-ene;
3β-O-(3',3'-Dimethylsuccinyl)-17β-(4-methylpiperazine-1-acetamido)-21-oxolup-18-ene;
3β-O-(3',3'-Dimethylsuccinyl)-17β-(R)-1-methyl-pyrrolidine-2-amido]-21-oxolup-18-ene;
3β-O-(3',3'-Dimethylsuccinyl)-17β-(S)-1-isopropyl-pyrrolidine-2-amido]-21-oxolup-18-ene;
3β-O-(3',3'-Dimethylsuccinyl)-17β-(S)-1-tert-butyloxycarbonyl-pyrrolidine-2-amido]-21-oxolup-18-ene;
3β-O-(3',3'-Dimethylsuccinyl)-17β-(R)-1-tert-butyloxycarbonyl-pyrrolidine-2-amido]-21-oxolup-18-ene;
3β-O-(3',3'-Dimethylsuccinyl)-17β-((RS)-2-dimethylamino-propionamido)-21-oxolup-18-ene;
3β-O-(3',3'-Dimethylsuccinyl)-17β-(1-imidazole-acetamido)-21-oxolup-18-ene;
3β-O-(3',3'-Dimethylsuccinyl)-17β-(2-carboxy-benzamido)-21-oxolup-18-ene;
3β-O-(3',3'-Dimethylsuccinyl)-17β-(5-cyclopropyl-[1,3,4]oxadiazole-2-amido)-21-oxolup-18-ene;
3β-O-(3',3'-Dimethylsuccinyl)-17β-(5-phenyl-[1,3,4]oxadiazole-2-amido)-21-oxolup-18-ene;
3β-O-(3',3'-Dimethylsuccinyl)-17β-(2,6-dimethylpyridin-4-yl)amido-21-oxolup-18-ene;
3β-O-(3',3'-Dimethylsuccinyl)-17β-((S)-1-methylpiperidine-2-amido)-21-oxolup-18-ene;
3β-O-(3',3'-Dimethylsuccinyl)-17β-((R)-1-methylpiperidine-2-amido)-21-oxolup-18-ene;
3β-O-(3',3'-Dimethylsuccinyl)-17β-(3-methyl-[1,2,4]oxadiazole-5-amido)-21-oxolup-18-ene;
3β-O-(3',3'-Dimethylsuccinyl)-17β-(5-methyl-[1,2,4]oxadiazole-3-amido)-21-oxolup-18-ene;
3β-O-(3',3'-Dimethylsuccinyl)-17β-(5-methyl-[1,3,4]oxadiazole-2-methyl-amido)-21-oxolup-18-ene;
3β-O-(3',3'-Dimethylsuccinyl)-17β-(8β-oxa-bicyclo[3.2.1]octane-3-amido)-21-oxolup-18-ene;
3β-O-(3',3'-Dimethylsuccinyl)-17β-(8α-oxa-bicyclo[3.2.1]octane-3-amido)-21-oxolup-18-ene;
3β-O-(3',3'-Dimethylsuccinyl)-17β-(2-methyl-1,3-thiazole-4-amido)-21-oxolup-18-ene;
3β-O-(3',3'-Dimethylsuccinyl)-17β-(1-azetidin-acetamido)-21-oxolup-18-ene;
3β-O-(3',3'-Dimethylsuccinyl)-17β-(N',N'-dimethyl-oxalamido)-21-oxolup-18-ene;
3β-O-(3',3'-Dimethylglutaryl)-17β-(5-methyl-[1,3,4]oxadiazole-2-amido)-21-oxolup-18-ene;
3β-O-(3',3'-Dimethylsuccinyl)-17β-(2-methyl-1,3-oxazole-4-amido)-21-oxolup-18-ene;
3β-O-(3',3'-Dimethylsuccinyl)-17β-(5-methyl-thiophene-2-amido)-21-oxolup-18-ene;
3β-O-(3',3'-Dimethylsuccinyl)-17β-(thiophene-3-amido)-21-oxolup-18-ene;
3β-O-(3',3'-Dimethylsuccinyl)-17β-(5-ethyl-[1,3,4]-oxadiazole-2-amido)-21-oxolup-18-ene;
3β-O-(3',3'-Dimethylsuccinyl)-17β-(5-methyl-[1,3]-oxazole-2-amido)-21-oxolup-18-ene;
3β-O-(cis-Cyclohexane-3'-carboxylic acid-1'-carboxyl)-17β-[(5-methyl-[1,3,4]oxadiazol-2-carbonyl)-amino]-21-oxolup-18-ene;
3β-O-(3',3'-Dimethylsuccinyl)-17β-(1H-pyrazole-4-amido)-21-oxolup-18-ene;
3β-O-(3',3'-Dimethylsuccinyl)-17β-(5-isopropyl-[1,3,4]-oxadiazole-2-amido)-21-oxolup-18-ene;
3β-O-(3',3'-Dimethylsuccinyl)-17β-methoxycarbonyl-lamino-21-oxolup-18-ene;
3β-O-(3',3'-Dimethylsuccinyl)-17β-isopropyloxycarbonylamino-21-oxolup-18-ene;
3β-O-(3',3'-Dimethylsuccinyl)-17β-cyclopropylmethoxycarbonylamino-21-oxolup-18-ene;
3β-O-(3',3'-Dimethylsuccinyl)-17β-cyclopentyloxycarbonylamino-21-oxolup-18-ene;
3β-O-(3',3'-Dimethylsuccinyl)-17β-cyclohexyloxycarbonylamino-21-oxolup-18-ene;
3β-O-(3',3'-Dimethylsuccinyl)-17β-[(1-carboxylic acid tert-butyl ester)-piperidine-4-oxycarbonylamino]-21-oxolup-18-ene;
3β-O-(3',3'-Dimethylsuccinyl)-17β-cyclohexylmethoxycarbonylamino-21-oxolup-18-ene;
3β-O-(3',3'-Dimethylsuccinyl)-17β-benzyloxycarbonylamino-21-oxolup-18-ene;
3β-O-(3',3'-Dimethylsuccinyl)-17β-cyclobutyloxycarbonylamino-21-oxolup-18-ene;
3β-O-(3',3'-Dimethylsuccinyl)-17β-(1-cyclopropylethoxycarbonylamino)-21-oxolup-18-ene;
3β-O-(3',3'-Dimethylsuccinyl)-17β-(1-methyl-cyclopropylmethoxycarbonylamino)-21-oxolup-18-ene;
3β-O-(3',3'-Dimethylsuccinyl)-17β-(1-amino-cyclopropylmethoxycarbonylamino)-21-oxolup-18-ene;
3β-O-(3',3'-Dimethylsuccinyl)-17β-((R)-1-methylpyrrolidine-3-oxycarbonylamino)-21-oxolup-18-ene;
3β-O-(3',3'-Dimethylsuccinyl)-17β-(tetrahydro-thiopyran-4-oxycarbonylamino)-21-oxolup-18-ene;
3β-O-(3',3'-Dimethylsuccinyl)-17β-(1,1-dioxo-tetrahydro-thiopyran-4-oxycarbonylamino)-21-oxolup-18-ene;
3β-O-(3',3'-Dimethylsuccinyl)-17β-(piperidine-4-oxycarbonylamino)-21-oxolup-18-ene;
3β-O-(3',3'-Dimethylsuccinyl)-17β-(1-methylpiperidine-4-oxycarbonylamino)-21-oxolup-18-ene;
3β-O-(3',3'-Dimethylsuccinyl)-17β-(1-methylpiperidine-4-methoxycarbonylamino)-21-oxolup-18-ene;
3β-O-(3',3'-Dimethylsuccinyl)-17β-(1-methylpiperidine-3-methoxycarbonylamino)-21-oxolup-18-ene;
3β-O-(3',3'-Dimethylsuccinyl)-17β-((S)1-methylpyrrolidine-2-methoxycarbonylamino)-21-oxolup-18-ene;
3β-O-(3',3'-Dimethylsuccinyl)-17β-(1-methylpyrrolidine-3-methoxycarbonylamino)-21-oxolup-18-ene;
3β-O-(3',3'-Dimethylsuccinyl)-17β-(2-cyclopropyl-1-ethoxycarbonylamino)-21-oxolup-18-ene;
3β-O-(3',3'-Dimethylsuccinyl)-17β-(2-pyrrolidin-1-ethoxycarbonylamino)-21-oxolup-18-ene;
3β-O-(3',3'-Dimethylsuccinyl)-17β-(2-(2-oxo-pyrrolidin)-1-ethoxycarbonylamino)-21-oxolup-18-ene;
3β-O-(cis-Cyclohexane-3'-carboxylic acid-1'-carboxyl)-17β-[N tert-butyloxycarbonyl-amino]-21-oxolup-18-ene;
3β-O-[(1'R,3'S)-1',2',2'-Trimethyl-cyclopentane-3'-carboxylic acid-1'-carboxyl]-17β-[N-tert-butyloxycarbonyl-amino]-21-oxolup-18-ene;
17β-Benzamido-3β-hydroxy-21-oxolup-18-ene;
17β-(pyridin-2-yl)amido-3β-hydroxy-21-oxolup-18-ene;
17β-(isopropylcarbonylamino)-3β-hydroxy-21-oxolup-18-ene; and
pharmaceutically acceptable salts thereof.

17. A compound selected from:

3β-O-acetyl-17β-amino-21-oxolup-18-ene;
3β-hydroxy-17β-amino-21-oxolup-18-ene;
3β-hydroxy-17β-[N'-(benzyl)ureido]-21-oxolup-18-ene;
3β-hydroxy-17β-[N'-3β-hydroxy-oxolup-18-ene 17β-ureido]-21-oxolup-18-ene;
3β-hydroxy-17β-benzamido-21-oxolup-18-ene;
3β-hydroxy-17β-(pyridin-2-yl)amido-21-oxolup-18-ene;
3β-hydroxy-17β-(5-methyl-[1,3,4]oxadiazole-2-amido)-21-oxolup-18-ene;
3β-hydroxy-17β-(1-tert-butyloxycarbonylpiperidine-4-amido)-21-oxolup-18-ene;
3β-hydroxy-17β-(pyridin-3-yl)amido-21-oxolup-18-ene;
3β-hydroxy-17β-(4-fluorobenzyl)amido-21-oxolup-18-ene;
3β-hydroxy-17β-(pyridin-4-yl)amido-21-oxolup-18-ene;
3β-hydroxy-17β-(pyrazin-2-yl)amido-21-oxolup-18-ene;
3β-hydroxy-17β-(1-methyl-1H-pyrazole-3-amido)-21-oxolup-18-ene;
3β-hydroxy-17β-(1-methyl-1H-imidazole-5-amido)-21-oxolup-18-ene;
3β-hydroxy-17β-(1-methyl-1H-imidazole-4-amido)-21-oxolup-18-ene;
3β-hydroxy-17β-(2-thiophene)amido-21-oxolup-18-ene;
3β-hydroxy-17β-(1,3-thiazole-2-amido)-21-oxolup-18-ene;
3β-O-acetyl-17β-(5-methyl-[1,3,4]oxadiazole-2-amido)-21-oxolup-18-ene;
3β-hydroxy-17β-(pyrimidine-5-amido)-21-oxolup-18-ene;
3β-hydroxy-17β-(5-methylisoxazole-3-amido)-21-oxolup-18-ene;
3β-hydroxy-17β-(pyrimidine-4-amido)-21-oxolup-18-ene;
3β-hydroxy-17β-(1-methyl-1H-imidazole-2-amido)-21-oxolup-18-ene;
3β-hydroxy-17β-(1,3-thiazole-4-amido)-21-oxolup-18-ene;
3β-hydroxy-17β-(1,3-thiazole-5-amido)-21-oxolup-18-ene;
3β-hydroxy-17β-(1-methyl-1H-pyrazole-5-amido)-21-oxolup-18-ene;
3β-hydroxy-17β-(1-methyl-1H-pyrazole-4-amido)-21-oxolup-18-ene;
3β-hydroxy-17β-(3-methylbenzamido)-21-oxolup-18-ene;
3β-hydroxy-17β-(2,6-dimethylpyridin-4-yl)amido-21-oxolup-18-ene;
3β-hydroxy-17β-((RS)1-methylpiperidine-2-amido)-21-oxolup-18-ene;
3β-hydroxy-17β-[2-(4-methylpiperazin-1-yl)-acetamido]-21-oxolup-18-ene;
3β-hydroxy-17β-(2-dimethylamino-acetamido)-21-oxolup-18-ene;
3β-hydroxy-17β-(2-methylpyridin-4-yl)amido-21-oxolup-18-ene;
3β-hydroxy-17β-((RS)2-dimethylamino-propionamido)-21-oxolup-18-ene;
3β-hydroxy-17β-(2-imidazol-1-yl-acetamido)-21-oxolup-18-ene;
3β-hydroxy-17β-(6-methylpyridin-3-yl)amido-21-oxolup-18-ene;
3β-hydroxy-17β-(4-methylpyridin-3-yl)amido-21-oxolup-18-ene;
3β-hydroxy-17β-(5-methylpyridin-3-yl)amido-21-oxolup-18-ene;
3β-hydroxy-17β-(2-methylpyridin-3-yl)amido-21-oxolup-18-ene;
3β-hydroxy-17β-(2-methylbenzamido)-21-oxolup-18-ene;
3β-hydroxy-17β-(3-pyrrolidin-1-yl-propionamido)-21-oxolup-18-ene;
3β-hydroxy-17β-(2-pyrrolidin-1-yl-acetamido)-21-oxolup-18-ene;
3β-hydroxy-17β-(4-pyrrolidin-1-yl-butyramido)-21-oxolup-18-ene;
3β-hydroxy-17β-(3-piperidin-1-yl-propionamido)-21-oxolup-18-ene;
3β-hydroxy-17β-[3-(2-oxo-pyrrolidin-1-yl)-propionamido]-21-oxolup-18-ene;
3β-hydroxy-17β-[(S)-1-methyl-pyrrolidine-2-amido]-21-oxolup-18-ene;
3β-hydroxy-17β-(1-isopropylazetidine-3-amido)-21-oxolup-18-ene;
3β-hydroxy-17β-(3-thiophene)amido-21-oxolup-18-ene;
3β-hydroxy-17β-(5-methyl-[1,3]-oxazole-2-amido)-21-oxolup-18-ene;
3β-hydroxy-17β-isopropyloxycarbonylamino-21-oxolup-18-ene;
3β-O-acetyl-17β-tert-butyloxycarbonylamino]-21-oxolup-18-ene;
3β-hydroxy-17β-tert-butyloxycarbonylamino-]-21-oxolup-18-ene;
3β-O-acetyl-17β-isopropyloxycarbonylamino-21-oxolup-18-ene;
3β-O-acetyl-17β-cyclopropylmethoxycarbonylamino-21-oxolup-18-ene;
3β-O-acetyl-17β-cyclopentyloxycarbonylamino-21-oxolup-18-ene;
3β-hydroxy-17β-cyclopentyloxycarbonylamino-21-oxolup-18-ene;
3β-O-acetyl-17β-cyclohexyloxycarbonylamino-21-oxolup-18-ene;
3β-hydroxy-17β-cyclohexyloxycarbonylamino-21-oxolup-18-ene;
3β-O-acetyl-17β-(1-tert-butoxycarbonylpiperidin-4-yloxycarbonylamino)-21-oxolup-18-ene;
3β-O-acetyl-17β-cyclohexylmethoxycarbonylamino-21-oxolup-18-ene;
3β-hydroxy-17β-cyclohexylmethoxycarbonylamino-21-oxolup-18-ene;
3β-O-acetyl-17β-benzyloxycarbonylamino-21-oxolup-18-ene;
3β-O-acetyl-17β-cyclopropylmethoxycarbonylamino-21-oxolup-18-ene;
3β-O-acetyl-17β-cyclopropylmethoxycarbonylamino-21-oxolup-18-ene;
3β-acetoxy-17β-cyclobutyloxycarbonylamino-21-oxolup-18-ene;
3β-acetoxy-17β-tetrahydro-thiopyran-4-yloxycarbonylamino-21-oxolup-18-ene;
3β-acetoxy-17β-(1-methyl-piperidin-4-yloxycarbonylamino)-21-oxolup-18-ene;
3β-acetoxy-17β-((S)-1-Methyl-pyrrolidin-2-yl)-methoxycarbonylamino-21-oxolup-18-ene;
3β-acetoxy-17β-(2-pyrrolidin-1-ylethoxycarbonylamino)-21-oxolup-18-ene;
3β-acetoxy-17β-cyclopropylethoxycarbonylamino-21-oxolup-18-ene;
3β-O-acetyl-17β-(1-tert-butoxycarbonylamino-cyclopropylmethoxycarbonylamino)-21-oxolup-18-ene;
3β-acetoxy-17β-(1-methyl-pyrrolidin-3-yloxycarbonylamino)-21-oxolup-18-ene;

3β-O-acetyl-17β-(1-methylpiperidin-4-ylmethoxycarbonylamino)-21-oxolup-18-ene;
3β-O-acetyl-17β-(1-methylpiperidin-3-ylmethoxycarbonylamino)-21-oxolup-18-ene;
3β-acetoxy-17β-(1-Methyl-pyrrolidin-3-yl)-methoxycarbonylamino-21-oxolup-18-ene;
3β-acetoxy-17β-[3-(2-oxo-pyrrolidin-1-yl)-propionamido]-21-oxolup-18-ene; and
pharmaceutically acceptable salts thereof.

18. A compound according to claim 16, wherein said compound is:
3β-O-(3',3'-Dimethylsuccinyl)-17β-tert-butyloxycarbonylamino-21-oxolup-18-ene;
3β-O-(3',3'-Dimethylsuccinyl)-17β-amino-21-oxolup-18-ene;
3β-O-(3',3'-Dimethylsuccinyl)-17β-(methylamino)-21-oxolup-18-ene;
3β-O-(3',3'-Dimethylsuccinyl)-17β[N'-(cyclohexyl)ureido]-21-oxolup-18-ene;
3β-O-(3',3'-Dimethylsuccinyl)-17β[N'-(cyclohexylmethyl)ureido]-21-oxolup-18-ene;
3β-O-(3',3'-Dimethylsuccinyl)-17β[N'-(pyridin-3-ylmethyl)ureido]-21-oxolup-18-ene;
3β-O-(3',3'-Dimethylsuccinyl)-17β-(N'-5-methyl-[1,3,4]oxadiazol-2-yl-ureido)-21-oxolup-18-ene;
3β-O-(3',3'-Dimethylsuccinyl)-17β[N'-(pyridin-4-ylmethyl)ureido]-21-oxolup-18-ene;
3β-O-(3',3'-Dimethylsuccinyl)-17β-benzamido-21-oxolup-18-ene;
3β-O— (3',3'-Dimethylsuccinyl)-17β-(5-methyl-[1,3,4]oxadiazole-2-amido)-21-oxolup-18-ene;
3β-O-(3',3'-Dimethylsuccinyl)-17β-(pyridin-3-yl)amido-21-oxolup-18-ene;
3β-O-(3',3'-Dimethylsuccinyl)-17β-(pyrazin-2-yl)amido-21-oxolup-18-ene;
3β-O-(3',3'-Dimethylsuccinyl)-17β-(1-methyl-1H-pyrazole-3-amido)-21-oxolup-18-ene;
3β-O-(3',3'-Dimethylsuccinyl)-17β-(1-methyl-1H-imidazole-5-amido)-21-oxolup-18-ene;
3β-O-(3',3'-Dimethylsuccinyl)-17β-(1,3-thiazole-2-amido)-21-oxolup-18-ene;
3β-O-(3',3'-Dimethylsuccinyl)-17β-(pyrimidine-2-amido)-21-oxolup-18-ene;
3β-O-(3',3'-Dimethylsuccinyl)-17β-(1,3-thiazole-4-amido)-21-oxolup-18-ene;
3β-O-(3',3'-Dimethylsuccinyl)-17β-phenylacetamido-21-oxolup-18-ene;
3β-O-(3',3'-Dimethylsuccinyl)-17β-tetrahydro-pyran-4-carbonylamino-21-oxolup-18-ene;
3β-O-(3',3'-Dimethylsuccinyl)-17β-(1-methyl-1H-pyrazole-4-amido)-21-oxolup-18-ene;
3β-O-(3',3'-Dimethylsuccinyl)-17β-(1-methylpiperidine-4-amido)-21-oxolup-18-ene;
3β-O-(3',3'-Dimethylsuccinyl)-17β-isopropyloxycarbonylamino-21-oxolup-18-ene;
3β-O-(3',3'-Dimethylsuccinyl)-17β-cyclohexyloxycarbonylamino-21-oxolup-18-ene;
3β-O-(3',3'-Dimethylsuccinyl)-17β-benzyloxycarbonylamino-21-oxolup-18-ene;
3β-O-(3',3'-Dimethylsuccinyl)-17β-(1-methylpiperidine-4-oxycarbonylamino)-21-oxolup-18-ene; and
pharmaceutically acceptable salts thereof.

19. A compound according to claim 16, wherein said compound is:
3β-O-(3',3'-Dimethylsuccinyl)-17β-amino-21-oxolup-18-ene hydrochloride salt;
3β-O-(3',3'-Dimethylsuccinyl)-17β-[N'-(3-pyridyl)ureido]-21-oxolup-18-ene hydrochloride salt;
3β-O-(3',3'-Dimethylsuccinyl)-17β-(N'-piperidin-4-yl-ureido)-21-oxolup-18-ene hydrochloride salt;
3β-O-(3',3'-Dimethylsuccinyl)-17β-(piperidine-4-amido)-21-oxolup-18-ene hydrochloride;
3β-O-(3',3'-Dimethylsuccinyl)-17β-benzamido-21-oxolup-18-ene sodium salt;
3β-O-(3',3'-Dimethylsuccinyl)-17β-(4-pyridyl)amido-21-oxolup-18-ene hydrochloride salt;
3β-O-(3',3'-Dimethylsuccinyl)-17β-(2-pyridyl)amido-21-oxolup-18-ene hydrochloride salt;
3β-O-(3',3'-Dimethylsuccinyl)-17β-(2-pyrazyl)amido-21-oxolup-18-ene hydrochloride salt;
3β-O-(3',3'-Dimethylsuccinyl)-17β-(1-methyl-1H-pyrazole-3-amido)-21-oxolup-18-ene hydrochloride salt;
3β-O-(3',3'-Dimethylsuccinyl)-17β-(1-methyl-1H-imidazole-5-amido)-21-oxolup-18-ene hydrochloride salt;
3β-O-(3',3'-Dimethylsuccinyl)-17β-(1-methyl-1H-imidazole-4-amido)-21-oxolup-18-ene hydrochloride salt;
3β-O-(3',3'-Dimethylsuccinyl)-17β-(1-methyl-1H-imidazole-2-amido)-21-oxolup-18-ene hydrochloride salt;
3β-O-(3',3'-Dimethylsuccinyl)-17β-(1-methyl-1H-pyrazole-5-amido)-21-oxolup-18-ene hydrochloride salt; or
3β-O-(3',3'-Dimethylsuccinyl)-17β-(1-methyl-1H-pyrazole-4-amido)-21-oxolup-18-ene hydrochloride salt.

20. A pharmaceutical composition comprising a compound according to claim 1 together with one or more pharmaceutically acceptable carrier.

* * * * *